(12) United States Patent
Koul et al.

(10) Patent No.: US 9,550,793 B2
(45) Date of Patent: Jan. 24, 2017

(54) SPIROCYCLIC COMPOUNDS, COMPOSITIONS AND MEDICINAL APPLICATIONS THEREOF

(71) Applicant: Advinus Therapeutics Limited, Bangalore (IN)

(72) Inventors: Summon Koul, Pune (IN); Debnath Bhuniya, Pune (IN); Kasim Mookhtiar, Pune (IN); Sandeep Bhosale, Pune (IN); Suresh Kurhade, Pune (IN); Keshav Naik, Pune (IN); Ravikumar Velayutham, Pune (IN); Videsh Salunkhe, Pune (IN)

(73) Assignee: Advinus Therapeutics Limited, Bangalore (IN)

( * ) Notice: Subject to any disclaimer, the term of this patent is extended or adjusted under 35 U.S.C. 154(b) by 0 days.

(21) Appl. No.: 14/430,469

(22) PCT Filed: Oct. 1, 2013

(86) PCT No.: PCT/IN2013/000600
§ 371 (c)(1),
(2) Date: Mar. 23, 2015

(87) PCT Pub. No.: WO2014/054053
PCT Pub. Date: Apr. 10, 2014

(65) Prior Publication Data
US 2015/0218187 A1    Aug. 6, 2015

(30) Foreign Application Priority Data
Oct. 3, 2012 (IN) .......................... 4129/CHE/2012

(51) Int. Cl.
| | |
|---|---|
| C07D 215/20 | (2006.01) |
| A61K 31/438 | (2006.01) |
| C07D 498/04 | (2006.01) |
| C07D 413/14 | (2006.01) |
| C07D 413/12 | (2006.01) |
| C07D 451/02 | (2006.01) |
| C07D 471/04 | (2006.01) |
| C07D 487/04 | (2006.01) |
| C07D 271/113 | (2006.01) |

(52) U.S. Cl.
CPC ......... *C07D 498/04* (2013.01); *C07D 271/113* (2013.01); *C07D 413/12* (2013.01); *C07D 413/14* (2013.01); *C07D 451/02* (2013.01); *C07D 471/04* (2013.01); *C07D 487/04* (2013.01)

(58) Field of Classification Search
CPC ... C07D 413/14; C07D 413/12; C07D 451/02; C07D 498/04; C07D 271/113; C07D 471/04
USPC .... 546/15, 16, 18; 544/70, 230; 514/210.18, 514/210.2, 211.05, 236.2, 249, 262.1, 514/264.11, 278
See application file for complete search history.

(56) References Cited

U.S. PATENT DOCUMENTS

| | | | |
|---|---|---|---|
| 7,795,283 B2 * | 9/2010 | Birch | C07D 271/113 514/364 |
| 2010/0317653 A1 * | 12/2010 | Birch | C07D 413/12 514/218 |
| 2011/0092547 A1 * | 4/2011 | Birch | C07D 413/12 514/340 |

FOREIGN PATENT DOCUMENTS

| | | |
|---|---|---|
| WO | 2006134317 A1 | 12/2006 |
| WO | 2007138311 A1 | 12/2007 |
| WO | 2009016462 A2 | 2/2009 |
| WO | 2010089685 A1 | 8/2010 |

* cited by examiner

*Primary Examiner* — Rita Desai
(74) *Attorney, Agent, or Firm* — Andrews Kurth Kenyon LLP; David Bradin

(57) ABSTRACT

The present disclosure relates to a series of spirocyclic compounds of formula (I), their stereoisomers, tautomers, prodrugs, pharmaceutically acceptable salts, polymorphs, solvates, hydrates, N-Oxides, Co crystals and formulations thereof. The disclosure also relates to process of preparation of these spirocyclic compounds.

Formula (I)

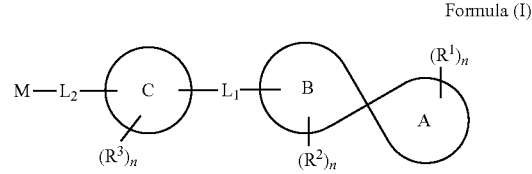

These compounds are useful in the treatment, prevention, prophylaxis, management, or adjunct treatment of all medical conditions related to inhibition of acyl CoA diacyl glycerol acyltransferase 1 (DGAT1).

7 Claims, No Drawings

SPIROCYCLIC COMPOUNDS, COMPOSITIONS AND MEDICINAL APPLICATIONS THEREOF

CROSS-REFERENCE TO RELATED APPLICATIONS

This application is a U.S. national phase entry, under the provisions of 35 U.S.C. §371, of International Patent Application No. PCT/IN13/000600 filed Oct. 1, 2013, which in turn claims priority to Indian Patent Application No. 4129/CHE/2012 filed Oct. 3, 2012. The disclosures of such international patent application and Indian priority patent application are hereby incorporated herein by reference in their respective entireties, for all purposes.

FIELD OF THE INVENTION

The present disclosure relates to a series of spirocyclic compounds, their stereoisomers, tautomers, prodrugs, pharmaceutically acceptable salts, polymorphs, solvates, hydrates, N-Oxides, Co crystals and formulations thereof. The invention also relates to process of preparation of these spirocyclic compounds. These compounds are useful in the treatment, prevention, prophylaxis, management, or adjunct treatment of all medical conditions related to inhibition of acyl CoA diacyl glycerol acyltransferase 1 (DGAT1).

BACKGROUND OF THE INVENTION

Diacylglycerol O-acyltransferase, also known as diglyceride acyltransferase or (DGAT), is found in the microsomal fraction of cells. DGAT plays an essential role in the metabolism of cellular diacylglycerol and is critically important for triglyceride production and energy storage homeostasis (*Eu. J. Biochem.* 1989, 182, 395-400). DGAT catalyses the final and rate limiting step in the triacylglycerol synthesis from 1,2-diacylglycerol (DAG) and long chain fatty acyl CoA as substrates (*Lipid Res.*, 1996, 35, 169-201). Although triglycerides are essential for normal physiology, excess triglyceride accumulation results in obesity and, particularly when it occurs in non adipose tissues, is associated with insulin resistance.

Two DGAT genes (DGAT 1 and DGAT 2) have been cloned and characterized. Both the encoded proteins share no sequence homology but they catalyze the same reaction (*Proc. Natl. Acad. Sci. USA*, 1998, 95, 13018-13023; *J. Biol. Chem.*, 2001, 276, 38870-38876). The enzymes are widely expressed; however some differences do exist in the relative abundance of expression in various tissues.

Studies in the gene knockout mice have indicated that pharmacological inhibition of DGAT1 would be of value in the treatment of Type II diabetes and obesity. DGAT1 knockout (DGAT1$^{-/-}$) mice are viable and capable of synthesizing triglycerides, as evidenced by normal fasting serum triglyceride levels and normal adipose tissue composition. DGAT1$^{-/-}$ mice have less adipose tissue than wild type mice at baseline and are resistant to diet induced obesity. Metabolic rate is ~20% higher in DGAT1$^{-/-}$ mice than in wild type mice on both regular and high fat diets (*Nature Genetics*, 2000, 25, 87-90). Increased physical activity in DGAT1$^{-/-}$ mice partially accounts for their increased energy expenditure. DGAT1$^{-/-}$ mice also exhibit increased insulin sensitivity. Thus phenotype of DGAT1 knock out mice suggests that DGAT1 inhibitors have utility for the treatment of obesity and associated complications like Type II diabetes and metabolic syndrome.

DGAT enzymes produce the fat that is stored in the droplets—important for HCV replication. DGAT1 interacts with one viral protein, the viral nucleocapsid core protein, required for viral particle assembly. The core protein normally associates with the surface of fat droplets but cannot do so when. DGAT1 is inhibited or missing in infected cells. Hence, HCV infection and viral particle production are severely impaired in liver cells that lack DGAT1 activity (*Nature Medicine*, 2010, 16, 1295-1298).

Several patent applications and publications describe the discovery of small molecule DGAT1 inhibitors (dibenzoxazepinones EP 1219716; substituted amino-pyrimidino oxazines, WO2004047755; amide compounds, WO2008011131; piperidine/piperazine derivatives, WO2008148840; pyrazine carboxamides, WO2010146395; oxadiazole and oxazole substituted benzimidazole and indole derivatives, WO2009040410; amino-dihydropyrido-pyrimidinone compounds, oxazole compounds, WO2010059602; US20100197590; substituted bicyclolactam compounds, WO2009016462; Imidazole derivatives, WO2012047772; WO2012009217, Spirocyclic compounds; Inhibitors of diacylglycerol acyltransferase: a review of 2008 patents, *Expert Opin. Ther. Patents*, 2010, 20(1), 19-29; *J. Med. Chem.* 2009, 52, 1558-1568; *J. Med. Chem.* 2008, 51, 380-383; *J. Med. Chem.*, 2011, 54 (7), 2433-2446; *ACS Med. Chem. Lett.*, 2011, 2 (5), 407-412; *ACS Med. Chem. Lett.*, 2012, 3 (5), 411-415; *Bioorg. Med. Chem. Lett.*, 2012, 22, 3873-3878. WO2006064189 describes oxadiazole compounds as DGAT1 inhibitors. However, only few small molecule DGAT1 inhibitors are in clinical trials. For example, LCQ-908 from Novartis is in Phase 2 clinical trials for the treatment of HCV, hypertriglyceridemia and T2D. Pfizer and AstraZeneca have recently discontinued their DGAT1 inhibitors from Phase 1 clinical trials. No DGAT1 inhibitor has yet reached the marketing stage. Therefore, there remains a need for discovering novel DGAT1 inhibitors possessing desirable properties such as pharmacokinetic/dynamic and or physicochemical and/or other drug like profiles to advance into clinics.

SUMMARY OF THE INVENTION

The present disclosure provides spirocyclic compounds of Formulae (I), their tautomers, polymorphs, stereoisomers, prodrugs, solvates, hydrates, N-Oxides, co-crystals, pharmaceutically acceptable salts, pharmaceutical compositions containing them and methods of treating conditions and diseases that are mediated by DGAT1 activity

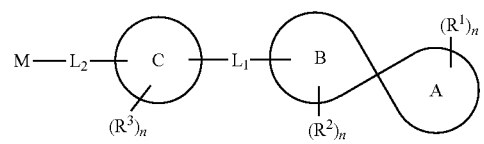

Formula (I)

wherein
M is selected from group consisting of

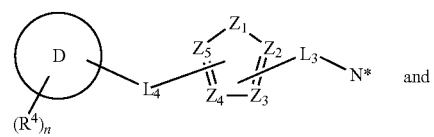

Attachment 1 and

-continued

Attachment 2

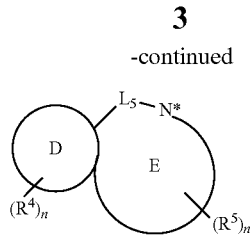

* represents point of attachment to $L_2$.
rings A and B represent a spirocyclic ring system wherein, A and B are same or different and independently represents a three to eight membered ring which may be saturated or partially unsaturated optionally having up to four heteroatoms selected from O, N or S;
ring C is absent or is 6 membered aromatic or heteroaromatic ring system;
ring D is selected from cycloalkyl, aryl, heterocyclyl or heteroaryl;
rings E represents a 5-12 membered ring including spirocyclic system, which is saturated, unsaturated or partially unsaturated optionally having upto three heteroatom independently selected from O, N or S;
$L_1$, $L_2$, $L_3$, $L_4$ and $L_5$ are independently absent or is $C_{1-4}$ alkylene wherein one or more methylene groups is optionally replaced by hetero atoms or groups such as —O—, —S(O)$_p$—, —N(R$^6$)—, —C(O)—, —C(S)— or —(CR$^a$R$^b$)—; alkylene is optionally substituted with hydroxy, amino, aminoalkyl, cyano, halogen, haloalkyl, perhaloalkyl, carboxy, carboxyalkyl, alkylcarboxy, alkoxy, hydroxyalkyl, alkoxyalkyl, alkoxyalkoxy or alkyl;
$Z_1$ is selected from O, N or S;
$Z_2$, $Z_3$, $Z_4$ and $Z_5$ are same or different and are independently selected from —CH or N provided that two of $Z_2$, $Z_3$, $Z_4$ and $Z_5$ represent N;
$R^1$, $R^2$, $R^3$, $R^4$ and $R^5$ are independently selected from hydrogen, halo, cyano, nitro, —(CR$^a$R$^b$)$_n$OR$^7$, —(CR$^a$R$^b$)$_n$C(O)R$^7$, —(CR$^a$R$^b$)$_n$SR$^7$, —(CR$^a$R$^b$)$_n$COOR$^7$, —(CR$^a$R$^b$)$_n$NR$^8$R$^9$, —(CR$^a$R$^b$)$_n$C(O)NR$^8$R$^9$, —(CR$^a$R$^b$)$_n$NR$^8$C(O)OR$^7$, —(CR$^a$R$^b$)$_n$NR$^8$C(O)NR$^8$R$^9$, —NR$^8$S(O)$_2$R$^7$, —S(O)$_p$R$^7$, —SO$_3$H, —S(O)$_2$NR$^8$R$^9$, azido, oxo, thiocarbonyl, $C_{1-6}$alkyl, $C_{2-6}$alkenyl, $C_{2-6}$alkynyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkenyl, cycloalkylalkyl aryl, arylalkyl, heterocyclyl, heterocyclylalkyl, heteroaryl or heteroarylalkyl wherein each substituent is unsubstituted or substituted with 1, 2, or 3 substituents independently selected from alkyl, halogen, haloalkyl, perhaloalkyl, haloalkoxy, perhaloalkoxy, cyano —(CR$^a$R$^b$)$_n$OR$^7$, —(CR$^a$R$^b$)$_n$COOR$^7$, —(CR$^a$R$^b$)$_n$NR$^8$R$^9$, —(CR$^a$R$^b$)$_n$C(O)NR$^8$R$^9$, —S(O)$_p$R$^7$ or —SO$_3$H.
$R^6$ is selected from hydrogen, cyano, alkyl or haloalkyl;
$R^7$ is selected from hydrogen, alkyl, haloalkyl, —(CR$^a$R$^b$)$_n$OR$^7$, —(CR$^a$R$^b$)$_n$COOR$^7$, —(CR$^a$R$^b$)$_n$C(O)R$^7$, aminocarbonyl, cycloalkyl, cycloalkylalkyl, aryl, arylalkyl, heteroaryl, heteroarylalkyl, heterocyclyl or heterocyclylalkyl;
$R^8$ and $R^9$ are independently selected from the group consisting of hydrogen, alkyl, haloalkyl, —(CR$^a$R$^b$)$_n$OR$^7$, —(CR$^a$R$^b$)$_n$C(O)R$^7$, aryl, arylalkyl, heteroaryl, heteroarylalkyl, cycloalkyl, cycloalkylalkyl, heterocyclyl and heterocyclylalkyl, or
$R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, —(CR$^a$R$^b$)$_n$OR$^7$, —(CR$^a$R$^b$)$_n$SR$^7$, —(CR$^a$R$^b$)$_n$NR$^8$R$^9$, oxo, alkylsulfonyl, —(CR$^a$R$^b$)$_n$COOR$^7$, —(CR$^a$R$^b$)$_n$C(O)NR$^8$R$^9$, cycloalkyl, cycloalkylalkyl, aryl, arylalkyl, heterocyclyl, heterocyclylalkyl, heteroaryl, or heteroarylalkyl;
$R^a$ and $R^b$ are independently selected from the group consisting of hydrogen, —OR$^7$, halogen, haloalkyl, perhaloalkyl and alkyl; or
$R^a$ and $R^b$ taken together form a monocyclic or a bicyclic ring system which is saturated or partially unsaturated and optionally have additional heteroatoms selected from O, N or S;
p=0-2;
n=0-4

The present disclosure discloses a process of preparation of compounds of formula (I), or its tautomers, polymorphs, stereoisomers, prodrugs, solvates, hydrates, N-Oxides, co-crystals or pharmaceutically acceptable salts thereof.

These and other features, aspects, and advantages of the present disclosure will become better understood with reference to the following description. This statement is provided to introduce a selection of concepts in simplified form. This statement is not intended to identify key features or essential features of the subject matter, nor is it intended to be used to limit the scope of the subject matter.

DETAILED DESCRIPTION OF THE INVENTION

Definitions

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methyl, ethyl, n-propyl, iso-propyl, n-butyl, iso-butyl, t-butyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkyl" or "substituted alkylene" refers to: (1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where $R^b$ is hydrogen, alkyl, aryl, heteroaryl or heterocyclyl. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_p R^c$, where $R^c$ is alkyl, aryl, or heteroaryl and p is 0, 1 or 2; or (2) an alkyl group or alkylene group as defined above that is interrupted by 1, 2, 3, 4, 5, 6, 7, 8, 9 or 10 atoms independently selected from oxygen, sulphur and $NR^d$, where $R^d$ is selected from hydrogen, alkyl, cycloalkyl, cycloalkenyl, aryl, heteroaryl and heterocyclyl, carbonylalkyl, carboxyester, carboxyamide and sulfonyl. All substituents may be optionally further substituted by alkyl, alkoxy, halogen, $CF_3$, amino, substituted amino, cyano, or —$S(O)_p R^c$, in which $R^c$ is alkyl, aryl, or heteroaryl and p is 0, 1, or 2; or (3) an alkyl or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl (—CH=$CH_2$), 1-propylene or allyl (—$CH_2$CH=$CH_2$), isopropylene (—C($CH_3$)=$CH_2$), bicyclo[2.2.1]heptene, and the like.

The term "alkenylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl, $SO_3H$, aryl, aryloxy, heteroaryl, aminocarbonylamino, heteroaryloxy, heterocyclyl, heterocyclyloxy, hydroxyamino, alkoxyamino, nitro, —$S(O)_2 NR^a R^a$, —$NR^a S(O)_2 R^a$ and —$S(O)_p R^b$ where each $R^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_p R^c$, where $R^c$ is alkyl, aryl, or heteroaryl and p is 0, 1 or 2.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl, —$CH_2$C≡CH), homopropargyl (or but-1-yn-4-yl, —$CH_2CH_2$C≡CH) and the like.

The term "alkynylene" refers to a diradical of a branched or an unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, am inocarbonyl, alkoxycarbonylamino, azido, cyano, halogen, hydroxy, keto, thiocarbonyl, carboxy, carboxyalkyl, —$SO_3H$, aryl, aryloxy, heteroaryl, aminocarbonylamino, heteroaryloxy, heterocyclyl, heterocyclyloxy, hydroxyamino, alkoxyamino, nitro, —$S(O)_2 NR^a R^a$, —$NR^a S(O)_2 R^a$ and —$S(O)_p R^b$, where each $R^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_p R^c$ where $R^c$ is alkyl, aryl, or heteroaryl and p is 0, 1 or 2.

The term "cycloalkyl" refers to unless otherwise mentioned, carbocyclic groups of from 3 to 20 carbon atoms having single cyclic ring or multiple condensed rings or spirocyclic rings or bridged rings which may be saturated or partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo[2.2.1]heptane, bicyclo[2.2.2]octane, 1,3,3-trimethylbicyclo[2.2.1]hept-2-yl, (2,3,3-trimethylbicyclo[2.2.1]hept-2-yl), or carbocyclic groups, to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, aminosulfonyl, aminocarbonylamino, heteroaryloxy, heterocyclyl, heterocyclyloxy, hydroxyamino, alkoxyamino, nitro, —C(O)R and —$S(O)_p R^b$, where R is hydrogen, hydroxyl, alkoxy, alkyl and cyclocalkyl, heterocyclyloxy where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_p R^c$, where $R^c$ is alkyl, aryl, or heteroaryl and p is 0, 1 or 2.

The term "spirocycle" refers to unless otherwise mentioned, a bicyclic organic compound with rings connected through just one atom. The rings can be different in nature or identical.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group R'''—O—, where R''' is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O)NR'R' where each R' is independently hydrogen, alkyl, aryl, heteroaryl, heterocyclyl or both R' groups are joined to form a heterocyclic group (e.g. morpholino). Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —S(O)$_p$R$^c$, where R$^c$ is alkyl, aryl, or heteroaryl and p is 0, 1 or 2.

The term "acylamino" refers to the group —NR''C(O)R'' where each R'' is independently hydrogen, alkyl, aryl, heteroaryl, or heterocyclyl. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —S(O)$_p$R$^c$, where R$^c$ is alkyl, aryl, or heteroaryl and p is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, or —S(O)$_p$R$^c$, where R$^c$ is alkyl, aryl, or heteroaryl and p is 0, 1 or 2.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

"Aryloxyalkyl" refers to the group -alkyl-O-aryl. Representative examples of aryloxyalkyl include but are not limited to phenoxymethyl, naphthyloxymethyl, phenoxyethyl, naphthyloxyethyl and the like.

"Di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Aminoalkyl" refers to an amino group that is attached to ($C_{1-6}$) alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —SO$_3$H, aryl, aryloxy, heteroaryl, aminosulfonyl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; where R$^b$ is hydrogen, alkyl, aryl, heterocyclyl or heteroaryl and p is 0, 1 or 2. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and —S(O)$_p$R$^c$ where R$^c$ is hydrogen, alkyl, aryl, or heteroaryl and p is 0, 1 or 2.

The term "arylalkyl" refers to an aryl group covalently linked to an alkylene group, where aryl and alkylene are defined herein.

"Optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group aryl-O— wherein the aryl group is as defined above, and includes optionally substituted aryl groups as also defined above.

The term "arylthio" refers to the group —S-aryl, where aryl is as defined herein including optionally substituted aryl groups as also defined above.

The term "substituted amino" refers to the group —NR'R' where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, $CF_3$, amino, substituted amino, cyano, and $—S(O)_pR^c$, where $R^c$ is alkyl, aryl, or heteroaryl and p is 0, 1 or 2.

The term "carboxyalkyl" refers to the groups -alkylene-C(O)OH.

The term "alkylcarboxyalkyl" refers to the groups -alkylene-C(O)OR$^d$ where R$^d$ is alkyl, cycloalkyl, where alkyl, cycloalkyl are as defined herein, and may be optionally further substituted by alkyl, halogen, $CF_3$, amino, substituted amino, cyano, or $—S(O)_pR^c$, in which R$^c$ is alkyl, aryl, or heteroaryl and p is 0, 1 or 2.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulphur within at least one ring. Such heteroaryl groups can have a single ring (e.g. pyridyl or furyl) or multiple condensed rings (e.g. indolizinyl, benzothiazolyl, or benzothienyl). Examples of heteroaryls include, but are not limited to, [1,2,4]oxadiazol, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The term "heteroarylene" refers to a diradical of a heteroaryl group as defined above.

Unless otherwise constrained the heteroaryl or heterarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, $—SO_3H$, aryl, aryloxy, heteroaryl, aminocarbonylamino, heteroaryloxy, heterocyclyl, heterocyclyloxy, hydroxyamino, alkoxyamino, nitro, $—S(O)_2NR^aR^a$, $—NR^aS(O)_2R^a$, and $—S(O)_pR^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; where R$^b$ is hydrogen, alkyl, aryl, heterocyclyl or heteroaryl, and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and $—S(O)_nR^c$, where R$^c$ is alkyl, aryl, or heteroaryl and n is 0, 1 or 2.

The term "heteroarylalkyl" refers to a heteroaryl group covalently linked to an alkylene group, where heteroaryl and alkylene are defined herein.

"Optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a, single ring or multiple condensed rings or spirocyclic rings, or bridged rings unless otherwise mentioned, having from 1 to 40 carbon atoms and from 1 to 10 hetero atoms, preferably 1, 2, 3 or 4 heteroatoms, selected from nitrogen, sulphur, phosphorus, and/or oxygen within the ring. Heterocyclic groups can have a single ring or multiple condensed rings, and include tetrahydrofuranyl, morpholinyl, piperidinyl, piperazinyl, dihydropyridinyl, tetrahydroquinolinyl and the like. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, $—C(O)R$ where R is hydrogen, hydroxyl, alkoxy, alkyl and cyclocalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and $—S(O)_pR^b$, where R$^b$ is hydrogen, alkyl, aryl, heterocyclyl or heteroaryl and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and $—S(O)R^c$, where R$^c$ is alkyl, aryl, or heteroaryl and n is 0, 1 or 2.

The term "heterocyclylalkyl" refers to a heterocyclyl group covalently linked to an alkylene group, where heterocyclyl and alkylene are defined herein.

"Optionally substituted heterocyclylalkyl" refers to an optionally substituted heterocyclyl group covalently linked to an optionally substituted alkylene group.

The term "heteroaryloxy" refers to the group heteroaryl-O—.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

"Substituted sulfoxide" refers to a group —S(O)R, in which R is substituted alkyl, substituted aryl, or substituted heteroaryl, as defined herein.

The term "sulfone" or "substituted sulfone" refers to a group $—S(O)_2R$, in which R is alkyl, aryl, or heteroaryl The compounds of the present disclosure may have the ability to crystallize in more than one form, a characteristic known as polymorphism, and all such polymorphic forms ("polymorphs") are encompassed within the scope of the disclosure. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the disclosure are congeners, analogs, hydrolysis products, metabolites and precursor or prodrugs of the compound. In general, unless otherwise indicated, all physical forms are equivalent for the uses contemplated herein and are intended to be within the scope of the present disclosure.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the disclosure are quaternary ammonium compounds wherein an equivalent of an anion (M-) is associated with the positive charge of the N atom. M- may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. M- is preferably an anion selected from chloride, bromide, iodide, sulphate, nitrate, acetate, maleate, oxalate, succinate or trifluoroacetate. More preferably M- is chloride, bromide, trifluoroacetate or methanesulphonate.

The present disclosure provides spirocyclic compounds of Formula (I), their tautomers, polymorphs, stereoisomers, prodrugs, solvates, hydrates, N-Oxides, co-crystals or a pharmaceutically acceptable salts, pharmaceutical compositions containing them and methods of treating conditions and diseases that are mediated by DGAT1 activity,

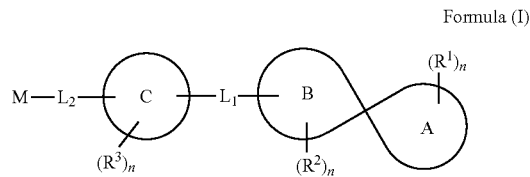

Formula (I)

wherein
M is selected from group consisting of

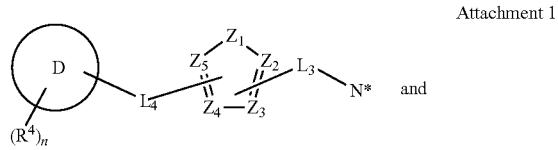

Attachment 1

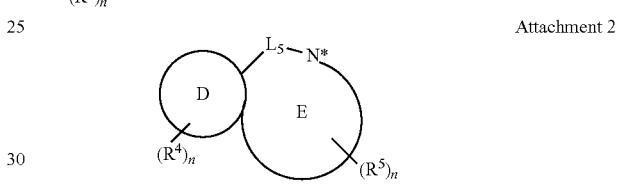

Attachment 2

* represents point of attachment to $L_2$.
rings A and B represent a spirocyclic ring system wherein, A and B are same or different and independently represents a three to eight membered ring which may be saturated or partially unsaturated optionally having upto four heteroatoms selected from O, N or S;
ring C is absent or is 6 membered aromatic or heteroaromatic ring system;
ring D is selected from cycloalkyl, aryl, heterocyclyl or heteroaryl;
rings E represents a 5-12 membered ring including spirocyclic system, which is saturated, unsaturated or partially unsaturated optionally having upto three heteroatom independently selected from O, N or S;
$L_1$, $L_2$, $L_3$, $L_4$ and $L_5$ are independently absent or is $C_{1-4}$ alkylene wherein one or more methylene groups is optionally replaced by hetero atoms or groups such as —O—, —S(O)$_p$—, —N(R$^6$)—, —C(O)—, —C(S)— or —(CR$^a$R$^b$)—; alkylene is optionally substituted with hydroxy, amino, aminoalkyl, cyano, halogen, haloalkyl, perhaloalkyl, carboxy, carboxyalkyl, alkylcarboxy, alkoxy, hydroxyalkyl, alkoxyalkyl, alkoxyalkoxy or alkyl;
$Z_1$ is selected from O, N or S;
$Z_2$, $Z_3$, $Z_4$ and $Z_5$ are same or different and are independently selected from —CH or N provided that two of $Z_2$, $Z_3$, $Z_4$ and $Z_5$ represent N;
$R^1$, $R^2$, $R^3$, $R^4$ and $R^5$ are independently selected from hydrogen, halo, cyano, nitro, —(CR$^a$R$^b$)$_n$OR$^7$, —(CR$^a$R$^b$)$_n$C(O)R$^7$, —(CR$^a$R$^b$)$_n$SR$^7$, —(CR$^a$R$^b$)$_n$COOR$^7$, —(CR$^a$R$^b$)$_n$NR$^8$R$^9$, —(CR$^a$R$^b$)$_n$C(O)NR$^8$R$^9$, —(CR$^a$R$^b$)$_n$NR$^8$C(O)OR$^7$, —(CR$^a$R$^b$)$_n$NR$^8$C(O)NR$^8$R$^9$, —NR$^8$S(O)$_2$R$^7$, —S(O)$_p$R$^7$, —SO$_3$H, —S(O)$_2$NR$^8$R$^9$, azido, oxo, thiocarbonyl, $C_{1-6}$alkyl, $C_{2-6}$alkenyl, $C_{2-6}$ alkynyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkenyl, cycloalkylalkyl, aryl, arylalkyl, heterocyclyl, heterocyclylalkyl, heteroaryl or heteroarylalkyl
  wherein each substituent is unsubstituted or substituted with 1, 2, or 3 substituents independently selected from alkyl, halogen, haloalkyl, perhaloalkyl, haloalkoxy, perhaloalkoxy, cyano —(CR$^a$R$^b$)$_n$OR$^7$, —(CR$^a$R$^b$)$_n$COOR$^7$, —(CR$^a$R$^b$)$_n$NR$^8$R$^9$, —(CR$^a$R$^b$)$_n$C(O)NR$^8$R$^9$, —S(O)$_p$R$^7$ or —SO$_3$H.

R$^6$ is selected from hydrogen, cyano, alkyl or haloalkyl;
R$^7$ is selected from hydrogen, alkyl, haloalkyl, —(CR$^a$R$^b$)$_n$OR$^7$, —(CR$^a$R$^b$)$_n$COOR$^7$, —(CR$^a$R$^b$)$_n$C(O)R$^7$, aminocarbonyl, cycloalkyl, cycloalkylalkyl, aryl, arylalkyl, heteroaryl, heteroarylalkyl, heterocyclyl or heterocyclylalkyl;
R$^8$ and R$^9$ are independently selected from the group consisting of hydrogen, alkyl, haloalkyl, —(CR$^a$R$^b$)$_n$OR$^7$, —(CR$^a$R$^b$)$_n$C(O)R$^7$, aryl, arylalkyl, heteroaryl, heteroarylalkyl, cycloalkyl, cycloalkylalkyl, heterocyclyl and heterocyclylalkyl, or
R$^8$ and R$^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, —(CR$^a$R$^b$)$_n$OR$^7$, —(CR$^a$R$^b$)$_n$SR$^7$, —(CR$^a$R$^b$)$_n$NR$^8$R$^9$, oxo, alkylsulfonyl, —(CR$^a$R$^b$)$_n$COOR$^7$, (CR$^a$R$^b$)$_n$C(O)NR$^8$R$^9$, cycloalkyl, cycloalkylalkyl, aryl, arylalkyl, heterocyclyl, heterocyclylalkyl, heteroaryl, or heteroarylalkyl;
R$^a$ and R$^b$ are independently selected from the group consisting of hydrogen, —OR$^7$, halogen, haloalkyl, perhaloalkyl and alkyl; or
R$^a$ and R$^b$ taken together form a monocyclic or a bicyclic ring system which is saturated or partially unsaturated and optionally have additional heteroatoms selected from O, N or S;
p=0-2;
n=0-4

According to another embodiment, the present disclosure relates to compounds of formula (I) or its tautomers, polymorphs, stereoisomers, prodrugs, solvates, hydrates, N-Oxides, co-crystals or a pharmaceutically acceptable salts thereof, wherein, rings A and B is selected from

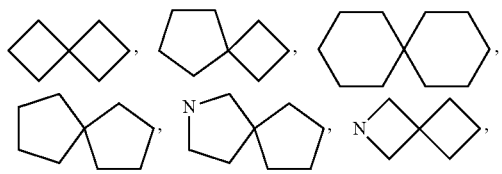

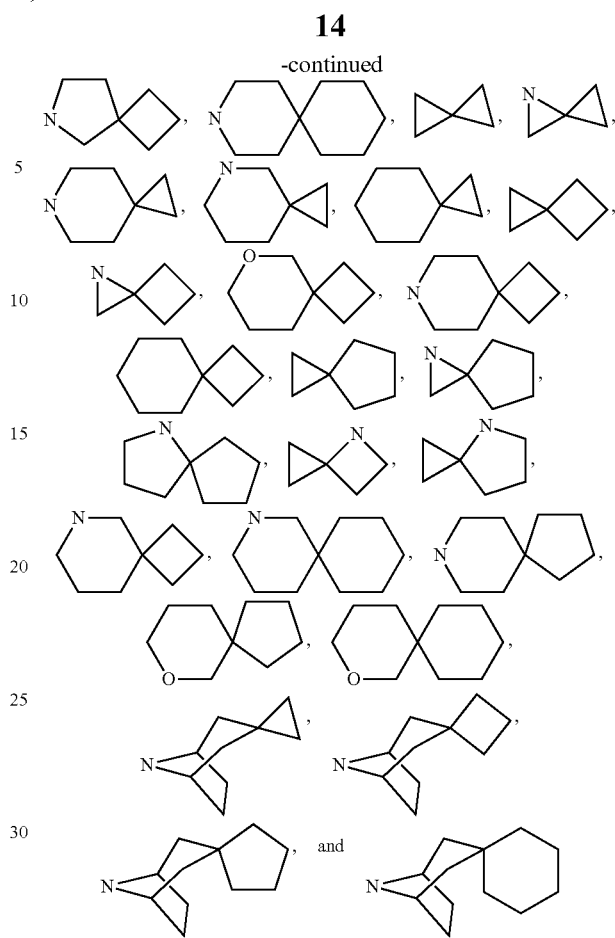

According to still another embodiment, the present disclosure relates to compounds of formula (I) or its tautomers, polymorphs, stereoisomers, prodrugs, solvates, hydrates, N-Oxides, co-crystals or a pharmaceutically acceptable salts thereof, wherein,
ring C is absent or selected from

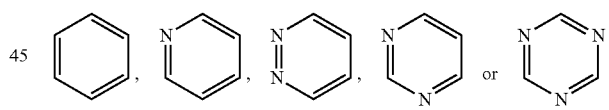

According to another embodiment, the present disclosure relates to compounds of formula (Ia) or its tautomers, polymorphs, stereoisomers, prodrugs, solvates, hydrates, N-Oxides, co-crystals or a pharmaceutically acceptable salts thereof, wherein, Formula (Ia)

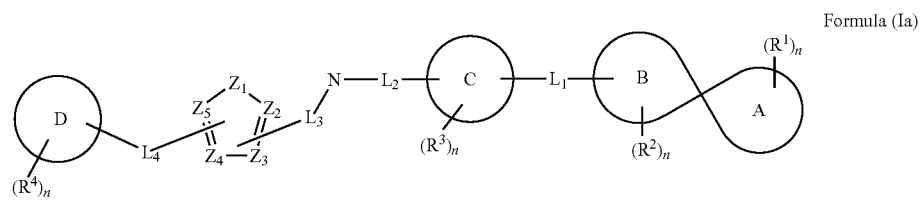

wherein rings A and B represent a spirocyclic ring system wherein, A and B are same or different and independently represents a three to eight membered ring which may be saturated or partially unsaturated optionally having upto four heteroatoms selected from O, N or S;

ring C is absent or is 6 membered aromatic or heteroaromatic ring system;

ring D is selected from cycloalkyl, aryl, heterocyclyl or heteroaryl;

$L_1$, $L_2$, $L_3$ and $L_4$ are independently absent or is $C_{1-4}$ alkylene wherein one or more methylene groups is optionally replaced by hetero atoms or groups such as —O—, —S(O)$_p$—, —N(R$^6$)—, —C(O)—, —C(S)— or —(CR$^a$R$^b$)—; alkylene is optionally substituted with hydroxy, amino, aminoalkyl, cyano, halogen, haloalkyl, perhaloalkyl, carboxy, carboxyalkyl, alkylcarboxy, alkoxy, hydroxyalkyl, alkoxyalkyl, alkoxyalkoxy or alkyl;

$Z_1$ is selected from O, N or S;

$Z_2$, $Z_3$, $Z_4$ and $Z_5$ are same or different and are independently selected from —CH or N provided that two of $Z_2$, $Z_3$, $Z_4$ and $Z_5$ represent N;

$R^1$, $R^2$, $R^3$ and $R^4$ are independently selected from hydrogen, halo, cyano, nitro, —(CR$^a$R$^b$)$_n$OR$^7$, —(CR$^a$R$^b$)$_n$C(O)R$^7$, —(CR$^a$R$^b$)$_n$SR$^7$, —(CR$^a$R$^b$)$_n$COOR$^7$, —(CR$^a$R$^b$)$_n$NR$^8$R$^9$, —(CR$^a$R$^b$)$_n$C(O)NR$^8$R$^9$, —(CR$^a$R$^b$)$_n$NR$^8$C(O)OR$^7$, —(CR$^a$R$^b$)$_n$NR$^8$C(O)NR$^8$R$^9$, —NR$^8$S(O)$_2$R$^7$, —S(O)$_p$R$^7$, —SO$_3$H, —S(O)$_2$NR$^8$R$^9$, azido, oxo, thiocarbonyl, $C_{1-6}$ alkyl, $C_{2-6}$ alkenyl, $C_{2-6}$ alkynyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkenyl, cycloalkylalkyl, aryl, arylalkyl, heterocyclyl, heterocyclylalkyl, heteroaryl or heteroarylalkyl wherein each substituent is unsubstituted or substituted with 1, 2, or 3 substituents independently selected from alkyl, halogen, haloalkyl, perhaloalkyl, haloalkoxy, perhaloalkoxy, cyano —(CR$^a$R$^b$)$_n$OR$^7$, —(CR$^a$R$^b$)$_n$COOR$^7$, —(CR$^a$R$^b$)$_n$NR$^8$R$^9$, —(CR$^a$R$^b$)$_n$C(O)NR$^8$R$^9$, —S(O)$_p$R$^7$ or —SO$_3$H.

$R^6$ is selected from hydrogen, cyano, alkyl or haloalkyl;

$R^7$ is selected from hydrogen, alkyl, haloalkyl, —(CR$^a$R$^b$)$_n$OR$^7$, —(CR$^a$R$^b$)$_n$COOR$^7$, —(CR$^a$R$^b$)$_n$C(O)R$^7$, aminocarbonyl, cycloalkyl, cycloalkylalkyl, aryl, arylalkyl, heteroaryl, heteroarylalkyl, heterocyclyl or heterocyclylalkyl;

$R^8$ and $R^9$ are independently selected from the group consisting of hydrogen, alkyl, haloalkyl, —(CR$^a$R$^b$)$_n$OR$^7$, —(CR$^a$R$^b$)$_n$C(O)R$^7$, aryl, arylalkyl, heteroaryl, heteroarylalkyl, cycloalkyl, cycloalkylalkyl, heterocyclyl and heterocyclylalkyl, or $R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, —(CR$^a$R$^b$)$_n$OR$^7$, —(CR$^a$R$^b$)$_n$SR$^7$, —(CR$^a$R$^b$)$_n$NR$^8$R$^9$, oxo, alkylsulfonyl, —(CR$^a$R$^b$)$_n$COOR$^7$, —(CR$^a$R$^b$)$_n$C(O)NR$^8$R$^9$, cycloalkyl, cycloalkylalkyl, aryl, arylalkyl, heterocyclyl, heterocyclylalkyl, heteroaryl, or heteroarylalkyl;

$R^a$ and $R^b$ are independently selected from the group consisting of hydrogen, —OR', halogen, haloalkyl, perhaloalkyl and alkyl; or $R^a$ and $R^b$ taken together form a monocyclic or a bicyclic ring system which is saturated or partially unsaturated and optionally have additional heteroatoms selected from O, N or S;

p=0-2;

n=0-4

According to another embodiment, the present disclosure relates to compounds of formula (Ia) or its tautomers, polymorphs, stereoisomers, prodrugs, solvates, hydrates, N-Oxides, co-crystals or a pharmaceutically acceptable salts thereof, wherein, $Z_1$-$Z_5$ forms ring selected from

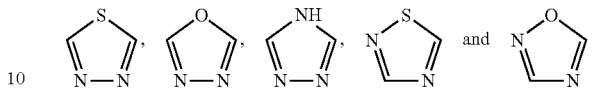

According to still another embodiment, the present disclosure relates to compounds of formula (Ia) or its tautomers, polymorphs, stereoisomers, prodrugs, solvates, hydrates, N-Oxides, co-crystals or a pharmaceutically acceptable salts thereof, wherein, D is selected from

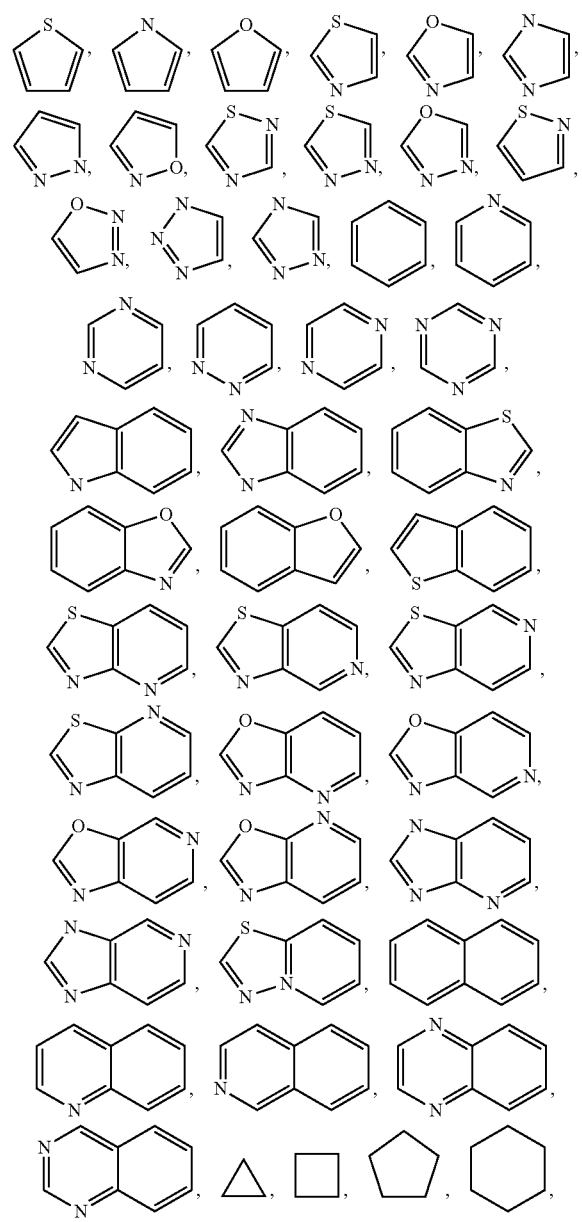

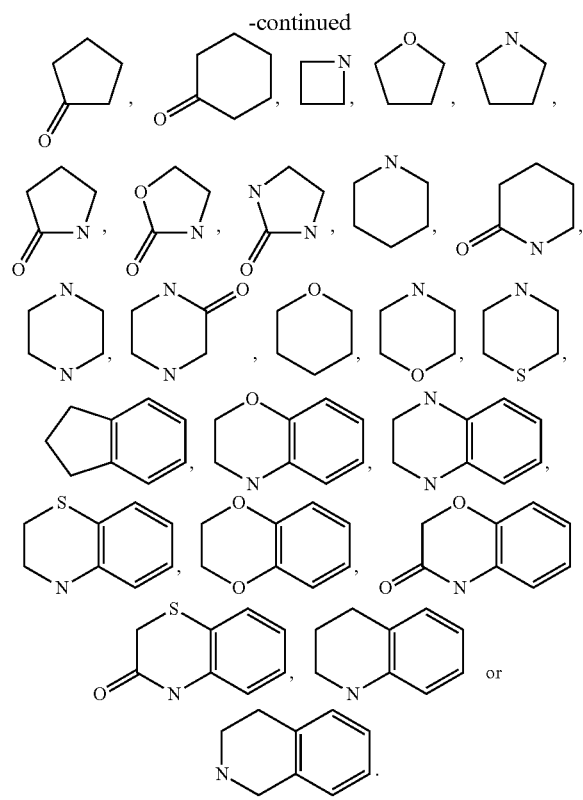

According to another embodiment, the present disclosure relates to compounds of formula (Ib) or its tautomers, polymorphs, stereoisomers, prodrugs, solvates, hydrates, N-Oxides; co-crystals or a pharmaceutically acceptable salts thereof, wherein, Formula (Ib)

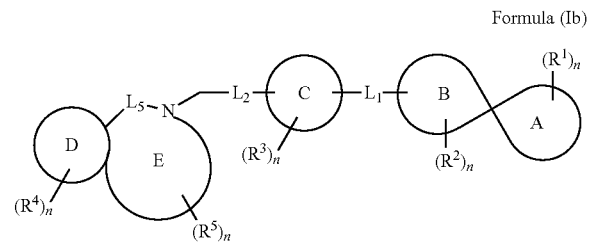

wherein
rings A and B represent a spirocyclic ring system wherein, A and B are same or different and independently represents a three to eight membered ring which may be saturated or partially unsaturated optionally having upto four heteroatoms selected from O, N or S;
ring C is absent or is 6 membered aromatic or heteroaromatic ring system;
ring D is selected from cycloalkyl, aryl, heterocyclyl or heteroaryl;
rings E represents a 5-12 membered ring including spirocyclic system, which is saturated, unsaturated or partially unsaturated optionally having upto three heteroatom independently selected from O, N or S;
$L_1$, $L_2$ and $L_5$ are independently absent or is $C_{1-4}$ alkylene wherein one or more methylene groups is optionally replaced by hetero atoms or groups such as —O—, —S$(O)_p$—, —N($R^6$)—, —C(O)—, —C(S)— or —(CR$^a$R$^b$)—; alkylene is optionally substituted with hydroxy, amino, aminoalkyl, cyano, halogen, haloalkyl, perhaloalkyl, carboxy, carboxyalkyl, alkylcarboxy, alkoxy, hydroxyalkyl, alkoxyalkyl, alkoxyalkoxy or alkyl;
$R^1$, $R^2$, $R^3$, $R^4$ and $R^5$ are independently selected from hydrogen, halo, cyano, nitro, —(CR$^a$R$^b$)$_n$OR$^7$, —(CR$^a$R$^b$)$_n$C(O)R$^7$, —(CR$^a$R$^b$)$_n$SR$^7$, —(CR$^a$R$^b$)$_n$COOR$^7$, —(CR$^a$R$^b$)$_n$NR$^8$R$^9$, —(CR$^a$R$^b$)$_n$C(O)NR$^8$R$^9$, —(CR$^a$R$^b$)$_n$NR$^8$C(O)OR$^7$, —(CR$^a$R$^b$)$_n$NR$^8$C(O)NR$^8$R$^9$, —NR$^8$S(O)$_2$R$^7$, —S(O)$_p$R$^7$, —SO$_3$H, —S(O)$_2$NR$^8$R$^9$, azido, oxo, thiocarbonyl, $C_{1-6}$ alkyl, $C_{2-6}$ alkenyl, $C_{2-6}$ alkynyl, cyanoalkyl, cyanoalkylcarbonyl, haloalkyl, perhaloalkyl, haloalkoxy, perhaloalkoxy, alkoxyalkoxy, alkoxyalkoxyalkyl, cycloalkyl, cycloalkenyl, cycloalkylalkyl, aryl, arylalkyl, heterocyclyl, heterocyclylalkyl, heteroaryl or heteroarylalkyl
wherein each substituent is unsubstituted or substituted with 1, 2, or 3 substituents independently selected from alkyl, halogen, haloalkyl; perhaloalkyl, haloalkoxy, perhaloalkoxy, cyano —(CR$^a$R$^b$)$_n$OR$^7$, —(CR$^a$R$^b$)$_n$COOR$^7$, —(CR$^a$R$^b$)$_n$NR$^8$R$^9$, —(CR$^a$R$^b$)$_n$C(O)NR$^8$R$^9$, —S(O)$_p$R$^7$ or —SO$_3$H.
$R^6$ is selected from hydrogen, cyano, alkyl or haloalkyl;
$R^7$ is selected from hydrogen, alkyl, haloalkyl, —(CR$^a$R$^b$)$_n$OR$^7$, —(CR$^a$R$^b$)$_n$COOR$^7$, —(CR$^a$R$^b$)$_n$C(O)R$^7$, aminocarbonyl, cycloalkyl, cycloalkylalkyl, aryl, arylalkyl, heteroaryl, heteroarylalkyl, heterocyclyl or heterocyclylalkyl;
$R^8$ and $R^9$ are independently selected from the group consisting of hydrogen, alkyl, haloalkyl, —(CR$^a$R$^b$)$_n$OR$^7$, —(CR$^a$R$^b$)$_n$C(O)R$^7$, aryl, arylalkyl, heteroaryl, heteroarylalkyl, cycloalkyl, cycloalkylalkyl, heterocyclyl and heterocyclylalkyl, or
$R^8$ and $R^9$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, —(CR$^a$R$^b$)$_n$OR$^7$, —(CR$^a$R$^b$)$_n$SR$^7$, —(CR$^a$R$^b$)$_n$NR$^8$R$^9$, oxo, alkylsulfonyl, —(CR$^a$R$^b$)$_n$COOR$^7$, —(CR$^a$R$^b$)$_n$C(O)NR$^8$R$^9$, cycloalkyl, cycloalkylalkyl, aryl, arylalkyl, heterocyclyl, heterocyclylalkyl, heteroaryl, or heteroarylalkyl;
$R^a$ and $R^b$ are independently selected from the group consisting of hydrogen, —OR$^7$, halogen, haloalkyl, perhaloalkyl and alkyl; or
$R^a$ and $R^b$ taken together form a monocyclic or a bicyclic ring system which is saturated or partially unsaturated and optionally have additional heteroatoms selected from O, N or S;
p=0-2;
n=0-4

According to another embodiment, the present disclosure relates to compounds of formula (Ib) or its tautomers, polymorphs, stereoisomers, prodrugs, solvates, hydrates, N-Oxides, co-crystals or a pharmaceutically acceptable salts thereof, wherein, Ring D-E is selected from

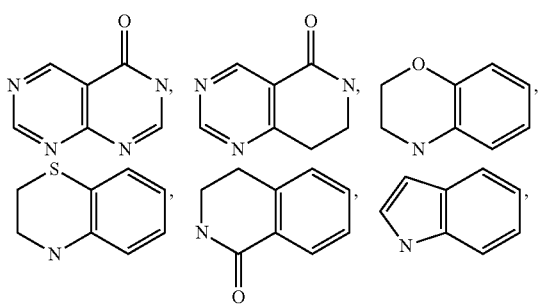

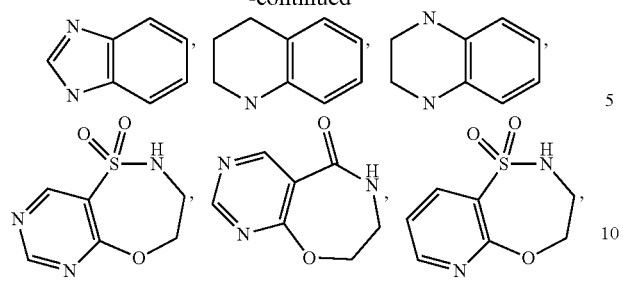

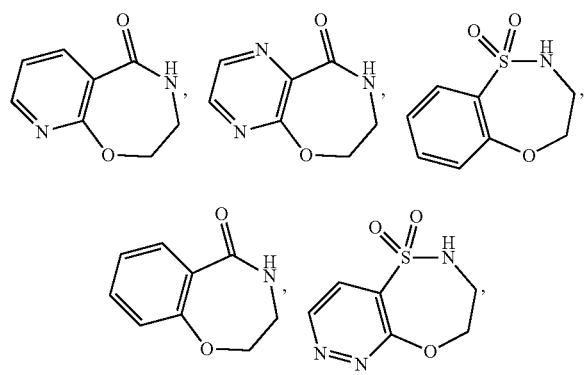

The compounds of formula (I), their tautomers, polymorphs, stereoisomers, prodrugs, solvates, hydrates, N-Oxides, co-crystals or a pharmaceutically acceptable salts thereof, may be prepared following independent general synthetic routes as outlined in the Schemes.

The compounds of Formula (I) may be prepared as outlined in the Scheme 1 and Scheme 2:

Scheme I: Preparation of compounds of Formula I wherein M is attachment 1 and $Z_1$, $Z_5$ are N; $Z_2$, $Z_4$ are C and $Z_3$ is O; $L_3$ is C(O)

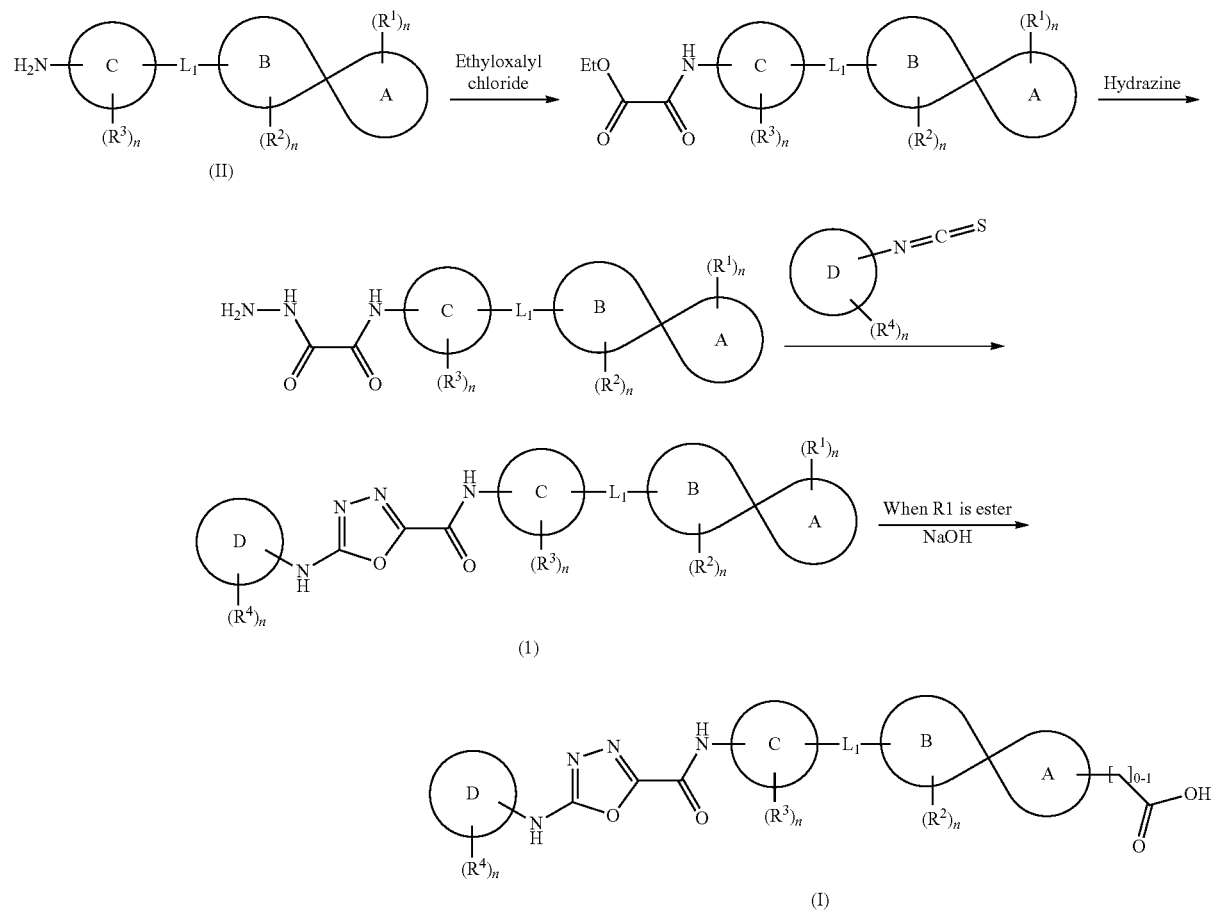

Compounds of Formula I when M is attachment 1 may be prepared from compounds of Formula II by treating them with ethyl oxalyl chloride followed by oxadiazole formation in 2 steps and finally hydrolysis (when R1=COOH in compounds of Formula I)

Scheme II: Preparation of compounds of Formula I wherein M is attachment 2; ring D is aminopyrimidine; ring E is oxazapinone; $L_2$ is absent and $L_5$ is C(O)

Compounds of Formula I when M is attachment 2 may be prepared by Buchwald coupling of compounds of Formula III with TBS protected appropriately substituted ethanol amines followed by amide coupling. Subsequently, base catalyzed cyclization to the lactam leads to compounds of Formula I.

Scheme III: Preparation of compounds of Formula I wherein M is attachment 2; ring D is aminopyrimidine; ring E is oxazapinone; $L_2$ is absent and $L_5$ is C(O); ring C is 6 membered aromatic or heteroaromatic ring system

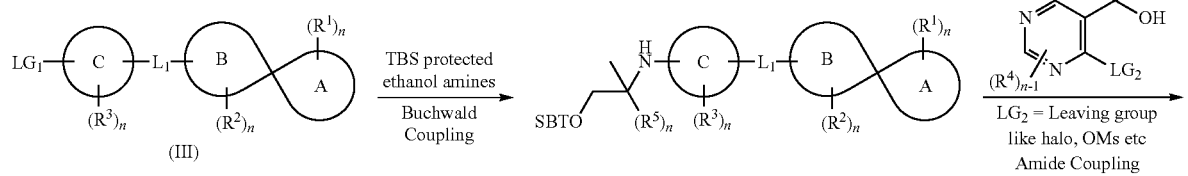

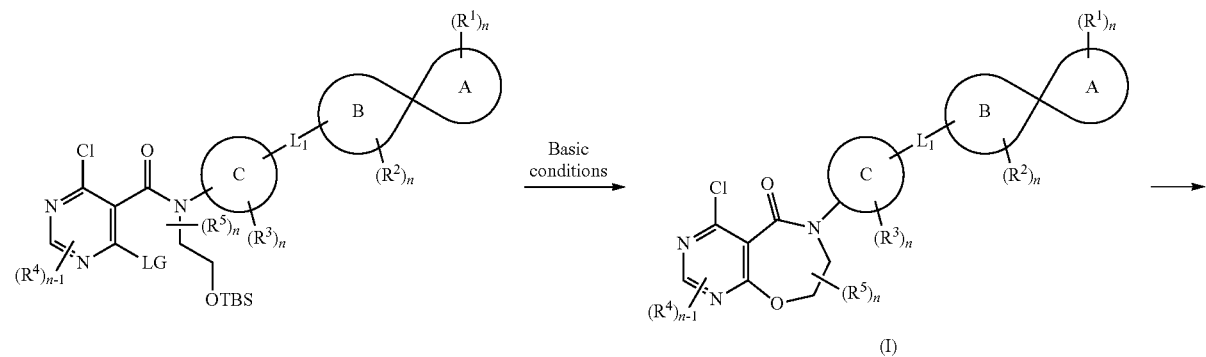

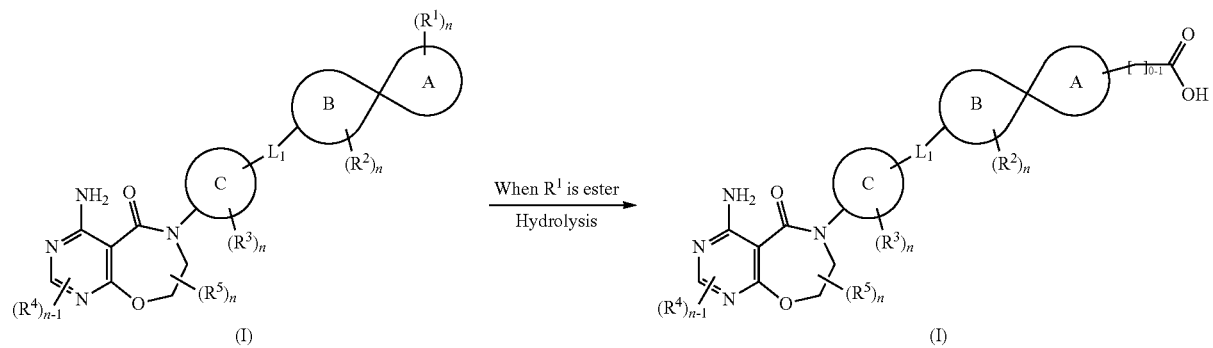

Scheme III

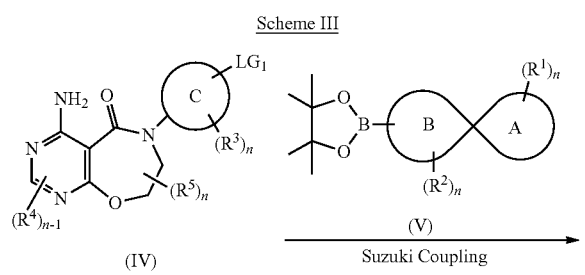

LG$_1$ is a halogen, preferably Br or I

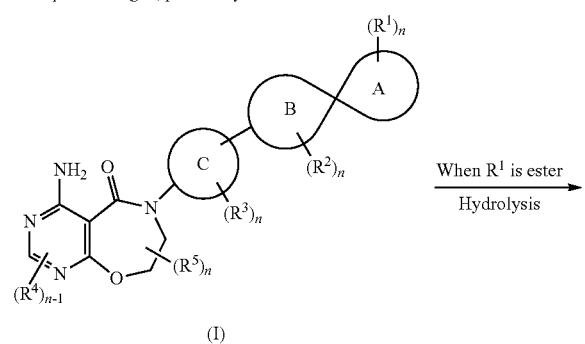

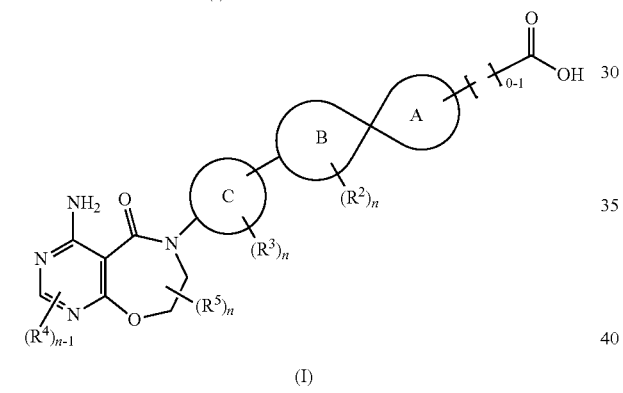

Alternatively compounds of Formula I can be prepared by Suzuki coupling of Intermediates of Formula IV with Intermediates of Formula V.

Scheme IV: Preparation of compounds of Formula I wherein M is attachment 2; ring D is aminopyrimidine; ring E is pyrimidinone; L$_2$ is absent and L$_5$ is C(O)

Scheme IV

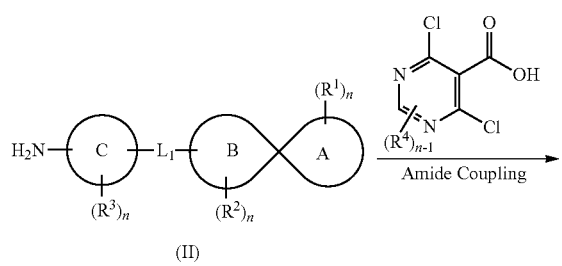

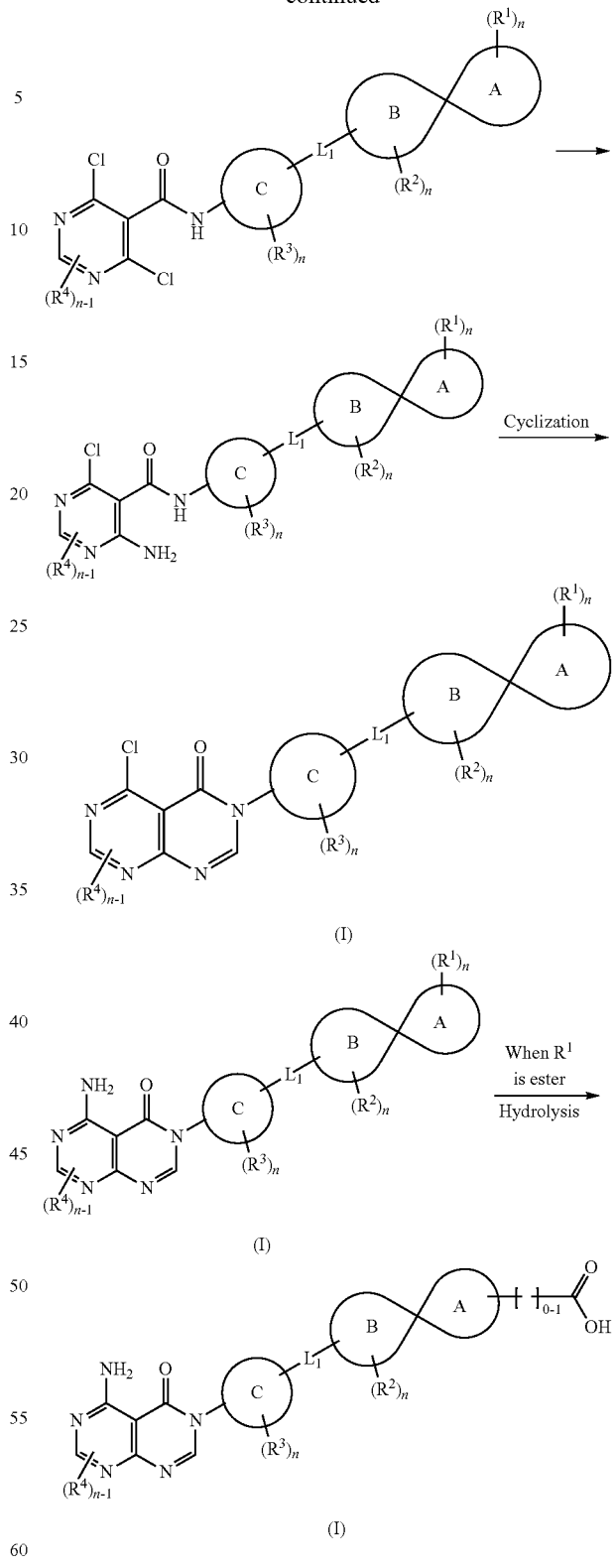

Compounds of Formula I when M is attachment 2 may be prepared by amide coupling of compounds of Formula II with ring D carboxylic acids. Subsequently, cyclization leads to compounds of Formula I.

Scheme V: Preparation of compounds of Formula I wherein M is attachment 2; ring D is aminopyrimidine; ring E is piperidinone; $L_2$ is absent and $L_5$ is C(O), ring C is 6 membered aromatic or heteroaromatic ring system

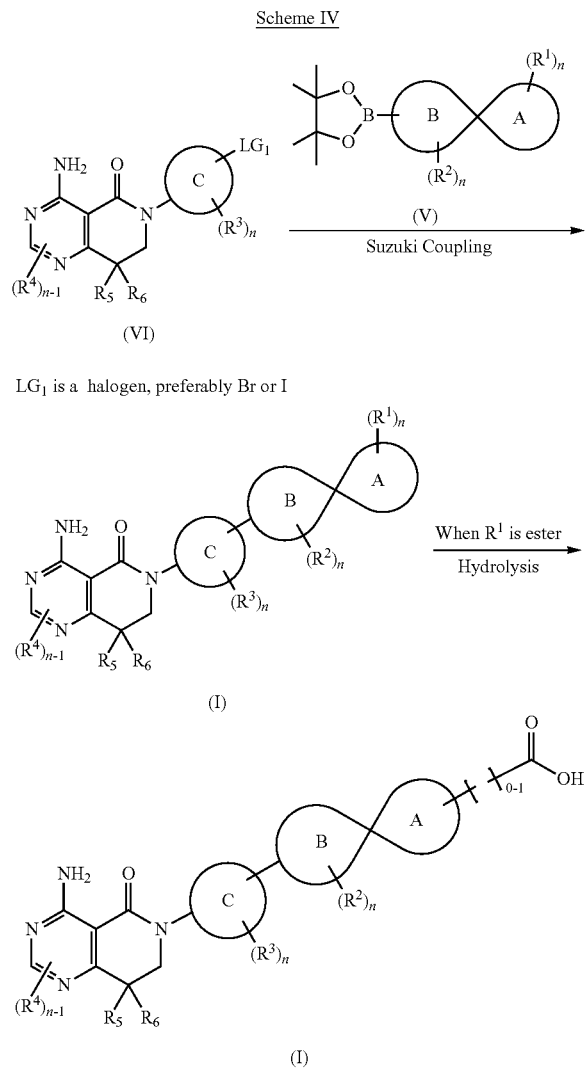

Compounds of Formula I can be prepared by Suzuki coupling of Intermediates of Formula VI with Intermediates of Formula V Suzuki Coupling:

Suzuki coupling is the organic reaction of an aryl- or vinyl-boronic acid with an aryl- or vinyl-halide catalyzed by a palladium(0) complex such as tetrakis(triphenylphosphine)palladium [*Chemical Reviews* 95 (7): 2457-2483]

Buchwald Coupling:

Buchwald coupling is a chemical reaction used for the synthesis of carbonnitrogen bonds via the palladium-catalyzed cross-coupling of amines with aryl halides [*Chem. Sci.* 2: 27-50, 2011]

Amide Coupling:

Amide coupling may be carried out using any suitable amide coupling regents such as oxalyl chloride, thionyl chloride, BOP-Cl, DCC, HOBt, HOAt, HATU, EDCI, alkylchloroformate and the like in the presence of organic non-nucleophilic bases such as triethyl amine, di-isopropylethyl amine, pyridine, N-methyl pyrrolidine, N,N-dimethylaminopyridine, DBU, DABCO, other hindered amines and pyridines. The amide coupling reaction may be carried out in the presence of solvents such as dichloromethane, dichloroethane, DMF, dimethylacetamide, THF, acetonitrile or mixture of them may be used at a temperature ranging from −5 to 150° C. The reaction may be carried out optionally in presence of catalytic amount of DMF. Amide coupling may also be carried out by heating ester and amine either in the absence of solvent or in presence of high boiling solvent like toluene, xylene, DMSO. Amide coupling may be carried out in presence of trialkyl aluminium (*Chem. Commun.,* 2008, 1100-1102).

Wherever desired or necessary, in any of the above mentioned processes, any of the compounds of formula (I) may be converted into a pharmaceutically acceptable salt or vice versa or converting one salt form into another pharmaceutically acceptable salt form.

According to another embodiment the present invention provides co-crystals comprising a compound of formula (I) wherein compounds of formula (I) that contain groups capable of acting as donors and/or acceptors for hydrogen bonds may be capable of forming co-crystals with suitable co-crystal formers. These co-crystals may be prepared from compounds of Formula (I) by known co-crystal forming procedures. Such procedures include grinding, heating, co-subliming, co-melting, or contacting in solution compounds of formula I with the co-crystal former under crystallization conditions and isolating co-crystals thereby formed.

According to another embodiment the present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

Yet another embodiment of the present invention is the use of a compound of the present invention or a pharmaceutically acceptable salt thereof for the manufacture of a medicament for the treatment or prophylaxis of diseases and disorders associated with DGAT1.

In one embodiment, the invention provides methods of treating or preventing a condition associated with DGAT1 in a subject, such as a mammal, i.e., a human or non-human mammal, comprising administering an effective amount of one or more compounds described herein to the subject.

In an embodiment, the compounds of the present invention are particularly useful for the delay or treatment of a range of DGAT1 mediated diseases or disorders selected from obesity, diabetes, Chylomicron disorders, familial chylomicronemia, impaired glucose tolerance, diabetic neuropathy, diabetic nephropathy, diabetic retinopathy, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, pancreatitis, metabolic acidosis, ketosis, steatosis, dysmetabolic syndrome and nonalcoholic fatty liver disease; cardiovascular diseases, such as atherosclerosis, arteriosclerosis, acute heart failure, congestive heart failure, coronary artery disease, cardiomyopathy, myocardial ischaemia, myocardial infarction, angina pectoris, hypertension, hypotension, stroke, ischemia, ischemic reperfusion injury, aneurysm, restenosis, peripheral vascular disease and vascular stenosis, diseases of the skin such as acne, infertility and polycystic ovary syndrome. The compounds of the present invention may be useful for the treatment of Hepatitis C infection.

In another embodiment, the DGAT1 mediated disorders of the present invention are selected from obesity, diabetes, Chylomicron disorders, familial chylomicronemia, impaired glucose tolerance, insulin resistance, impaired glucose tolerance, diabetic neuropathy, diabetic nephropathy, diabetic retinopathy, hypercholesterolemia, hypertriglyceridemia and hyperlipidemia.

In another embodiment, the present invention provides a method for the treatment of diseases or disorders mediated by DGAT1, comprising administering to a mammal in need thereof a therapeutically effective amount of a compound of formula 1, or a pharmaceutically acceptable salt or prodrug thereof.

In a further embodiment, the present invention provides a method for the treatment of Type II diabetes, obesity and Hepatitis C infection comprising administering to a mammal in need thereof a therapeutically effective amount of a compound of formula 1, or a pharmaceutically acceptable salt or prodrug thereof.

EXAMPLES

The disclosure is further illustrated by the following examples which in no way should be construed as being further limiting. One skilled in the art will readily appreciate that the specific methods and results described are merely illustrative.

Intermediate 1-IX

Methyl 2-[9-(5-amino-2-pyridyl)spiro[5.5]undecan-3-yl]acetate

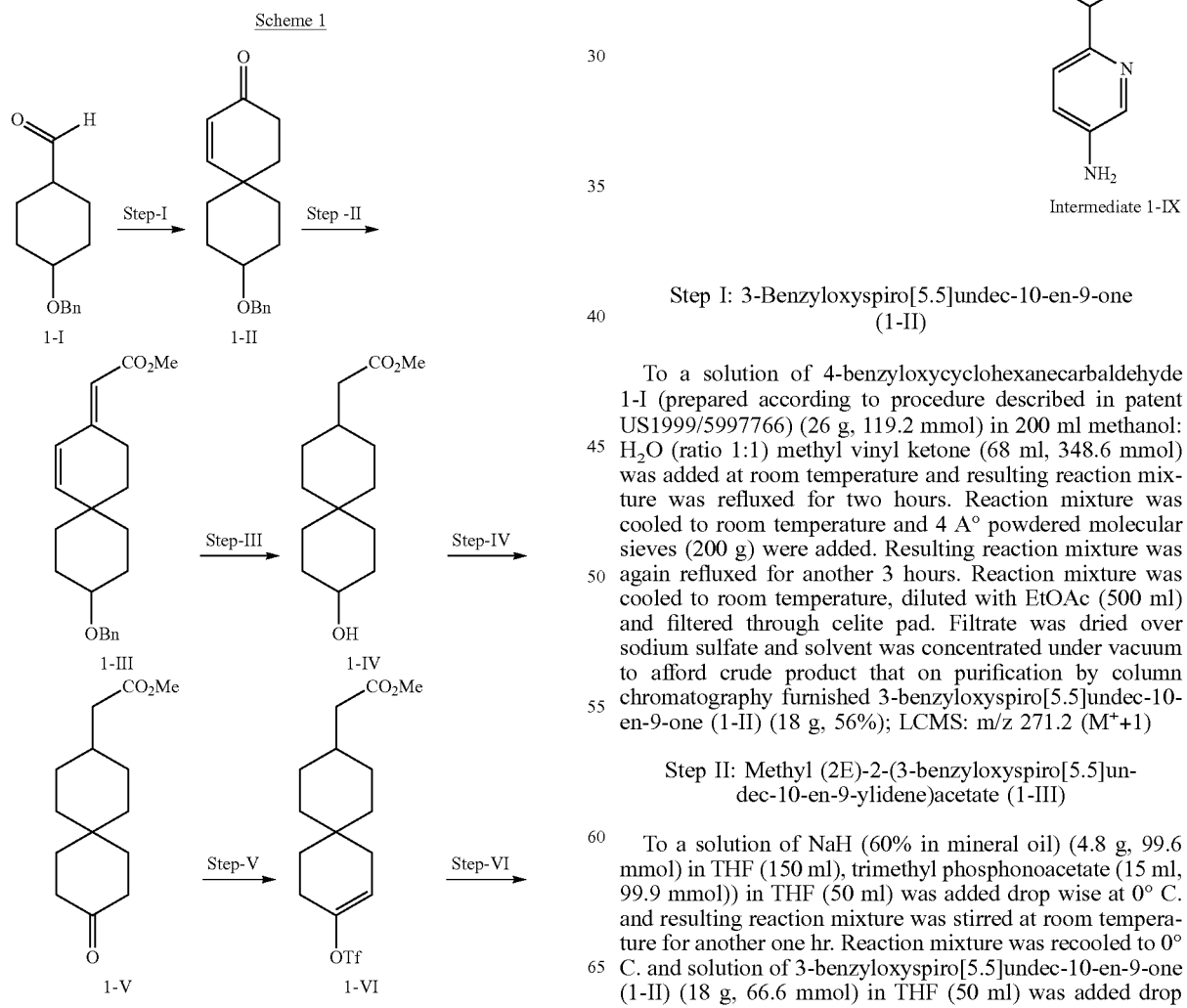

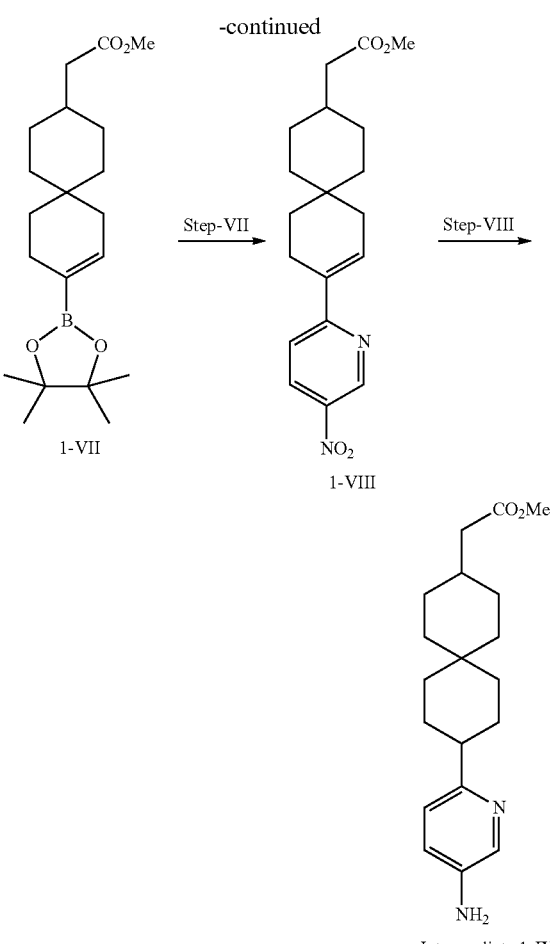

Step I: 3-Benzyloxyspiro[5.5]undec-10-en-9-one (1-II)

To a solution of 4-benzyloxycyclohexanecarbaldehyde 1-I (prepared according to procedure described in patent US1999/5997766) (26 g, 119.2 mmol) in 200 ml methanol:H$_2$O (ratio 1:1) methyl vinyl ketone (68 ml, 348.6 mmol) was added at room temperature and resulting reaction mixture was refluxed for two hours. Reaction mixture was cooled to room temperature and 4 A° powdered molecular sieves (200 g) were added. Resulting reaction mixture was again refluxed for another 3 hours. Reaction mixture was cooled to room temperature, diluted with EtOAc (500 ml) and filtered through celite pad. Filtrate was dried over sodium sulfate and solvent was concentrated under vacuum to afford crude product that on purification by column chromatography furnished 3-benzyloxyspiro[5.5]undec-10-en-9-one (1-II) (18 g, 56%); LCMS: m/z 271.2 (M$^+$+1)

Step II: Methyl (2E)-2-(3-benzyloxyspiro[5.5]undec-10-en-9-ylidene)acetate (1-III)

To a solution of NaH (60% in mineral oil) (4.8 g, 99.6 mmol) in THF (150 ml), trimethyl phosphonoacetate (15 ml, 99.9 mmol)) in THF (50 ml) was added drop wise at 0° C. and resulting reaction mixture was stirred at room temperature for another one hr. Reaction mixture was recooled to 0° C. and solution of 3-benzyloxyspiro[5.5]undec-10-en-9-one (1-II) (18 g, 66.6 mmol) in THF (50 ml) was added drop wise and resulting reaction mixture was heated to 50° C. for 18 hrs. Reaction mixture was cooled to room temperature and diluted with saturated NH$_4$Cl (150 ml) and extracted with EtOAc (200 ml×4). Combined organic layer was washed with brine (100 ml) and dried over sodium sulfate. Crude product obtained after evaporation of solvent gave desired product (1-III) along with hydrolyzed product. This crude product was taken in methanol (200 ml) and thionyl chloride (5 ml) was added at 0° C. followed by reflux for 3 hours. Excess of methanol was removed by evaporation. Purification of crude product by silica gel chromatography furnished title compound (1-III) (12.5 g, 58%); LCMS: m/z 327.2 (M$^+$+1)

Step III:
2-(9-hydroxyspiro[5.5]undecan-3-yl)acetate (1-IV)

To a solution of (2E)-2-(3-benzyloxyspiro[5.5]undec-10-en-9-ylidene)acetate (1-III) (3.3 g, 10.1 mmol) in EtOAc (100 ml) was added Pd(OH)$_2$ (0.5 g) and reaction mixture was shaken on parr apparatus at 40 psi for 4 hrs. Catalyst was removed by filtration on celite bed and washed with EtOAc (100 ml). Filtrate was concentrated under vacuum to yield methyl 2-(9-hydroxyspiro[5.5]undecan-3-yl)acetate (1-IV) (2.6 g, 97%)

Step IV: Methyl
2-(9-oxospiro[5.5]undecan-3-yl)acetate (1-V)

Dess Martin periodinate (6.6 g, 15.6 mmol) was added to a solution of 2-(9-hydroxyspiro[5.5]undecan-3-yl)acetate (1-IV) in DCM (25 ml) at 0° C. and reaction mixture was stirred at room temperature for 3 hrs. Reaction mixture was diluted with water and extracted with DCM (25 ml×3). Combined organic layer was washed with 10% aqueous sodium thiosulfate (50 ml) and dried over sodium sulfate. Organic solvent was evaporated under vacuum to afford crude product which was purified by column chromatography to furnish methyl 2-(9-oxospiro[5.5]undecan-3-yl)acetate (1-V) (2.1 g, 85%); LCMS: m/z 239.3 (M$^+$+1)

Step V: Methyl 2-[9-(trifluoromethylsulfonyloxy)spiro[5.5]undec-9-en-3-yl]acetate (1-VI)

To a solution of 2-(9-oxospiro[5.5]undecan-3-yl)acetate (1-V) (7 g, 29.4 mmol) in THF (40 ml), NaHMDS (1 M in THF) (32 ml, 32.3 mmol) was added drop wise during 30 min at −78° C. and reaction mixture was stirred at same temperature for another 1 hr. In another flask N-phenyl bis-(trifluoromethanesulfonamide) was taken in THF (20 ml) and transferred into the reaction mixture through cannula. Reaction mixture was stirred for another 2 hrs, diluted with saturated NH$_4$Cl (20 ml) solution and extracted using EtOAc (50 ml×3). Combined organic layer was dried over sodium sulfate and evaporated to dryness to yield crude product which was purified by column chromatography to furnish methyl 2-[9-(trifluoromethylsulfonyloxy)spiro[5.5]undec-9-en-3-yl]acetate (1-VI) (13.8 gm, containing N-phenyl triflimide as a minor impurity); LCMS: m/z 371.3 (M$^+$+1)

Step VI: Methyl 2-[9-(4,4,5,5-tetramethyl-1,3,2-dioxaborolan-2-yl)spiro[5.5]undec-9-en-3-yl]acetate (1-VII)

A mixture of crude methyl 2-[9-(trifluoromethylsulfonyloxy)spiro[5.5]undec-9-en-3-yl]acetate (1-VI) from previous step (13.8 g, 37.2 mmol), bispinacolo diborane (10.4 g, 41.0 mmol) and KOAc (10.98 g, 111.8 mmol) in 1,4 dioxane (100 ml) was degassed using argon for one hr. DPPF.PdCl$_2$: DCM complex was added and reaction mixture was heated to 100° C. for 18 hrs. Reaction mixture was cooled to room temperature and filtered through celite pad followed by extraction using EtOAc (50 ml×4). Combined organic layer was washed with brine (100 ml) and dried over anhydrous Na$_2$SO$_4$. Crude product obtained after evaporation of solvent on purification by column chromatography furnished methyl 2-[9-(4,4,5,5-tetramethyl-1,3,2-dioxaborolan-2-yl)spiro[5.5]undec-9-en-3-yl]acetate (1-VII) (7.2 g, 38% over two steps); LCMS: m/z 349.2 (M$^+$+1)

Step VII: Methyl 2-[9-(5-nitro-2-pyridyl)spiro[5.5]undec-9-en-3-yl]acetate (1-VIII)

A solution containing 2-bromo-3-nitropyridine (1 g, 4.9 mmol), boronate ester (1-VII) (1.7 g, 4.9 mmol) and 2M aqueous K$_2$CO$_3$ (6.6 ml) in 1,4-dioxane (20 ml) was degassed for one hr. Pd(PPh$_3$)$_4$ (0.3 g, 0.245 mmol) was added and reaction mixture was heated to 100° C. for 16 hrs. Reaction mixture was cooled to room temperature and filtered through celite pad followed by extraction using EtOAc (20 ml×4). Combined organic layer was washed with brine (30 ml) and dried over Na$_2$SO$_4$. Crude product obtained after evaporation of solvent was purified by column chromatography to furnish title compound (1-VIII) (1.1 g, 65%)

Step VIII: Methyl 2-[9-(5-amino-2-pyridyl)spiro[5.5]undecan-3-yl]acetate (Intermediate 1-IX)

To a solution of methyl 2-[9-(5-nitro-2-pyridyl)spiro[5.5]undec-9-en-3-yl]acetate (1-VIII) (1.1 g, 31.9 mmol) in EtOAc (20 ml) was added 10% Pd/C under argon atmosphere and resulting reaction mixture was stirred under hydrogen atmosphere (balloon pressure) for 18 hrs. Catalyst was removed by filtration using celite pad and filtrate was concentrated under vacuum to yield methyl 2-[9-(5-amino-2-pyridyl)spiro[5.5]undecan-3-yl]acetate (Intermediate 1-IX) (0.9 g, 93%).
$^1$HNMR (400 MHz, CDCl$_3$): δ 0.86-1.20 (m, 4H), 1.16-1.34 (m, 6H), 1.41-1.68 (m, 6H), 2.01-2.17 (m, 2H), 2.21 (d, J=14.4 Hz, 2H), 3.66 (s, 3H), 6.95 (d, J=1.6 Hz, 1H), 7.27-7.29 (m, 1H), 8.03 (app. t, J=2 Hz, 1H)
LCMS: m/z 317.2 (M$^+$+1)

Intermediate 2-X: Methyl 2-[9-(4-aminophenyl)spiro[5.5]undecan-3-yl]acetate

Scheme 2

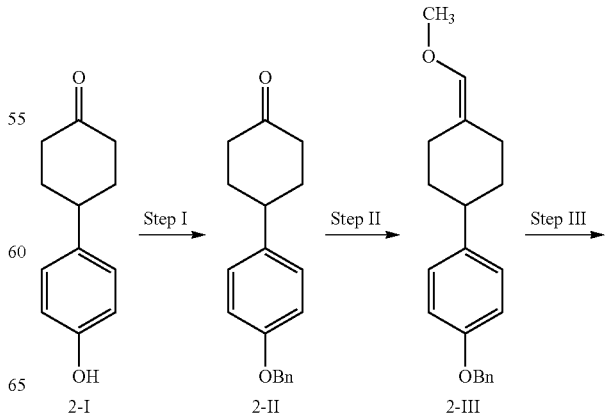

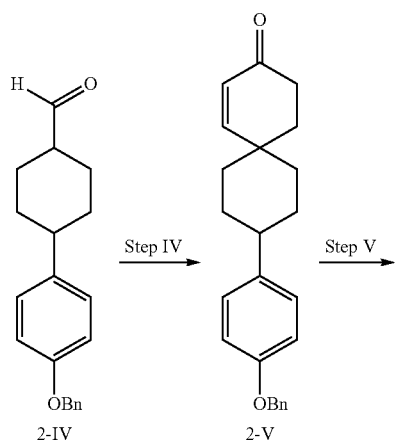

Intermediate 2-X

Step I: 4-(4-benzyloxyphenyl)cyclohexanone (2-II)

To a solution of commercially available 4-(4-hydroxyphenyl)cyclohexanone (2-I) (25 g, 131.57 mmol) in DMF (200 ml) was added powdered potassium carbonate (36.32 gm, 263.15 mmol) and benzyl bromide (28.13 gm, 164.47 mmol) at room temperature and reaction mixture was heated overnight at 110° C. After completion of reaction, solid was filtered and filtrate was concentrated under vacuum. The residue was poured on ice-water; resulting solid was filtered and washed with water and hexane. Solid was dried on high vacuum to afford title compound (2-II) (60.58 gm, 82%); LCMS: m/z 281.20 (M$^+$+1)

Step II: 1-Benzyloxy-4-[4-methoxymethylene)cyclohexyl]benzene (2-III)

To a suspension of (Methoxymethyl)triphenylphosphonium chloride (79.57 gm, 232.14 mmol) in THF (500 ml) at 0° C. was added NaH (60% in mineral oil, 7.14 gm, 178.57 mmol). Reaction mixture was then allowed to stir for 8 hrs at room temperature. 4-(4-benzyloxyphenyl)cyclohexanone (2-II) (50 g, 178.57 mmol) was dissolved in THF (200 ml) and was added to above suspension at 0° C. Reaction mixture was stirred overnight at room temperature. After completion of reaction, reaction mixture was poured over saturated solution of ammonium chloride and diluted with ethyl acetate, layers were separated, aqueous layer was extracted with ethyl acetate and combined organic layers were washed with water and brine, dried over anhydrous sodium sulfate and concentrated under vacuum. Purification was done by column chromatography using 9% ethyl acetate in hexane as eluent to afford title compound (2-III) (36.5 g, 66.3%); LCMS: m/z 309.20 (M$^+$+1)

Step III: 4-(4-benzyloxyphenyl)cyclohexanecarbaldehyde (2-IV)

To a solution of 1-benzyloxy-4-[4-methoxymethylene)cyclohexyl]benzene (2-III) (36.50 g) in THF (300 ml) was added 6N HCl (100 ml) and reaction mixture was heated at 64° C. for 3 hrs. After completion of reaction, solvent was evaporated under vacuum. Reaction mixture was neutralized with saturated solution of sodium bicarbonate. Organic layer was dried over anhydrous sodium sulfate and concentrated under vacuum to afford title compound (2-IV) (34 g, 97%); LCMS: m/z 295.30 (M$^+$+1)

Step IV: 3-(4-benzyloxyphenyl)spiro[5.5]undec-10-en-9-one (2-V)

To a solution of 4-(4-benzyloxyphenyl)cyclohexanecarbaldehyde (2-IV) (34 g, 115.6 mmol) in THF (2500 ml) was added methyl vinyl ketone (12.96 g, 185.03 mmol) at 0° C. 3N KOH in ethanol (195 ml) was added drop wise to it. Reaction mixture was stirred at room temperature overnight. After completion of reaction, solvent was removed under reduced pressure. Reaction was neutralized with 1N HCl and extracted with ethyl acetate; organic layer was dried over anhydrous sodium sulfate and concentrated under vacuum. Purification was done by column chromatography using 15% ethyl acetate in hexane to afford title compound (2-V) (23.48 g, 58%); LCMS: m/z 347.10 (M$^+$+1)

Step V: Methyl (2Z)-2-[3-(4-benzyloxyphenyl)spiro[5.5]undec-10-en-9-ylidene]acetate (2-VI)

2-VI was prepared from 2-V following similar procedure as used for the synthesis of 1-III from 1-II (Scheme 1); LCMS: m/z 403.10 (M$^+$+1)

Step VI: Methyl 2-[9-(4-hydroxyphenyl)spiro[5.5]undecan-3-yl]acetate (2-VII)

2-VII was prepared from 2-VI following similar procedure as used for the synthesis of 1-IV from 1-III (Scheme 1); LCMS: m/z 317.20 (M$^+$+1)

Step VII: Methyl 2-[9-[4-(trifluoromethylsulfonyloxy)phenyl]spiro[5.5]undecan-3-yl]acetate (2-VIII)

To a solution of (2-VII) (10 g, 31.6 mmol) in DCM (140 ml) at –20° C. was added triethylamine (6.3 g, 63.2 mmol) followed by triflic anhydride (13.39 g, 47.4 mmol) and stirred at room temperature for 2 hr. After completion of reaction, the reaction mixture was diluted with DCM and washed with water and brine, dried over anhydrous sodium sulfate and concentrated under vacuum. Purification was done by column chromatography using 3-5% ethyl acetate in hexane as eluent to afford title compound (2-VIII) (10.5 g, 74%).

$^1$H NMR (400 MHz, CDCl$_3$): δ 0.95-1.88 (m, 15H), 2.04-2.06 (m, 2H), 2.23 (d, J=7.6 Hz, 2H), 2.44-2.51 (m, 1H), 3.67 (s, 3H), 7.17 (d, J=8.8 Hz, 2H), 7.27 (d, J=8.4 Hz, 2H)

Step VIII: Methyl 2-[9-[4-(benzyl amino)phenyl]spiro[5.5]undecan-3-yl]acetate (2-IX)

A mixture of 2-VIII (10.5 g, 23.6 mmol), benzyl amine (3.7 g, 35.4 mmol), X-Phos (3.3 g, 7.0 mmol) and cesium carbonate (23.1 g, 70.9 mmol) in 1,4-dioxane (120 ml) was degassed for 1 hr. Palladium acetate (0.51 g, 2.2 mmol) was added and reaction mixture was heated at 101° C. overnight. After completion of reaction, reaction mixture was filtered on celite bed and filtrate was concentrated under vacuum. Purification was done by column chromatography using 3-10% ethyl acetate in hexane as eluent to afford title compound (2-IX) (9.3 g, 97%); LCMS: m/z 406.20 (M$^+$+1)

Step IX: Methyl 2-[9-(4-aminophenyl)spiro[5.5]undecan-3-yl]acetate (Intermediate 2-X)

To a solution of 2-IX (9.3 g) in ethyl acetate (40 ml) was added palladium hydroxide (2 g) and 2-3 drops of conc. HCl. Reaction mixture was then stirred under 50 psi pressure for 6 hrs. After completion of reaction, reaction mixture was filtered on celite bed and filtrate was concentrated under vacuum. Purification was done by column chromatography using 10-15% ethyl acetate in hexane as eluent to afford title compound Intermediate 2-X (6.6 g, 92%)

$^1$HNMR (400 MHz, CDCl$_3$): δ 0.95-1.60 (m, 13H), 1.74-1.76 (m, 1H), 1.84-1.86 (m, 2H), 2.04 (t, J=13.4 Hz, 1H), 2.22 (d, J=7.2 Hz, 1H), 2.35 (t, J=7.8 Hz, 2H), 3.67 (s, 3H), 6.65 (d, J=8.4 Hz, 2H), 7.01 (app t, J=6.8 Hz, 2H)

LCMS: m/z 316.20 (M$^+$+1)

Intermediate 3-II: Methyl 2-(9-aminospiro[5.5]undecan-3-yl)acetate

Scheme 3

Step I: Methyl 2-[9-(benzyl amino)spiro[5.5]undecan-3-yl]acetate (3-I)

To a solution of methyl 2-(9-oxospiro[5.5]undecan-3-yl)acetate (1-V) (0.15 g, 0.6 mmol) in methanol (3 ml), were added 4 A° molecular sieves (500 mg) and benzyl amine (0.2 g, 1.8 mmol) and resulting reaction mixture was stirred at room temperature for 2 hours. Sodium cyanoborohydride (0.26 g, 1.26 mmol) was added and stirring was continued for another 18 hrs. Reaction mixture was filtered through celite pad, washed with EtOAc and filtrate obtained was evaporated to yield crude title compound (3-I) (0.23 g crude) which was used for next step without further purification Step II: Methyl 2-(9-aminospiro[5.5]undecan-3-yl)acetate (Intermediate 3-II)

To a solution of 3-I (0.23 g, 0.70 mmol) in EtOAc (20 ml), were added 10% Pd/C (100 mg) and Pd(OH)$_2$ (100 mg) and reaction mixture was hydrogenated using parr shaker at 50 psi for 4 hrs. Catalyst was removed by filtration using celite pad and filtrate was evaporated to furnish crude title compound, Intermediate 3-II (102 mg) which was used for next step without further purification Intermediate 4-V: Methyl 2-[9-(5-amino-2-pyridyl)-9-azaspiro[5.5]undecan-3-yl]acetate

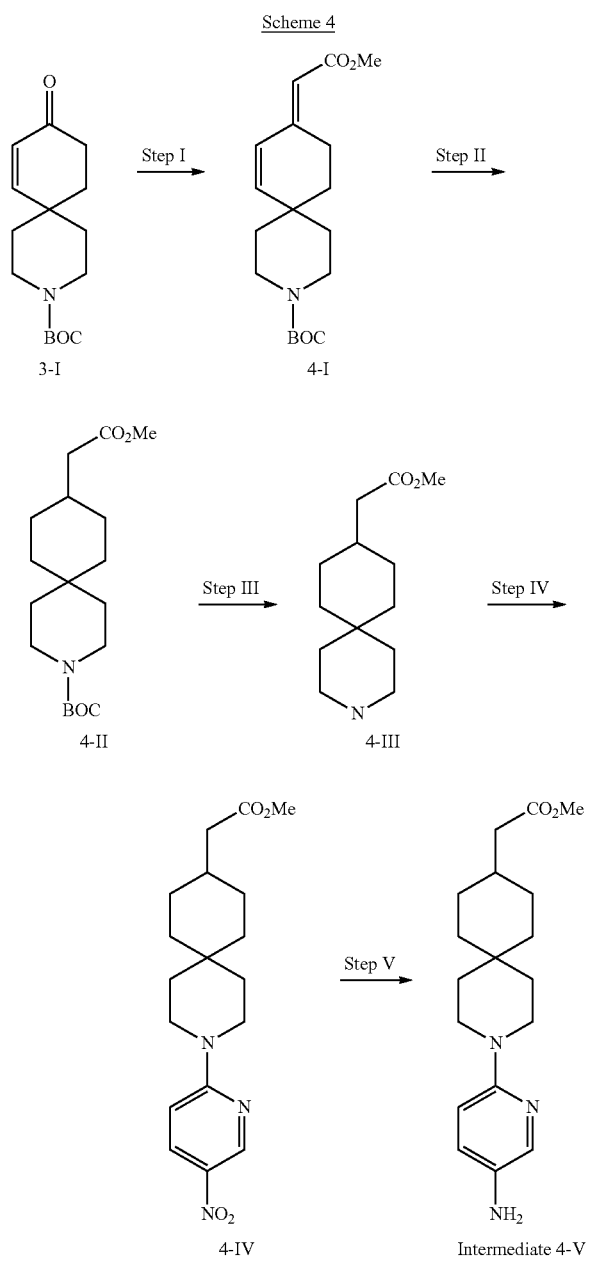 [SMILES: CC(C)(C)OC(=O)N1CCC2(C=CC(=O)CC2)CC1 ; COC(=O)/C=C1/C=CC2(CC1)CCN(C(=O)OC(C)(C)C)CC2 ; COC(=O)CC1CCC2(CC1)CCN(C(=O)OC(C)(C)C)CC2 ; COC(=O)CC1CCC2(CCNCC2)CC1 ; COC(=O)CC1CCC2(CC1)CCN(c1ccc([N+](=O)[O-])cn1)CC2 ; COC(=O)CC1CCC2(CC1)CCN(c1ccc(N)cn1)CC2]

Scheme 4

Step I: t-butyl (3E)-3-(2-methoxy-2-oxo-ethyl-idene)-9-azaspiro[5.5]undec-4-ene-9-carboxylate (4-I)

4-I was prepared from 3-I following similar procedure as used for the synthesis of 1-III from 1-II (Scheme 1); LCMS: m/z 266.2 (M$^+$+1)

Step-II: t-butyl 3-(2-methoxy-2-oxo-ethyl)-9-azaspiro[5.5]undecane-9-carboxylate (4-II)

To a solution of 4-I (16 g, 49.84 mmol) in EtOAc (150 ml) was added Pd(OH)$_2$ (3 g). Resulting reaction mixture was stirred under hydrogen balloon for 17 hrs. Catalyst was removed by filtration through celite pad and filtrate was evaporated under vacuum to furnish title compound (4-II) (14.8 g, 91%)

Step-III: Methyl 2-(9-azaspiro[5.5]undecan-3-yl)acetate (4-III)

To a solution of 4-II (14.8 g, 45.53 mmol) in DCM (200 ml) was added 3.0% TFA in DCM (30 ml) at 0° C. and resulting reaction mixture was stirred at room temperature for 2 hrs. Solvent was removed under reduced pressure to yield crude product (4-III) as TFA salt. (10.1 g). Crude product was used in next step without purification: LCMS: m/z 226.2 (M$^+$+1)

Step-IV: Methyl 2-[9-(5-nitro-2-pyridyl)-9-azaspiro[5.5]undecan-3-yl]acetate (4-IV)

To a solution of 2-chloro-5-nitropyridine (7.09 g, 44.88 mmol) in DCM (100 ml) was added methyl 2-(9-azaspiro[5.5]undecan-3-yl)acetate TFA salt (4-III) (10.1 g, 44.88 mmol) in DCM (50 ml) followed by triethyl amine (31.3 ml, 224.4 mmol) and reaction mixture was stirred at room temperature for 24 hrs. Reaction mixture was evaporated under reduced pressure and resulting solid was suspended in EtOAc (500 ml) and water (200 ml). EtOAc layer was separated and washed with brine (100 ml) and organic layer was dried over anhydrous Na$_2$SO$_4$. Crude product obtained after evaporation of organic layer was purified by silica gel column chromatography to furnish methyl 2-[9-(5-nitro-2-pyridyl)-9-azaspiro[5.5]undecan-3-yl]acetate (4-IV) (14 g, 90%); LCMS: m/z 348.2 (M$^+$+1)

Step-V: Methyl 2-[9-(5-amino-2-pyridyl)-9-azaspiro[5.5]undecan-3-yl]acetate (Intermediate 4-V)

To a solution of methyl 2-[9-(5-nitro-2-pyridyl)-9-azaspiro[5.5]undecan-3-yl]acetate (4-IV) (14 g, 40.34 mmol) in EtOAc (120 ml) was added 10% Pd(OH)$_2$ under argon atmosphere and resulting reaction mixture was stirred under hydrogen balloon for 18 hrs. Catalyst was removed by filtration using celite pad and filtrate was concentrated under reduced pressure. Crude product thus obtained was purified by silica gel column chromatography to furnish title compound methyl 2-[9-(5-amino-2-pyridyl)-9-azaspiro[5.5]undecan-3-yl]acetate (Intermediate 4-V) (11.8 g, 93%)

$^1$HNMR (400 MHz, CDCl$_3$): δ 1.1-1.26 (m, 4H), 1.46 (t, J=5.6 Hz, 2H), 1.55-1.63 (m, 4H), 1.69-1.77 (m, 3H), 2.24 (d, J=7.2 Hz, 2H), 3.29-3.34 (m, 4H), 3.66 (s, 3H), 6.59 (d, J=8.8 Hz, 1H), 6.98 (dd, J=8.8, 3.2 Hz, 1H), 7.79 (d, J=2.8 Hz, 1H)

LCMS: m/z 318.2 (M$^+$+1)

Intermediate 5-VII: Ethyl 2-[7-(4-aminophenyl)spiro[3.5]nonan-2-yl]acetate

Scheme 5

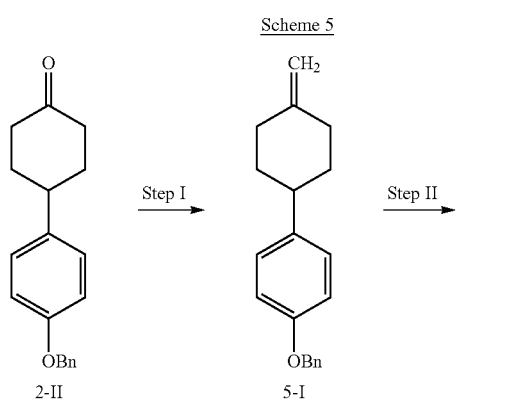

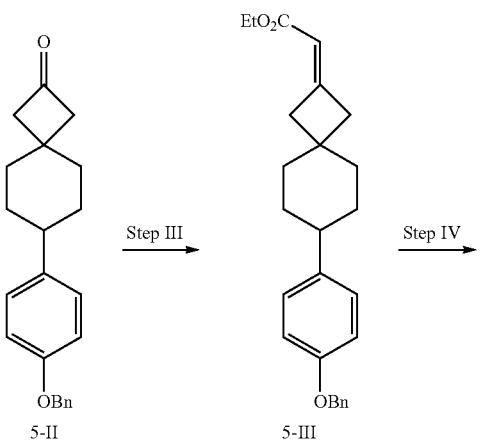

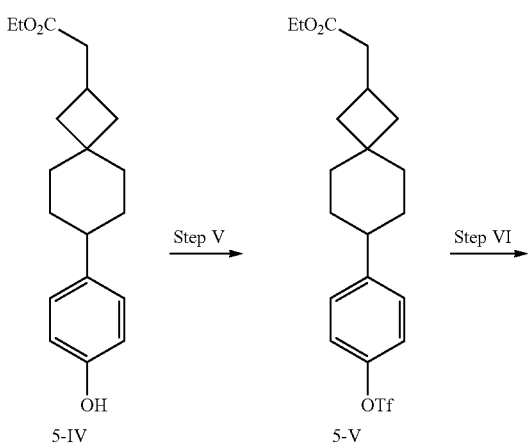

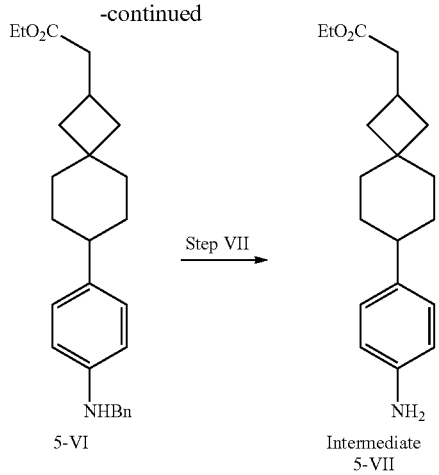

Step I: 1-Benzyloxy-4-(4-methylenecyclohexyl)benzene (5-I)

A suspension of methyltriphenylphosphonium bromide (200 g, 561.6 mmol) in THF (500 mL) was cooled to 0° C. and KO'Bu (63 g, 561.6 mmol) was added portion wise. The mixture was warmed to room temperature and after being stirred for 1 h at room temperature, it was again cooled to 0° C. and treated with a solution of ketone 2-II (52.5 g, 187.5 mmol) in THF (500 mL) via cannula. The reaction mixture was slowly warmed to room temperature and stirred for 18 h. On completion of the reaction (monitored by TLC), water (200 mL) was added and extracted with ethyl acetate (200 ml×3). The organic layer was separated and washed with water (100 ml) followed by brine and dried over anhydrous sodium sulfate. Solvent was removed under reduced pressure to afford crude product which was purified on column chromatography (Silica gel 100-200 mesh, 4% EtOAc: hexane as eluent) to provide title compound 5-I (42 g, 79% yield); LCMS: m/z 279.0 (M$^+$+1)

Step II: 7-(4-benzyloxyphenyl)spiro[3.5]nonan-2-one (5-II)

To a suspension of zinc-copper couple (6.97 g, 107.20 mmol) and alkene 5-I (4.6 g, 16.5 mmol) in Et$_2$O (35 ml) was added a solution of trichloroacetyl chloride (7.4 mL, 66.18 mmol) in Et$_2$O (10 mL) drop wise at room temperature. After stirring the mixture at room temperature for 18 h, it was poured into an aqueous solution of NaHCO$_3$ at 0° C., and filtered. The filtrate was extracted with ethyl acetate. The extract was washed with brine, dried, and evaporated to afford brown oil. To a solution of this oil in MeOH (150 ml) at 0° C. was added NH$_4$Cl (7.0 g, 132.0 mmol) in one portion followed by zinc dust (12.85 g, 198.0 mmol) portion wise at 0° C. The reaction mixture was warmed to room temperature and stirred for 18 h. On completion of reaction (monitored by TLC), the mixture was filtered. The filtrate was concentrated in vacuo. The residue was purified on column chromatography (Silica gel 100-200 mesh, 10% EtOAc:hexane as eluent) to provide title compound 5-II (0.9 g, 75% yield); LCMS: m/z 321.2 (M$^+$+1)

Steps III-VII: Intermediate 5-VII was prepared from 5-II following similar sequence of procedures as used for the preparation of Intermediate 2-X from 2-V (Scheme 2)

$^1$HNMR (400 MHz, DMSO-d6): δ 1.17 (t, J=6.8 Hz, 3H), 1.30-1.52 (m, 8H), 1.55-1.68 (m, 2H), 1.78-1.91 (m, 2H), 2.01-2.11 (m, 1H), 2.16-2.25 (m, 1H), 2.38-2.41 (m, 2H), 4.03 (q, J=6.8 Hz, 2H), 5.03 (bs, 2H), 6.49 (d, J=8.3 Hz, 2H), 6.84 (d, J=8.3 Hz, 2H)

LCMS: m/z 302.2 ($M^+$+1)

Intermediate 6-III: Methyl 7-(4-aminophenyl)spiro[3.5]nonane-2-carboxylate

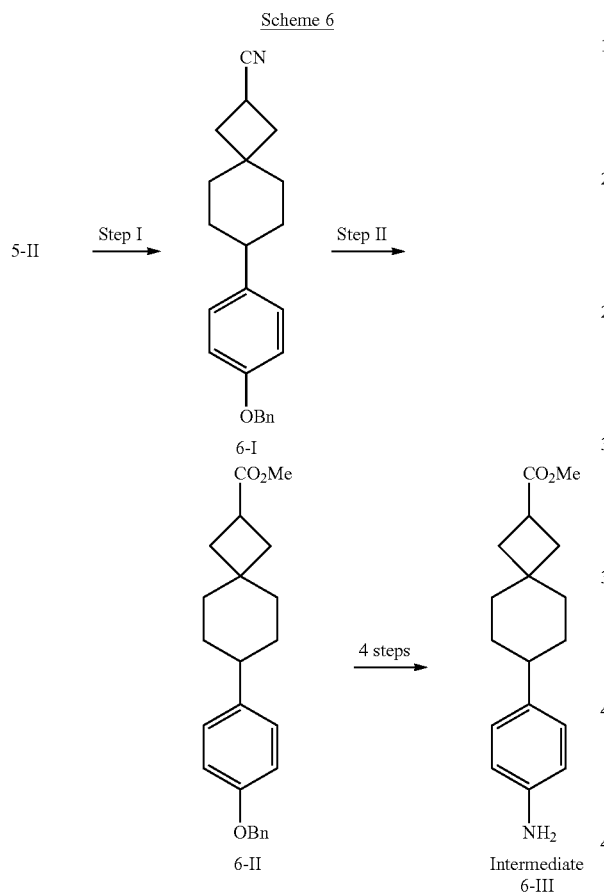

Step I: 7-(4-Benzyloxyphenyl)spiro[3.5]nonane-2-carbonitrile (6-1)

A suspension of 5-II (2.8 g, 8.75 mmol) and toluene sulphonyl methyl isocyanide (1.79 g, 9.18 mmol) in DME (9 mL) was cooled to 0° C. and a solution of KO$^t$Bu in a mixture of DME (5 mL) and $^t$BuOH (5 mL) was added drop wise via syringe and the mixture was stirred at the same temperature for 30 min and then at room temperature for 18 h. After completion of reaction, the mixture was treated with water (150 mL) and then extracted with ethyl acetate (100 ml×3). Organic layer was washed with water (40 ml) followed by brine and dried over anhydrous sodium sulfate. Solvent was removed under reduced pressure to afford crude product which was purified by column chromatography (Silica gel 100-200 mesh, 25% EtOAc:hexane as eluent) to provide title compound 6-I (1.1 g, 38% yield)

Step II: Methyl 7-(4-benzyloxyphenyl)spiro[3.5]nonane-2-carboxylate (6-II)

A mixture of 6-I (1.1 g, 3.30 mmol) and KOH (1.53 g, 8.2 mmol) in ethylene glycol (7 mL) was heated to 180° C. for 18 h. After completion of reaction, the mixture was dissolved in MeOH (150 mL) and the mixture was treated with NaH$_2$PO$_4$ (2 g) and then filtered. The filtrate was concentrated and the residue was dissolved in MeOH (10 mL) and cooled to 0° C. To the cold solution, SOCl$_2$ (6 mL) was added drop wise and the mixture was allowed to warm to room temperature and stirred for 18 h. After completion of reaction, the solvent was removed in vacuo. The resultant residue was dissolved in ethyl acetate (150 mL) and washed with water (40 ml) followed by brine and dried over anhydrous sodium sulfate. Solvent was removed under reduced pressure to afford crude product which was purified by column chromatography (Silica gel 100-200 mesh, 8% EtOAc:hexane as eluent) to provide 6-II (0.9 g, 75% yield); LCMS: m/z 386.2 ($M^+$+Na).

Step III: Methyl 7-(4-aminophenyl)spiro[3.5]nonane-2-carboxylate (Intermediate 6-III)

6-II was transformed to Intermediate 6-III following the same sequence of procedures as used for the preparation of Intermediate 5-VII from 5-III $^1$H NMR (400 MHz, CDCl$_3$): δ 1.34-1.43 (m, 4H), 1.65-1.79 (m, 4H), 1.86-1.88 (m, 1H), 1.92-2.17 (m, 3H), 2.25-2.35 (m, 1H), 3.06 (p, J=8.8 Hz, 1H), 3.68 (s, 3H), 6.62 (d, J=8.4 Hz, 2H), 6.98 (d, J=8.8 Hz, 2H)

LCMS: m/z 274.9 ($M^+$+1)

Intermediate 7-VIII: Ethyl 2-[7-(5-amino-2-pyridyl)-7-azaspiro[3.5]nonan-2-yl]acetate

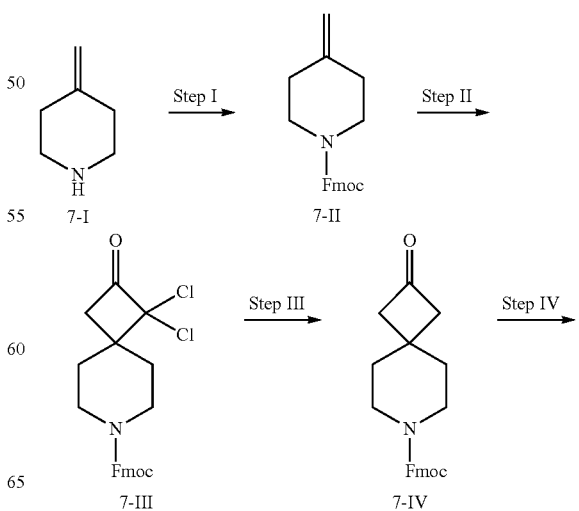

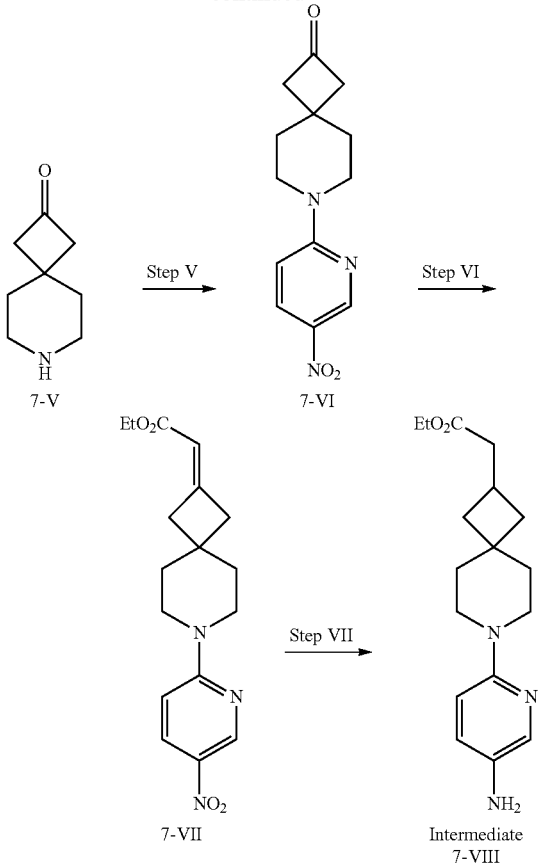

Step I: 9H-fluoren-9-ylmethyl 4-methylenepiperidine-1-carboxylate (7-II)

To a cooled solution of 4-methylenepiperidine TFA salt 7-I (prepared according to the procedure mentioned in US 20050261322 A1) (18.00 g, 85.23 mmol, 1.0 equiv.) in THF (85 mL) was added sodium bicarbonate (21.48 g, 255.68 mmol) in water (43 mL) and stirred at 0° C. To this reaction mixture Fmoc chloride (26.46 g, 102.27 mmol) was added in 4 equal portions and stirred for 15 hours at room temperature. After completion of reaction, reaction mixture was diluted with water (50 ml) and extracted with ethyl acetate (4×50 mL). Organic layer was washed with water (40 mL) followed by brine (40 mL) and dried over anhydrous sodium sulfate. Solvent was removed under reduced pressure to afford crude product which was purified by column chromatography (Silica gel 100-200 mesh, 5% EtOAc:hexane as eluent) to provide pure product (7-II) (25.42 g, 93.4%); LCMS: m/z 218.0 ($M^+$+1)

Step II: 9H-fluoren-9-ylmethyl 3,3-dichloro-2-oxo-7-azaspiro[3.5]nonane-7-carboxylate (7-III)

To a stirred solution of (7-II) (20.0 g, 62.62 mmol) in 1,2-dimethoxyethane (310 mL) was added zinc-copper couple (40.95 g, 626.17 mmol). To this stirred suspension, trichloroacetyl chloride (56.90 g, 312.99 mmol) was added in such a way that reaction mixture started gentle reflux (addition of trichloroacetyl chloride was very slow as to maintain gentle reflux 1 h). After completion of reaction, reaction mixture was filtered through celite pad, diluted with water (200 mL) and extracted with ethyl acetate (4×500 mL). Organic layer was washed with water (400 mL) followed by brine (400 mL) and dried over anhydrous sodium sulfate. Solvent was removed under reduced pressure to afford crude product which was purified by column chromatography (Silica gel 100-200 mesh, 15% EtOAc:hexane as eluent) to provide pure product (7-III) (19.13 g, 71%); LCMS: m/z 430.1 ($M^+$+1)

Step III: 9H-fluoren-9-ylmethyl 2-oxo-7-azaspiro[3.5]nonane-7-carboxylate (7-IV)

To a cooled solution of 9H-fluoren-9-ylmethyl 3,3-dichloro-2-oxo-7-azaspiro[3.5]nonane-7-carboxylate (7-III) (20.0 g, 46.48 mmol) in methanol (230 mL) was added ammonium chloride (7.46 g, 139.44 mmol, 3.0 equiv.). To this stirred suspension, zinc dust (30.39 g, 464.79 mmol) was added in 4 equal portions at 0° C. in such a way that temperature of reaction mixture should not rise above 10° C. and stirred for 14 hours at room temperature. After completion of reaction, reaction mixture was filtered through celite pad; methanol was removed under reduced pressure and then diluted with ethyl acetate (4×250 mL). Organic layer was washed with water (400 mL) and saturated $NaHCO_3$ (400 mL) followed by brine (400 mL) and dried over anhydrous sodium sulfate. Solvent was removed under reduced pressure to afford crude product which was purified by column chromatography (Silica gel 100-200 mesh, 15% EtOAc:hexane as eluent) to provide pure product 7-IV (12.76 g, 76%); LCMS: m/z 362.1 ($M^+$+1)

Step IV: 7-azaspiro[3.5]nonan-2-one (7-V)

To a stirred solution of 9H-fluoren-9-ylmethyl 2-oxo-7-azaspiro[3.5]nonane-7-carboxylate (7-IV) (15 g, 41.51 mmol) in DMF (42 mL) was added piperidine (7.06 g, 83.02 mmol) and stirred for 3 hours at room temperature. After completion of reaction, reaction mixture was poured on ice (150 g). Solid separated was filtered through celite pad and aqueous layer was extracted with ethyl acetate (4×200 mL). Organic layer was washed with brine (200 mL) and dried over anhydrous sodium sulfate. Solvent was removed under reduced pressure to afford crude product (7-V) (12.46 g) which was used for next step without any purification; LCMS: m/z 140.1 ($M^+$+1)

Step V: 7-(5-nitro-2-pyridyl)-7-azaspiro[3.5]nonan-2-one (7-VI)

7-VI was prepared from 7-V following similar procedure as used for the preparation of 4-IV from 4-III (Scheme 4); LCMS: m/z 262.1 ($M^+$+1)

Step VI: Ethyl 2-[7-(5-nitro-2-pyridyl)-7-azaspiro[3.5]nonan-2-ylidene]acetate (7-VII)

To a solution of 7-(5-nitro-2-pyridyl)-7-azaspiro[3.5]nonan-2-one (0.20 g, 0.76 mmol) (7-VI) in toluene (7.6 mL) was added carbethoxy methylene triphenylphosphorane (0.20 g, 1.53 mmol). The reaction mixture was refluxed for 18 h. After completion of reaction, reaction mixture was diluted with ethyl acetate (50 ml) and washed with water (2×20 mL) followed by brine (20 mL) and dried over anhydrous sodium sulfate. Solvent was removed under reduced pressure to afford crude product which was purified by column chromatography (Silica gel 100-200 mesh, 5%

EtOAc:hexane as eluent) to provide pure product (7-VII) (0.258 g, 81.4%); LCMS: m/z 332.1 (M⁺+1)

Step VII: Ethyl 2-[7-(5-amino-2-pyridyl)-7-azaspiro [3.5]nonan-2-yl]acetate (Intermediate 7-VIII)

To a solution of ethyl 2-[7-(5-nitro-2-pyridyl)-7-azaspiro [3.5]nonan-2-ylidene]acetate (7-VII) (0.25 g, 0.75 mmol) in ethyl acetate (7.5 mL) was added palladium on carbon 10% w/w (0.050 g). The reaction mixture was stirred under hydrogen atmosphere for 14 hours. After completion of reaction, reaction mixture was diluted with ethyl acetate (50 ml) and filtered through celite pad and washed with ethyl acetate (2×10 mL). Solvent was removed under reduced pressure to afford crude product
Intermediate 7-VIII (0.178 g) which was used for next reaction without any purification $^1$H NMR (400 MHz, CDCl$_3$): δ 0.88 (t, J=7.1 Hz, 3H), 1.51 (t, J=9.0 Hz, 2H), 1.60 (t, J=5.4 Hz, 2H), 1.72 (t, J=5.4 Hz, 2H), 2.04-2.20 (m, 4H), 2.43 (d, J=7.6 Hz, 2H), 2.66 (quin., 1H), 3.24 (t, J=5.4 Hz, 2H), 3.32 (t, J=5.4 Hz, 2H), 4.11 (q, J=7.1 Hz, 2H), 6.59 (d, J=9.0 Hz, 1H), 6.97 (dd, J=8.8 & 2.7 Hz, 1H), 7.78 (d, J=2.2 Hz, 1H)
LCMS: m/z 304.2 (M⁺+1)

Intermediate 8-III: Ethyl 7-(5-amino-2-pyridyl)-7-azaspiro[3.5]nonane-2-carboxylate Scheme 8

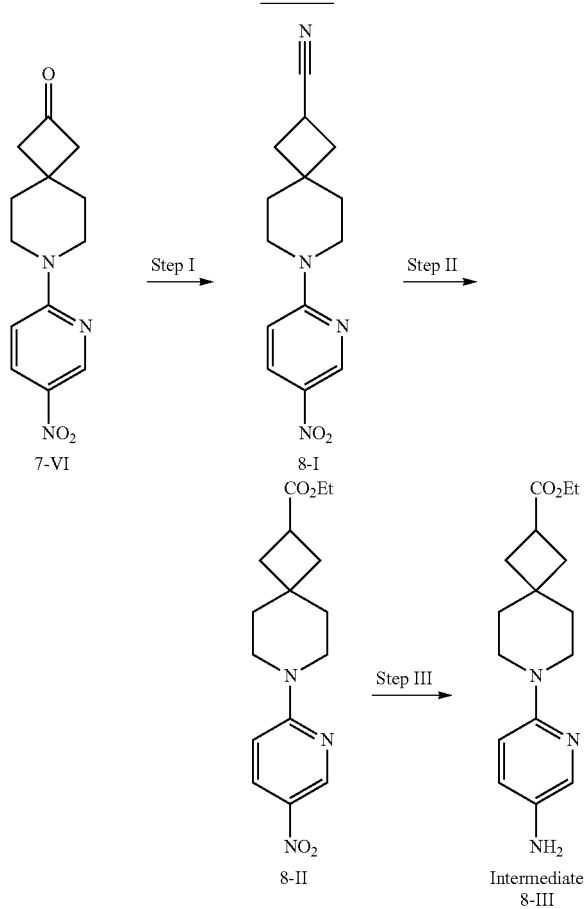

Step I: 7-(5-nitro-2-pyridyl)-7-azaspiro[3.5]nonane-2-carbonitrile (8-I)

To a cooled solution of 7-(5-nitro-2-pyridyl)-7-azaspiro [3.5]nonan-2-one (7-VI) (0.20 g, 0.76 mmol) in 1,2-dimethoxyethane (28 mL) was added TOSMIC (0.164 g, 0.84 mmol) at 0° C. To this stirred solution t-BuOK (0.172 g, 1.53 mmol) was added in 1:1 mixture of 1,2-dimethoxyethane and t-butanol (1.6 mL) at 0° C. and stirred for 14 hours at room temperature. After completion of reaction, reaction mixture was poured on ice-water (20 mL) and extracted with ethyl acetate (3×25 mL). Organic layer was washed with water (40 mL) followed by brine (40 mL) and dried over anhydrous sodium sulfate. Solvent was removed under reduced pressure to afford crude product which was purified by column chromatography (Silica gel 100-200 mesh, 25% EtOAc:hexane as eluent) to provide pure product (8-I) (0.115 g, 55.3%); LCMS: m/z 273.1 (M⁺+1)

Step II: Ethyl 7-(5-nitro-2-pyridyl)-7-azaspiro[3.5] nonane-2-carboxylate (8-II)

To a solution of 7-(5-nitro-2-pyridyl)-7-azaspiro[3.5] nonane-2-carbonitrile 8-I (0.110 g, 0.40 mmol) in ethanol (8 mL) was added conc. sulfuric acid (0.8 mL). The reaction mixture was stirred at reflux temperature for 5 h. After completion of reaction, reaction mixture was diluted with ethyl acetate (20 ml) and neutralized with saturated NaHCO$_3$ to pH ~8 and extracted with ethyl acetate (2×20 mL), washed with brine (20 mL) and dried over anhydrous sodium sulfate. Solvent was removed under reduced pressure to afford crude product which was purified by column chromatography (Silica gel 100-200 mesh, 25% EtOAc: hexane as eluent) to provide pure product (8-II) (0.071 g, 55%); LCMS: m/z 320.1 (M⁺+1)

Step III: Ethyl 7-(5-amino-2-pyridyl)-7-azaspiro [3.5]nonane-2-carboxylate (Intermediate 8-III)

To a solution of Ethyl 7-(5-nitro-2-pyridyl)-7-azaspiro [3.5]nonane-2-carboxylate 8-II (0.15 g, 0.47 mmol, 1.0 equiv.) in ethyl acetate (4.6 mL) was added palladium on carbon 10% w/w (0.050 g). This reaction mixture was stirred under hydrogen atmosphere for 14 h. Reaction was monitored by TLC. On completion of reaction, reaction mixture was diluted with ethyl acetate (50 mL) and filtered through celite pad washed with ethyl acetate (2×10 mL). Solvent was removed under reduced pressure to afford crude product Intermediate 8-III (0.130 g) which was used for next reaction without any purification $^1$H NMR (400 MHz, CDCl$_3$): δ 1.25 (t, J=7.1 Hz, 3H), 1.50-1.72 (m, 2H), 1.66 (t, J=5.6 Hz, 2H), 1.72 (t, J=5.6 Hz, 2H), 2.01 (d, J=8.9 Hz, 4H), 3.08 (quin., 1H), 3.25 (t, J=5.6 Hz, 2H), 3.33 (t, J=5.6 Hz, 2H), 4.13 (q, J=7.1 Hz, 2H), 6.59 (d, J=8.8 Hz, 1H), 6.97 (dd, J=8.8 & 2.9 Hz, 1H), 7.78 (d, J=3.0 Hz, 1H)
LCMS: m/z 290.2 (M⁺+1)

Intermediate 9-V: Methyl 6-(4-aminophenyl)spiro[2.5]octane-2-carboxylate

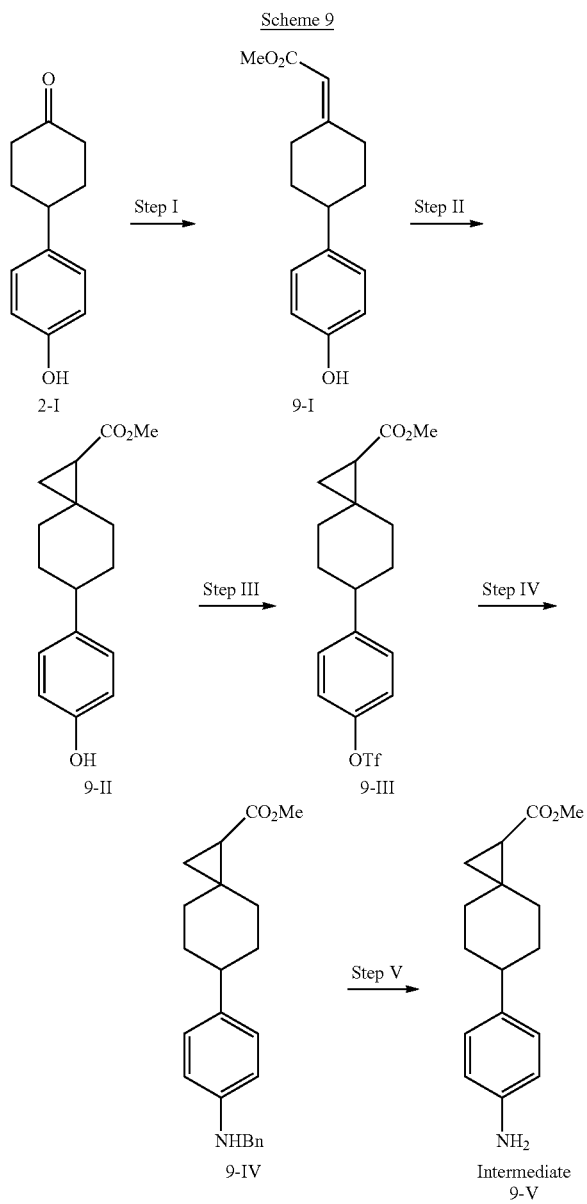

Scheme 9

Step I: Methyl 2-[4-(4-hydroxyphenyl)cyclohexylidene]acetate (9-I)

To a suspension of sodium hydride (6.3 g, 263.1 mmol) in THF (300 mL) was added trimethyl phosphonoacetate (23 g, 126.3 mmol) at 0° C. and reaction mixture was stirred at room temperature for 1 hr. 4-(4-hydroxyphenyl)cyclohexanone (2-I) (20 g, 105.2 mmol) in THF (100 mL) was added drop wise at 0° C. and reaction mixture was stirred overnight at room temperature. After completion of reaction, solvent was evaporated and reaction was quenched with saturated solution of ammonium chloride, extracted with ethyl acetate and washed with water and brine. Organic layer was dried over anhydrous sodium sulfate and concentrated in vacuo. Purification was done by column chromatography using 2-5% ethyl acetate in hexane to afford title compound (9-I) (25 g, 96%).

Step II: Methyl 6-(4-hydroxyphenyl)spiro[2.5]octane-2-carboxylate (9-II)

To a suspension of sodium hydride (60% in mineral oil, 3.90 g, 162.6 mmol) in DMSO (75 mL) at 0° C. was added trimethyl sulfoxonium iodide (26.8 g, 121.9 mmol) portion wise and reaction mixture was stirred for 30 minutes. Methyl 2-[4-(4-hydroxyphenyl)cyclohexylidene]acetate (9-I) (10 g, 40.6 mmol) in 75 mL DMSO was added drop wise. Reaction mixture was stirred for 3 hr at room temperature. After completion of reaction, reaction mixture was diluted with diethyl ether and washed with water; organic layer was dried over anhydrous sodium sulfate and concentrated in vacuo. Purification was done by column chromatography using 15-20% ethyl acetate in hexane to afford title compound (9-II) (5.5 g, 52%); LCMS: m/z 261.1 (M$^+$+1)

Step III: Methyl 6-[4-(trifluoromethyl sulfonyloxy)phenyl]spiro[2.5]octane-2-carboxylate (9-III)

To a solution of methyl 6-(4-hydroxyphenyl)spiro[2.5]octane-2-carboxylate (9-II) (5.8 g, 22.6 mmol) in DCM at 0° C. was added triethylamine (4.5 g, 45.3 mmol) followed by triflic anhydride (9.5 g, 33.9 mmol) and reaction mixture was allowed to stir for 2 hr at room temperature. After completion of reaction, reaction mixture was diluted with DCM and washed with water and brine. Organic layer was dried over anhydrous sodium sulfate and concentrated in vacuo. Purification was done by column chromatography using 10-15% ethyl acetate in hexane to afford title compound (9-III) (8.0 g, 91%); LCMS: m/z 393.10 (M$^+$+1)

Step IV: Methyl 6-[4-(benzyl amino)phenyl]spiro[2.5]octane-2-carboxylate (9-IV)

A mixture of methyl 6-[4-(trifluoromethyl sulfonyloxy)phenyl]spiro[2.5]octane-2-carboxylate (9-III) (7.3 g, 18.6 mmol), benzyl amine (2.9 g, 27.9 mmol), cesium carbonate (18.2 g, 55.9 mmol) and X-Phos (2.6 g, 5.5 mmol) in toluene was degassed for 1 hr and Palladium acetate (0.8 g, 3.7 mmol) was added. Reaction mixture was then heated at 120° C. overnight. After completion of reaction, reaction mixture was filtered on celite bed and filtrate was concentrated in vacuo. Purification was done by column chromatography using 6-8% ethyl acetate in hexane as eluent to afford title compound (9-IV) (6.1 g, 94%); LCMS: m/z 350.20 (M$^+$+1)

Step V: Methyl 6-(4-aminophenyl)spiro[2.5]octane-2-carboxylate (Intermediate 9-V)

To a solution of methyl 6-[4-(benzyl amino)phenyl]spiro[2.5]octane-2-carboxylate (9-IV) (10.6 g, 30.3 mmol) in ethyl acetate (100 mL) was added palladium hydroxide (1.5 g) and 2-3 drops of conc. HCl. Reaction mixture was then stirred overnight under hydrogen atmosphere. After completion of reaction, reaction mixture was filtered on celite bed and filtrate was concentrated in vacuo. Purification was done by column chromatography using 10-15% ethyl acetate in hexane as eluent to afford title compound (Intermediate 9-V) (5.4 g, 69%)

$^1$H NMR (400 MHz, CDCl$_3$): δ 0.90-0.94 (m, 1H), 0.98-1.02 (m, 1H), 1.13-1.24 (m, 2H), 1.49-1.86 (m, 6H), 1.93-2.05 (m, 1H), 2.43-2.50 (m, 1H). 3.58 (bs, 2H), 3.69 (s, 3H), 6.64 (dd, J=2.0 Hz, J=6.8 Hz, 2H), 7.01 (d, J=8.4 Hz, 2H)

LCMS: m/z 260.10 (M$^+$+1)

Intermediate 10-VI: Ethyl 7-(5-amino-2-pyridyl)-7-azaspiro[2.5]octane-2-carboxylate

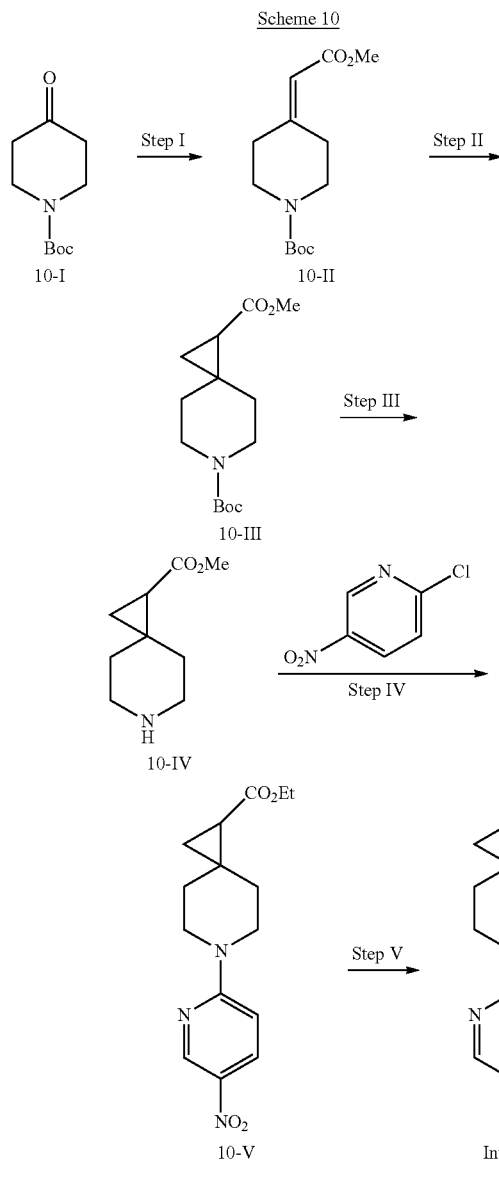

Step I: t-butyl-4-(2-ethoxy-2-oxo-ethylidene)piperidine-1-carboxylate (10-II)

10-II was prepared from commercially available N-Boc piperidone following similar procedure as used for preparation of 7-VII from 7-VI (Scheme 7); LCMS: m/z 170.2 [M$^+$-100 (M$^+$-Boc)]

Step II: 4-Aza-spiro[2.5]octane-1,4-dicarboxylic acid 4-tert-butyl ester 1-ethyl ester (10-III)

10-III was prepared from 10-II following similar procedure as for preparation of 9-II from 9-I (Scheme 9)

Step III: Ethyl-6-azaspiro[2.5]octane-2-carboxylate (10-IV)

10-IV was prepared from 10-III following similar procedure as for the preparation of 4-III from 441 (Scheme 4); LCMS: m/z 184.20 (M$^+$+1)

Step IV: Ethyl 6-(5-nitro-2-pyridyl)-6-azaspiro[2.5]octane-2-carboxylate (10-V)

10-V was prepared from 10-IV following similar procedure as for preparation of 4-IV from 4-III (Scheme 4); LCMS: m/z 306.2 (M$^+$+1)

Step V: Ethyl 6-(5-amino-2-pyridyl)-6-azaspiro[2.5] octane-2-carboxylate (Intermediate 10-VI)

Intermediate 10-VI was prepared from 10-V following similar procedure as used for preparation of Intermediate 7-VIII from 7-VII (Scheme 7)

$^1$H NMR (400 MHz, CDCl$_3$): δ 0.93-0.96 (m, 1H), 1.18-1.21 (m, 1H), 1.26 (t, J=6.8 Hz, 3H), 1.50-1.60 (m, 2H), 1.78-2.04 (m, 2H), 3.22-3.28 (m, 1H), 3.40-3.52 (m, 4H), 4.13 (q, J=6.8 Hz, 2H), 6.60 (d, J=8.8 Hz, 1H), 6.98 (dd, J=2.4 Hz, J=8.8 Hz, 1H), 7.79 (d, J=2.8 Hz, 1H)

LCMS: m/z 276.2 (M$^+$+1)

Intermediate 11-VI: Ethyl 7-(5-amino-2-pyridyl)-7-azaspiro[2.5]octane-2-carboxylate

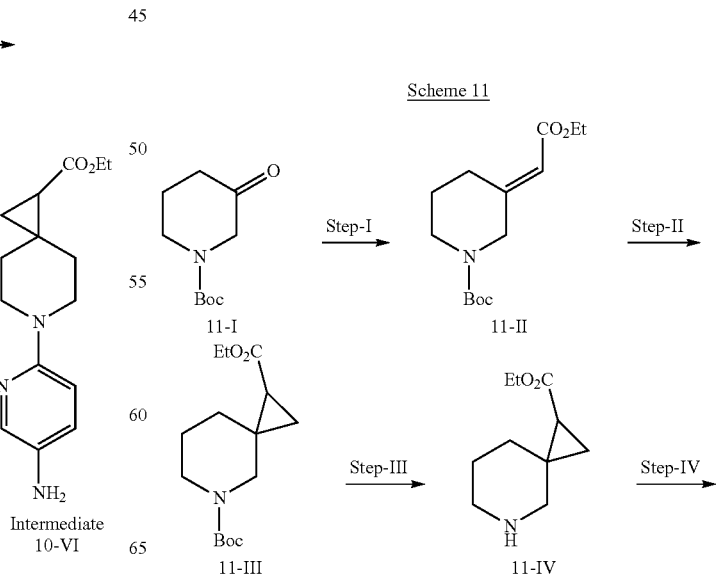

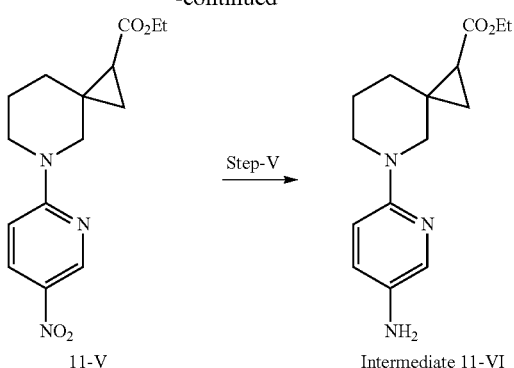

Intermediate 11-VI was prepared from 11-I following similar sequence of procedures as used for the preparation of Intermediate 10-VI from 10-I (Scheme 10); LCMS: m/z 276.1 (M$^+$+1)

Intermediate 12-VI: Methyl 6-(4,4,5,5-tetramethyl-1,3,2-dioxaborolan-2-yl)spiro[2.5]oct-6-ene-2-carboxylate

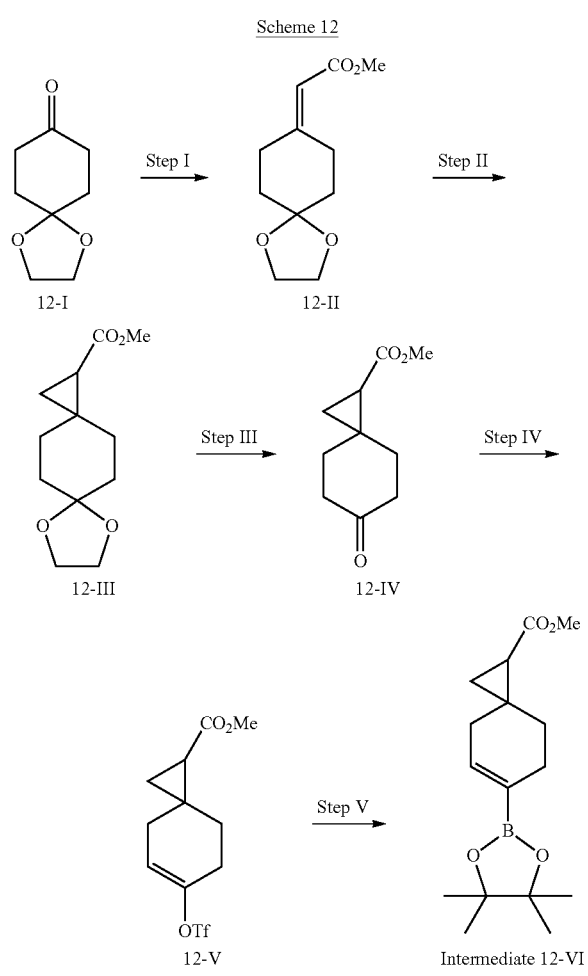

Step I: Methyl 2-(1,4-dioxaspiro[4.5]decan-8-ylidene)acetate (12-II)

To a stirred suspension of sodium hydride [60% in mineral oil (14.10 g, 352.56 mmol] in THF (1 L) was added trimethyl phosphonoacetate (64.17 g, 352.56 mmol) in THF (200 mL) drop wise under nitrogen at 0° C. The temperature was maintained at 0° C. for 1 h and then allowed to attain room temperature. The reaction mixture was stirred at room temperature for 2 h. Commercially available 1,4-dioxaspiro[4.5]decan-8-one (12-I) (50 g, 320.51 mmol) in THF (400 mL) was added at 0° C. and reaction mixture was stirred at room temperature for 6 h. After completion of reaction, the reaction mixture was quenched with ice (1000 g), extracted with ethyl acetate (2×1 L), washed with water (2×500 mL) followed by brine solution (500 ml) and dried over anhydrous sodium sulfate. Solvent was removed under reduced pressure to give crude product (12-II) (61.52 g) which was used for next reaction without further purification; LCMS: m/z 213.1 (M$^+$+1)

Step II: Methyl 7,10-dioxadispiro[2.2.4.6.2.3]dodecane-2-carboxylate (12-III)

12-III was prepared from 12-II following similar procedure as for the preparation of 9-II from 9-I (Scheme 9)

Step III: Methyl 6-oxospiro[2.5]octane-2-carboxylate (12-IV)

To a stirred solution of methyl 7,10-dioxadispiro[2.2.4^6.2^3]dodecane-2-carboxylate (12-III) (29.0 g, 128.31 mmol) in acetone (2.1 L) was added 1N aqueous HCl (522 mL) at room temperature and the reaction mixture was stirred at 50° C. for 3 h. After completion of reaction, acetone was removed under reduced pressure and extracted with ethyl acetate (2×500 ml), washed with brine solution (250 ml) and dried over anhydrous sodium sulfate. Solvent was removed under reduced pressure to give crude product which was purified by column chromatography (Silica gel 100-200 mesh, 15% EtOAc:hexane as eluent) to provide pure title product (12-IV) (19 g, 81.4%); LCMS: m/z 183.1 (M$^+$+1)

Step IV: Methyl 6-(trifluoromethylsulfonyloxy)spiro[2.5]oct-6-ene-2-carboxylate (12-V)

12-V was prepared from 12-IV following similar procedure as used for the preparation of 1-VI from 1-V (Scheme 1); LCMS: m/z 315.0 (M$^+$+1)

Step V: Methyl 6-(4,4,5,5-tetramethyl-1,3,2-dioxaborolan-2-yl)spiro[2.5]oct-6-ene-2-carboxylate (Intermediate 12-VI)

Intermediate 12-VI was prepared from 12-V following similar procedure as used for the preparation of 1-VII from 1-VI (Scheme 1)

$^1$H NMR (400 MHz, CDCl$_3$): δ 0.85-0.93 (m, 1H), 1.16 (t, J=4.8 Hz, 1H), 1.21-1.32 (m, 13H), 1.49-1.57 (m, 1H), 1.62-1.76 (m, 2H), 2.02-2.08 (m, 2H), 2.15-2.23 (m, 1H), 3.65 (s, 3H), 6.48-6.51 (m, 1H)

LCMS: m/z 293.2 (M$^+$+1)

Intermediate 13-II: Methyl 6-(5-amino-2-pyridyl)spiro[2.5]octane-2-carboxylate Scheme 13

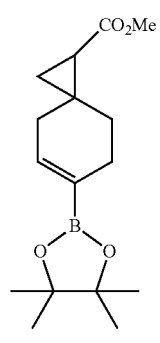

Intermediate 12-VI

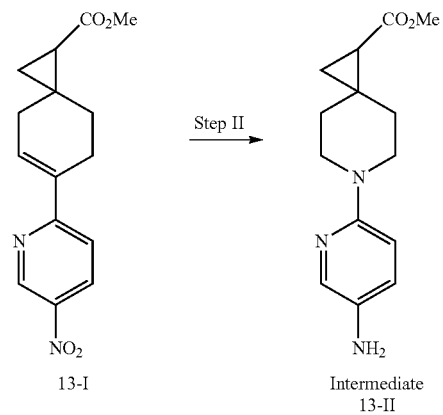

Intermediate 13-II was prepared from Intermediate 12-VI following similar sequence of procedures as followed for the synthesis of Intermediate 1-IX from 1-VII (Scheme 1)

$^1$H NMR (400 MHz, CDCl$_3$): δ 1.22-1.28 (m, 2H), 1.87-1.99 (m, 3H), 2.00-2.02 (m, 1H), 2.17-2.20 (m, 2H), 2.38-2.42 (m, 2H), 2.58-2.60 (m, 2H), 3.56 (bs, 2H), 3.67 (s, 3H), 6.46 (s, 1H), 6.96 (dd, J=4.4 Hz, J=2.8 Hz, 1H), 8.05 (s, 1H)

LCMS: m/z 261.10 (M$^+$+1)

Intermediate 14-II: Ethyl 6-(4-aminophenyl)-6-azaspiro[2.5]octane-2-carboxylate Scheme 14

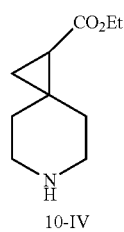

10-IV

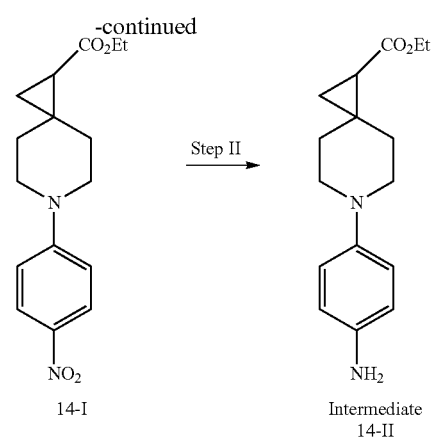

Step I: Ethyl 6-(4-nitrophenyl)-6-azaspiro[2.5]octane-2-carboxylate (14-I)

To a stirred solution of trifluoroacetate salt of ethyl 6-azaspiro[2.5]octane-2-carboxylate (10-IV) (2.0 g, 7.1 mmol) in DMF (15 mL) was added potassium carbonate (3.0 g, 21.4 mmol) and 4-fluoronitrobenzene (1.2 g, 8.6 mmol) and heated at 120° C. After stirring for 72 h, reaction mixture was cooled to room temperature, quenched with the addition of water (50 mL) and stirred for 20 min. The resulting solid was filtered, dried under vacuum to give (2.0 g, 60%) of title compound (14-I); LCMS: m/z 291.2 (M$^+$+1)

Step II: Ethyl 6-(4-aminophenyl)-6-azaspiro[2.5]octane-2-carboxylate (Intermediate 14-II)

Intermediate 14-II was prepared from 14-I following the similar sequence of procedures as used for the preparation of Intermediate 1-IX from 1-VII (Scheme 1)

$^1$H NMR (400 MHz, DMSO-d6): δ 0.97-1.00 (m, 2H), 1.47-1.78 (m, 4H), 2.69-2.73 (m, 1H), 2.86-2.90 (m, 1H), 2.95-2.97 (m, 2H), 3.59 (s, 1H), 4.80 (bs, 2H), 6.49 (d, J=8.0 Hz, 2H), 6.70 (d, J=8.4 Hz, 2H)

LCMS: m/z 261.2 (M$^+$+1)

Intermediate 15-V: Ethyl 8-(5-amino-2-pyridyl)spiro[8-azabicyclo[3.2.1]octane-3,2'-cyclopropane]-1'-carboxylate Scheme 15

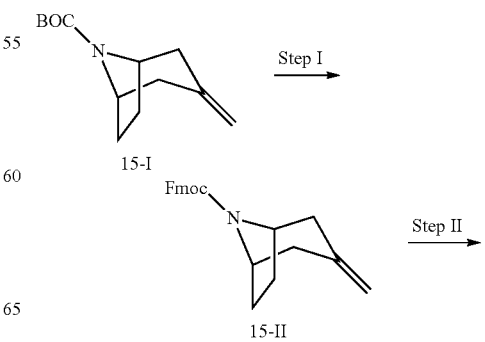

53

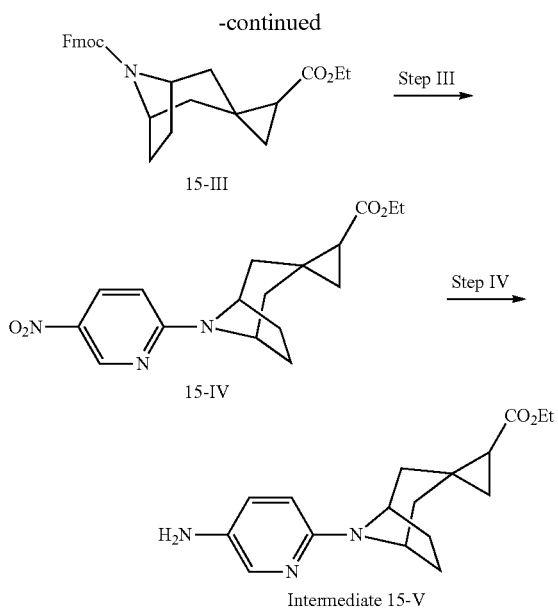

Step I: 9H-fluoren-9-ylmethyl 3-methylene-8-azabi-cyclo[3.2.1]octane-8-carboxylate (15-II)

A mixture of 15-I (prepared according to the procedure mentioned in WO 2010138490) (1.5 g, 6.76 mmol) and HCl (20 mL, 4 N soln. in 1,4-dioxane) was stirred at room temperature for 2 h. On completion of reaction, the mixture was concentrated in vacuo and used for next step. To a solution of this residue in a mixture of THF (35 mL) and water (15 mL) at 0° C. was added NaHCO$_3$ (2.27 g, 27.04 mmol) and Fmoc chloride (2.27 g, 8.78 mmol) and stirred at room temperature for 18 h. The mixture was extracted with ethyl acetate (100 ml×3). Organic layer was washed with water (40 ml) followed by brine and dried over anhydrous sodium sulfate. Solvent was removed under reduced pressure to afford crude product which was purified on column chromatography (Silica gel 100-200 mesh, 5% EtOAc:hexane as eluent) to provide 15-II (2.0 g, 86% yield); LCMS: m/z 346.2 (M$^+$+1)

Step II: 1'-ethyl-8-(9H-fluoren-9-ylmethyl)spiro[8-azabicyclo[3.2.1]octane-3,2'-cyclopropane]-1',8-dicarboxylate (15-III)

A solution of ethyl diazoacetate (1.83 mL, 17.37 mmol) in CH$_2$Cl$_2$ (20 mL) was added to a suspension of 15-II (2.0 g, 5.79 mmol) and Rh$_2$(OAc)$_4$ (0.015 g, 0.034 mmol) in CH$_2$Cl$_2$ (100 mL) at room temperature over a period of 6 h via syringe pump. After completion of addition, the mixture was stirred for another 10 h at room temperature and then concentrated in vacuo. The residue was purified by column chromatography (Silica gel 100-200 mesh, 22% EtOAc:hexane as eluent) to provide 15-III (2.0 g, 80% yield); LCMS: m/z 432.2 (M$^+$+1)

Step III: Ethyl 8-(5-nitro-2-pyridyl)spiro[8-azabicyclo[3.2.1]octane-3,2'-cyclopropane]-1'-carboxylate (15-IV)

15-IV was prepared from 15-III following the same sequence of procedures used for the preparation of 7-VI from 7-IV (Scheme 7); LCMS: m/z 332.2 (M$^+$+1)

54

Step IV: Ethyl 8-(5-amino-2-pyridyl)spiro[8-azabicyclo[3.2.1]octane-3,2'-cyclopropane]-1'-carboxylate (Intermediate 15-V)

Intermediate 15-V was prepared from 15-IV following the same procedure used for the preparation of compound Intermediate 7-VIII from 7-VII (Scheme 7)

$^1$H NMR (400 MHz, CDCl$_3$): δ 0.75 (d, J=12.8 Hz, 1H), 0.84-0.88 (m, 1H), 1.14 (dd, J=8.0, 3.6 Hz, 1H), 1.21 (t, J=7.2 Hz, 3H), 1.36 (t, J=4.4 Hz, 1H), 1.49 (d, J=13.2 Hz, 2H), 1.94-2.08 (m, 4H), 2.39 (d, J=12.8 Hz, 1H), 4.05 (q, J=7.2 Hz, 2H), 4.43-4.46 (m, 2H), 6.48 (d, J=8.8 Hz, 1H), 6.99 (dd, J=8.8, 2.8 Hz, 1H), 7.79 (d, J=2.8 Hz, 1H)

LCMS: m/z 301.9 (M$^+$+1)

Intermediate 16-IV: Ethyl 8-(5-amino-2-pyridyl)spiro[8-azabicyclo[3.2.1]octane-3,3'-cyclobutane]-1'-carboxylate Scheme 16

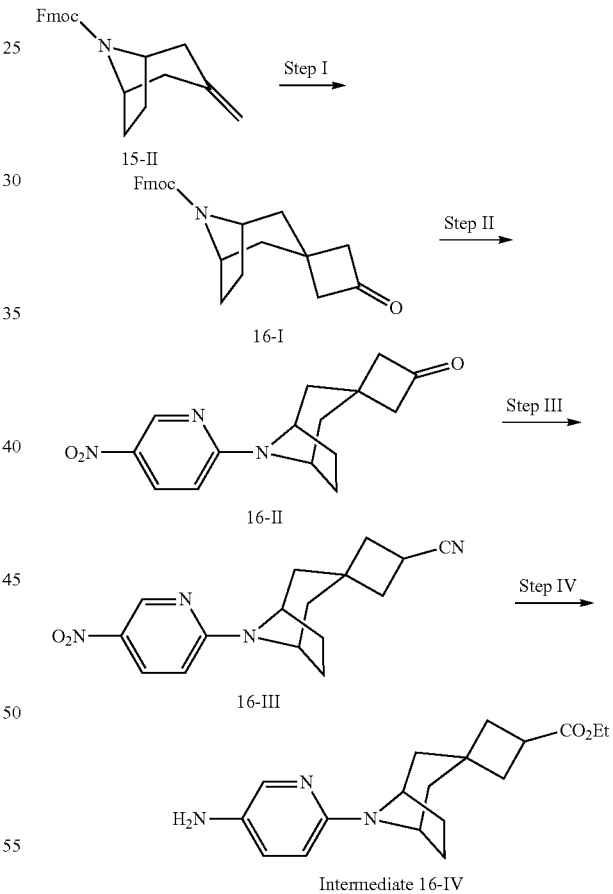

Step I: 9H-fluoren-9-ylmethyl 3'-oxospiro[8-azabicyclo[3.2.1]octane-3,1'-cyclobutane]-8-carboxylate (16-I)

Compound 16-I was prepared from 15-II following the same sequence of procedures used for the preparation of compound 5-II from 5-I (Scheme 5); LCMS: m/z 388.1 (M$^+$+1)

Step II: 8-(5-nitro-2-pyridyl)spiro[8-azabicyclo[3.2.1]octane-3,3'-cyclobutane]-1'-one (16-II)

Compound 16-II was prepared from 16-I following the same sequence of procedures used for the preparation of compound 7-VI from 7-IV (Scheme 7)

Step III: 8-(5-nitro-2-pyridyl)spiro[8-azabicyclo[3.2.1]octane-3,3'-cyclobutane]-1'-carbonitrile (16-III)

16-III was prepared from 16-II following the procedure used for the preparation of compound 8-I from 7-VI (Scheme 8)

Step IV: Ethyl 8-(5-nitro-2-pyridyl)spiro[8-azabicyclo[3.2.1]octane-3,3'-cyclobutane]4'-carboxylate (Intermediate 16-IV)

Intermediate 16-IV was prepared from 16-III following the same sequence of procedures as used for the preparation of Intermediate 8-III from 8-II (Scheme 8)

$^1$H NMR (400 MHz, CDCl$_3$): δ1.22 (t, J=7.2 Hz, 3H), 1.67 (dd, J=13.6, 1.6 Hz, 1H), 1.76-1.86 (m, 4H), 1.90-2.01 (m, 3H), 2.27-2.39 (m, 2H), 2.49-2.55 (m, 2H), 3.07 (p, J=8.8 Hz, 1H), 4.10 (q, J=7.2 Hz, 2H), 4.29 (br s, 1H), 4.41 (br s, 1H), 6.45 (d, J=8.8 Hz, 1H), 6.97 (dd, J=8.8, 2.8 Hz, 1H), 7.79 (d, J=3.2 Hz, 1H)

LCMS: m/z 316.2 (M$^+$+1)

Intermediate 17-VI: 6-(2,2-difluoro-7-azaspiro[3.5]nonan-7-yl)pyridin-3-amine Scheme 17

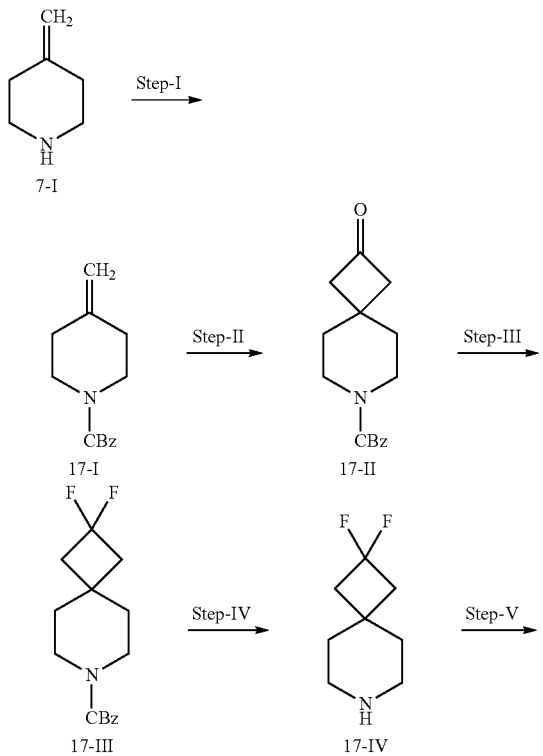

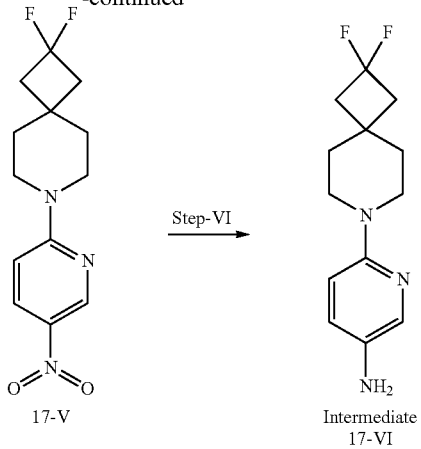

Step I: Benzyl 4-methylenepiperidine-1-carboxylate (17-I)

To a cool solution of 4-methylenepiperidine TFA salt 7-I (50 g, 236.74 mmol, 1.0 equiv.) in THF (473 mL) was added sodium bicarbonate (99.43 g, 1183 mmol, 5.0 equiv.) in water (236 mL) and stirred at 0° C. To this reaction mixture benzoyl chloride (33.8 mL, 236.74 mmol, 1.0 equiv.) was added dropwise at 0° C. This reaction mixture was stirred for 15 hours at room temperature. Reaction was monitored by TLC. On completion of reaction, reaction mixture was diluted with water (500 ml) and extracted with ethyl acetate (4×500 mL). Organic layer was washed with water (400 mL) followed by brine (400 mL) and dried over anhydrous sodium sulfate. Solvent was removed under reduced pressure to afford crude product which was purified by column chromatography (Silica gel 100-200 mesh, 10% EtOAc:hexane as eluent) to provide pure product 17-I (28.0 g, 52%); LCMS: m/z 232.2 (M$^+$+1)

Step II: Benzyl 2-oxo-7-azaspiro[3.5]nonane-7-carboxylate (17-II)

To a stirred solution of benzyl 4-methylenepiperidine-1-carboxylate 17-I (14.0 g, 60.57 mmol, 1.0 equiv.) in 1,2-dimethoxyethane (302 mL) was added zinc-copper couple (39.61 g, 302.85 mmol, 5.0 equiv.). To this stirred suspension, trichloroacetyl chloride (34.1 mL, 302.85 mmol, 5.0 equiv.) was added slowly over a period of 1 h in such a way that reaction mixture started refluxing gently. Reaction was monitored by TLC. The reaction mixture was further stirred at room temperature for 2 h and cooled to 0° C. Ammonium chloride (16.2 g, 302.85 mmol, 5.0 equiv.) was added followed by zinc dust (39.61 g, 6053 mmol, 10.0 equiv.) Zinc dust was added in 4 equal portions at 0° C. in such a way that temperature of reaction mixture did not rise above 10° C. The resulting reaction mixture was stirred for 14 hours at room temperature. Reaction was monitored by TLC. On completion of reaction, reaction mixture was filtered through celite pad, washed with ethyl acetate (4×250 mL). Organic layer was washed with water (400 mL), with sat. NaHCO3 (400 mL) followed by brine (400 mL), and dried over anhydrous sodium sulfate. Solvent was removed under reduced pressure to afford crude product which was purified by column chromatography (Silica gel 100-200 mesh, 15% EtOAc:hexane as eluent) to provide pure product 17-II (10.28 g, 62%); LCMS: m/z 274.1 (M⁺+1).

Step III: Benzyl 2,2-difluoro-7-azaspiro[3.5]nonane-7-carboxylate

To a solution of 17-II (2 g, 7.3 mmol, 1.0 equiv.) in DCM (25 mL) was added Deoxofluor (3.37 mL, 18.25 mmol, 2.5 equiv.) at 0° C. This reaction mixture was stirred for 15 hours at room temperature. Reaction was monitored by TLC. On completion of reaction, reaction mixture was diluted with DCM (30 ml) and washed with water (20 mL), with brine (20 mL) and dried over anhydrous sodium sulfate. Solvent was removed under reduced pressure to afford crude yellow coloured product which was purified by column chromatography (Silica gel 100-200 mesh, 20% EtOAc: hexane as eluent) to provide pure product 17-III (1.50 g, 69%); LCMS: m/z 296.2 (M⁺+1).

Step IV: 2,2-Difluoro-7-azaspiro[3.5]nonane (17-IV)

To a solution of 17-III (1.80 g, 6.10 mmol, 1.0 equiv.) in methanol (20 mL) was added palladium hydroxide on carbon 10% w/w (0.35 g). The reaction mixture was stirred under hydrogen atmosphere for 18 h. Reaction was monitored by TLC. On completion of reaction, reaction mixture was diluted with ethyl acetate (50 ml) and filtered through celite pad and washed with ethyl acetate (2×10 mL). Solvent was removed under reduced pressure to afford crude product 17-IV (0.95 g, 97%) which was used for next reaction without any purification; LCMS: m/z 162.2 (M⁺+1).

Step V: 2,2-difluoro-7-(5-nitro-2-pyridyl)-7-azaspiro[3.5]nonane (17-V)

17-V was prepared from 17-IV following similar procedure as for the preparation of 4-IV from 4-III
$^1$H NMR (400 MHz, CDCl$_3$): δ 1.77 (t, J=5.6 Hz, 4H), 2.44 (t, J=12.5 Hz, 4H), 3.72 (t, J=5.6 Hz, 4H), 6.59 (d, J=9.5 Hz, 1H), 8.19 (dd, J=9.5 & 2.9 Hz, 1H), 9.03 (d, J=2.7 Hz, 1H).
LCMS: m/z 284.2 (M⁺+1)

Step VI: 6-(2,2-difluoro-7-azaspiro[3.5]nonan-7-yl)pyridin-3-amine (Intermediate 17-VI)

Intermediate 17-VI was prepared from 17-V following the similar procedure as used for the preparation of Intermediate 8-III from 8-II; LCMS: m/z 254.2 (M⁺+1)

Intermediate 18-IV: 7-(5-amino-2-pyridyl)-7-azaspiro[3.5]nonan-2-ol

Scheme 18

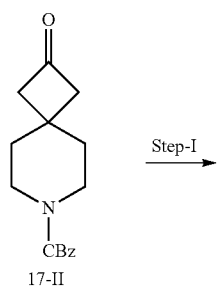

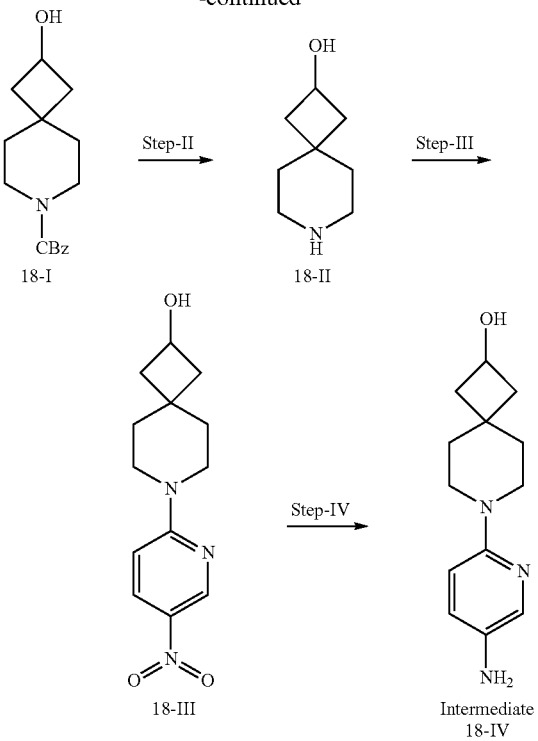

Step I: Benzyl 2-hydroxy-7-azaspiro[3.5]nonane-7-carboxylate (18-I)

To a solution of benzyl 2-oxo-7-azaspiro[3.5]nonane-7-carboxylate 17-II (3.0 g, 10.97 mmol, 1.0 equiv.) in methanol (33 mL) was added sodium borohydride (0.42 g, 10.98 mmol, 1.0 equiv.) in portions. The reaction mixture was stirred at room temperature for 3 h. Reaction was monitored by TLC. On completion of reaction, volatiles were removed under reduced pressure. Reaction mixture was diluted with water (50 ml) and extracted with ethyl acetate (3×50 mL). Organic layer was washed with brine (50 mL), dried over anhydrous sodium sulfate and solvent was removed under reduced pressure to afford crude product which was purified by silica gel column chromatography (100-200 mesh size) using 10-15% ethyl acetate in hexane as a eluent to give pure product 18-I (2.84 g, 94%); LCMS: m/z 276.1 (M⁺+1)

Step II: 7-azaspiro[3.5]nonan-2-ol (18-II)

To a solution of 18-I (1.20 g, 4.36 mmol) in ethanol (22 mL) was added palladium on carbon 10% w/w (0.120 g). This reaction mixture was stirred under hydrogen atmosphere for 14 h. Reaction was monitored by TLC. On completion of reaction, reaction mixture was diluted with ethyl acetate (50 ml) and filtered through celite pad and washed with ethyl acetate (2×10 mL). Solvent was removed under reduced pressure to afford crude product 18-II (0.60 g, 98%) which was used for next reaction without any purification; LCMS: m/z 276.3 (M⁺+1)

Step III: 7-(5-nitro-2-pyridyl)-7-azaspiro[3.5]nonan-2-ol (18-III)

18-III was prepared from 18-II following similar procedure as used for the preparation of 4-IV from 4-III; LCMS: m/z 264.2 (M⁺+1)

Step IV: 7-(5-amino-2-pyridyl)-7-azaspiro[3.5]nonan-2-ol (Intermediate 18-IV)

Intermediate 18-IV was prepared from 18-III following similar procedure as used for the preparation of Intermediate 8-III from 8-II ¹H NMR (400 MHz, CDCl₃): 1.61-1.72 (m, 7H), 2.28-2.33 (m, 1H), 3.26 (t, J=5.6 Hz, 2H), 3.31 (t, J=5.6 Hz, 2H), 4.34 (quin., 1H), 6.59 (d, J=8.8 Hz, 1H), 6.97 (dd, J=8.8 & 2.9 Hz, 1H), 7.77 (d, J=2.9 Hz, 1H)
LCMS: m/z 234.2 (M⁺+1)

Intermediate 19-V: 6-(2-fluoro-7-azaspiro[3.5]nonan-7-yl)pyridin-3-amine

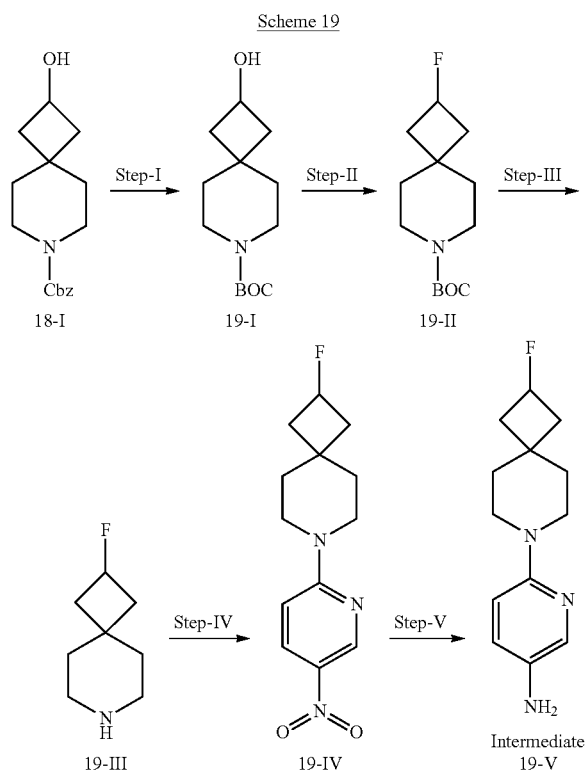

Scheme 19

Step I: t-butyl 2-hydroxy-7-azaspiro[3.5]nonane-7-carboxylate (19-I)

To a solution of 18-I (3.0 g, 10.90 mmol, 1.0 equiv.) in ethyl acetate (17 mL) was added palladium on carbon 10% w/w (0.700 g) followed by Boc-anhydride (7.32 g, 32.70 mmol, 3.0 equiv.). This reaction mixture was stirred under hydrogen atmosphere for 14 h. Reaction was monitored by TLC. On completion of reaction, reaction mixture was diluted with ethyl acetate (50 ml), filtered through celite pad and washed with ethyl acetate (2×10 mL). Solvent was removed under reduced pressure to give crude product which was purified by column chromatography to afford 19-I (3.11 g, 99%); LCMS: m/z 242.2 (M⁺+1)

Step II: t-butyl 2-fluoro-7-azaspiro[3.5]nonane-7-carboxylate (19-II)

To an ice cool solution of 19-I (3.10 g, 12.85 mmol, 1.0 equiv.) in DCM (95 mL) was added DAST (2.38 mL, 17.99 mmol, 1.4 equiv.). The reaction mixture was stirred under argon atmosphere for 2 h. Reaction was monitored by TLC. On completion of reaction, reaction mixture was diluted with DCM (50 ml) and washed with water (20 mL), with brine (20 mL) and finally dried over anhydrous sodium sulfate. Solvent was removed under reduced pressure to afford crude yellow colored product which was purified by column chromatography (Silica gel 100-200 mesh, 5-8% EtOAc:hexane as eluent) to provide pure product 19-II (2.35 g, 75%); LCMS: m/z 188.2 (M⁺-t-Bu)

Step III: 2-fluoro-7-azaspiro[3.5]nonane (19-III)

To a cooled solution of 19-II (2.34 g, 9.62 mmol, 1.0 equiv) in DCM (10 mL) was added TFA (7.6 mL, 96.23 mmol, 10.0 equiv) at 0° C. and resulting reaction mixture was stirred at room temperature (25° C.) for 2 hrs. Solvent was removed under reduced pressure to yield crude product 19-III as TFA salt (1.35 g, 99%) which was used for next step without further purification

Step IV: 2-fluoro-7-(5-nitro-2-pyridyl)-7-azaspiro[3.5]nonane (19-IV)

19-IV was prepared from 19-III following similar procedure as used for the preparation of 4-IV from 4-III ¹H NMR (400 MHz, CDCl₃): 1.58-1.74 (m, 2H), 1.96 (t, J=12.5 Hz, 2H), 2.40 (dd, J=19.8 & 7.4 Hz, 2H), 3.36 (dt, J=13.2 & 2.4 Hz, 2H), 4.34-4.46 (m, 2H), 5.14 (dd, 17.1 & 10.3 Hz, 2H), 5.70-5.88 (m, 1H), 6.59 (d, J=9.6 Hz, 1H), 8.19 (dd, J=9.5 & 2.7 Hz, 1H), 9.02 (d, J=2.7 Hz, 1H)
LCMS: m/z 266.2 (M⁺+1)

Step V: 6-(2-fluoro-7-azaspiro[3.5]nonan-7-yl)pyridin-3-amine (Intermediate 19-V)

To a solution of 19-IV (2.30 g, 8.69 mmol, 1.0 equiv.) in ethanol (25 mL) was added iron powder (0.97 g, 17.38 mmol, 2.0 equiv.) followed by ammonium chloride (2.77 g, 52.05 mmol, 6.0 equiv.). The reaction mixture was stirred at 65° C. for 2 hours. Reaction was monitored by TLC. On completion of reaction, ethanol was removed under reduced pressure; reaction mixture was diluted with ethyl acetate (50 ml), filtered through celite pad and washed with ethyl acetate (2×10 mL). Solvent was removed under reduced pressure to afford crude product which was purified by column chromatography (Silica gel 100-200 mesh, 25-30% EtOAc:hexane as eluent) to provide pure product Intermediate 19-V (1.21 g, 59%); LCMS: m/z 236.3 (M⁺+1)

Intermediate 20-IV: 6-(2-methyl-7-azaspiro[3.5]nonan-7-yl)pyridin-3-amine

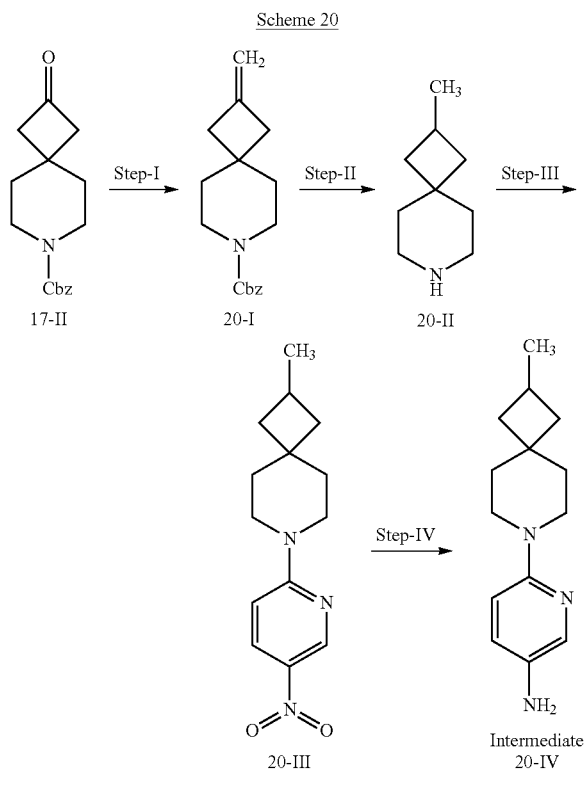

Step I: Benzyl 2-methylene-7-azaspiro[3.5]nonane-7-carboxylate (20-I)

To a stirred suspension of methyl triphenylphosphonium bromide (34.69 g, 154.00 mmol) in THF (100 mL) at 0° C., was added t-BuOK (17.33 g, 154 mmol) in portions (20 minutes). The reaction mixture was stirred for 2 hours, at 0° C. till it attained orange color. To this reaction mixture, a solution of 17-II (9.0 g, 38 mmol) in dry THF (50 mL) was added drop wise at 0° C., and the stirring was continued while allowing the reaction mixture to attain room temperature. The reaction mixture was allowed to stir for 16 hours and reaction was monitored by TLC. On completion of reaction, reaction mixture was poured into saturated aqueous ammonium chloride solution (100 mL), and the organic materials were extracted in ethyl acetate (3×100 mL). The organic layer was washed with brine solution (300 mL), dried over anhydrous sodium sulfate and finally concentrated under reduced pressure to obtain a crude compound which was purified by column chromatography (silica gel 100-200 mesh, eluent: 5% ethyl acetate in hexanes) to provide pure product 20-I (7.00 g, 78%); LCMS: m/z 272.3 ($M^+$+1)

Step II: 2-methyl-7-azaspiro[3.5]nonane (20-II)

20-II was prepared from 20-I following similar procedure as used for the preparation of 18-II from 18-I; LCMS: m/z 140.2 ($M^+$+1)

Step III: 2-methyl-7-(5-nitro-2-pyridyl)-7-azaspiro[3.5]nonane (20-III)

20-III was prepared from 20-II following similar procedure as used for the preparation of 4-IV from 4-III $^1$H NMR (400 MHz, CDCl$_3$): 1.11 (d, J=6.6 Hz, 3H), 1.42 (t, J=10.7 Hz, 2H), 1.50-1.62 (m, 2H), 1.68 (t, J=5.6 Hz, 2H), 2.04 (t, J=10.5 Hz, 2H), 2.32-2.42 (m, 1H), 3.63 (t, J=5.4 Hz, 2H), 3.70 (t, J=5.4 Hz, 2H), 6.55 (d, J=9.5 Hz, 1H), 8.15 (dd, J=9.6 & 2.9 Hz, 1H), 9.01 (d, J=2.6 Hz, 1H)

LCMS: m/z 262.3 ($M^+$+1)

Step IV: 6-(2-methyl-7-azaspiro[3.5]nonan-7-yl)pyridin-3-amine (Intermediate 20-IV)

Intermediate 20-IV was prepared from 20-III following similar procedure as used for the preparation of Intermediate 8-III from 8-II; LCMS: m/z 232.4 ($M^+$+1)

Intermediate 21-IX: 6-[2-(1-methyltetrazol-5-yl)-7-azaspiro[3.5]nonan-7-yl]pyridin-3-amine

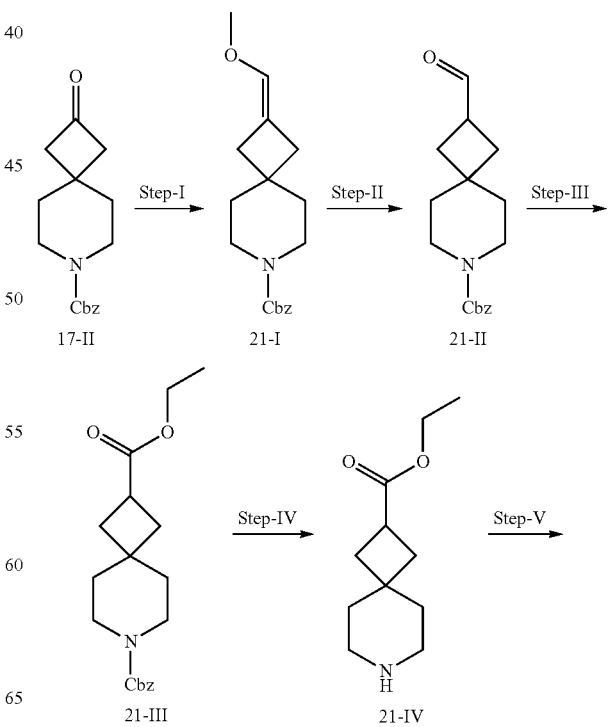

-continued

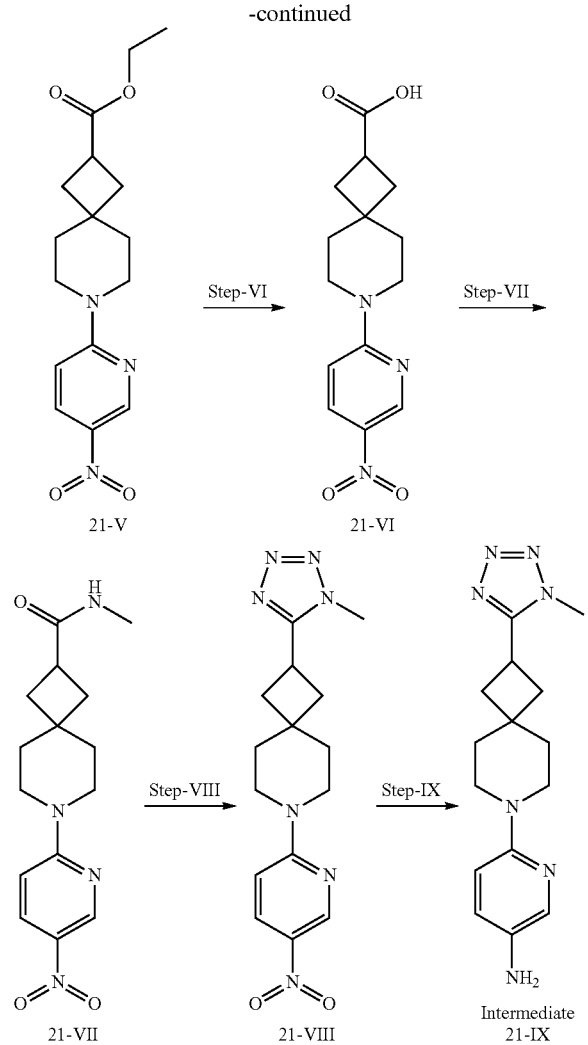

Step I: benzyl 2-(methoxymethylene)-7-azaspiro[3.5]nonane-7-carboxylate (21-I)

To a stirred suspension of methoxymethyl triphenylphosphonium chloride (67.72 g, 197.56 mmol, 3.0 equiv.) in THF (100 mL) was added t-BuOK (22.17 g, 197.56 mmol, 3.0 equiv.) in portions (20 minutes) at 0° C. The reaction mixture was stirred for 2 h at 0° C. (blood red colour). To this reaction mixture, a solution of 17-II (15.0 g, 65.85 mmol, 1.0 equiv.) in dry THF (32 mL) was added drop wise at −78° C. and the stirring was continued at 0° C. for 1 h. The reaction was monitored by TLC. On completion of reaction, reaction mixture was poured into saturated aqueous ammonium chloride solution (100 mL) and the organic materials were extracted in ethyl acetate (3×100 mL). The organic layer was washed with brine solution (300 mL), dried over anhydrous sodium sulfate and finally concentrated under reduced pressure to obtain a crude compound which was purified by column chromatography (Neutral alumina, eluent: 5% ethyl acetate in hexanes) to provide pure product 21-I (12.0 g, 60%); LCMS: m/z 302.0 (M$^+$+1)

Step II: Benzyl 2-formyl-7-azaspiro[3.5]nonane-7-carboxylate (21-II)

To a solution of 21-I (12.0 g, 39.86 mmol, 1.0 equiv.) in acetonitrile (120 ml) was added 2M aq. HCl (60 mL) and reaction mixture was stirred at room temperature for 4 h. Reaction was monitored by TLC. On completion of reaction, volatiles were removed under reduced pressure. Aqueous layer was extracted with ethyl acetate (100 mL×3) and organic layer was washed with water (100 mL), with brine (100 mL) and dried over anhydrous sodium sulfate. Solvent was removed under reduced pressure to afford crude product (11.0 g, 96%), which was used for next reaction without any purification; LCMS: m/z 288.2 (M$^+$+1)

Step III: 7-benzyl-2-ethyl 7-azaspiro[3.5]nonane-2,7-dicarboxylate (21-III)

To a solution of 21-II (11.0 g, 38.30 mmol, 1.0 equiv.) in ethanol (383 ml) was added oxone (23.55 g, 38.30 mmol, 1.0 equiv.) and reaction mixture was stirred at room temperature for 20 h. Reaction was monitored by TLC. On completion of reaction, reaction mixture was filtered through the celite pad, washed with ethanol (50 ml). Solvent was removed under reduced pressure to afford crude product which was purified by column chromatography (Silica gel 100-200 mesh, 15% EtOAc:hexane as eluent) to provide pure product 21-III (9.0 g, 71%); LCMS: m/z 332.2 (M$^+$+1)

Step IV: Ethyl 7-azaspiro[3.5]nonane-2-carboxylate (21-IV)

To a solution of 21-III (9.0 g, 27.19 mmol, 1.0 equiv.) in ethanol (50 mL) was added palladium on carbon 10% w/w (1.0 g). The reaction mixture was stirred under hydrogen atmosphere for 18 h. Reaction was monitored by TLC. On completion of reaction, reaction mixture was diluted with ethyl acetate (50 ml) and filtered through celite pad and washed with ethyl acetate (2×10 mL). Solvent was removed under reduced pressure to afford crude product (5.1 g, 95%) which was used for next reaction without any purification; LCMS: m/z 198.2 (M$^+$+1)

Step V: Ethyl 7-(5-nitro-2-pyridyl)-7-azaspiro[3.5]nonane-2-carboxylate (21-V)

To a solution of ethyl 21-IV (1.50 g, 9.31 mmol, 1.0 equiv.) in DCM (18 ml) was added 2-chloro-5-nitropyridine (2.2 g, 13.97 mmol, 1.5 equiv.) followed by triethyl amine (3.8 ml, 27.93 mmol, 3.0 equiv.) and reaction mixture was stirred at room temperature for 18 hrs. Reaction was monitored by TLC. On completion of reaction, reaction mixture was diluted with DCM (30 ml) and washed with water (20 mL), with brine (20 mL) and dried over anhydrous sodium sulfate. Solvent was removed under reduced pressure to afford crude yellow colored product which was purified by column chromatography (Silica gel 100-200 mesh, 10% EtOAc:hexane as eluent) to provide pure product 21-V (yellow colored, 1.70 g, 58%); LCMS: m/z 320.2 (M$^+$+1)

Step VI: 7-(5-nitro-2-pyridyl)-7-azaspiro[3.5]nonane-2-carboxylic acid (21-VI)

To a solution of 21-V (1.70 g, 5.32 mmol, 1.0 equiv.) in THF:MeOH:H2O (3:2:1) (60 ml), LiOH.H$_2$O (1.18 g, 26.63 mmol, 5.0 equiv.) was added and resulting reaction mixture was stirred at room temperature for 16 hrs. Reaction mixture was evaporated and acidified with 1N HCl. Resulting solid was filtered out and dried under vacuum to furnish title compound 21-VI (1.55 g, 97%); LCMS: m/z 292.2 (M$^+$+1)

Step VII: N-methyl-7-(5-nitro-2-pyridyl)-7-azaspiro[3.5]nonane-2-carboxamide (21-VII)

To the stirred solution of 21-VI (0.50 g, 0.103 mmol, 1.0 equiv.) in N,N-DMF (3.4 mL) was added 2M methyl amine solution in THF (5.0 mL) followed by HATU (0.97 g, 2.56 mmol, 1.5 equiv.) and stirred at room temperature for 16 h. The reaction progress was monitored using TLC. After completion of the reaction, reaction mixture was poured on ice-water (10 mL) and extracted with ethyl acetate (3×20 mL). Organic layer was washed with water (20 mL) followed by brine (20 mL) and dried over anhydrous sodium sulfate. Solvent was removed under reduced pressure to afford crude product (0.50 g, 96%) which was used for next reaction without any purification; LCMS: m/z 305.3 (M$^+$+1)

Step VIII: 2-(1-methyltetrazol-5-yl)-7-(5-nitro-2-pyridyl)-7-azaspiro[3.5]nonane (21-VIII)

To a solution of 21-VII (0.51 g, 1.87 mmol, 1.0 equiv.) in DCM (15 mL) was added triflic anhydride (0.49 mL, 5.61 mmol, 3.0 equiv.) at −15° C. The reaction mixture was stirred for 30 min. at same temperature. Sodium azide (0.219 g, 3.36 mmol, 1.8 equiv.) was added to the reaction mixture followed by DIPEA (1.0 mL, 5.61 mmol, 3.0 equiv.) and stirred at room temperature for 15 hr. After completion of reaction, the reaction mixture was diluted with DCM (30 mL) and washed with water (20 mL) followed by brine (20 mL) and dried over anhydrous sodium sulfate. Solvent was removed under reduced pressure to afford crude yellow colored product which was purified by column chromatography (Silica gel 100-200 mesh, 10%-20% EtOAc:hexane as eluent) to provide pure product 21-VIII (yellow colored, 0.17 g, 31%)

$^1$H NMR (400 MHz, CDCl$_3$): δ 1.77 (t, J=5.6 Hz, 2H), 1.86 (t, J=5.6 Hz, 2H), 2.38-2.51 (m, 4H), 3.61-3.70 (m, 3H), 3.82 (t, J=5.6 Hz, 4H), 3.95 (s, 3H), 6.59 (d, J=9.5 Hz, 1H), 8.18 (dd, J=9.5 & 2.7 Hz, 1H), 9.02 (d, J=2.7 Hz, 1H)

LCMS: m/z 330.2 (M$^+$+1)

Step IX: 6-[2-(1-methyltetrazol-5-yl)-7-azaspiro[3.5]nonan-7-yl]pyridin-3-amine (Intermediate 21-IX)

To a solution of 21-VIII (0.17 g, 0.51 mmol, 1.0 equiv.) in a mixture of ethanol (10 mL), ethyl acetate (3 mL) and DCM (1 mL) was added palladium on carbon 10% w/w (0.05 g). The resulting reaction mixture was stirred under hydrogen atmosphere for 14 h. Reaction was monitored by TLC. On completion of reaction, reaction mixture was diluted with ethyl acetate (50 ml) and filtered through celite pad and washed with ethyl acetate (2×10 mL). Solvent was removed under reduced pressure to afford crude product, Intermediate 21-IX (0.15 g, 97%) which was used for next reaction without any purification; LCMS: m/z 300.3 (M$^+$+1)

Intermediate 22-X: Ethyl 2-[6-(5-amino-2-pyridyl)-6-azaspiro[3.3]heptan-2-yl]acetate

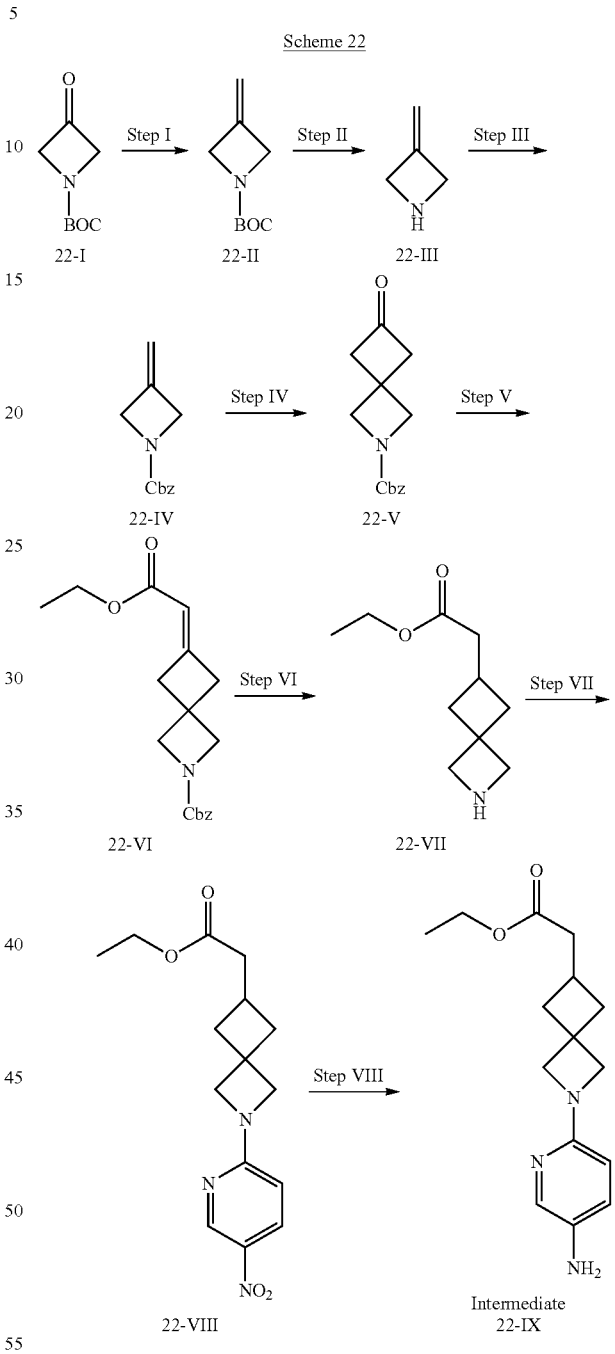

Scheme 22

Step I: tert-butyl 3-methyleneazetidine-1-carboxylate (22-II)

To a stirred suspension of methyl triphenylphosphonium bromide (259.9 gm, 719.29 mmole) in diethylether (1 L) was added potassium-t-butoxide (80.7 gm, 719.29 mmoles) portion wise under nitrogen atmosphere. The resulting yellow suspension was refluxed for 3 hours and solution of 22-I (82 g, 479.53 mmoles) in diethyl ether (350 mL) was added drop wise. The reaction mixture was refluxed for 16 hours. After completion of reaction (monitored by TLC), reaction mixture was decanted, residue was dissolved in diethyl ether, washed with water, dried over sodium sulfate and concentrated under reduced pressure. The crude product so obtained was stirred in pentane and the solid that precipitated out was filtered off and concentrated to give target product 22-II as a crude yellow liquid (60 g).

$^1$H NMR (400 MHz, CDCl$_3$): δ 1.44 (s, 9H), 4.46 (s, 4H), 4.97 (s, 2H)

Step II: 3-methyleneazetidine (22-III)

To a stirred solution of 22-II (60 g) in dichloromethane (250 mL) was added slowly trifluoroacetic acid (135 mL, 1773 mmoles) over a period of 20 minutes. The reaction mixture was allowed to stir at room temperature for another 1 hour. Reaction mixture was evaporated to dryness and the crude product 22-III was used as such for next step.

Step III: Benzyl 3-methyleneazetidine-1-carboxylate (22-IV)

To a stirred solution of 22-III (64.5 g, 351.1 mmol) in THF (350 mL) at 0° C. was added portion wise suspension of sodium bicarbonate (147 gms, 1755 mmol) in water (175 mL). Benzylchloroformate (75.2 mL, 5273 mmol) was added drop wise over a period of 30 minutes and reaction mixture was stirred at room temperature for 16 hours. THF was evaporated and residue was dissolved in diethyl ether. Water was added and organic layer was extracted. Aqueous layer was again extracted with diethyl ether. Combined organic layer was washed with water, dried over anhydrous sodium sulfate and concentrated under reduced pressure to afford 22-IV as a crude oil (40 g).

$^1$H NMR (400 MHz, CDCl$_3$): δ 4.56 (s, 4H), 4.69 (s, 2H), 5.01 (s, 2H), 7.33 (m, 5H)

Step IV: Benzyl 2-oxo-6-azaspiro[3.3]heptane-6-carboxylate (22-V)

To a stirred suspension of 22-IV (40 gms, 196.9 mmol) in 1,2-dimethoxyethane (800 mL) was added trichloroacetyl chloride (~5-10 mL) to initiate the reaction. When the reaction mixture started refluxing, trichloroacetyl chloride (70 mL) was added drop wise in such a manner that reaction should remain refluxing. After complete addition, reaction was stirred at room temperature and monitored by TLC. After completion of reaction, reaction mixture was cooled to −5° C. and ammonium chloride (3.9 g, 78.83 mmole) in water (20 mL) was added drop wise. Zn dust (5.1 g, 78.75 mmole) was added portion wise over a period of one hour and stirred further for one hour at same temperature. After completion of reaction, reaction mixture was filtered through celite bed and washed thoroughly with ethyl acetate. Solvent was concentrated under reduced pressure and crude product so obtained was purified by column chromatography using 40% ethyl acetate in hexane to afford target product 22-V (29 g, 60%) as a thick oil; LCMS: m/z 246 (M$^+$+1)

$^1$H NMR (400 MHz, CDCl$_3$): δ 3.32 (s, 4H), 4.13 (s, 4H), 5.03 (s, 2H), 7.53 (s, 5H)

Step V: Benzyl 2-(2-ethoxy-2-oxo-ethylidene)-6-azaspiro[3.3]heptane-6-carboxylate (22-VI)

A mixture of 22-V (29 g, 8.16 mmol) and carboethoxymethyltriphenylphospharane (5.68 g, 16.32 mmol) in toluene (40 mL) was refluxed for 16 hours. After completion of reaction (monitored by TLC), water was added and crude product was extracted with ethyl acetate. Organic layer was separated, washed with water followed by brine, dried over anhydrous sodium sulphate and concentrated under reduced pressure. Crude product so obtained was purified by column chromatography using 20% ethyl acetate in hexane to afford target product 22-VI (25 g, 67%) as a solid compound; LCMS: m/z 316 (M$^+$+1)

$^1$H NMR (400 MHz, CDCl$_3$): δ 1.26 (t, J=8.0 Hz, 3H), 3.01 (s, 2H), 3.30 (s, 2H), 4.05 (m, 4H), 4.15 (q, J=4 Hz, 2H), 5.09 (s, 2H), 5.65 (s, 1H), 7.34 (s, 5H)

Step VI: Ethyl 2-(6-azaspiro[3.3]heptan-2-yl)acetate (22-VII)

To a stirred solution of 22-VI (7 gms, 22.22 mmole) in ethanol (100 mL) was added Pd/C (10%, 1.3 g) and reaction was stirred under hydrogen atmosphere for 7-8 hours. After completion of reaction, reaction mixture was filtered through celite and washed with ethyl acetate. Solvent was concentrated under reduced pressure to afford title compound 22-VII (4 g, 90%); LCMS: m/z 184 (M$^+$+1)

Step VII: [6-[2-(2-ethoxy-2-oxo-ethyl)-6-azaspiro[3.3]heptan-6-yl]-3-pyridyl]azinic acid (22-VIII)

To a stirred solution of 22-VII (0.50 g, 4.5 mmol) in dichloromethane (25 mL) was added triethylamine (1.3 mL, 9.9 mmol). 2-chloro, 5-nitropyridine was added at room temperature under inert atmosphere and reaction mixture was stirred for 16 hours. After completion of reaction (monitored by TLC), water was added to reaction mixture and crude product was extracted with dichloromethane. Organic layer was washed with brine and dried over anhydrous sodium sulphate to give crude compound which was purified by silica gel column chromatography to give title compound 22-VIII (0.50 g, 66%) as a yellow solid; LCMS: m/z 307 (M$^+$+1)

Step VIII: ethyl 2-[6-(5-amino-2-pyridyl)-6-azaspiro[3.3]heptan-2-yl]acetate (Intermediate 22-IX)

To a stirred solution of 22-VIII (0.50 g, 1.62 mmole) in ethanol (10 mL) was added Pd/C (10%, 0.10 g) and reaction was stirred under hydrogen atmosphere for 16 hours. After completion of reaction, reaction mixture was filtered through celite, washed with ethyl acetate and solvent was concentrated under reduced pressure to give title compound Intermediate 22-IX (0.30 g, 66%); LCMS: m/z 276 (M$^+$+1)

Intermediate 23-IX: Ethyl 7-(4-aminophenyl)-7-azaspiro[3.5]nonane-2-carboxylate

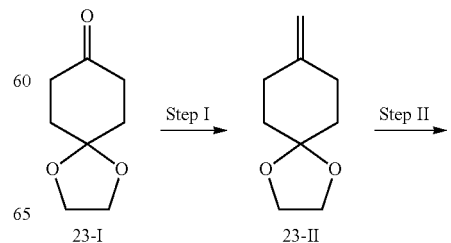

Scheme 23

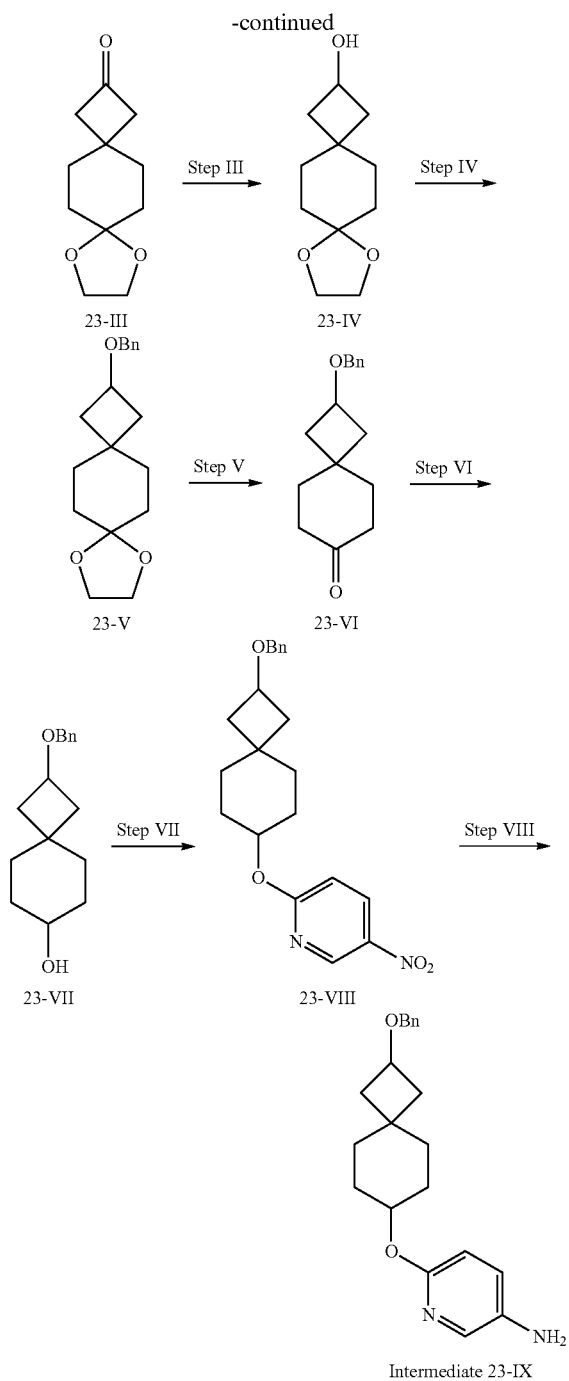

ous exothermic reaction takes place). After stirring the mixture at room temperature for 1 hour, it was cooled to −5° C. and NH$_4$Cl (5.20 g, 97.26 mmol) was added slowly in portions. Finally zinc dust (21.19 g, 324.2 mmol) was added in portions over the period of 1 hour at −5° C. Reaction mixture was allowed to warm to room temperature, celite was added and the thick mass formed was filtered over celite pad. Celite pad was washed with excess ethyl acetate. Combined organic layer was washed with brine solution, dried over anhydrous sodium sulfate and concentrated under reduced pressure to provide crude compound which was purified by silica gel column chromatography (15-20% ethyl acetate in hexanes) to provide title compound 23-III (3.1 g, 49%).

$^1$H NMR (400 MHz, CDCl$_3$): δ 1.22-1.30 (m, 2H), 1.57-1.69 (m, 2H), 1.78-1.86 (m, 2H), 3.79 (s, 2H), 3.39 (s, 4H), 3.54 (s, 2H), 3.96 (s, 2H)

Step III: 8,11-dioxadispiro[3.2.4.2]tridecan-2-ol (23-IV)

To a stirred solution of 23-III (5.0 g, 25.47 mmol) in methanol (50 mL), sodium borohydride (0.48 g, 12.73 mmol) was added portion wise and stirred for 30 minutes. Reaction mixture was concentrated to give the crude product which was purified by silica gel column chromatography (20-30% ethyl acetate in hexanes as eluent) to provide title compound 23-IV (5.0 g, 99%); LCMS: m/z 199.2 (M$^+$+1).

Step IV: 2-Benzyloxy-8,11-dioxadispiro[3.2.4.2]tridecane (23-V)

To a stirred solution of 23-IV (5.0 g, 25.22 mmol) in anhydrous THF (126 mL), sodium hydride (60% in mineral oil, 1.51 g, 37.83 mmol) was added portion wise at room temperature and stirred for 2.5 hours. Finally benzyl bromide (3.77 mL, 31.52 mmol) was added drop wise and the reaction mixture was further allowed to stir for 12 hours. The reaction mixture was poured over ice-water mixture (200 mL), extracted with ethyl acetate (3×100 mL), organic layer was washed with brine solution, dried over anhydrous sodium sulfate and concentrated under reduced pressure to provide title compound 23-V (7.0 g, 96%) as a liquid.

Step V: 2-benzyloxyspiro[3.5]nonan-7-one (23-VI)

A mixture of 23-V (7.2 g, 24.96 mmol) in THF (30 mL) and 1N HCl (30 mL) was refluxed for 3 hours. After completion of reaction, the reaction mixture was diluted with ethyl acetate (100 mL), organic layer was washed with water followed by brine solution, dried over anhydrous sodium sulfate, filtered and concentrated under reduced pressure to afford title compound 23-VI as a crude product (6.15 g) as a liquid which was used for next step without further purification.

Step VI: 2-Benzyloxyspiro[3.5]nonan-7-ol (23-VII)

To a stirred solution of 23-VI (6.15 g, 25.17 mmol) in methanol (100 mL), sodium borohydride (0.476 g, 12.58 mmol) was added portion wise at 0° C. and stirred for 30 minutes at same temperature. Reaction mixture was concentrated to give the crude product which was purified by column chromatography over silica gel using 15-20% ethyl acetate in hexane as eluent to provide title compound 23-VII (5.8 g, 93%).

Step I: 8-methylene-1,4-dioxaspiro[4.5]decane (23-II)

23-II was prepared from 23-I following similar procedure as used for the preparation of 5-I from 2-II Step II: 8,11-dioxadispiro[3.2.4.2]tridecan-2-one (23-III)

To a stirred suspension of 23-II (5.0 g, 32.42 mmol) and zinc-copper couple (21.06 g, 162.1 mmol) in DME (100 mL) was added trichloroacetyl chloride (9.45 mL, 84.30 mmol) drop wise (controlled addition) at room temperature (vigor- $^1$H NMR (400 MHz, CDCl$_3$): δ 1.28-1.45 (m, 4H), 1.61-1.84 (m, 6H), 2.05-2.15 (m, 1H), 2.16-2.24 (m, 1H), 3.60 (br. s, 1H), 3.98-4.06 (m, 1H), 4.40 (s, 2H), 7.27-7.34 (aromatics, 5H)

Step VII: 2-(2-benzyloxyspiro[3.5]nonan-7-yl)oxy-5-nitro-pyridine (23-VIII)

To a stirred solution of 23-VII (0.5 g, 2.02 mmol) in anhydrous THF (10 mL), 60% sodium hydride (0.105 g, 2.63 mmol) was added portion wise at room temperature and stirred for 2.5 hours. Finally 2-chloro-5-nitro-pyridine (0.486 g, 3.03 mmol) was added and the reaction mixture was heated at 70° C. for 12 hours. The reaction mixture was poured over ice-water mixture (10 mL), extracted with ethyl acetate (3×10 mL), organic layer was washed with brine solution, dried over anhydrous sodium sulfate and concentrated under reduced pressure to afford crude product which was purified by silica gel column chromatography (15-20% ethyl acetate in hexanes) to provide title compound 23-VIII (0.45 g, 60%).

$^1$H NMR (400 MHz, CDCl$_3$): δ 1.40-1.53 (m, 2H), 1.57-1.66 (m, 2H), 1.68-1.82 (m, 4H), 1.84-1.97 (m, 1H), 2.21-2.80 (m, 1H), 4.01-4.10 (m, 1H), 4.41 (s, 2H), 5.09-5.19 (m, 1H), 6.74 (d, J=9.0 Hz, 1H), 7.28-7.35 (aromatics, 5H), 8.32 (dd, J=9.0, 2.9 Hz, 1H), 9.04 (d, J=2.7 Hz, 1H). MS (EI) m/z: 369.3 (M+1).

Step VIII: 6-(2-benzyloxyspiro[3.5]nonan-7-yl)oxy-pyridin-3-amine (Intermediate 23-IX)

To a solution of 23-VIII (0.45 g, 1.22 mmol) in ethyl acetate (10 mL) was added 10% Pd/C (0.10 g). Hydrogenation was carried out at 1 atmospheric pressure of molecular hydrogen (balloon pressure) at room temperature for 16 hours. The reaction mixture was filtered through short pad of celite and washed thoroughly with ethyl acetate. The filtrate was condensed under reduced pressure to obtain crude product which was purified by silica gel preparative TLC (45% ethyl acetate in hexanes) to afford title compound Intermediate 23-IX (0.26 g, 63%); LCMS: 339.3 (M$^+$+1).

$^1$H NMR (400 MHz, CDCl$_3$): δ 1.38-1.57 (m, 4H), 1.64-1.79 (m, 4H), 1.81-1.92 (m, 2H), 2.07-2.16 (m, 1H), 2.17-2.28 (m, 1H), 3.35 (br.s, 2H), 3.98-4.08 (m, 1H), 4.40 (s, 2H), 4.74-4.90 (m, 1H), 6.54 (d, J=8.4 Hz, 1H), 7.01 (d, J=7.9 Hz, 1H), 7.27-7.40 (aromatics, 5H), 7.63 (s, 1H). MS (EI) m/z: 339.3 (M+1).

Intermediate 24-X: Ethyl 7-(4-aminophenyl)-7-azaspiro[3.5]nonane-2-carboxylate

Scheme 24

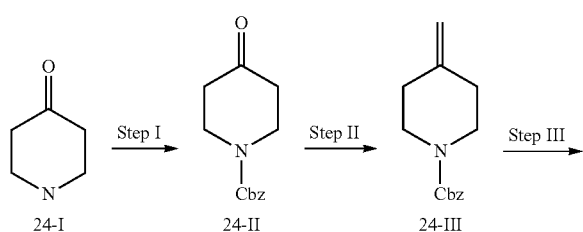

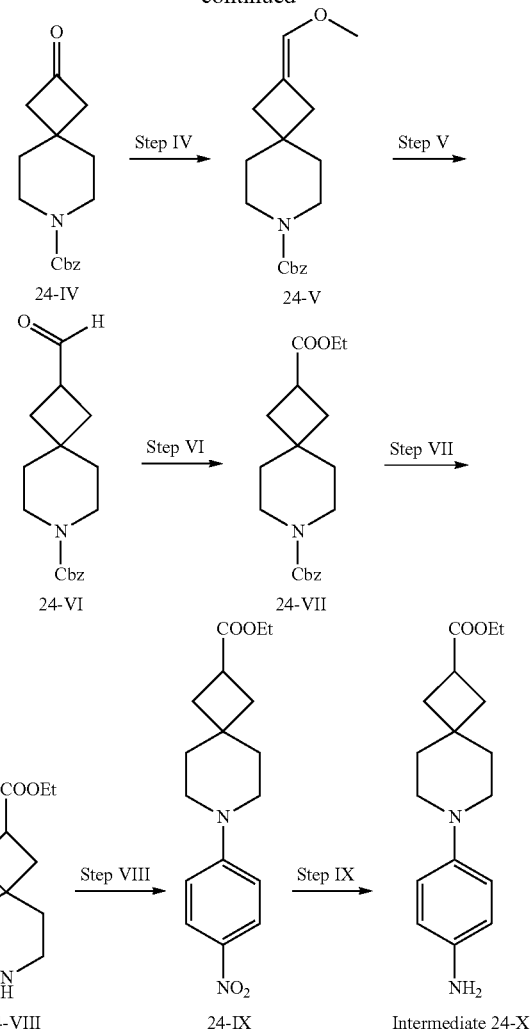

Step I: Benzyl 4-oxopiperidine-1-carboxylate (24-II)

To a stirred solution of 4-piperidone monohydrate hydrochloride (50 g, 325.49 mmol) in THF (500 mL) at 0° C. was added a solution of sodium bicarbonate (136.7 g, 1627 mmol) in water (230 mL) and the resulting reaction mixture was stirred at 0° C. for 30 minutes. Benzylchloroformate (46.5 mL, 325.49 mmol) was added drop wise to the reaction mixture and stirred at 0° C. for 30 minutes. The reaction mixture was allowed to attain room temperature and stirred for 16 hours. After completion of reaction (monitored by TLC), solvent was evaporated under reduced pressure. The residue was taken in water and ethyl acetate, organic layer washed with brine, dried over Na$_2$SO$_4$ and concentrated under reduced pressure to afford title compound 24-II (69 g, 92%) as a yellowish liquid; LCMS: m/z 233.3

$^1$HNMR (400 MHz, CDCl$_3$): δ 2.45 (m, 4H), 3.81-3.78 (m, 4H), 5.17 (s, 2H), 7.38-7.26 (m, 5H)

Step II: Benzyl 4-methylenepiperidine-1-carboxylate (24-III)

To a stirred suspension of methyl triphenylphosphonium bromide (317.0 g, 887.42 mmol) in THF (1000 mL) was added potassium ter-butoxide (99.5 g, 887.42 mmol) portion wise under nitrogen atmosphere at 0° C. The reaction mixture was allowed to attain room temperature and stirred for 3 hours. Subsequently reaction mixture was again cooled to 0° C. and a solution of 24-II (69 g, 295.8 mmol) in THF (500 mL) was added through addition funnel. Reaction mixture was further stirred for 16 hours at room temperature. After completion of reaction, saturated ammonium chloride solution was added to the reaction mixture and product was extracted with ethyl acetate. Organic layer was washed with brine, dried over anhydrous $Na_2SO_4$ and concentrated under reduced pressure to afford title compound 24-III (50 g, 58%) as a brownish liquid;

LCMS: m/z 231.0, $(M^++1)$

Step III: Preparation of (d): benzyl 2-oxo-7-azaspiro[3.5]nonane-7-carboxylate (24-IV)

To a solution of 24-III (50 g, 216.17 mmol) in 1,2 dimethoxyethane (1000 mL) at room temperature was added Zinc-Copper couple (139.34 g, 1080.85 mmol). After 10 minutes, trichloroacetyl chloride (121.31 mL, 1080.85 mmol) was added to reaction mixture through addition funnel and resulting reaction mixture was stirred for 2 hours [Note: First half portion of Trichloroacetyl chloride was added in one portion and remaining amount was added slowly after exothermic reaction started in the reaction mixture]. The reaction was cooled down to room temperature and ammonium chloride (57.81 g, 1080.85 mmol) was added portion wise to reaction mixture at 0° C. Subsequently zinc dust (141.35 g, 1080.85 mmol) was added portion wise to reaction maintaining temperature below 0° C. and the reaction mixture was stirred at room temperature for 16 hours. After completion of reaction (monitored by TLC), crude reaction mixture was filtered through celite bed and washed thoroughly with ethyl acetate. Organic layer was washed with water, saturated $NaHCO_3$ solution, followed by brine and dried over anhydrous $Na_2SO_4$. Solvent was evaporated under reduced pressure and crude product so obtained was purified by silica gel column chromatography using 15% ethyl acetate in hexanes as eluent to afford target compound 24-IV (48 g, 81%) as a yellow color liquid; LCMS: m/z 273.3 $(M^++1)$

Step IV: Benzyl 2-(methoxymethylene)-7-azaspiro [3.5]nonane-7-carboxylate (24-V)

To a solution of (Methoxymethyl)triphenylphosphonium chloride (18.81 g, 54.87 mmol) in THF (30 mL) at −4° C. was added potassium tert.butoxide (6.16 g, 54.87 mmol) followed by t-butanol (5.2 mL, 54.87 mmol) and the resulting reaction mixture was stirred at 0° C. for 1 hour. A solution of 24-IV (5 g, 18.29 mmol) in THF (20 mL) was added dropwise to the reaction mixture at −78° C. The reaction mixture was slowly allowed to attain room temperature and stirring was continued for 1 hour. After completion of reaction (monitored by TLC), water was added to the reaction mixture and product was extracted with ethyl acetate. Organic layer was washed with brine, aqueous saturated ammonium chloride solution followed by brine and dried over anhydrous $Na_2SO_4$. Solvent was concentrated under reduced pressure and the crude product so obtained was purified by silica gel column chromatography using 5% ethyl acetate in hexanes as eluent to afford title compound 24-V (8.3 g, 40%) as a yellow liquid; LCMS: m/z 301.4 $(M^++1)$

Step V: Benzyl 2-formyl-7-azaspiro[3.5]nonane-7-carboxylate (24-VI)

To a solution of 24-V (2.2 g, 7.29 mmol) in acetonitrile was added at room temperature 2M HCl solution and the resulting reaction mixture was stirred for 4 hours. After completion of reaction (monitored by TLC), reaction mixture, was evaporated to dryness and residue was extracted with ethyl acetate. Organic layer was washed with water followed by brine and dried over anhydrous $Na_2SO_4$. Solvent was evaporated under reduced pressure to afford 24-VI (1.93 g, 92%) as a colorless liquid; LCMS: m/z 287.35 $(M^++1)$.

$^1$HNMR (400 MHz, $CDCl_3$): δ 1.43-1.62 (m, 4H), 1.96-2.08 (m, 4H), 3.13-3.17 (m, 1H), 3.35-3.38 (m, 2H), 3.42-3.45 (m, 2H), 5.11 (s, 2H), 7.26-7.35 (m, 5H), 9.75 (s, 1H)

Step VI: O7-benzyl O2-ethyl 7-azaspiro[3.5]nonane-2,7-dicarboxylate (24-VII)

To a solution of 24-VI (1.94 g, 6.75 mmol) in EtOH (65 mL) at room temperature was added oxone (4.15 g, 6.75 mmol). The resulting reaction mixture was stirred at room temperature for 16 hours. Reaction mixture was filtered through celite bed and filtrate was concentrated under reduced pressure. The crude product so obtained was purified by silica gel column chromatography using 10% ethyl acetate in hexanes to afford title compound 24-VII (1.58 g, 71%) as a colourless liquid; LCMS: m/z $(M^++1)$ $^1$HNMR (400 MHz, $CDCl_3$): δ 1.23-1.27 (t, J=8 Hz, 3H), 1.54-1.65 (m, 4H), 2.04-2.07 (m, 4H), 3.03-3.09 (m, 1H), 3.35-3.38 (m, 2H), 3.41-3.44 (m, 2H), 4.10-4.15 (q, J=4 Hz, 8 Hz, 2H), 5.11 (s, 2H), 7.26-7.35 (m, 5H)

Step VII: Ethyl 7-azaspiro[3.5]nonane-2-carboxylate (24-VIII)

A solution of 24-VII (1.6 g, 5.04 mmol) in EtOH (30 mL) was degassed under nitrogen at room temperature and Pd/C (10%, 1 g) was added to the reaction mixture. Reaction was stirred under hydrogen atmosphere for 16 hours. Reaction mixture was filtered through celite bed. Filtrate was concentrated and dried under vacuum to provide target compound 24-VIII (0.85 g, 90%) as an off white semi solid; LCMS: m/z 197.27 $(M^++1)$ $^1$HNMR (400 MHz, DMSO-D6): 1.15-1.18 (t, 8 Hz, 3H), 1.43-1.45 (m, 2H), 1.53-1.55 (m, 2H), 1.85-1.90 (m, 2H), 1.96-2.01 (m, 2H), 2.61-2.62 (m, 2H), 2.68-2.69 (m, 2H), 3.03-3.12 (m, 2H), 4.02-4.07 (q, 8 Hz, 16 Hz, 2H), 4.20-4.60 (br., s, 1H)

Step VIII: Ethyl 7-(4-nitrophenyl)-7-azaspiro[3.5] nonane-2-carboxylate (24-IX)

A solution of 24-VIII (2.0 g, 10.13 mmol), 1-fluoro-4-nitrobenzene (1.57 g, 11.15 mmol) and potassium carbonate (0.004 g, 30.39 mmol) in DMF (15 mL) was stirred under nitrogen at room temperature for 16 hours. Reaction mixture was cooled to 0° C. and ice cold water was added to it. The solid product so obtained was filtered and washed with water followed by hexanes and dried under vacuum to furnish title compound 24-IX (2.7 g, 86%) as a yellow solid; LCMS: m/z 318.1 $(M^++1)$

Step IX: Ethyl 7-(4-aminophenyl)-7-azaspiro[3.5] nonane-2-carboxylate (Intermediate 24-X)

A solution of 24-IX (2.8 g, 8.8 mmol) in ethyl acetate (40 mL) was degassed under nitrogen at room temperature. Pd/C (10%, 2 g) was added to the reaction mixture. Reaction was stirred under hydrogen atmosphere for 16 hours. Reaction mixture was filtered through celite bed and washed with ethyl acetate. Filtrate was concentrated under vacuum to afford title compound Intermediate 24-X (2.3 g, 92%) as a brownish liquid; LCMS: m/z 288.18 (M$^+$+1)

Intermediate 25-IV: Ethyl 2-[7-(4-aminophenyl)-7-azaspiro[3.5]nonan-2-yl]acetate Scheme 25

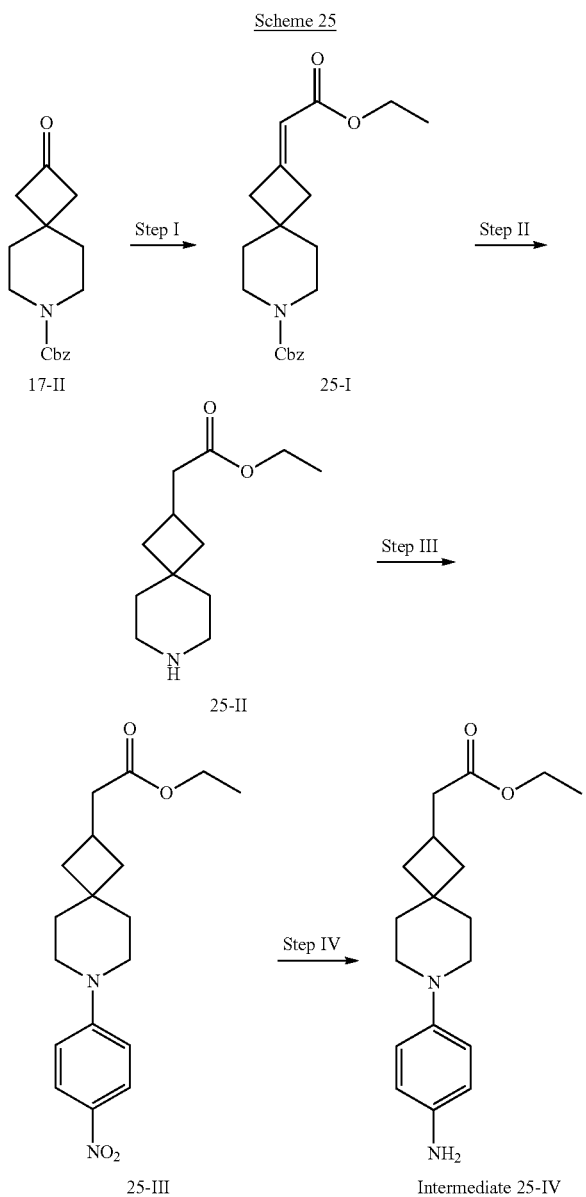

Step I: Benzyl 2-(2-ethoxy-2-oxo-ethylidene)-7-azaspiro[3.5]nonane-7-carboxylate (25-I)

To a stirred suspension of 17-II (15 gm, 54 mmol) in toluene (200 mL) was added carboethoxymethyltriphenylphosphorane (22 gm, 65 mmole) and the resulting reaction mixture was refluxed for 16 hours. After completion of reaction, water was added and the product was extracted with ethyl acetate. Organic layer was separated, washed with water, followed by brine and dried over anhydrous sodium sulphate. Solvent was evaporated under reduced pressure and the crude product so obtained was purified by column chromatography using 10% ethyl acetate in hexanes to afford title compound 25-I (10 g, 53%).

$^1$H NMR (400 MHz, CDCl$_3$): δ 1.27 (t, J=8.0 Hz, 3H), 1.40 (s, 4H), 2.58 (s, 2H), 2.88 (s, 2H), 3.41 (m, 4H), 4.15 (q, J=4 Hz, 2H), 5.12 (s, 2H), 5.70 (s, 1H), 7.34 (s, 5H) LCMS: m/z 361 (M$^+$+1)

Step II: Ethyl 2-(7-azaspiro[3.5]nonan-2-yl)acetate (25-II)

To a stirred solution of 25-I (9.5 g, 27 mmol) in ethanol (100 mL) was added of Pd/C (10%, 2.5 g) and reaction was carried out under hydrogen atmosphere for 16 hours. After completion of reaction (monitored by TLC), reaction mixture was filtered through celite pad and washed with ethyl acetate. Solvent was concentrated under reduced pressure to give title compound 25-II (5 g, 86%); LCMS: m/z 212 (M$^+$+1)

Step III: Ethyl 2-[7-(4-nitrophenyl)-7-azaspiro[3.5]nonan-2-yl]acetate (25-III)

25-III was prepared from 25-II following similar procedure as used for the synthesis of 24-IX from 24-VIII.

$^1$H NMR (400 MHz, CDCl$_3$): δ 1.26 (t, J=5.6 Hz, 3H), 1.51 (t, J=9 Hz, 2H), 1.63 (t, J=6 Hz, 2H), 1.75 (t, J=5.6 Hz, 2H), 2.10 (t, J=11 Hz, 2H), 2.44 (d, J=7.6 Hz, 2H), 2.67-2.69 (m, 1H), 3.22 (t, J=5.2 Hz, 2H), 3.41 (t, J=5.2 Hz, 2H), 4.12 (q, J=7.2 Hz, 2H), 6.80 (d, J=9.2 Hz, 2H), 8.09 (d, J=9.6 Hz, 2H) LCMS: m/z 333 (M$^+$+1)

Step IV: Ethyl 2-[7-(4-aminophenyl)-7-azaspiro[3.5] nonan-2-yl]acetate (Intermediate 25-IV)

Intermediate 25-IV was prepared from 25-III following similar procedure as used for the synthesis of Intermediate 24-X from 24-IX; LCMS: m/z 303 (M$^+$+1)

Example A1 methyl 2-[9-[5-[[5-(3,4-difluoroanilino)-1,3,4-oxadiazole-2-carbonyl]amino]-2-pyridyl]spiro[5.5]undecan-3-yl]acetate Scheme 26

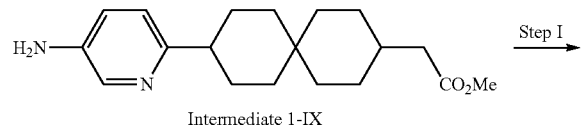

Intermediate 1-IX

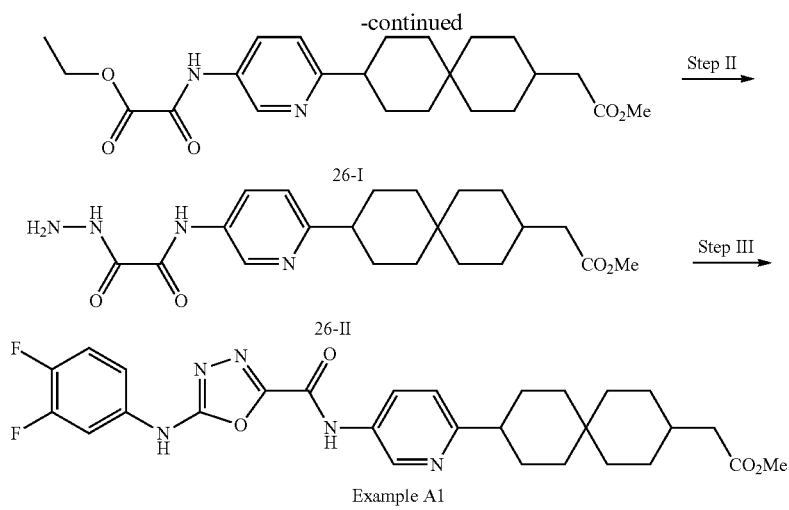

Step I: Ethyl 2-[[6-[3-(2-methoxy-2-oxo-ethyl)spiro[5.5]undecan-9-yl]-3-pyridyl]amino]-2-oxo-acetate (26-I)

Ethyl chlorooxoacetate (0.34 ml, 3.0 mmol) was added to a stirred solution of Intermediate 1-IX (0.8 g, 2.53 mmol) and pyridine (0.54 ml, 5.56 mmol) in DCM (20 ml). The resulting solution was stirred at room temperature for 2 hrs. Reaction mixture was diluted with DCM (50 ml) and washed with brine (50 ml). Combined organic layer was dried over $Na_2SO_4$. Evaporation of solvent under reduced pressure furnished the crude title product 26-I (1.1 g) that was used for next step without further purification; LCMS: m/z 417.2 ($M^+$+1)

Step II: Methyl 2-[9-[5-[(2-hydrazino-2-oxo-acetyl)amino]-2-pyridyl]spiro[5.5]undecan-3-yl]acetate (26-II)

To a solution of 26-I (1.1 g, 2.64 mmol) in EtOH (100 ml), hydrazine hydrate (0.15 g, 3.17 mmol) was added at room temperature and resulting suspension was stirred for 3 hrs. Solid that separated in the reaction mixture was filtered off and dried under vacuum to furnish title compound 26-II (0.76 g, 74%); LCMS: m/z 403.2 ($M^+$+1)

Step III: Methyl 2-[9-[5-[[5-(3,4-difluoroanilino)-1,3,4-oxadiazole-2-carbonyl]amino]-2-pyridyl]spiro[5.5]undecan-3-yl]acetate (Example A1)

3,4-difluorophenylisothiocyanate (0.1 ml, 0.54 mmol) was added to the solution of methyl 2-[9-[5-[(2-hydrazino-2-oxo-acetyl)amino]-2-pyridyl]spiro[5.5]undecan-3-yl]acetate (26-II) (0.2 g, 0.49 mmol) in N,N-dimethylacetamide and resulting reaction mixture was stirred at 45° C. for 90 min. Reaction mixture was cooled to room temperature and EDCI (0.113 g, 0.59 mmol) was added and reaction mixture was again heated to 85° C. for 3 hrs. Reaction mixture was added to crushed ice and resulting solid was collected by filtration followed by recrystallization using hot EtOH to furnish title compound (Example A1) (0.17 g, 66%)

$^1$HNMR (400 MHz, $CDCl_3$): δ 0.89-1.37 (m, 6H), 1.45-1.60 (m, 6H), 1.98 (d, J=12.8 Hz, 4H), 2.01 (d, J=6.8 Hz, 2H), 2.48-2.65 (m, 2H), 3.55 (s, 3H), 7.26 (d, J=8.8 Hz, 1H), 7.30-7.34 (m, 1H), 7.48 (dd, J=9.2, 19.2 Hz, 1H), 7.64-7.70 (m, 1H), 8.05 (dd, J=2 Hz, 1H), 8.81 (d, J=14.4 Hz, 1H), 11.21 (s, 1H), 11.28 (s, 1H)

LCMS: m/z 540.2 ($M^+$+1)

Following compounds were prepared from their corresponding intermediates (given in parentheses) using the same sequence of procedures as used for preparation of Example A1 from Intermediate 1-IX:

| Example No | Structure and IUPAC name | Characterization Data | Intermediate from which prepared |
|---|---|---|---|
| A2 | methyl 2-[9-[5-[(5-anilino-1,3,4-oxadiazole-2-carbonyl)amino]-2-pyridyl]spiro[5.5]undecan-3-yl]acetate | LCMS: m/z 504.3 ($M^+$ + 1) $^1$HNMR (400 MHz, DMSO-d6): δ 0.93-1.03 (m, 2H), 1.07-1.16 (m, 1H), 1.18-1.35 (m, 5H), 1.40-1.51 (m, 2H), 1.53-1.72 (m, 4H), 2.01 (d, J = 12.8 Hz, 2H), 2.20 (d, J = 6.8 Hz, 2H), 2.53-2.65 (m, 2H), 3.56 (s, 3H), 7.06 (t, J = 7.6 Hz, 1H), 7.26 (d, J = 8.4 Hz, 1H), 7.37 (t, J = 7.6 Hz, 2H), 7.59 (d, J = 8.0 Hz, 2H), 8.06 (dd, J = 2.4 Hz, J = 8.4 Hz, 1H), 8.81 (d, J = 2.4 Hz, 1H), 11.00 (s, 1H), 11.29 (s, 1H) | 1-IX |

-continued

| Example No | Structure and IUPAC name | Characterization Data | Intermediate from which prepared |
|---|---|---|---|
| A3 | 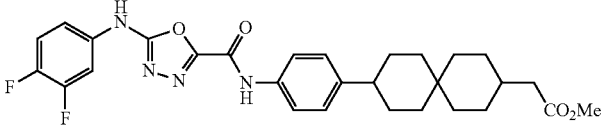 [SMILES: COC(=O)CC1CCC2(CC1)CCC(c1ccc(NC(=O)c3nnc(Nc4ccc(F)c(F)c4)o3)cc1)CC2]<br>methyl 2-[9-[4-[[5-(3,4-difluoroanilino)-1,3,4-oxadiazole-2-carbonyl]amino]phenyl]spiro[5.5]undecan-3-yl]acetate | LCMS: m/z 539.2 (M$^+$ + 1)<br>$^1$HNMR (400 MHz, CDCl$_3$): δ 0.85-0.94 (m, 2H), 1.01-1.20 (m, 2H), 1.25-1.33 (m, 6H), 1.37-1.42 (m, 2H), 1.62-1.65 (m, 2H), 1.74-1.78 (m, 1H), 2.07 (d, J = 13.2 Hz, 2H), 2.24 (d, J = 6.8 Hz, 2H), 2.44-2.46 (m, 1H), 3.67 (s, 3H), 7.15-7.22 (m, 3H), 7.40-7.43 (m, 1H), 7.52-7.57 (m, 3H), 7.62-7.64 (m, 1H), 8.00 (s, 1H), 8.73 (s, 1H). | 2-X |
| A4 | 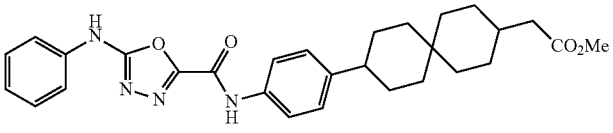 [SMILES: COC(=O)CC1CCC2(CC1)CCC(c1ccc(NC(=O)c3nnc(Nc4ccccc4)o3)cc1)CC2]<br>methyl 2-[9-[4-[(5-anilino-1,3,4-oxadiazole-2-carbonyl)amino]phenyl]spiro[5.5]undecan-3-yl]acclate | LCMS: m/z 503.2 (M$^+$ + 1)<br>$^1$HNMR (400 MHz, CDCl$_3$): δ 0.95-1.08 (m, 2H), 1.09-1.15 (m, 1H), 1.23-1.42 (m, 7H), 1.47-1.63 (m, 4H), 1.76-1.78 (m, 1H), 2.07 (d, J = 11.6 Hz, 2H), 2.23 (d, J = 7.2 Hz, 2H), 2.42-2.52 (m, 1H), 3.67 (s, 3H), 7.14 (t, J = 7.6 Hz, 1H), 7.20-7.23 (m, 2H), 7.38-7.45 (m, 2H), 7.51-7.58 (m, 4H), 7.71 (s, 1H), 8.73 (s, 1H). | 2-X |
| A5 | 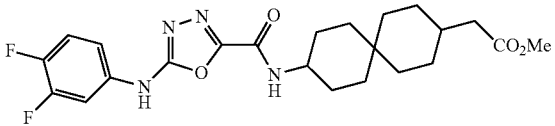 [SMILES: COC(=O)CC1CCC2(CC1)CCC(NC(=O)c1nnc(Nc3ccc(F)c(F)c3)o1)CC2]<br>methyl 2-[9-[[5-(3,4-difluoroanilino)-1,3,4-oxadiazole-2-carbonyl]amino]spiro[5.5]undecan-3-yl]acetate | LCMS: m/z 463.2 (M$^+$ + 1) | 3-II |
| A6 | 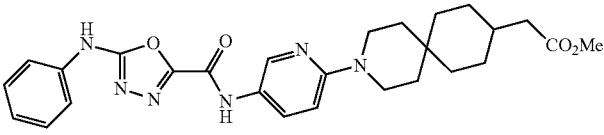 [SMILES: COC(=O)CC1CCC2(CC1)CCN(c1ccc(NC(=O)c3nnc(Nc4ccccc4)o3)cn1)CC2]<br>methyl 2-[9-[5-[(5-anilino-1,3,4-oxadiazole-2-carbonyl)amino]-2-pyridyl]-9-azaspiro[5.5]undecan-3-yl]acetate | LCMS: m/z 504.7 (M$^+$ + 1)<br>$^1$HNMR (400 MHz, DMSO-d6): δ 1.07-1.21 (m, 4H), 1.34 (t, J = 5.6 Hz, 2H), 1.47-1.50 (m, 4H), 1.66 (d, J = 10.8 Hz, 3H), 2.23 (d, J = 7.2 Hz, 2H), 3.44 (d, J = 10.8 Hz, 4H), 3.58 (s, 3H), 6.82 (d, J = 9.2 Hz, 1H), 7.05 (t, J = 7.2 Hz, 1H), 7.39 (t, J = 7.6 Hz, 2H), 7.60 (d, J = 8.0 Hz, 2H), 7.88 (dd, J = 2.4 Hz, J = 9.2 Hz, 1H), 8.45 (d, J = 2.4 Hz, 1H), 10.92 (s, 1H), 10.98 (s, 1H) | 4-V |
| A7 | 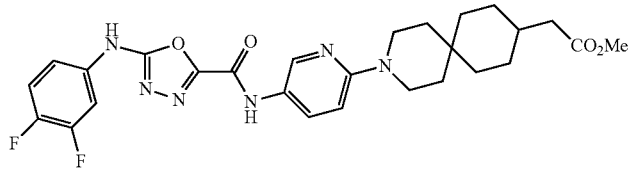 [SMILES: COC(=O)CC1CCC2(CC1)CCN(c1ccc(NC(=O)c3nnc(Nc4ccc(F)c(F)c4)o3)cn1)CC2]<br>methyl 2-[9-[5-[[5-(3,4-difluoroanilino)-1,3,4-oxadiazole-2-carbonyl]amino]-2-pyridyl]-9-azaspiro[5.5]undecan-3-yl]acetate | LCMS: m/z 540.6 (M$^+$ + 1)<br>$^1$HNMR (400 MHz, DMSO-d6): δ 1.10-1.19 (m, 4H), 1.34 (t, J = 5.6 Hz, 2H), 1.47-1.50 (m, 4H), 1.66 (d, J = 10.8 Hz, 3H), 2.24 (d, J = 7.2 Hz, 2H), 3.45 (d, J = 10.4 Hz, 4H), 3.58 (s, 3H), 6.82 (d, J = 9.2 Hz, 1H), 7.34 (d, J = 9.2 Hz, 1H), 7.47 (dd, J = 8.8 Hz, J = 19.2 Hz, 1H), 7.67-7.72 (m, 1H), 7.88 (dd, J = 2.4 Hz, J = 9.6 Hz, 1H), 8.45 (d, J = 2.4 Hz, 1H), 10.96 (s, 1H), 11.26 (s, 1H) | 4-V |

| Example No | Structure and IUPAC name | Characterization Data | Intermediate from which prepared |
|---|---|---|---|
| A8 | 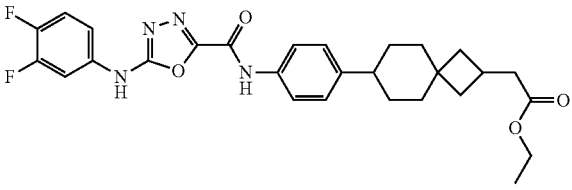 [SMILES: CCOC(=O)CC1CC2(CCC(c3ccc(NC(=O)c4nnc(Nc5ccc(F)c(F)c5)o4)cc3)CC2)C1]<br>ethyl 2-[7-[4-[[5-(3,4-difluoroanilino)-1,3,4-oxadiazole-2-carbonyl]amino]phenyl]spiro[3.5]nonan-2-yl]acetate | LCMS: m/z 525.3 (M$^+$ + 1)<br>$^1$HNMR (400 MHz, DMSO-d6): δ 1.17 (t, J = 7.2 Hz, 3H), 1.33-1.47 (m, 6H), 1.49-1.63 (m, 4H), 1.81-1.90 (m, 2H), 2.07 (t, J = 8.0 Hz, 1H), 2.38 (d, J = 7.6 Hz, 3H), 4.04 (q, J = 7.2 Hz, 2H), 7.19 (d, J = 8.4 Hz, 2H), 7.34 (d, J = 8.8 Hz, 1H), 7.49 (dd, J = 2.8 Hz, J = 19.2 Hz, 1H), 7.67-7.72 (m, 3H), 11.01 (s, 1H), 11.28 (s, 1H) | 5-VII |
| A9 | 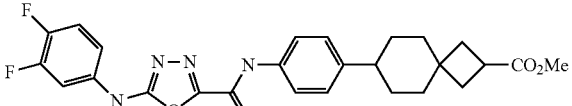<br>methyl 7-[4-[[5-(3,4-difluoroanilino)-1,3,4-oxadiazole-2-carbonyl]amino]phenyl]spiro[3.5]nonane-2-carboxylate | LCMS: m/z 497.3 (M$^+$ + 1)<br>$^1$HNMR (400 MHz, DMSO-d6): δ 1.35-1.45 (m, 4H), 1.59-1.67 (m, 3H), 1.93 (d, J = 8.8 Hz, 4H), 2.11-2.16 (m, 1H), 2.35-2.45 (m, 1H), 3.08-3.16 (m, 1H), 3.60 (s, 3H), 7.15-7.21 (m, 2H), 7.34 (d, J = 8.8 Hz, 1H), 7.48 (dd, J = 9.2 Hz, J = 19.6 Hz, 1H), 7.66-7.33 (m, 3H), 11.02 (s, 1H), 11.29 (bs, 1H) | 6-III |
| A10 | 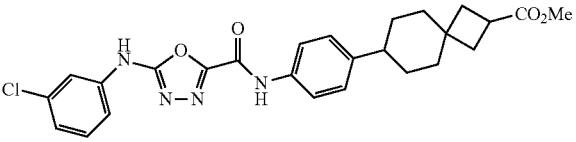 [SMILES: COC(=O)C1CC2(CCC(c3ccc(NC(=O)c4nnc(Nc5cccc(Cl)c5)o4)cc3)CC2)C1]<br>methyl 7-[4-[[5-(3-chloroanilino)-1,3,4-oxadiazole-2-carbonyl]amino]phenyl]spiro[3.5]nonane-2-carboxylate | LCMS: m/z 495.1 (M$^+$ + 1), 497.1 (M$^+$ + 3)<br>1HNMR (400 MHz, DMSO-d6): δ 1.30-1.50 (m, 4H), 1.55-1.75 (m, 4H), 1.92 (d, J = 8.8 Hz, 4H), 2.12 (t, J = 9.6 Hz, 1H), 2.35-2.42 (m, 1H), 3.12 (t, J = 8.0 Hz, 1H), 3.60 (s, 3H), 7.10-7.19 (m, 3H), 7.36-7.49 (m, 3H), 7.68-7.74 (m, 1H), 10.96 (s, 1H), 11.01 (s, 1H) | 6-III |
| A11 | 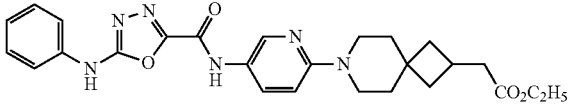<br>ethyl 2-[7-[5-[(5-anilino-1,3,4-oxadiazole-2-carbonyl)amino]-2-pyridyl]-7-azaspiro[3.5]nonan-2-yl]acetate | LCMS: m/z 491.2 (M$^+$ + 1) | 7-VIII |
| A12 | 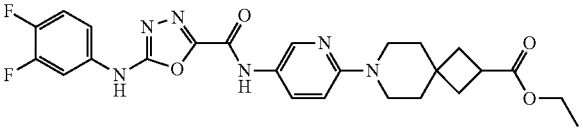 [SMILES: CCOC(=O)C1CC2(CCN(c3ccc(NC(=O)c4nnc(Nc5ccc(F)c(F)c5)o4)cn3)CC2)C1]<br>ethyl 7-[5-[[5-(3,4-difluoroanilino)-1,3,4-oxadiazole-2-carbonyl]amino]-2-pyridyl]-7-azaspiro[3.5]nonane-2-carboxylate | LCMS: m/z 513.3 (M$^+$ + 1)<br>400 MHz, DMSO-d6: δ 1.18 (t, J = 7.2 Hz, 3H), 1.51 (t, J = 5.6 Hz, 2H), 1.61 (t, J = 4.8 Hz, 2H), 1.91-1.98 (m, 2H), 2.05 (t, J = 9.6 Hz, 2H), 3.14 (q, J = 8.8 Hz, 1H), 3.38 (t, J = 5.6 Hz, 2 H), 3.45 (t, J = 5.2 Hz, 2H), 4.07 (q, J = 7.2 Hz, 2H), 6.86 (d, J = 9.2 Hz, 1H), 7.33-7.36 (m, 1H), 7.42-7.50 (m, 1H), 7.71 (dd, J = 2.4 Hz, J = 7.2 Hz, 1H), 7.88 (dd, J = 2.8 Hz, J = 9.2 Hz, 1H), 8.45 (d, J = 2.4 Hz, 1H), 10.96 (s, 1H), 11.26 (s, 1H) | 8-III |

| Example No | Structure and IUPAC name | Characterization Data | Intermediate from which prepared |
|---|---|---|---|
| A13 | ethyl 7-[5-[[5-[[6-(2,2,2-trifluoroethoxy)-3-pyridyl]amino]-1,3,4-oxadiazole-2-carbonyl]amino]-2-pyridyl]-7-azaspiro[3.5]nonane-2-carboxylate | LCMS: m/z 576.3 (M$^+$ + 1) | 8-III |
| A14 | methyl 6-[4-[[5-(3,4-difluoroanilino)-1,3,4-oxadiazole-2-carbonyl]amino]phenyl]spiro[2.5]octane-2-carboxylate | LCMS: m/z 483.2 (M$^+$ + 1)<br>1HNMR (400 MHz, DMSO-d6): δ 0.97-1.33 (m, 4H), 1.48-1.60 (m, 3H), 1.68-1.84 (m, 3H), 1.88-2.00 (m, 1H), 2.55-2.62 (m, 1H), 3.63 (s, 3H), 7.19 (d, J = 7.6 Hz, 2H), 7.34 (d, J = 7.6 Hz, 1H), 7.50 (dd, J = 9.6 Hz, J = 18.8 Hz, 1H), 7.68-7.72 (m, 3H), 11.03 (s, 1H), 11.30 (s, 1H) | 9-V |
| A15 | methyl 6-[4-[[5-[[6-(2,2,2-trifluoroethoxy)-3-pyridyl]amino]-1,3,4-oxadiazole-2-carbonyl]amino]phenyl]spiro[2.5]octane-2-carboxylate | LCMS: m/z 546.2 (M$^+$ + 1)<br>$^1$HNMR (400 MHz, DMSO-d6): δ 0.97-1.08 (m, 2H), 1.50-1.60 (m, 3H), 1.70-1.78 (m, 3H), 1.81 (d, J = 12.8 Hz, 1H), 1.93 (t, J = 12.8 Hz, 1H), 2.56-2.61 (m, 1H), 3.42 (q, J = 6.4 Hz, 1H), 3.63 (s, 3H), 4.36 (t, J = 4.8 Hz, 1H), 4.97 (q, J = 9.2 Hz, 2H), 7.08 (d, J = 8.8 Hz, 1H), 7.19 (d, J = 7.6 Hz, 2H), 7.68 (d, J = 7.6 Hz, 2H), 8.03 (d, J = 9.2 Hz, 1H), 8.43 (s, 1H), 10.01 (s, 1H), 11.10 (s, 1H) | 9-V |
| A16 | methyl 6-[4-[[5-(3-chloroanilino)-1,3,4-oxadiazole-2-carbonyl]amino]phenyl]spiro[2.5]octane-2-carboxylate | LCMS: m/z 481.1 (M$^+$ + 1)<br>$^1$HNMR (400 MHz, DMSO-d6): δ 0.94-0.99 (m, 1H), 1.01-1.03 (m, 1H), 1.07-1.13 (m, 2H), 1.49-1.59 (m, 2H), 1.71-1.73 (m, 2H), 1.81-1.92 (m, 1H), 1.91-1.95 (m, 1H), 2.54-2.65 (m, 2H), 3.62 (s, 3H), 7.10 (dd, J = 0.8 Hz, J = 15.2 Hz, 1H), 7.17 (d, J = 8.4 Hz, 2H), 7.40 (t, J = 8.4 Hz, 1H), 7.48 (t, J = 8.4 Hz, 1H), 7.69 (dd, J = 2.0 Hz, J = 8.0 Hz, 2H), 11.02 (s, 1H), 11.25 (s, 1H) | 9-V |
| A17 | ethyl 6-[5-[(5-anilino-1,3,4-oxadiazole-2-carbonyl)amino]-2-pyridyl]-6-azaspiro[2.5]octane-2-carboxylate | LCMS: m/z 463.2 (M$^+$ + 1) | 10-VI |

-continued

| Example No | Structure and IUPAC name | Characterization Data | Intermediate from which prepared |
|---|---|---|---|
| A18 | 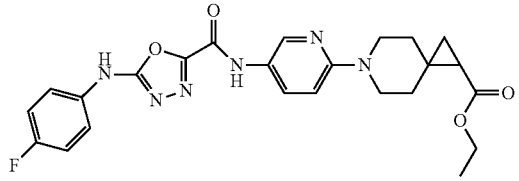 [SMILES: CCOC(=O)C1CC12CCN(c1ccc(NC(=O)c3nnc(Nc4ccc(F)cc4)o3)cn1)CC2]<br>ethyl 6-[5-[[5-(4-fluoroanilino)-1,3,4-oxadiazole-2-carbonyl]amino]-2-pyridyl]-6-azaspiro[2.5]octane-2-carboxylate | LCMS: m/z 481.2 (M⁺ + 1) | 10-VI |
| A19 | <br>ethyl 6-[5-[[5-(3,4-difluoroanilino)-1,3,4-oxadiazole-2-carbonyl]amino]-2-pyridyl]-6-azaspiro[2.5]octane-2-carboxylate | LCMS: m/z 498.2 (M⁺ + 1) | 10-VI |
| A20 | 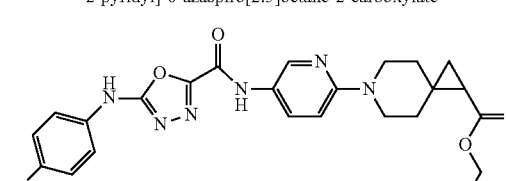<br>ethyl 6-[5-[[5-(4-methylanilino)-1,3,4-oxadiazole-2-carbonyl]amino]-2-pyridyl]-6-azaspiro[2.5]octane-2-carboxylate | LCMS: m/z 477.2 (M⁺ + 1) | 10-VI |
| A21 | 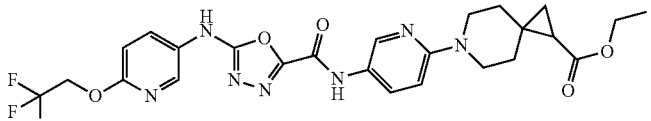<br>ethyl 6-[5-[[5-[[6-(2,2,2-trifluoroethoxy)-3-pyridyl]amino]-1,3,4-oxadiazole-2-carbonyl]amino]-2-pyridyl]-6-azaspiro[2.5]octane-2-carboxylate | LCMS: m/z 562.2 (M⁺ + 1)<br>¹HNMR (400 MHz, DMSO-d6): δ 0.98-1.08 (m, 2H), 1.18 (t, J = 6.8 Hz, 3H), 1.40-1.56 (m, 2H), 1.66 (t, J = 6.8 Hz, 3H), 3.44-3.53 (m, 2H), 3.55-3.68 (m, 2H), 4.07 (q, J = 6.4 Hz, 2H), 4.97 (q, J = 9.2 Hz, 2H), 6.89 (d, J = 9.2 Hz, 1H), 7.08 (d, J = 8.8 Hz, 1H), 7.90 (d, J = 8.4 Hz, 1H), 8.03 (d, J = 8.4 Hz, 1H), 8.45 (d, J = 19.2 Hz, 2H), 10.97 (s, 1H), 11.09 (bs, 1H) | 10-VI |
| A22 | 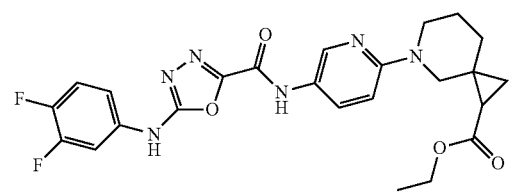 [SMILES: CCOC(=O)C1CC12CCCN(c1ccc(NC(=O)c3nnc(Nc4ccc(F)c(F)c4)o3)cn1)C2]<br>ethyl 7-[5-[[5-(3,4-difluoroanilino)-1,3,4-oxadiazole-2-carbonyl]amino]-2-pyridyl]-7-azaspiro[2.5]octane-2-carboxylate | LCMS: m/z 499.2 (M⁺ + 1) | 11-VI |
| A23 | 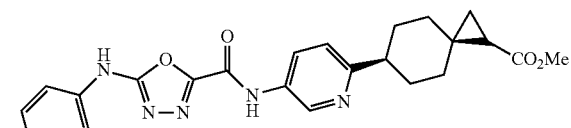<br>Cis-methyl 6-[5-[(5-anilino-1,3,4-oxadiazole-2-carbonyl)amino]-2-pyridyl]spiro[2.5]octane-2-carboxylate [Tentative assignment of isomerism] | LCMS: m/z 448.2 (M⁺ + 1) | 13-II |

| Example No | Structure and IUPAC name | Characterization Data | Intermediate from which prepared |
|---|---|---|---|
| A24 | 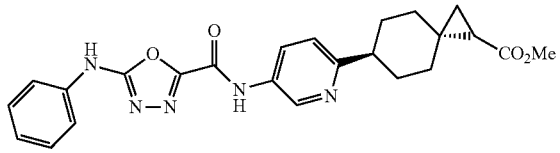<br>Trans-methyl 6-[5-[(5-anilino-1,3,4-oxadiazole-2-carbonyl)amino]-2-pyridyl]spiro[2.5]octane-2-carboxylate [Tentative assignment of isomerism] | LCMS: m/z 448.2 (M$^+$ + 1) | 13-II |
| A25 | 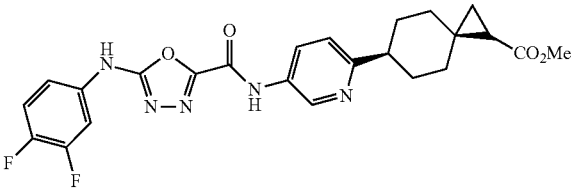<br>Cis-methyl 6-[5-[[5-(3,4-difluoroanilino)-1,3,4-oxadiazole-2-carbonyl]amino]-2-pyridyl]spiro[2.5]octane-2-carboxylate [Tentative assignment of isomerism] | LCMS: m/z 484.2 (M$^+$ + 1) | 13-II |
| A26 | 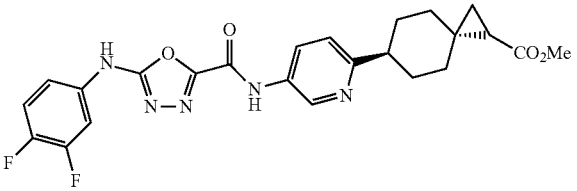<br>Trans-methyl 6-[5-[[5-(3,4-difluoroanilino)-1,3,4-oxadiazole-2-carbonyl]amino]-2-pyridyl]spiro[2.5]octane-2-carboxylate [Tentative assignment of isomerism] | LCMS: m/z 484.2 (M$^+$ + 1) | 13-II |
| A27 | 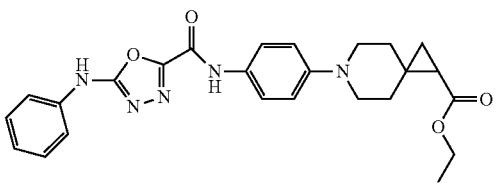 [SMILES: CCOC(=O)C1CC12CCN(c1ccc(NC(=O)c3nnc(Nc4ccccc4)o3)cc1)CC2]<br>ethyl 6-[4-[(5-anilino)-1,3,4-oxadiazole-2-carbonyl]amino]phenyl]-6-azaspiro[2.5]octane-2-carboxylate | LCMS: m/z 462.2 (M$^+$ + 1) | 14-II |
| A28 | 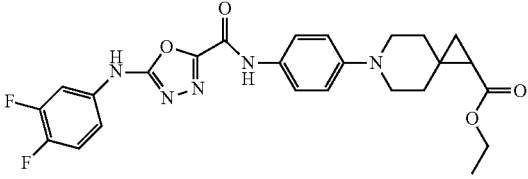 [SMILES: CCOC(=O)C1CC12CCN(c1ccc(NC(=O)c3nnc(Nc4ccc(F)c(F)c4)o3)cc1)CC2]<br>ethyl 6-[4-[[5-(3,4-difluoroanilino)-1,3,4-oxadiazole-2-carbonyl]amino]phenyl]-6-azaspiro[2.5]octane-2-carboxylate | LCMS: m/z 498.2 (M$^+$ + 1) | 14-II |

-continued

| Example No | Structure and IUPAC name | Characterization Data | Intermediate from which prepared |
|---|---|---|---|
| A29 | ethyl 6-[4-[[5-(4-fluoroanilino)-1,3,4-oxadiazole-2-carbonyl]amino]phenyl]-6-azaspiro[2.5]octane-2-carboxylate | LCMS: m/z 480.2 (M⁺ + 1) | 14-II |
| A30 | ethyl 8-[5-[[5-(3,4-difluoroanilino)-1,3,4-oxadiazole-2-carbonyl]amino]-2-pyridyl]spiro[8-azabicyclo[3.2.1]octane-3,2'-cyclopropane]-1'-carboxylate | LCMS: m/z 525.3 (M⁺ + 1)<br>¹HNMR (400 MHz, DMSO-d6): δ 0.88 (d, J = 13.2 Hz, 1H), 1.12 (t, J = 6.4 Hz, 3H), 1.21-1.28 (m, 3H), 1.39 (d, J = 14.0 Hz, 1H), 1.79 (d, J = 12.4 Hz, 1H), 1.90-2.06 (m, 4H), 2.12 (d, J = 11.6 Hz, 1H), 3.91-4.04 (m, 2H), 4.52 (d, J = 18.0 Hz, 2H), 4.53 (s, 1H), 6.76 (d, J = 9.2 Hz, 1H), 7.34 (d, J = 8.4 Hz, 1H), 7.49 (dd, J = 9.2 Hz, J = 19.2 Hz, 1H), 7.67-7.72 (m, 1H), 7.90 (dd, J = 2.4 Hz, J = 8.8 Hz, 1H), 8.47 (d, J = 2.4 Hz, 1H), 10.97 (s, 1H), 11.27 (s, 1H) | 15-V |
| A31 | ethyl 8-[5-[[5-(3,4-difluoroanilino)-1,3,4-oxadiazole-2-carbonyl]amino]-2-pyridyl]spiro[8-azabicyclo[3.2.1]octane-3,3'-cyclobutane]-1'-carboxylate | LCMS: m/z 539.2 (M⁺ + 1)<br>¹HNMR (400 MHz, DMSO-d6): δ 1.15 (t, J = 7.2 Hz, 3H), 1.60-1.82 (m, 4H), 1.84-2.04 (m, 3H), 2.26 (t, J = 9.6 Hz, 1H), 2.67-2.77 (m, 4H), 3.10 (t, J = 8.8 Hz, 1H), 4.01 (q, J = 7.2 Hz, 2H), 4.38 (s, 1H), 4.46 (s, 1H), 6.69 (dd, J = 4.4 Hz, J = 9.2 Hz, 1H), 7.27 (s, 1H), 7.41-7.52 (m, 1H), 7.67-7.72 (m, 1H), 7.79-7.91 (s, 1H), 8.41 (s, 1H), 1018 (s, 1H), 10.93 (s, 1H) | 16-IV |
| A32 | ethyl 2-[7-[5-[[5-(3,4-difluoroanilino)-1,3,4-oxadiazole-2-carbonyl]amino]-2-pyridyl]-7-azaspiro[3.5]nonan-2-yl]acetate | LCMS: m/z 527.1 (M⁺ + 1) | 7-VIII |
| A33 | ethyl 2-[7-[5-[[5-(2-fluoroanilino)-1,3,4-oxadiazole-2-carbonyl]amino]-2-pyridyl]-7-azaspiro[3.5]nonan-2-yl]acetate | LCMS: m/z 509.2 (M⁺ + 1) | 7-VIII |
| A34 | ethyl 7-[5-[(5-anilino-1,3,4-oxadiazole-2-carbonyl)amino]-2-pyridyl]-7-azaspiro[3.5]nonane-2-carboxylate | LCMS: m/z 477.0 (M⁺ + 1)<br>¹HNMR (400 MHz, DMSO-D6): 1.16-1.23 (t, J = 8 Hz, 3H), 1.49-1.52 (m, 2H), 1.60-1.61 (m, 2H), 1.92-1.95 (m, 2H), 1.97-2.05 (m, 2H), 3.12-3.27 (m, 1H), 3.40-3.44 (m, 2H), 3.45-3.46 (m, 2H), 4.04-4.09 (q, J = 8 Hz, 16 Hz, 2H), 6.84-6.87 (d. J = 12 Hz, 1H), | 8-III |

| Example No | Structure and IUPAC name | Characterization Data | Intermediate from which prepared |
|---|---|---|---|
| | | 7.04-7.07 (m, 1H), 7.37-7.41 m, 2H), 7.59-7.61 (m, 2H), 7.88 (d, J = 8 Hz, 1H), 8.45 (s, 1H), 10.91 (s, 1H) | |
| A35 | 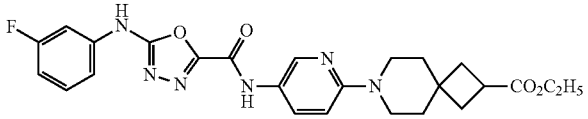 [SMILES: CCOC(=O)C1CC2(CCN(c3ccc(NC(=O)c4nnc(Nc5cccc(F)c5)o4)cn3)CC2)C1]<br>ethyl 7-[5-[[5-(3-fluoroanilino)-1,3,4-oxadiazole-2-carbonyl]amino]-2-pyridyl]-7-azaspiro[3.5]nonane-2-carboxylate | LCMS: m/z 495 (M⁺ + 1)<br>¹HNMR (400 MHz, DMSO-D6): δ 1.14 (t, J = 4 Hz, 3H), 1.56-1.58 (m, 2H), 1.66-1.69 (m, 2H), 1.98-2.03 (m, 2H), 2.09-2.14 (m, 2H), 3.19-3.23 (m, 1H), 3.42-3.46 (m, 2H), 3.50-3.53 (m, 2H), 4.10-4.15<br>(q, J = 4 Hz, 12 Hz, 2H), 6.92-6.97 (m, 2H), 7.40-7.47 (m, 1H), 7.49-7.50 (m. 1H), 7.58-7.61 (m, 1H), 7.94-7.97 (m, 1H), 8.52 (s, 1H), 11.05 (s, 1H), 11.35 (s, 1H) | 8-III |
| A36 | 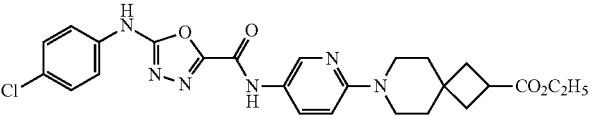 [SMILES: CCOC(=O)C1CC2(CCN(c3ccc(NC(=O)c4nnc(Nc5ccc(Cl)cc5)o4)cn3)CC2)C1]<br>ethyl 7-[5-[[5-(4-chloroanilino)-1,3,4-oxadiazole-2-carbonyl]amino]-2-pyridyl]-7-azaspiro[3.5]nonane-2-carboxylate | LCMS: m/z 511 (M⁺ + 1), 512 (M⁺ + 2)<br>¹HNMR (400 MHz, DMSO-D6): δ 1.18 (t, J = 8 Hz, 3H), 1.51 (m, 2H), 1.61 (m, 2H), 1.92-1.96 (m, 2H), 2.03-2.08 (m, 2H), 3.12-3.14 (m, 1H), 3.38 (m, 2H), 3.45 (m, 2H),<br>4.04-4.09 (q, J = 8 Hz, 16 Hz, 2H), 6.84-6.87 (d, 1H), 7.45-7.47 (m, 2H), 7.61-7.63 (m, 2H), 7.87-7.89 (d, 1H), 8.45 (s, 1H), 10.95 (s, 1H), 11.17 (s, 1H) | 8-III |
| A37 | 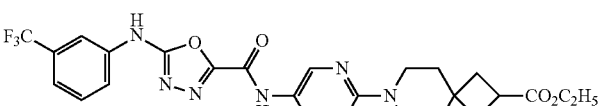<br>ethyl 7-[5-[[5-[3-(trifluoromethyl)anilino]-1,3,4-oxadiazole-2-carbonyl]amino]-2-pyridyl]-7-azaspiro[3.5]nonane-2-carboxylate | LCMS: m/z 545 (M⁺ + 1)<br>¹HNMR (400 MHz, DMSO-D6): δ1.18 (t, J = 8 Hz, 3H), 1.49-1.52 (m, 2H), 1.60-1.63 (m, 2H), 1.92-1.97 (m, 2H), 2.03-2.08 (m, 2H), 3.10-3.19 (m, 1H), 3.34-3.40 (m, 2H), 3.44-3.45 (m, 2H), 4.06 (q, J =<br>8 Hz, 16 Hz, 2H), 6.86 (d, J = 12 Hz, 1H), 7.40-7.44 (m, 1H), 7.62-7.66 (m, 1H), 7.84-7.88 (m, 2H), 8.00 (m, 1H), 8.45- 8.46 (m, 1H), 10.96 (s, 1H), 11.39 (s, 1H) | 8-III |
| A38 | 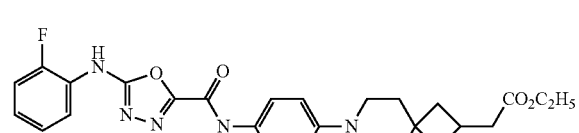<br>ethyl 2-[7-[4-[[5-(2-fluoroanilino)-1,3,4-oxadiazole-2-carbonyl]amino]phenyl]-7-azaspiro[3.5]nonan-2-yl]acetate | LCMS: m/z 508.1 (M⁺ + 1) | 25-IV |
| A39 | 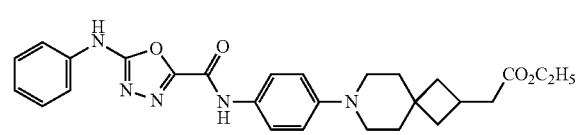 [SMILES: CCOC(=O)CC1CC2(CCN(c3ccc(NC(=O)c4nnc(Nc5ccccc5)o4)cc3)CC2)C1]<br>ethyl 2-[7-[4-[(5-anilino-1,3,4-oxadiazole-2-carbonyl)amino]phenyl]-7-azaspiro[3.5]nonan-2-yl]acetate | LCMS: m/z 490.1 (M⁺ + 1) | 25-IV |

-continued

| Example No | Structure and IUPAC name | Characterization Data | Intermediate from which prepared |
|---|---|---|---|
| A40 | 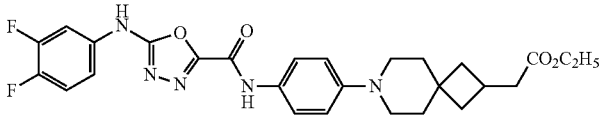 [SMILES: CCOC(=O)CC1CC2(CCN(c3ccc(NC(=O)c4nnc(Nc5ccc(F)c(F)c5)o4)cc3)CC2)C1]<br>ethyl 2-[7-(4-[[5-(3,4-difluoroanilino)-1,3,4-oxadiazole-2-carbonyl]amino]phenyl]-7-azaspiro[3.5]nonan-2-yl]acetate | LCMS: m/z 526.2 (M$^+$ + 1) | 25-IV |
| A41 | 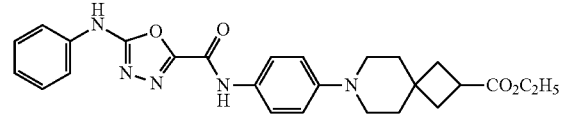<br>ethyl 7-[4-[(5-anilino-1,3,4-oxadiazole-2-carbonyl)amino]phenyl]-7-azaspiro[3.5]nonane-2-carboxylate | LCMS: m/z 476.0 (M$^+$ + 1)<br>$^1$HNMR (400 MHz, DMSO-D6): 1.41 (t, J = 4 Hz, 3H), 1.55-1.60 (m, 2H), 1.65-1.70 (m, 2H), 1.88-1.93 (m, 2H), 2.04-2.48 (m, 2H), 2.98-3.00 (m, 2H), 3.05-3.07 (m, 2H), 3.08-3.10 (m, 1H), 4.03 (q, 2H), 6.89 (d, J = 8 Hz, 1H), 7.02-7.04 (m, 1H), 7.34-7.36 (m, 3H), 7.56-7.60 (m, 4H), 10.79 (s, 1H), 10.94 (s, 1H) | 24-X |
| A42 | 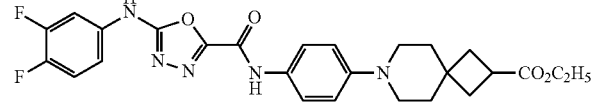<br>ethyl 7-[4-[[5-(3,4-difluoroanilino)-1,3,4-oxadiazole-2-carbonyl]amino]phenyl]-7-azaspiro[3.5]nonane-2-carboxylate | LCMS: m/z 512.0 (M$^+$ + 1) | 24-X |
| A43 | 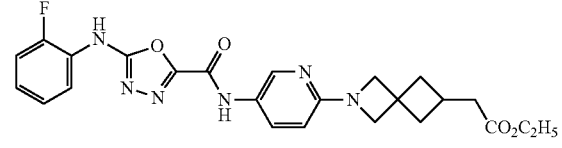 [SMILES: CCOC(=O)CC1CC2(C1)CN(c1ccc(NC(=O)c3nnc(Nc4ccccc4F)o3)cn1)C2]<br>ethyl 2-[6-[5-[[5-(2-fluoroanilino)-1,3,4-oxadiazole-2-carbonyl]amino]-2-pyridyl]-6-azaspiro[3.3]heptan-2-yl]acetate | LCMS: m/z 481.1 (M$^+$ + 1) | 22-IX |
| A44 | 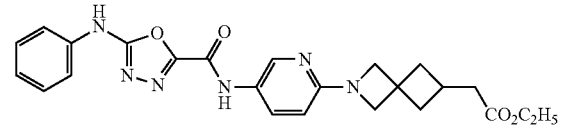 [SMILES: CCOC(=O)CC1CC2(C1)CN(c1ccc(NC(=O)c3nnc(Nc4ccccc4)o3)cn1)C2]<br>ethyl 2-[6-[5-[(5-anilino-1,3,4-oxadiazole-2-carbonyl)amino]-2-pyridyl]-6-azaspiro[3.3]heptan-2-yl]acetate | LCMS: m/z 463.2 (M$^+$ + 1) | 22-IX |
| A45 | 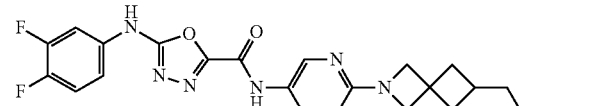<br>ethyl 2-[6-[5-[[5-(3,4-difluoroanilino)-1,3,4-oxadiazole-2-carbonyl]amino]-2-pyridyl]-6-azaspiro[3.3]heptan-2-yl]acetate | LCMS: m/z 499.1 (M$^+$ + 1) | 22-IX |

Example B1

2-[9-[5-[[5-(3,4-difluoroanilino)-1,3,4-oxadiazole-2-carbonyl]amino]-2-pyridyl]spiro[5.5]undecan-3-yl] acetic acid

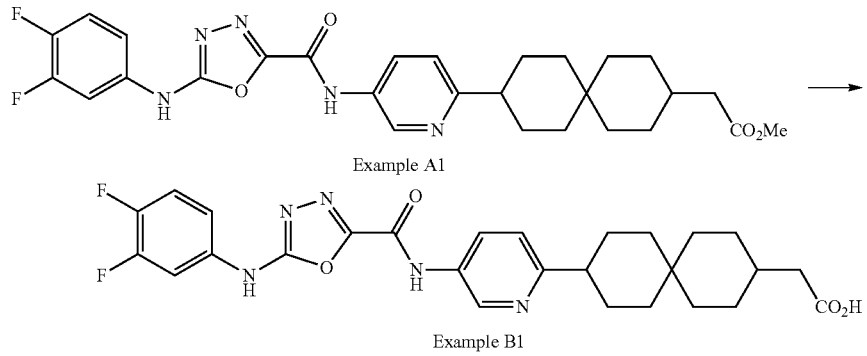

Example A1

Example B1

To a solution of methyl 2-[9-[5-[[5-(3,4-difluoroanilino)-1,3,4-oxadiazole-2-carbonyl]amino]-2-pyridyl]spiro[5.5]undecan-3-yl]acetate (Example A1) (0.17 g, 0.31 mmol) in THF:MeOH:H₂O (3:2:1) (10 ml), LiOH.H₂O (64 mg, 1.57 mmol) was added and resulting reaction mixture was stirred at room temperature for 6 hrs. Reaction mixture was evaporated and salt was neutralized to pH ~7. Resulting solid was collected by filtration and dried under vacuum and recrystallized in hot methanol to furnish title compound (Example B1) (0.076 g, 40%)

$^1$H NMR (400 MHz, DMSO-d6): δ 0.88-1.37 (m, 9H), 1.45-1.70 (m, 5H), 1.98-2.05 (m, 4H), 2.48-2.58 (m, 2H), 7.12-7.16 (m, 1H), 7.22-7.28 (m, 2H), 7.61 (ddd, J=9.6, 7.6, 2 Hz, 1H), 8.05 (dd, J=8.4, 2.4 Hz, 1H), 8.80 (d, J=2.8 Hz, 1H), 11.21 (s, 1H), 11.28 (s, 1H)

LCMS: m/z 526.1 (M$^+$+1)

Following compounds were prepared from their corresponding starting materials (given in parentheses) using the same sequence of procedures as used for preparation of Example B1 from Example A1:

| Example No | Structure and IUPAC name | Characterization data | Starting Compounds from which prepared |
|---|---|---|---|
| B2 | 2-[9-[5-[(5-anilino-1,3,4-oxadiazole-2-carbonyl) amino]-2-pyridyl] spiro [5.5] undecan-3-yl] acetic acid | LCMS: m/z 490.2 (M$^+$ + 1)<br>$^1$HNMR (400 MHz, DMSO-d6):<br>δ 0.91-1.03 (m, 2H), 1.07-1.16 (m, 1H), 1.20-1.26 (m, 2H), 1.29-1.32 (m, 1H), 1.34-1.40 (m, 2H), 1.47-1.50 (m, 2H), 1.61-1.67 (m, 4H), 1.69-1.76 (m, 1H), 2.01-2.04 (m, 2H), 2.08-2.12 (m, 2H), 2.55-2.67 (m, 1H), 7.06 (t, J = 7.2 Hz, 1H), 7.28 (d, J = 8.8 Hz, 1H), 7.39 (t, J = 8.0 Hz, 2H), 7.60 (d, J = 8.4 Hz, 2H), 8.08 (dd, J = 2.8 Hz, J = 8.4 Hz, 1H), 8.83 (d, J = 2.4 Hz, 1H), 11.15 (bs, 2H) | A2 |
| B3 | 2-[9-[4-[[5-(3,4-difluoroanilino)-1,3,4-oxadiazole-2-carbonyl] amino] phenyl] spiro [5.5] undecan-3-yl] acetic acid | LCMS: m/z 525.2 (M$^+$ + 1)<br>$^1$HNMR (400 MHz, DMSO-d6):<br>δ 0.86-1.01 (m, 2H), 1.05-1.20 (m, 1H), 1.21-1.40 (m, 6H), 1.44-1.62 (m, 6H), 2.01-2.08 (m, 2H), 2.11-2.13 (m, 1H), 2.39-2.55 (m, 2H). 7.23 (d, J = 8.8 Hz, 2H), 7.34 (d, J = 9.2 Hz, 1H), 7.44-7.52 (m, 1H), 7.67-7.72 (m, 3H), 10.98 (s, 1H) | A3 |

-continued

| Example No | Structure and IUPAC name | Characterization data | Starting Compounds from which prepared |
|---|---|---|---|
| B4 | 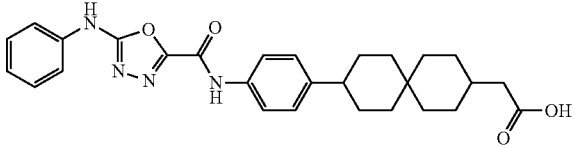 [SMILES: O=C(O)CC1CCC2(CC1)CCC(c1ccc(NC(=O)c3nnc(Nc4ccccc4)o3)cc1)CC2]<br>2-[9-[4-[(5-anilino-1,3,4-oxadiazole-2-carbonyl) amino] phenyl] spiro [5.5] undecan-3-yl] acetic acid | LCMS: m/z 489.2 (M$^+$ + 1)<br>$^1$HNMR (400 MHz, DMSO-d6) : δ 0.91-1.05 (m, 2H), 1.08-1.17 (m, 1H), 1.21-1.40 (m, 6H), 1.47-1.63 (m, 6H), 2.01-2.08 (m, 2H), 2.11-2.12 (m, 1H), 2.39-2.55 (m, 2H), 7.04-7.07 (m, 1H), 7.23 (d, J = 8.4 Hz, 2H), 7.39 (t, J = 8.0 Hz, 2H), 7.60 (d, J = 8.0 Hz, 2H), 7.68 (d, J = 8.4 Hz, 2H), 10.96 (bs, 2H), 11.97 (s, 1H) | A4 |
| B5 | 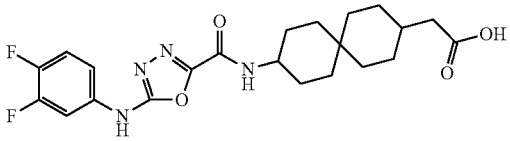 [SMILES: O=C(O)CC1CCC2(CC1)CCC(NC(=O)c1nnc(Nc3ccc(F)c(F)c3)o1)CC2]<br>2-[9-[[5-(3, 4-difluoroanilino)-1,3,4-oxadiazole-2-carbonyl] amino] spiro [5.5] undecan-3-yl] acetic acid | LCMS: m/z 499.2 (M$^+$ + 1)<br>$^1$HNMR (400 MHz, DMSO): δ 0.82-0.98 (m, 2H), 0.99-1.13 (m, 2H), 1.13-1.37 (m, 5H), 1.44-1.69 (m, 6H), 1.93 (t, J = 12 Hz, 2H), 2.07 (d, J = 6.8 Hz, 2H), 3.63-3.74 (m, 1H), 7.20-7.26 (m, 1H), 7.36 (dd, J = 8.8, 19.3 Hz, 1H), 7.64 (ddd, J = 2.4, 7.2, 13.2 Hz, 1H), 0.92 (d, J = 8.8 Hz, 1H), 9.53 (bs, 1H), 9.63 (bs, 1H) | A5 |
| B6 | 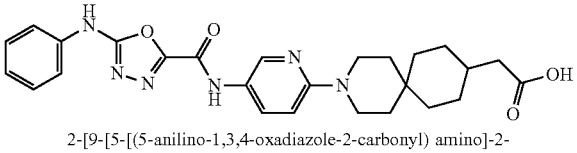<br>2-[9-[5-[(5-anilino-1,3,4-oxadiazole-2-carbonyl) amino]-2-pyridyl]-9-azaspiro [5.5] undecan-3-yl] acetic acid. | LCMS: m/z 490.7 (M$^+$ + 1)<br>$^1$HNMR (400 MHz, DMSO): δ 1.04-1.19 (m, 4H), 1.31 (t, J = 5.6 Hz, 2H), 1.45-1.53 (m, 4H), 1.63 (d, J = 10.8 Hz, 3H), 2.10 (d, J = 7.2 Hz, 2H), 3.42 (t, J = 10.4 Hz, 4H), 6.79 (d, J = 9.6 Hz, 1H), 7.02 (app.t, J = 7.6 Hz, 1H), 7.36 (t, J = 7.6 Hz, 2H), 7.57 (d, J = 8.0 Hz, 2H), 7.85 (dd, J = 9.6, J = 2.8 Hz, 1H), 8.42 (d, J = 2.4 Hz, 1H), 10.89 (s, 1H), 10.92-11.02 (bs, 1H), 11.88-12.20 (bs, 1H) | A6 |
| B7 | 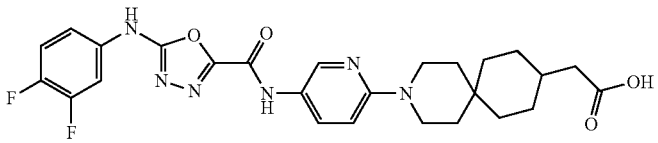 [SMILES: O=C(O)CC1CCC2(CC1)CCN(c1ccc(NC(=O)c3nnc(Nc4ccc(F)c(F)c4)o3)cn1)CC2]<br>2-[9-[5-[[5-(3,4-difluoroanilino)-1,3,4-oxadiazole-2-carbonyl] amino]-2-pyridyl]-9-azaspiro [5.5] undecan-3-yl] acetic acid | LCMS: m/z 526.6 (M$^+$ + 1)<br>$^1$HNMR (400 MHz, DMSO-d6): δ 1.05-1.32 (m, 4H), 1.34 (t, J = 5.2 Hz, 2H), 1.47-1.56 (m, 5H), 1.66 (d, J = 10.4 Hz, 2H), 2.13 (d, J = 6.8 Hz, 2H), 3.45 (t, J = 10 Hz, 4H), 6.82 (d, J = 9.2 Hz, 1H), 7.32-7.38 (m, 1H), 7.48 (dd, J = 19.6, 9.2 Hz, 1H), 7.69 (ddd, J = 2.8, 7.2, 12.8 Hz, 1H), 7.88 (dd, J = 9.2, 2.4 Hz, 1H), 8.45 (d, J = 2.8 Hz, 1H), 10.95 (s, 1H), 11.52 (bs, 1H), 11.95 (bs, 1H) | A7 |
| B8 | 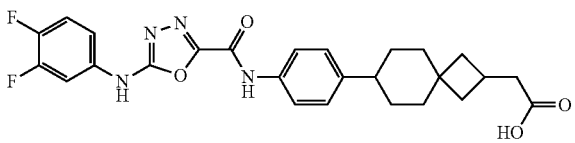 [SMILES: O=C(O)CC1CC2(CCC(c3ccc(NC(=O)c4nnc(Nc5ccc(F)c(F)c5)o4)cc3)CC2)C1]<br>2-[7-[4-[[5-(3,4-difluoroanilino)-1,3,4-oxadiazole-2-carbonyl] amino] phenyl] spiro [3.5] nonan-2-yl] acetic acid | LCMS: m/z 497.2 (M$^+$ + 1)<br>$^1$HNMR (400 MHz, DMSO-d6): δ 1.31-1.48 (m, 4H), 1.55-1.68 (m, 4H), 1.81-1.89 (m, 2H), 2.04-2.09 (m, 1H), 2.30-2.34 (m, 3H), 2.39-2.44 (m, 2H), 7.14-7.27 (m, 1H), 7.19 (d, J = 8.4 Hz, 2H) merged signals, 7.34 (d, J = 5.2 Hz, 1H), 7.50 (dd, J = 9.2, J = 19.2 Hz, 1H), 7.68 (d, J = 8.4 Hz, 2H), 7.70-7.73 (m, 1H), 11.01 (s, 1H), 11.29 (s, 1H), 11.97 (bs, 1H) | A8 |

-continued

| Example No | Structure and IUPAC name | Characterization data | Starting Compounds from which prepared |
|---|---|---|---|
| B9 | 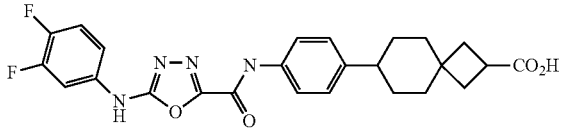 [SMILES: O=C(Nc1ccc(C2CCC3(CC2)CC(C(=O)O)C3)cc1)c1nnc(Nc2ccc(F)c(F)c2)o1]<br>7-[4-[[5-(3,4-difluoroanilino)-1,3,4-oxadiazole-2-carbonyl] amino] phenyl] spiro [3.5] nonane-2-carboxylic acid | LCMS: m/z 483.2 ($M^+ + 1$)<br>$^1$HNMR (400 MHz, DMSO-d6): δ 1.39-1.49 (m, 4H), 1.60-1.68 (m, 3H), 1.82-1.93 (m, 4H), 2.05-2.11 (m, 1H), 2.35-2.45 (m, 1H), 2.95-3.03 (m, 1H), 7.19 (d, J = 8.0 Hz, 2H), 7.34 (s, 1H), 7.47 (dd, J = 9.6 Hz, J = 18.4 Hz, 1H), 7.68 (d, J = 8.0 Hz, 3H), 10.99 (s, 1H), 11.61-11.74 (bs, 2H) | A9 |
| B10 | 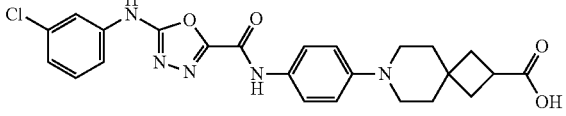<br>7-[4-[[5-(3-chloroanilino)-1,3,4-oxadiazole-2-carbonyl] amino] phenyl] spiro [3.5] nonane-2-carboxylic acid | LCMS: m/z 481.1 ($M^+ + 1$), 482.1, ($M^+ + 2$)<br>$^1$HNMR (400 MHz, DMSO-d6): δ 1.37-1.46 (m, 4H), 1.58-1.75 (m, 4H), 1.87-1.97 (m, 4H), 2.06-2.11 (m, 1H), 2.35-2.45 (m, 1H), 2.97-3.01 (m, 1H), 7.07 (d, J = 6.8 Hz, 1H), 7.19 (d, J = 8.4 Hz, 2H), 7.39 (t, J = 7.6 Hz, 1H), 7.48 (d, J = 8.4 Hz, 1H), 7.68 (d, J = 8.4 Hz, 2H), 7.72 (s, 1H), 10.82-11.02 (bs, 2H) | A10 |
| B11 | 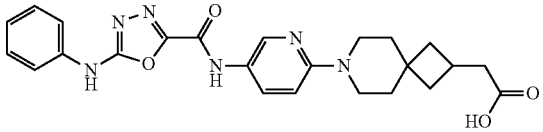 [SMILES: O=C(O)CC1CC2(CCN(c3ccc(NC(=O)c4nnc(Nc5ccccc5)o4)cn3)CC2)C1]<br>2-[7-[5-[(5-anilino-1,3,4-oxadiazole-2-carbonyl) amino]-2-pyridyl]-7-azaspiro [3.5] nonan-2-yl] acetic acid | LCMS: m/z 463.2 ($M^+ + 1$)<br>$^1$HNMR (400 MHz, DMSO-d6): δ 1.42-1.48 (m, 4H), 1.58 (t, J = 5.4 Hz, 2H), 1.97 (t, J = 12.0 Hz, 2H), 2.31-2.32 (m, 1H), 2.33 (d, J = 7.6 Hz, 2H), 3.53 (t, J = 4.7 Hz, 2H), 3.44 (t, J = 5.1 Hz, 2H), 6.83 (d, J = 9.0 Hz, 1H), 7.04 (t, J = 7.6 Hz, 1H), 7.37 (t, J = 7.6 Hz, 2H), 7.58 (d, J = 7.8 Hz, 2H), 7.86 (dd, J = 2.7 Hz, J = 9.3 Hz, 1H), 8.43 (d, J = 2.5 Hz, 1H), 10.89 (s, 1H), 10.95 (bs, 1H), 11.94 (bs, 1H) | A11 |
| B12 | 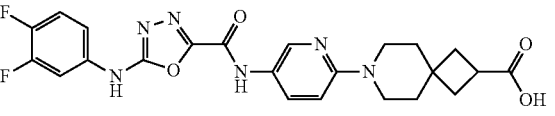 [SMILES: O=C(Nc1ccc(N2CCC3(CC2)CC(C(=O)O)C3)nc1)c1nnc(Nc2ccc(F)c(F)c2)o1]<br>7-[5-[[5-(3,4-difluoroanilino)-1,3,4-oxadiazole-2-carbonyl] amino]-2-pyridyl]-7-azaspiro [3.5] nonane-2-carboxylic acid | LCMS: m/z 485.2 ($M^+ + 1$)<br>$^1$HNMR (400 MHz, DMSO-d6): δ 1.50 (t, J = 5.4 Hz, 2H), 1.60 (t, J = 5.4 Hz, 2H), 1.96 (t, J = 12.3 Hz, 2H), 2.03 (t, J = 12.2 Hz, 2H), 3.01-3.10 (m, 1H), 3.39-3.41 (m, 2H), 3.45 (t, J = 5.1 Hz, 2H), 6.86 (d, J = 9.3 Hz, 1H), 7.30-7.38 (m, 1H), 7.49 (dd, J = 9.0 Hz, J = 19.5 Hz, 1H), 7.67-7.73 (m, 1H), 7.88 (dd, J = 2.4 Hz, J = 9.0 Hz, 1H), 8.45 (d, J = 2.7 Hz, 1H), 10.96 (s, 1H) | A12 |
| B13 | 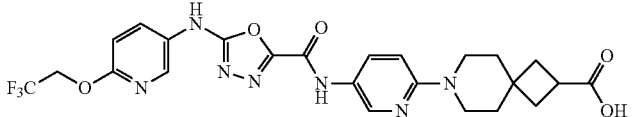 [SMILES: O=C(Nc1ccc(N2CCC3(CC2)CC(C(=O)O)C3)nc1)c1nnc(Nc2ccc(OCC(F)(F)F)nc2)o1]<br>7-[5-[[5-[[6-(2,2,2-trifluoroethoxy)-3-pyridyl]amino]-1,3,4-oxadiazole-2-carbonyl]amino]-2-pyridyl]-7-azaspiro[3.5]nonane-2-carboxylic acid | LCMS: m/z 547.5 ($M^+ + 1$)<br>$^1$HNMR (400 MHz, DMSO-d6): δ 1.46-1.50 (m, 2H), 1.54-1.58 (m, 2H), 1.88-1.94 (m, 4H), 2.88-2.92 (m, 1H), 3.35-3.41 (m, 4H), 4.90 (q, J = 9.2 Hz, 2H), 6.82 (d, J = 9.2 Hz, 1H), 6.91 (d, J = 8.8 Hz, 1H), 7.86 (dd, J = 2.4 Hz, J = 8.8 Hz, 1H), 7.98 (dd, J = 2.4 Hz, 8.8 Hz, 1H), 8.28 (d, J = 2.0 Hz, 1H), 8.43 (d, J = 2.4 Hz, 1H), 10.66 (bs, 1H) | A13 |

| Example No | Structure and IUPAC name | Characterization data | Starting Compounds from which prepared |
|---|---|---|---|
| B14 | 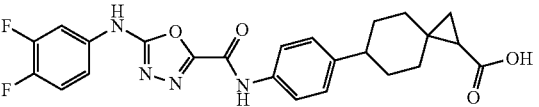 [SMILES: O=C(Nc1ccc(C2CCC3(CC2)CC3C(=O)O)cc1)c1nnc(Nc2ccc(F)c(F)c2)o1]<br>6-[4-[[5-(3,4-difluoroanilino)-1,3,4-oxadiazole-2-carbonyl] amino] phenyl] spiro [2.5] octane-2-carboxylic acid | LCMS: m/z 469.2 (M⁺ + 1)<br>¹HNMR (400 MHz, DMSO-d6): δ 0.84-0.91 (m, 1H), 0.96-098 (m, 1H), 1.03 (d, J = 12.8 Hz, 1H), 1.18-1.31 (m, 1H), 1.47 (t, J = 6.0 Hz, 1H), 1.52-1.66 (m, 1H), 1.77 (dd, J = 29.2, 12.4 Hz, 4H), 1.93 (t, J = 12.8 Hz, 1H), 2.56-2.64 (m, 1H), 7.19 (d, J = 8.0 Hz, 2H), 7.28-7.39 (m, 1H), 7.47 (dd, J = 8.8 Hz, J = 18.4 Hz, 1H), 7.64-7.68 (m, 3H), 11.0 (s, 1H), 11.2 (bs, 1H), 12.24 (bs, 1H) | A14 |
| B15 | 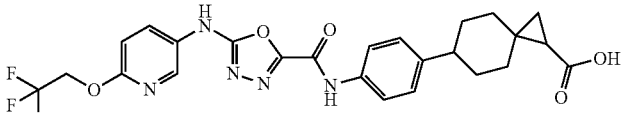<br>6-[4-[[5-[[6-(2,2,-trifluoroethoxy)-3-pyridyl] amino]-1,3,4-oxadiazole-2-carbonyl] amino] phenyl] spiro [2.5] octane-2-carboxylic acid | LCMS: m/z 532.3 (M⁺ + 1)<br>¹HNMR (400 MHz, DMSO-d6): δ 0.82-0.91 (m, 1H), 0.93-0.98 (m, 1H), 1.01 (d, J = 12.0 Hz, 1H), 1.14-1.29 (m, 1H), 1.45 (t, J = 6.0 Hz, 1H), 1.55 (q, J = 12.4 Hz, 1H), 1.74 (dd, J = 28.0, 12.8 Hz, 4H), 1.85-1.97 (m, 1H), 2.45-2.62 (m, 1H), 4.94 (q, J = 9.2 Hz, 2H), 7.05 (d, J = 8.8 Hz, 1H), 7.17 (d, J = 8.8 Hz, 2H), 7.68 (d, J = 8.8 Hz, 2H), 8.0 (dd, J = 2.8, J = 8.8 Hz, 1H), 8.40 (d, J = 2.4 Hz, 1H), 10.96 (s, 1H), 11.40-12.01 (bs, 2H) | A15 |
| B16 | 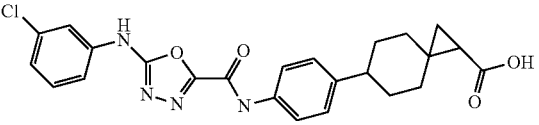 [SMILES: O=C(Nc1ccc(C2CCC3(CC2)CC3C(=O)O)cc1)c1nnc(Nc2cccc(Cl)c2)o1]<br>6-[4-[[5-(3-chloroanilino)-1,3,4-oxadiazole-2-carbonyl] amino] phenyl] spiro [2.5] octane-2-carboxylic acid | LCMS: m/z 467.1 (M⁺ + 1), 468.1 (M⁺ + 2)<br>¹HNMR (400 MHz, DMSO-d6): δ 0.84-0.93 (m, 1H), 0.96-0.98 (m, 1H), 1.03 (d, J = 11.6 Hz, 1H), 1.16-1.30 (m, 2H), 1.47 (t, J = 6.4 Hz, 1H), 1.52-1.64 (m, 1H), 1.66-1.85 (m, 3H), 1.93 (t, J = 11.6 Hz, 1H), 2.54-2.65 (m, 1H), 7.12 (d, J = 8.0 Hz, 1H), 7.20 (d, J = 7.6 Hz, 2H), 7.42 (app.t, J = 7.6 Hz, 1H), 7.50 (app.t, J = 7.6 Hz, 1H), 7.71 (d, J = 8.0 Hz, 2H), 7.73 (s, 1H), 11.02 (s, 1H), 11.25 (bs, 1H), 12.05 (bs, 1H) | A16 |
| B17 | 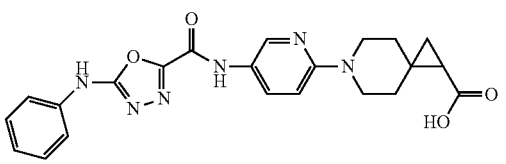 [SMILES: O=C(Nc1ccc(N2CCC3(CC2)CC3C(=O)O)nc1)c1nnc(Nc2ccccc2)o1]<br>6-[5-[(5-anilino-1,3,4-oxadiazole-2-carbonyl) amino]-2-pyridyl]-6-azaspiro [2.5] octane-2-carboxylic acid | LCMS: m/z 435.2 (M⁺ + 1)<br>¹HNMR (400 MHz, DMSO-d6): δ 0.94-0.99 (m, 2H), 1.44-1.49 (m, 2H), 1.54-1.57 (m, 1H), 1.67-1.71 (m, 2H), 3.35-3.63 (m, 4H), 6.89 (d, J = 9.3 Hz, 1H), 7.06 (t, J = 7.2 Hz, 1H), 7.39 (t, J = 8.3 Hz, 2H), 7.60 (d, J = 8.3 Hz, 2H), 7.91 (dd, J = 2.7 Hz, J = 9.1 Hz, 1H), 8.48 (d, J = 2.5 Hz, 1H), 11.00 (bs, 1H) | A17 |
| B18 | 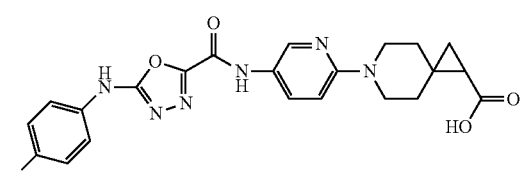<br>6-[5-[[5-(4-fluoroanilino)-1,3,4-oxadiazole-2-carbonyl] amino]-2-pyridyl]-6-azaspiro [2.5] octane-2-carboxylic acid | LCMS: m/z 452.9 (M⁺ + 1)<br>¹HNMR (400 MHz, DMSO-d6): δ 0.93-1.01 (m, 2H), 1.40-1.54 (m, 2H), 1.56 (dd, J = 7.6, 5.6 Hz, 1H), 1.62-1.76 (m, 2H), 3.54-3.67 (m, 4H), 6.89 (d, J = 9.2 Hz, 1H), 7.25 (t, J = 8.4 Hz, 2H), 7.58-7.65 (m, 2H), 7.90 (dd, J = 9.2, J = 2.4 Hz, 1H), 8.47 (d, J = 2 Hz, 1H), 10.96 (s, 1H), 11.06 (bs, 1H) | A18 |

-continued

| Example No | Structure and IUPAC name | Characterization data | Starting Compounds from which prepared |
|---|---|---|---|
| B19 | 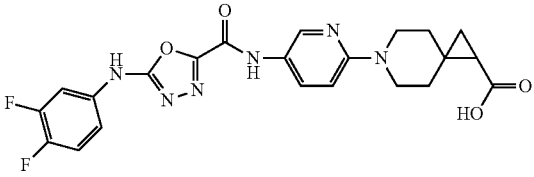 [SMILES: O=C(Nc1ccc(N2CCC3(CC2)CC3C(=O)O)nc1)c1nnc(Nc2ccc(F)c(F)c2)o1]<br>6-[5-[[5-(3,4-difluoroanilino)-1,3,4-oxadiazole-2-carbonyl] amino]-2-pyridyl]-6-azaspiro [2.5] octane-2-carboxylic acid | LCMS: m/z 471.1 (M$^+$ + 1)<br>$^1$HNMR (400 MHz, DMSO-d6): δ 0.94-1.01 (m, 2H), 1.39-1.54 (m, 2H), 1.56 (dd, J = 5.2, 7.6 Hz, 1H), 1.62-1.76 (m, 2H), 3.36-3.43 (m, 1H), 3.47-3.68 (m, 3H), 6.89 (d, J = 9.2 Hz, 1H), 7.31-7.38 (m, 1H), 7.49 (dd, J = 19.2, 9.2 Hz, 1H), 7.70 (ddd, J = 12.8, J = 7.2, J = 2.8 Hz, 1H), 7.90 (dd, J = 9.2, J = 2.8 Hz, 1H), 8.79 (d, J = 2.8 Hz, 1H), 10.98 (s, 1H), 11.29 (bs, 1H), 12.09 (bs, 1H) | A19 |
| B20 | 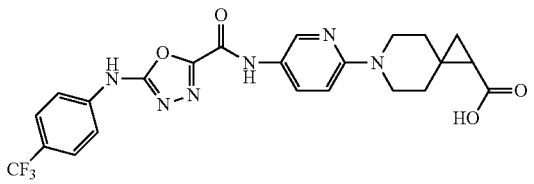<br>6-[5-[[5-(4-methylanilino)-1,3,4-oxadiazole-2-carbonyl] amino]-2-pyridyl]-6-azaspiro [2.5] octane-2-carboxylic acid | LCMS: m/z 503.2 (M$^+$ + 1)<br>$^1$HNMR (400 MHz, DMSO-d6): δ 0.93-1.01 (m, 2H), 1.41-1.51 (m, 2H), 1.52-1.58 (m, 1H), 1.66-1.73 (m, 2H), 3.43-3.68 (m, 4H), 6.89 (d, J = 9.2 Hz, 1H), 7.74 (d, J = 9.2 Hz, 2H), 7.79 (d, J = 8.8 Hz, 2H), 7.91 (dd, J = 9.2, J = 2.4 Hz, 1H), 8.48 (d, J = 2.8 Hz, 1H), 10.95 (bs, 2H) | A20 |
| B21 | 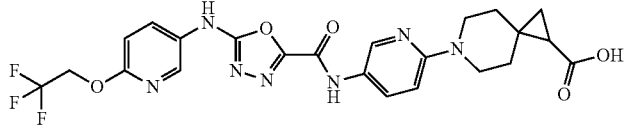 [SMILES: O=C(Nc1ccc(N2CCC3(CC2)CC3C(=O)O)nc1)c1nnc(Nc2ccc(OCC(F)(F)F)nc2)o1]<br>6-[5-[[5-[[6-(2,2,2-trifluoroethoxy)-3-pyridyl] amino]-1,3,4-oxadiazole-2-carbonyl] amino]-2-pyridyl]-6-azaspiro [2.5] octane-2-carboxylic acid | LCMS: m/z 534.1 (M$^+$ + 1)<br>$^1$HNMR (400 MHz, DMSO-d6): δ 0.91-1.03 (m, 2H), 1.38-1.51 (m, 3H), 1.61-1.76 (m, 2H), 3.46-3.69 (m, 4H), 4.96 (q, J = 8.8 Hz, 2H), 6.88 (d, J = 8.8 Hz, 1H), 7.07 (d, J = 8.4 Hz, 1H), 7.90 (d, J = 8.4 Hz, 1H), 8.03 (d, J = 8.0 Hz, 2H), 8.45 (d, J = 23.6 Hz, 1H), 10.94 (s, 1H), 11.2 (bs, 1H), 12.2 (bs, 1H) | A21 |
| B22 | 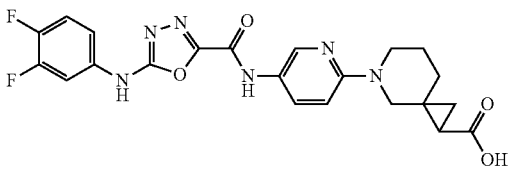 [SMILES: O=C(Nc1ccc(N2CCCC3(CC3C(=O)O)C2)nc1)c1nnc(Nc2ccc(F)c(F)c2)o1]<br>7-[5-[[5-(3,4-difluoroanilino)-1,3,4-oxadiazole-2-carbonyl] amino]-2-pyridyl]-7-azaspiro [2.5] octane-2-carboxylic acid | LCMS: m/z 471.1 (M$^+$ + 1)<br>$^1$HNMR (400 MHz, DMSO-d6): δ 0.87-0.91 (m, 1H), 0.97-1.01 (m, 1H), 1.46-1.77 (m ,4H), 3.30-3.65 (m, 5H), 6.85 (d, J = 9.6 Hz, 1H), 7.29-7.35 (m, 1H), 7.40-7.50 (m, 1H), 7.69-7.72 (m, 1H), 7.85-7.90 (m, 1H), 8.42-8.44 (m, 1H), 10.96 (bs, 3H) | A22 |
| B23 | Cis-6-[5-[(5-anilino-1,3,4-oxadiazole-2-carbonyl) amino]-2-pyridyl] spiro [2.5] octane-2-carboxylic acid [Tentative assignment of isomerism] | LCMS: m/z 434.2 (M$^+$ + 1)<br>$^1$HNMR (400 MHz, DMSO-d6): δ 0.83-0.86 (m, 1H), 0.89-0.91 (m, 1H), 1.04-1.06 (m, 1H), 1.50-1.55 (m, 1H), 1.56-1.75 (m, 4H), 1.81-1.95 (m, 3H), 2.71-2.77 (m, 1H), 7.04 (t, J = 7.6 Hz, 1H), 7.24 (d, J = 8.4 Hz, 1H), 7.37 (t, J = 7.6 Hz, 2H), 7.59 (d, J = 8.0 Hz, 2H), 8.08 (dd, J = 2.4 Hz, J = 8.4 Hz, 1H), 8.83 (d, J = 2.8 Hz, 1H). 11.15 (s, 2H) | A23 |
| B24 | Trans-6-[5-[(5-anilino-1,3,4-oxadiazole-2-carbonyl) amino]-2-pyridyl] spiro [2.5] octane-2-carboxylic acid [Tentative assignment of isomerism] | LCMS: m/z 434.2 (M$^+$ + 1)<br>$^1$HNMR (400 MHz, DMSO-d6): δ 0.84-0.87 (m, 1H), 0.92-0.94 (m, 1H), 1.00-1.03 (m, 1H), 1.33-1.38 (m, 1H), 1.41-1.44 (m, 1H), 1.65-1.68 (m, 2H), 1.71-1.73 (m, 1H), 1.78-1.83 (m, 2H), 1.87-1.93 (m, 1H), 2.64-2.74 (m, 1H), 7.04 (t, J = 7.6 Hz, 1H), 7.24 (d, J = 8.4 Hz, 1H), 7.37 (t, J = 7.6 Hz, | A24 |

| Example No | Structure and IUPAC name | Characterization data | Starting Compounds from which prepared |
|---|---|---|---|
| | | 2H), 7.59 (d, J = 8.0 Hz, 2H), 8.08 (dd, J = 2.4 Hz, J = 8.4 Hz, 1H), 8.83 (d, J = 2.8 Hz, 1H). 11.15 (s, 2H) | |
| B25 | Cis-6-[5-[[5-(3,4-difluoroanilino)-1,3,4-oxadiazole-2-carbonyl] amino]-2-pyridyl] spiro [2.5] octane-2-carboxylic acid [Tentative assignment of isomerism] | LCMS: m/z 470.1 (M$^+$ + 1) $^1$HNMR (400 MHz, DMSO-d6): δ 0.84-0.87 (m, 1H), 0.89-0.90 (m, 1H), 1.02-1.07 (m, 1H), 1.48-1.52 (m, 1H), 1.56-1.75 (m, 4H), 1.81-1.95 (m, 3H), 2.71-2.77 (m, 1H), 7.30 (d, J = 8.4 Hz, 1H), 7.34 (d, J = 9.2 Hz, 1H), 7.48 (dd, J = 9.2 Hz, J = 19.6 1H), 7.67-7.72 (m, 1H), 8.08 (dd, J = 2.4 Hz, J = 8.4 Hz, 1H), 8.85 (d, J = 2.4 Hz, 1H). 11.28 (s, 2H) | A25 |
| B26 | Trans-6-[5-[[5-(3,4-difluoroanilino)-1,3,4-oxadiazole-2-carbonyl] amino]-2-pyridyl] spiro [2.5] octane-2-carboxylic acid [Tentative assignment of isomerism] | LCMS: m/z 470.1 (M$^+$ + 1) $^1$HNMR (400 MHz, DMSO-d6): δ 0.87-0.90 (m, 1H), 0.94-0.97 (m, 1H), 1.03-1.06 (m, 1H), 1.35-1.39 (m, 1H), 1.45-1.47 (m, 1H), 1.66-1.76 (m, 3H), 1.80-1.83 (m, 2H), 1.86-1.95 (m, 1H) 2.70-2.76 (m, 1H), 7.26 (d, J = 8.8 Hz, 1H), 7.34 (d, J = 9.2 Hz, 1H), 7.48 (dd, J = 8.8 Hz, J = 19.6 Hz, 1H), 7.67-7.72 (m, 1H), 8.08 (dd, J = 2.4 Hz, J = 8.8 Hz, 1H), 8.85 (d, J = 2.4 Hz, 1H). 11.25 (s, 2H), 12.01 (bs, 1H) | A26 |
| B27 | 6-[4-[(5-anilino-1,3,4-oxadiazole-2-carbonyl) amino] phenyl]-6-azaspiro [2.5] octane-2-carboxylic acid | LCMS: m/z 433.9 (M$^+$ + 1) $^1$HNMR (400 MHz, CD$_3$OD): δ 1.09-1.18 (m, 1H), 1.21 (t, J = 4.8 Hz, 1H), 1.28 (s, 1H), 1.73-1.81 (m, 2H), 2.08-2.18 (m, 2H), 3.34 (s, 1H), 3.50-3.67 (m, 3H), 7.09 (app.t, J = 7.2 Hz, 1H), 7.37 (t, J = 7.6 Hz, 2H), 7.41-7.54 (m, 2H), 7.57 (d, J = 7.6 Hz, 2H), 7.81-7.91 (m, 2H) | A27 |
| B28 | 6-[4-[[5-(3,4-difluoroanilino)-1,3,4-oxadiazole-2-carbonyl] amino] phenyl]-6-azaspiro [2.5] octane-2-carboxylic acid | LCMS: m/z 470.2 (M$^+$ + 1) $^1$HNMR (400 MHz, DMSO-d6): δ 0.92-1.01 (m, 2H), 1.45-1.63 (m, 3H), 1.71-1.84 (m, 2H), 2.96-3.07 (m, 1H), 3.08-3.29 (m, 3H), 6.95 (d, J = 8.8 Hz, 2H), 7.31-7.37 (m, 1H), 7.49 (dd, J = 19.2, 9.2 Hz, 1H), 7.64 (d, J = 9.2 Hz, 2H), 7.70 (ddd, J = 12.8, J = 6.8, J = 2.4 Hz, 1H), 10.89 (s, 1H), 11.26 (s, 1H), 12.09 (bs, 1H) | A28 |
| B29 | 6-[4-[[5-(4-fluoroanilino)-1,3,4-oxadiazole-2-carbonyl] amino] phenyl]-6-azaspiro [2.5] octane-2-carboxylic acid | LCMS: m/z 451.9 (M$^+$ + 1) $^1$HNMR (400 MHz, CD$_3$OD): δ 1.20 (dd, J = 9.6, J = 4.4 Hz, 1H), 1.26 (t, J = 5.2 Hz, 1H), 1.84 (dd, J = 8.4, J = 5.6 Hz, 1H), 2.24-2.33 (m, 2H), 3.34 (s, 3H) 3.73-3.82 (m, 3H), 7.12 (t, J = 8.8 Hz, 2H), 7.46-7.61 (m, 2H), 7.74 (d, J = 9.2 Hz, 2H), 8.02 (d, J = 8.8 Hz, 2H) | A29 |

| Example No | Structure and IUPAC name | Characterization data | Starting Compounds from which prepared |
|---|---|---|---|
| B30 | 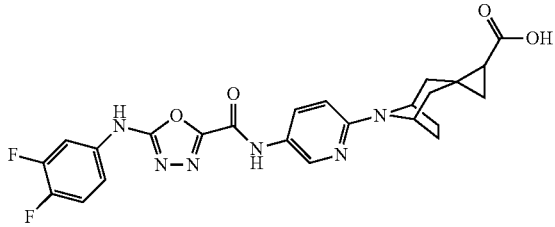 [SMILES: O=C(Nc1ccc(N2C3CCC2CC2(C3)CC2C(=O)O)nc1)c1nnc(Nc2ccc(F)c(F)c2)o1]<br>8-[5-[[5-(3,4-difluoroanilino)-1,3,4-oxadiazole-2-carbonyl]amino]-2-pyridyl] spiro [8-azabicyclo [3.2.1] octane-3,2'-cyclopropane]-1'-carboxylic acid | LCMS: m/z 497.1 (M$^+$ + 1)<br>$^1$HNMR (400 MHz, DMSO-d6): δ 0.85 (d, J = 14.0 Hz, 1H), 1.13-1.21 (m, 3H), 1.39 (d, J = 12.8 Hz, 1H), 1.81 (d, J = 12.0 Hz, 1H), 1.90-2.05 (m, 4H), 2.12 (d, J = 11.6 Hz, 1H), 4.49 (s, 1H), 4.53 (s, 1H), 6.76 (d, J = 9.2 Hz, 1H), 7.34 (d, J = 9.2 Hz, 1H), 7.47 (dd, J = 9.2 Hz, J = 19.2 Hz, 1H), 7.68-7.72 (m, 1H), 7.90 (dd, J = 2.4 Hz, J = 9.2 Hz, 1H), 8.48 (d, J = 2.8 Hz, 1H), 10.95 (s, 1H) | A30 |
| B31 | 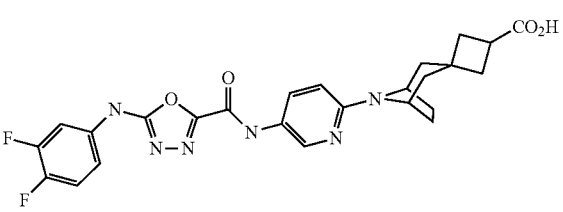 [SMILES: O=C(Nc1ccc(N2C3CCC2CC2(CC(C(=O)O)C2)C3)nc1)c1nnc(Nc2ccc(F)c(F)c2)o1]<br>8-[5-[[5-(3,4-difluoroanilino)-1,3,4-oxadiazole-2-carbonyl] amino]-2-pyridyl] spiro [8-azabicyclo [3.2.1] octane-3,3'-cyclobutane]-1'-carboxylic acid | LCMS: m/z 511.1 (M$^+$ + 1)<br>$^1$HNMR (400 MHz, D$_2$O): δ 1.63-1.69 (m, 4H), 1.74-1.76 (m, 2H), 1.87-1.95 (m, 5H), 2.23-2.26 (m, 1H), 2.93-2.97 (m, 1H), 4.36 (s, 1H), 4.45 (s, 1H), 6.69 (d, J = 8.4 Hz, 1H), 7.30 (s, 1H), 7.43 (dd, J = 10.0 Hz, J = 18.8 Hz, 1H), 7.66-7.71 (m, 1H), 7.84 (d, J = 7.2 Hz, 1H), 8.41 (s, 1H) | A31 |
| B32 | 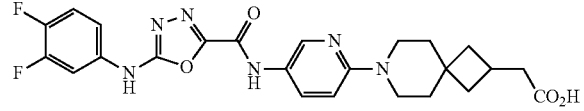<br>2-[7-[5-[[5-(3,4-difluoroanilino)-1,3,4-oxadiazole-2-carbonyl]amino]-2-pyridyl]-7-azaspiro[3.5]nonan-2-yl]acetic acid | LCMS: m/z 499.4 (M$^+$ + 1)<br>$^1$HNMR (400 MHz, DMSO-d6): δ 1.43-1.48 (m, 4H), 1.59 ( br s, 2H), 2.00 (t, J = 8.0 Hz, 2H), 2.34 (d, J = 8.0 Hz, 3H), 3.31 (br s, 2H), 3.45 (br s, 2H), 6.84 (d, J = 8.8 Hz, 1H), 7.29 (br s, 1H ), 7.41 (m, 1H), 7.65-7.70 (m, 1H), 7.88 (d, J = 8.0 Hz, 1H), 8.45 (s, 1H) 10.82 (s, 1H), 10.61 (s, 1H) | A32 |
| B33 | 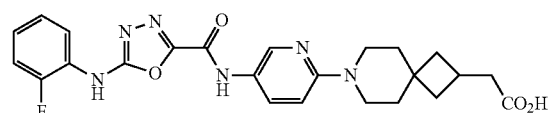<br>2-[7-[5-[[5-(2-fluoroanilino)-1,3,4-oxadiazole-2-carbonyl]amino]-2-pyridyl]-7-azaspiro[3.5]nonan-2-yl]acetic acid | LCMS: m/z 481.2 (M$^+$ + 1)<br>1HNMR (400 MHz, DMSO-d6): δ 1.41-1.46 (m, 4H), 1.57 (br s, 2H), 1.97 (t, J = 8.0 Hz, 2H), 2.32 (d, J = 8.0 Hz, 3H), 3.31 (br s, 2H), 3.43 (br s, 2H), 6.82 (d, J = 8.0 Hz, 1H), 7.12-7.15 (m, 1H), 7.22-7.31 (m, 2H), 7.84 (d, J = 8.0 Hz 1H), 8.03 (t, J = 8.0 Hz, 1H), 8.41 (s, 1H) 10.76 (br.s, 1H), 10.90 (s, 1H) 11.95 (s, 1H) | A33 |
| B34 | 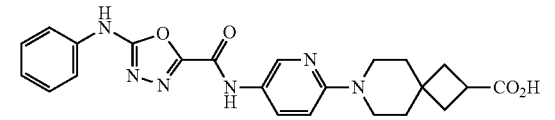<br>7-[5-[(5-anilino-1,3,4-oxadiazole-2-carbonyl)amino]-2-pyridyl]-7-azaspiro[3.5]nonane-2-carboxylic acid | LCMS: m/z 449.1 (M$^+$ + 1)<br>$^1$HNMR (400 MHz, DMSO-D6): 1.49 (br.s, 2H), 1.55 (br.s, 2H), 1.83-1.92 (m, 4H), 2.67-2.74 (m, 1H), 3.36-3.43 (m, 4H), 6.83 (d, J = 9.2 Hz, 1H), 6.96 (t, J = 6.8 Hz, 1H), 7.32 (t, J = 8 Hz, 2H), 7.57 (d, J = 8 Hz, 2H), 7.88 (d, J = 8.8 Hz, 1H), 8.45 (s, 1H) | A34 |
| B35 | 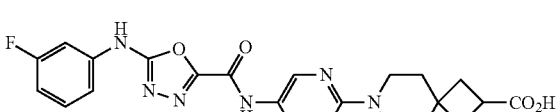<br>7-[5-[[5-(3-fluoroanilino)-1,3,4-oxadiazole-2-carbonyl]amino]-2-pyridyl]-7-azaspiro[3.5]nonane-2-carboxylic acid | LCMS: m/z 467.1 (M$^+$ + 1)<br>$^1$HNMR (400 MHz, DMSO-D6): δ 1.51 (br.s, 2H), 1.59 (br. s, 2H), 1.92-2.01 (m, 4H), 2.67 (br.s, 1H), 2.94-2.98 (m, 2H), 3.44 (br.s, 2H), 6.75 (br.s, 1H), 6.84 (d, J = 8 Hz, 1H), 7.26-7.34 (m, 2H), 7.49 (d, J = 12 Hz, 1H), 7.87-7.90 (m, 1H), 8.45 (d, J = 2.8 Hz, 1H), 10.79 (s, 1H) | A35 |

| Example No | Structure and IUPAC name | Characterization data | Starting Compounds from which prepared |
|---|---|---|---|
| B36 | 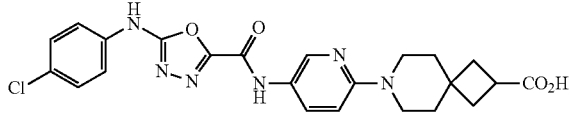 [SMILES: O=C(Nc1ccc(N2CCC3(CC2)CC(C(=O)O)C3)nc1)c1nnc(Nc2ccc(Cl)cc2)o1]<br>7-[5-[[5-(4-chloroanilino)-1,3,4-oxadiazole-2-carbonyl]amino]-2-pyridyl]-7-azaspiro[3.5]nonane-2-carboxylic acid | LCMS: m/z 483.1 ($M^+$ + 1), 484.1 ($M^+$ + 2)<br>$^1$HNMR (400 MHz, DMSO-D6): 1.50 (br.s, 2H), 1.58 (br.s, 2H), 1.88-1.97 (m, 3H), 2.88-2.92 (m, 1H), 3.37 (br.s, 3H), 3.42 (br. s, 2H), 6.83 (d, J = 8.8 Hz, 1H), 7.35 (d, J = 8.4 Hz, 2H), 7.57 (d, J = 8.8 Hz, 2H), 7.88 (dd, J = 2.4 Hz, 6.4 Hz, 1H), 8.45 (d, J = 2 Hz, 1H) | A36 |
| B37 | 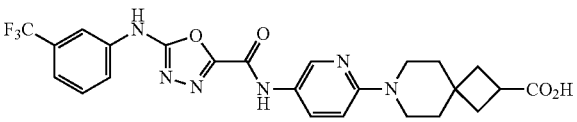 [SMILES: O=C(Nc1ccc(N2CCC3(CC2)CC(C(=O)O)C3)nc1)c1nnc(Nc2cccc(C(F)(F)F)c2)o1]<br>7-[5-[[5-[3-(trifluoromethyl)anilino]-1,3,4-oxadiazole-2-carbonyl]amino]-2-pyridyl]-7-azaspiro[3.5]nonane-2-carboxylic acid | LCMS: m/z 517.1 ($M^+$ + 1)<br>$^1$HNMR (400 MHz, DMSO-D6): δ 1.50 (m, 2H), 1.59 (m, 2H), 1.89-2.01 (m, 4H), 2.95-3.00 (m, 1H), 3.36-3.37 (m, 2H), 3.44 (m, 2H), 6.54 (s, 1H), 6.85 (d, J = 8 Hz, 1H), 7.17 (d, J = 4 Hz, 1H), 7.45 (t, J = 8 Hz, 1H), 7.71 (d, J = 8 Hz, 1H), 7.87-7.91 (m, 2H), 8.45 (s, 1H), 10.72 (s, 1H) | A37 |
| B38 | 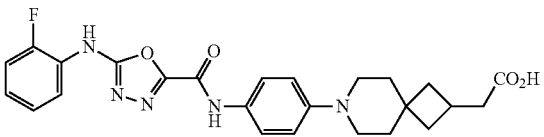 [SMILES: O=C(O)CC1CC2(CCN(c3ccc(NC(=O)c4nnc(Nc5ccccc5F)o4)cc3)CC2)C1]<br>2-[7-[4-[[5-(2-fluoroanilino)-1,3,4-oxadiazole-2-carbonyl]amino]phenyl]-7-azaspiro[3.5]nonan-2-yl]acetic acid | LCMS: m/z 480.4 ($M^+$ + 1)<br>$^1$HNMR (400 MHz, DMSO-d6): δ 1.46 (t, J = 8.0 Hz, 2H), 1.56 (br s, 2H), 1.67 (br s, 2H), 1.97 (t, J = 8.0 Hz, 2H), 2.34 (d, J = 8.0 Hz, 3H), 2.99 (br s, 2H), 3.08 (br s, 2H), 6.91 (d, J = 8.0 Hz, 2H), 7.10-7.16 (m, 1H), 7.25-7.33 (m, 2H), 7.60 (d, J = 12.0 Hz, 2H), 8.06 (t, J =8.0 Hz, 1H), 10.77 (s, 1H), 10.83 (s, 1H), 11.97 (s, 1H) | A38 |
| B39 | 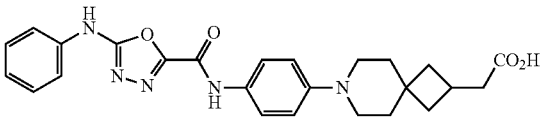 [SMILES: O=C(O)CC1CC2(CCN(c3ccc(NC(=O)c4nnc(Nc5ccccc5)o4)cc3)CC2)C1]<br>2-[7-[4-[(5-anilino-1,3,4-oxadiazole-2-carbonyl)amino]phenyl]-7-azaspiro[3.5]nonan-2-yl]acetic acid | LCMS: m/z 462.1 ($M^+$ + 1)<br>$^1$HNMR (400 MHz, DMSO-d6): δ 1.46 (t, J = 8.0 Hz, 2H), 1.56 (br s, 2H), 1.67 (br s, 2H), 1.98 (t, J = 8.0 Hz, 2H), 2.34 (d, J = 8.0 Hz, 3H), 2.99 (br s, 2H), 3.08 (br s, 2H), 6.91 (d, J = 8.0 Hz, 2H), 7.05 (t, J = 8.0 Hz, 1H), 7.40 (t, J = 8.0 Hz, 2H), 7.60 (m, 4H), 10.83 (s, 1H) 10.98 (s, 1H), 11.98 (s, 1H) | A39 |
| B40 | 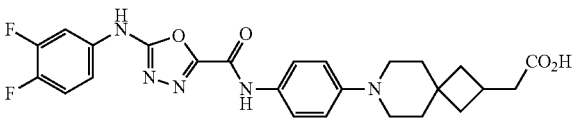<br>2-[7-[4-[[5-(3,4-difluoroanilino)-1,3,4-oxadiazole-2-carbonyl]amino]phenyl]-7-azaspiro[3.5]nonan-2-yl]acetic acid | LCMS: m/z 498.2 ($M^+$ + 1)<br>$^1$HNMR (400 MHz, DMSO-d6): δ 1.45 (t, J = 8.0 Hz, 2H), 1.56 (br.s, 2H), 1.67 (br. s, 2H), 1.97 (t, J = 8.0 Hz, 2H), 2.33 (d, J = 8.0 Hz, 3H), 2.99 (br s, 2H), 3.08 (br s, 2H), 6.91 (d, J = 8.0 Hz, 2H), 7.31 (br.s, 1H), 7.42-7.48 (m, 1H), 7.61 (d, J = 8.0 Hz, 2H), 7.68-7.71 (m, 1H), 10.82 (s, 1H) 11.60 (s, 2H) | A40 |
| B41 | 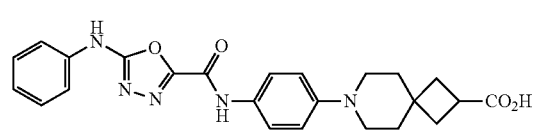<br>7-[4-[(5-anilino-1,3,4-oxadiazole-2-carbonyl)amino]phenyl]-7-azaspiro[3.5]nonane-2-carboxylic acid | LCMS: m/z 448.1 ($M^+$ + 1)<br>$^1$HNMR (400 MHz, DMSO-D6): δ 1.65-1.74 (m, 4H), 1.95-2.04 (m, 4H), 3.48-3.10 (m, 5H), 7.06 (br.s, 4H), 7.39 (br.s, 1H), 7.68-7.59 (m, 4H), 10.99 (m, 1H), 12.01 (br. s, 1H) | A41 |

| Example No | Structure and IUPAC name | Characterization data | Starting Compounds from which prepared |
|---|---|---|---|
| B42 | 7-[4-[[5-(3,4-difluoroanilino)-1,3,4-oxadiazole-2-carbonyl]amino]phenyl]-7-azaspiro[3.5]nonane-2-carboxylic acid | LCMS: m/z 484.1 (M$^+$ + 1) $^1$HNMR (400 MHz, DMSO-D6): δ 1.64 (br.s, 2H), 1.73 (br.s, 2H), 1.98-2.05 (m, 4H), 3.07-3.13 (m, 5H), 6.98 (d, J = 8 Hz, 2H), 7.35 (m, 1H), 7.49 (m, 1H), 7.66-7.73 (m, 3H), 10.82 (s, 1H) | A42 |
| B43 | 2-[6-[5-[[5-(2-fluoroanilino)-1,3,4-oxadiazole-2-carbonyl]amino]-2-pyridyl]-6-azaspiro[3.3]heptan-2-yl]acetic acid | LCMS: m/z 453.1 (M$^+$ + 1) $^1$HNMR (400 MHz, DMSO-d6): δ 1.91 (t, J = 10.4, 2H), 2.30-2.32 (m, 5H), 3.81 (s, 2H), 3.93 (s, 2H), 6.38 (d, J = 12.0 Hz, 1H), 7.05 (br s, 1H), 7.18-7.21 (m, 2H), 7.85-7.88 (m, 1H), 8.06 (t, J = 8.4 Hz, 1H), 8.40 (s, 1H) 10.81 (s, 1H). | A43 |
| B44 | 2-[6-[5-[(5-anilino-1,3,4-oxadiazole-2-carbonyl)amino]-2-pyridyl]-6-azaspiro[3.3]heptan-2-yl]acetic acid | LCMS: m/z 435.1 (M$^+$ + 1) $^1$HNMR (400 MHz, DMSO-d6): δ 1.89 (t, J = 10.4 Hz, 2H), 2.31-2.33 (m, 5H), 3.81 (s, 2H), 3.95 (s, 2H), 6.37 (d, J = 12.0 Hz, 1H), 7.05 (t, J = 6.8 Hz, 1H), 7.39 (t, J = 7.2 Hz, 2H), 7.61 (d, J = 12.0 Hz 2H), 7.88 (d, J = 8.0 Hz, 1H), 8.40 (s, 1H) 10.93 (s, 1H), 11.01 (s, 1H) 12.02 (s, 1H) | A44 |
| B45 | 2-[6-[5-[[5-(3,4-difluoroanilino)-1,3,4-oxadiazole-2-carbonyl]amino]-2-pyridyl]-6-azaspiro[3.3]heptan-2-yl]acetic acid | LCMS: m/z 471.1 (M$^+$ + 1) $^1$HNMR (400 MHz, DMSO-d6): δ 1.89 (t, J = 10.8 Hz, 2H), 2.32 (s, 5H), 3.8 (s, 2H), 3.9 (s, 2H), 6.37 (d, J = 12.0 Hz, 1H), 7.32 (br s, 1H), 7.45-7.52 (dd, J = 9.6 Hz, 9.2 Hz, 1H), 7.67-7.71 (m, 1H), 7.86-7.88 (m, 1H), 8.40 (s, 1H) 10.93 (s, 1H), 12.00 (s, 1H) | A45 |

Example C1

5-(3,4-difluoroanilino)-N-[6-[2-(pyrrolidine-1-carbonyl)-7-azaspiro[3.5]nonan-7-yl]-3-pyridyl]-1,3,4-oxadiazole-2-carboxamide

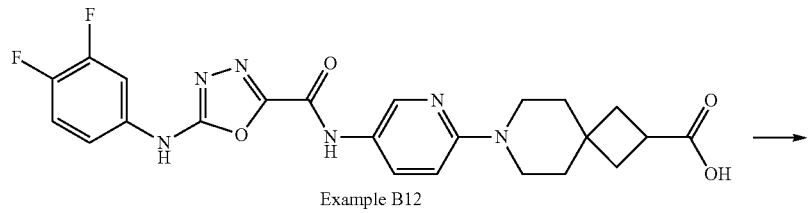

Example B12

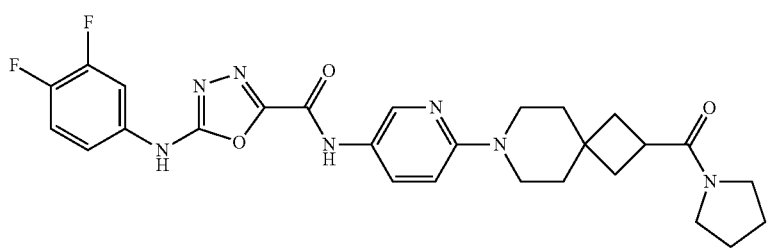

Example C1

To a stirred solution of 7-[5-[[5-(3,4-difluoroanilino)-1,3,4-oxadiazole-2-carbonyl]amino]-2-pyridyl]-7-azaspiro[3.5]nonane-2-carboxylic acid Example B12 (0.05 g, 0.103 mmol, 1.0 equiv.) in N,N dimethyl formamide (1 mL, 10 mL/mmol) was added pyrrolidine (7.3 mg, 0.103 mmol, 1.0 equiv.), HATU (0.039 g, 0.103 mmol, 1.0 equiv.) followed by N,N-diisopropylethyl amine (0.025 g, 0.206 mmol, 2.0 equiv.) and stirred at room temperature for 16 h. The reaction was monitored by TLC. After completion of the reaction, reaction mixture was poured into ice-water (10 mL) and extracted with ethyl acetate (3×20 mL). Organic layer was washed with water (20 mL) followed by brine (20 mL) and dried over anhydrous sodium sulfate. Solvent was removed under reduced pressure to afford crude product which was purified by preparative HPLC or by triturating with ethyl acetate to provide pure product Example C1 (32.1 mg, 58%).

$^1$H NMR (400 MHz, DMSO-d6): δ 1.46 (t, J=5.4 Hz, 2H), 1.61 (t, J=5.4 Hz, 2H), 1.70-1.76 (m, 2H), 1.78-1.99 (m, 6H), 3.16-3.30 (m, 5H), 3.36 (t, J=5.4 Hz, 2H), 3.45 (t, J=5.4 Hz, 2H), 6.83 (d, J=9.1 Hz, 1H), 7.30-7.33 (m, 1H), 7.47 (q, J=9.1 Hz, 1H), 7.64-7.70 (m, 1H), 7.86 (dd, J=9.3 & 2.7 Hz, 1H), 8.43 (d, J=2.7 Hz, 1H), 10.94 (s, 1H), 11.25 (bs, 1H)

MS (EI): m/z 538.3 (M$^+$+1)

Following compounds were prepared from Example B12 using similar procedure as used for the preparation of Example C1 from B12:

| Example No | Structure and IUPAC Name | Characterization Data |
|---|---|---|
| C2 | 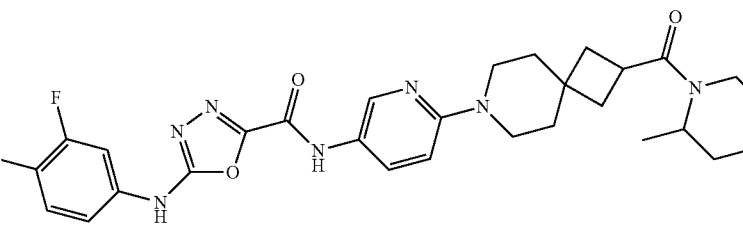<br>5-(3,4-difluoroanilino)-N-[6-[2-(2-methylpiperidine-1-carbonyl)-7-azaspiro[3.5]nonan-7-yl]-3-pyridyl]-1,3,4-oxadiazole-2-carboxamide | LCMS: m/z 566.3 (M$^+$ + 1)<br>$^1$HNMR (400 MHz, DMSO-d6): δ 1.02 (d, J = 7.2 Hz, 2H), 1.12 (d, J = 6.8 Hz, 2H), 1.40-1.54 (m, 4H), 1.56-1.66 (m, 3H), 1.82-2.02 (m, 4H), 2.55-2.67 (m, 1H), 2.94-2.99 (m, 1H), 3.22-3.27 (m, 1H), 3.32-3.37 (m, 2H), 3.43-3.47 (m, 2H), 3.96-4.01 (m, 1H), 4.22-4.27 (m, 1H), 4.64-4.68 (m, 1H), 6.83 (d, J = 9.2 Hz, 1H), 7.32 (d, J = 9.2 Hz, 1H), 7.47 (dd, J = 9.2 Hz, J = 19.6 Hz, 1H), 7.65-7.70 (m, 1H), 7.68 (dd, J = 2.8 Hz, J = 9.2 Hz, 1H), 8.43 (d, J = 2.4 Hz, 1H), 10.93 (s, 1H), 11.24 (s, 1H) |
| C3 | 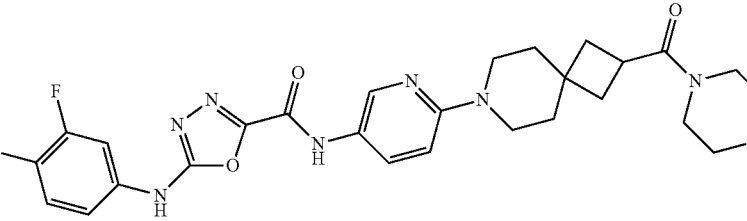<br>5-(3,4-difluoroanilino)-N-[6-[2-(morpholine-4-carbonyl)-7-azaspiro[3.5]nonan-7-yl]-3-pyridyl]-1,3,4-oxadiazole-2-carboxamide | LCMS: m/z 554.3 (M$^+$ + 1)<br>$^1$HNMR (400 MHz, DMSO-d6): δ 1.44 (t, J = 5.6 Hz, 2H), 1.61 (t, J = 5.2 Hz, 2H), 1.91-2.08 (m, 4H), 3.25-3.30 (m, 1H), 3.34-3.36 (m, 3H), 3.41-3.46 (m, 5H), 3.48-3.54 (m, 4H), 6.84 (d, J = 9.2 Hz, 1H), 7.32 (d, J = 9.6 Hz, 1H), 7.47 (dd, J = 9.6 Hz, J = 19.2 Hz, 1H), 7.65-7.70 (m, 1H), 7.86 (dd, J = 2.4 Hz, J = 9.2 Hz, 1H), 8.43 (d, J = 2.4 Hz, 1H), 10.94 (s, 1H), 11.23 (s, 1H) |
| C4 | 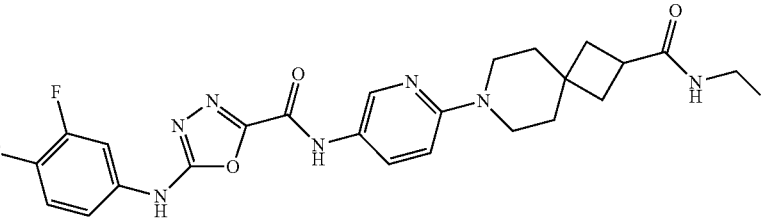<br>5-(3,4-difluoroanilino)-N-[6-[2-(2,2,2-trifluoroethylcarbamoyl)-7-azaspiro[3.5]nonan-7-yl]-3-pyridyl]-1,3,4-oxadiazole-2-carboxamide | LCMS: m/z 566.3 (M$^+$ + 1)<br>$^1$HNMR (400 MHz, DMSO-d6): δ 1.51 (t, J = 5.6 Hz, 2H), 1.60 (t, J = 5.6 Hz, 2H), 1.89-2.00 (m, 4H), 3.03-3.10 (m, 1H), 3.36 (t, J = 5.2 Hz, 2H), 3.46 (t, J = 5.2 Hz, 2H), 3.85-3.91 (m, 2H), 6.86 (d, J = 9.2 Hz, 1H), 7.34 (d, J = 8.4 Hz, 1H), 7.49 (dd, J = 9.2 Hz, J = 18.8 Hz, 1H), 7.67-7.72 (m, 1H), 7.88 (dd, J = 2.4 Hz, J = 9.2 Hz, 1H), 8.38 (t, J = 6.4 Hz, 1H), 8.46 (d, J = 2.4 Hz, 1H), 10.97 (s, 1H), 11.27 (s, 1H) |

| Example No | Structure and IUPAC Name | Characterization Data |
|---|---|---|
| C5 | 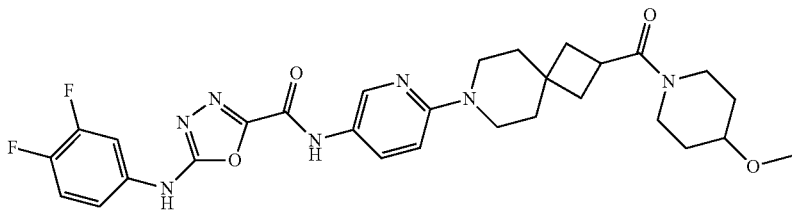<br>5-(3,4-difluoroanilino)-N-[6-[2-(4-methoxypiperidine-1-carbonyl)-7-azaspiro[3.5]nonan-7-yl]-3-pyridyl]-1,3,4-oxadiazole-2-carboxamide | LCMS: m/z 582.4 (M⁺ + 1)<br>¹HNMR (400 MHz, DMSO-d6): δ 1.23-1.34 (m, 2H), 1.42-1.50 (m, 2H), 1.60-1.68 (m, 2H), 1.72-1.86 (m, 2H), 1.91-2.02 (m, 4H), 3.03-3.11 (m, 4H), 3.24 (s, 3H), 3.34-3.37 (m, 1H), 3.44-3.56 (m, 4H), 3.80-3.85 (m, 1H), 6.86 (d, J = 9.2 Hz, 1H), 7.34 (d, J = 8.4 Hz, 1H), 7.49 (dd, J = 9.2 Hz, J = 19.2 Hz, 1H), 7.69 (t, J = 4.8 Hz, 1H), 7.88 (d, J = 8.8 Hz, 1H), 8.45 (s, 1H), 10.96 (s, 1H), 11.26 (s, 1H) |
| C6 | 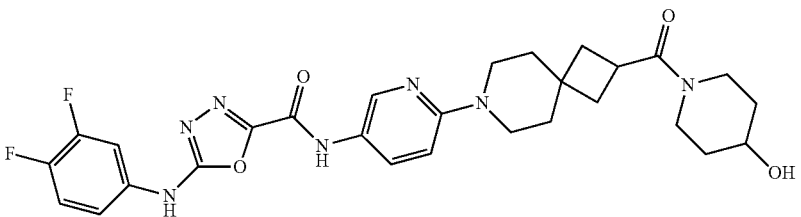<br>5-(3,4-difluoroanilino)-N-[6-[2-(4-hydroxypiperidine-1-carbonyl)-7-azaspiro[3.5]nonan-7-yl]-3-pyridyl]-1,3,4-oxadiazole-2-carboxamide | LCMS: m/z 568.4 (M⁺ + 1)<br>¹HNMR (400 MHz, DMSO-d6): δ 1.20-1.32 (m, 2H), 1.44-1.52 (m, 2H), 1.66 (t, J = 5.2 Hz, 2H), 1.70-1.78 (m, 1H), 1.93-2.04 (m, 4H), 2.96-3.09 (m, 2H), 3.31-3.36 (m, 2H), 3.38-3.44 (m, 2H), 3.50 (t, J = 5.2 Hz, 2H), 3.54-3.60 (m, 1H), 3.66-3.71 (m, 1H), 3.90-3.96 (m, 1H), 4.75 (d, J = 4.4 Hz, 1H), 6.88 (d, J = 9.2 Hz, 1H), 7.36 (d, J = 9.6 Hz, 1H), 7.51 (dd, J = 9.6 Hz, J = 19.6 Hz, 1H), 7.69-7.74 (m, 1H), 7.90 (dd, J = 2.4 Hz, J = 9.2 Hz, 1H), 8.48 (d, J = 2.8 Hz, 1H), 10.98 (s, 1H), 11.29 (s, 1H) |
| C7 | 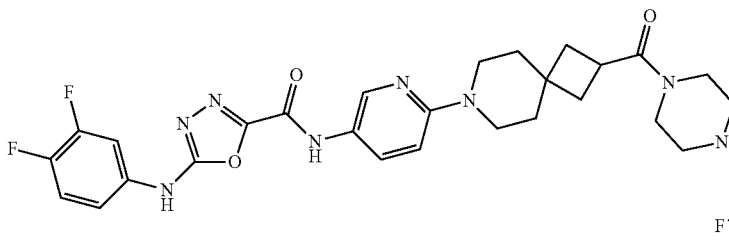<br>5-(3,4-difluoroanilino)-N-[6-[2-[3-(trifluoromethyl)-6,8-dihydro-5H-[1,2,4]triazolo[4,3-a]pyrazine-7-carbonyl]-7-azaspiro[3.5]nonan-7-yl]-3-pyridyl]-1,3,4-oxadiazole-2-carboxamide | LCMS: m/z 659.4 (M⁺ + 1)<br>¹HNMR (400 MHz, DMSO-d6): δ 1.42-1.50 (m, 2H), 1.62-1.68 (m, 2H), 1.88-1.98 (m, 2H), 2.01-2.08 (m, 3H), 3.43-3.48 (m, 4H), 3.84 (t, J = 4.8 Hz, 1H), 3.92-3.95 (m, 1H), 4.10-4.17 (m, 2H), 4.86 (s, 2H), 6.85 (d, J = 9.2 Hz, 1H), 7.32 (d, J = 9.6 Hz, 1H), 7.49 (dd, J = 9.6 Hz, 19.6 Hz, 1H), 7.65-7.70 (m, 1H), 7.86 (dd, J = 2.4 Hz, J = 9.2 Hz, 1H), 8.43 (d, J = 2.4 Hz, 1H), 10.94 (s, 1H), 11.25 (s, 1H) |
| C8 | 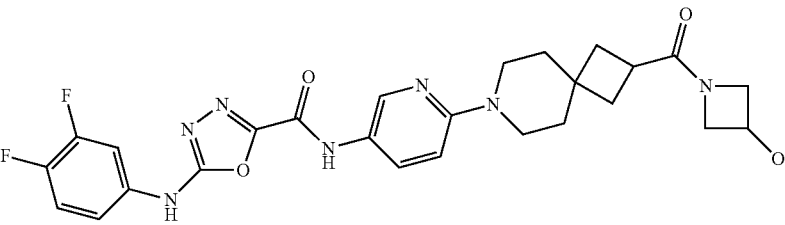<br>5-(3,4-difluoroanilino)-N-[6-[2-(3-hydroxyazetidine-1-carbonyl)-7-azaspiro[3.5]nonan-7-yl]-3-pyridyl]-1,3,4-oxadiazole-2-carboxamide | LCMS: m/z 540.4 (M⁺ + 1)<br>¹HNMR (400 MHz, DMSO-d6): δ 1.46 (t, J = 5.2 Hz, 2H), 1.59 (t, J = 5.2 Hz, 2H), 1.83-1.93 (m, 4H), 3.00-3.06 (m, 1H), 3.44 (t, J = 5.2 Hz, 2H), 3.50-3.56 (m, 1H), 3.70-3.74 (m, 1H), 3.95-4.01 (m, 1H), 4.15-4.19 (m, 1H), 4.36-4.44 (m, 1H), 5.68 (d, J = 6.4 Hz, 1H), 6.83 (d, J = 9.2 Hz, 1H), 7.31 (d, J = 8.8 Hz, 1H), 7.40-7.52 (m, 2H), 7.64-7.70 (m, 1H), 7.84-7.91 (m, 2H), 8.43 (d, J = 2.4 Hz, 1H), 10.83 (bs, 2H) |

| Example No | Structure and IUPAC Name | Characterization Data |
|---|---|---|
| C9 | 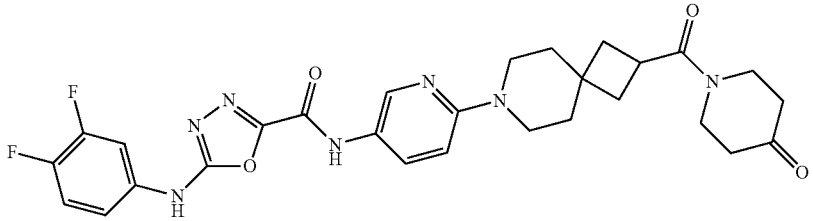<br>5-(3,4-difluoroanilino)-N-[6-[2-(4-oxopiperidine-1-carbonyl)-7-azaspiro[3.5]nonan-7-yl]-3-pyridyl]-1,3,4-oxadiazole-2-carboxamide | LCMS: m/z 566.4 (M⁺ + 1)<br>¹HNMR (400 MHz, DMSO-d6): δ 1.44-1.52 (m, 2H), 1.62-1.69 (m, 2H), 1.98-2.08 (m, 4H), 2.32-2.39 (m, 4H), 3.45-3.52 (m, 2H), 3.34-3.43 (m, 3H), 3.63 (t, J = 5.9 Hz, 2H), 3.72 (t, J = 5.9 Hz, 2H), 6.87 (d, J = 9.0 Hz, 1H), 7.30-7.35 (m, 1H), 7.48 (q, J = 10.3 Hz, 1H), 7.67-7.72 (m, 1H), 7.88 (d, J = 9.3 Hz, 1H), 8.46 (s, 1H), 10.95 (s, 1H), 11.28 (bs, 1H) |

Example D1

5-(3,4-difluoroanilino)-N-[6-(2,2-difluoro-7-azaspiro[3.5]nonan-7-yl)-3-pyridyl]-1,3,4-oxadiazole-2-carboxamide

Scheme 27

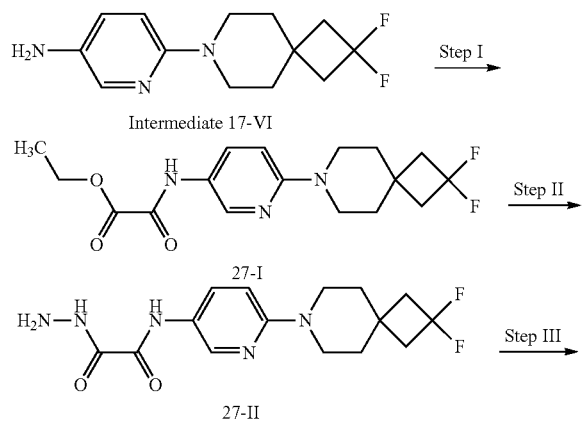

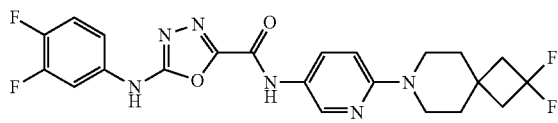

Example D1

Example D1 was prepared starting from Intermediate 17-VI following the same sequence of procedures as used for the synthesis of Example A1 from Intermediate 1-IX (Scheme 26)

¹H NMR (400 MHz, DMSO-d6): δ 1.58-1.66 (m, 4H), 2.42 (t, J=13.2 Hz, 4H), 3.46 (t, J=5.1 Hz, 4H), 6.89 (d, J=9.2 Hz, 1H), 7.34 (d, J=8.8 Hz, 1H), 7.48 (q, J=9.5 Hz, 1H), 7.67-7.72 (m, 1H), 7.90 (dd, J=9.1 & 2.2 Hz, 1H), 8.47 (d, J=2.2 Hz, 1H), 10.99 (s, 1H), 11.29 (bs, 1H)

LCMS: MS (EI): m/z 538.3 (M⁺+1)

Following compounds were prepared from their corresponding intermediates (given in table) using the same sequence of procedures as used for preparation of Example D1 from Intermediate 17-VI:

| Example No | Structure and IUPAC Name | Characterization Data | Intermediate from which prepared |
|---|---|---|---|
| D2 | 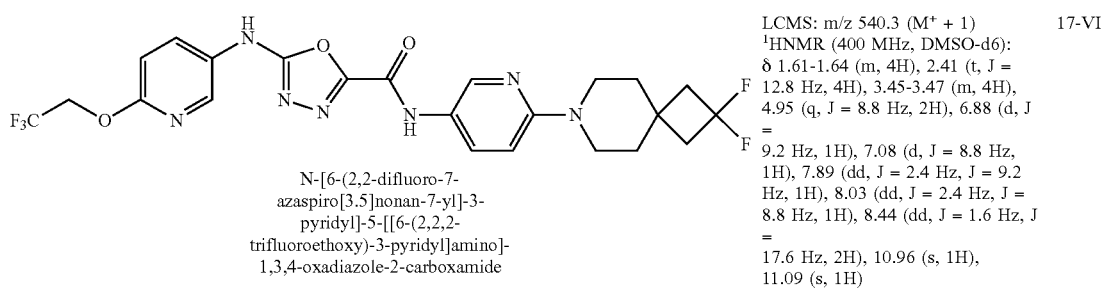<br>N-[6-(2,2-difluoro-7-azaspiro[3.5]nonan-7-yl)-3-pyridyl]-5-[[6-(2,2,2-trifluoroethoxy)-3-pyridyl]amino]-1,3,4-oxadiazole-2-carboxamide | LCMS: m/z 540.3 (M⁺ + 1)<br>¹HNMR (400 MHz, DMSO-d6): δ 1.61-1.64 (m, 4H), 2.41 (t, J = 12.8 Hz, 4H), 3.45-3.47 (m, 4H), 4.95 (q, J = 8.8 Hz, 2H), 6.88 (d, J = 9.2 Hz, 1H), 7.08 (d, J = 8.8 Hz, 1H), 7.89 (dd, J = 2.4 Hz, J = 9.2 Hz, 1H), 8.03 (dd, J = 2.4 Hz, J = 8.8 Hz, 1H), 8.44 (dd, J = 1.6 Hz, J = 17.6 Hz, 2H), 10.96 (s, 1H), 11.09 (s, 1H) | 17-VI |

| Example No | Structure and IUPAC Name | Characterization Data | Intermediate from which prepared |
|---|---|---|---|
| D3 | 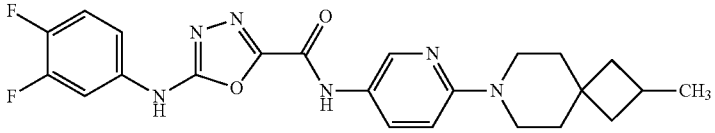<br>5-(3,4-difluoroanilino)-N-[6-(2-methyl-7-azaspiro[3.5]nonan-7-yl)-3-pyridyl]-1,3,4-oxadiazole-2-carboxamide | LCMS: m/z 455.3 (M$^+$ + 1)<br>$^1$HNMR (400 MHz, DMSO-d6): δ 1.06 (d, J = 6.8 Hz, 3H), 1.35 (t, J = 9.2 Hz, 2H), 1.47-1.49 (m, 2H), 1.56-1.58 (m, 2H), 1.98 (t, J = 10.0 Hz, 2H), 2.32-2.35 (m, 1H), 3.35-3.39 (m, 2H), 3.43-3.45 (m, 2H), 6.84 (d, J = 9.2 Hz, 1H), 7.34 (d, J = 8.0 Hz, 1H), 7.50 (dd, J = 9.2 Hz, J = 18.8 Hz, 1H), 7.69 (dd, J = 7.2 Hz, J = .10.4 Hz, 1H), 7.87 (d, J = 7.6 Hz, 1H), 8.44 (s, 1H), 10.96 (s, 1H), 11.27 (s, 1H) | 20-IV |
| D4 | 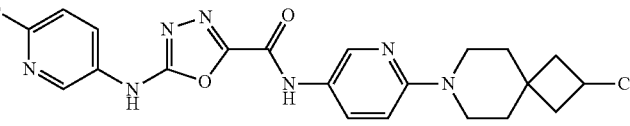<br>N-[6-(2-methyl-7-azaspiro[3.5]nonan-7-yl)-3-pyridyl]-5-[[6-(2,2,2-trifluoroethoxy)-3-pyridyl]amino]-1,3,4-oxadiazole-2-carboxamide | LCMS: m/z 518.3 (M$^+$ + 1)<br>$^1$HNMR (400 MHz, DMSO-d6): δ 1.04 (d, J = 6.8 Hz, 3H), 1.33 (t, J = 9.6 Hz, 2H), 1.46-1.49 (m, 2H), 1.54-1.58 (m, 2H), 1.96 (t, J = 10.4 Hz, 2H), 2.29-2.35 (m, 1H), 3.32-3.35 (m, 2H), 3.40-3.43. (m, 2H), 4.95 (q, J = 8.8 Hz, 2H), 6.82 (d, J = 9.6 Hz, 1H), 7.06 (d, J = 8.8 Hz, 1H), 7.85 (dd, J = 1.6 Hz, J = 8.8 Hz, 1H), 8.00 (dd, J = 2.4 Hz, J = 8.8 Hz, 1H), 8.42 (dd, J = 1.6 Hz, J = 9.2 Hz, 2H), 10.91 (s, 1H), 11.06 (s, 1H) | 20-IV |
| D5 | 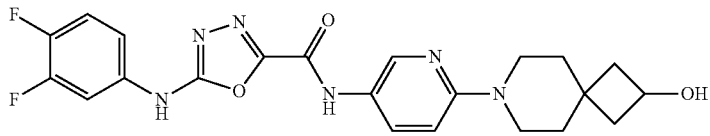<br>5-(3,4-difluoroanilino)-N-[6-(2-hydroxy-7-azaspiro[3.5]nonan-7-yl)-3-pyridyl]-1,3,4-oxadiazole-2-carboxamide | LCMS: m/z 457.3 (M$^+$ + 1)<br>$^1$HNMR (400 MHz, DMSO-d6): δ 1.46-1.55 (m, 4H), 1.58 (t, J = 9.6 Hz, 2H), 2.13-2.18 (m, 2H), 3.37-3.44 (m, 4H), 4.09-4.15 (m, 1H), 4.93 (d, J = 6.0 Hz, 1H), 6.84 (d, J = 8.8 Hz, 1H), 7.33 (d, J = 8.8 Hz, 1H), 7.48 (dd, J = 9.2 Hz, J = 19.2 Hz, 1H), 7.66-7.72 (m, 1H), 7.86 (dd, J = 2.4 Hz, J = 8.8 Hz, 1H), 8.44 (d, J = 2.4 Hz, 1H), 10.95 (s, 1H), 11.26 (bs, 1H) | 18-IV |
| D6 | 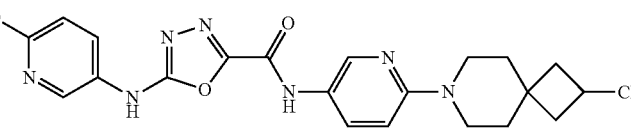<br>N-[6-(2-hydroxy-7-azaspiro[3.5]nonan-7-yl)-3-pyridyl]-5-[[6-(2,2,2-trifluoroethoxy)-3-pyridyl]amino]-1,3,4-oxadiazole-2-carboxamide | LCMS: m/z 520.3 (M$^+$ + 1)<br>$^1$HNMR (400 MHz, DMSO-d6): δ 1.49-1.52 (m, 4H), 1.58 (t, J = 9.2 Hz, 2H), 2.16 (t, J = 9.6 Hz, 2H), 3.37-3.44 (m, 4H), 4.09-4.15 (m, 1H), 4.92-5.00 (m, 3H), 6.84 (d, J = 9.2 Hz, 1H), 7.08 (d, J = 8.8 Hz, 1H), 7.86 (dd, J = 2.4 Hz, 9.2 Hz, 1H), 8.02 (dd, J = 2.4 Hz, 8.8 Hz, 1H), 8.43 (dd, J = 2.4 Hz, J = 9.6 Hz, 2H), 10.93 (s, 1H), 11.08 (s, 1H) | 18-IV |
| D7 | 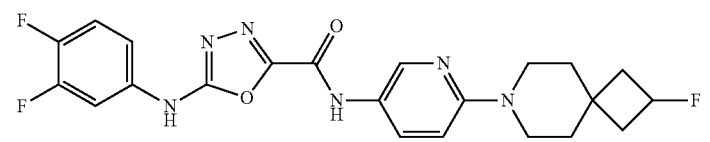<br>5-(3,4-difluoroanilino)-N-[6-(2-fluoro-7-azaspiro[3.5]nonan-7-yl)-3-pyridyl]-1,3,4-oxadiazole-2-carboxamide | LCMS: m/z 459.3 (M$^+$ + 1)<br>$^1$HNMR (400 MHz, DMSO-d6): δ 1.53-1.64 (m, 1H), 1.66-1.69 (m, 1H), 1.73-1.78 (m, 2H), 2.5 (d, J = 7.2 Hz, 1H), 2.40 (d, J = 7.6 Hz, 1H), 3.07-3.13 (m, 2H), 4.00-4.05 (d, J = 13.2 Hz, 2H), 5.09 (d, J = 2.8 Hz, 1H), 5.13 (s, 1H), 5.75-5.85 (m, 1H), 6.90 (d, J = 9.2 Hz, 1H), 7.32 (d, J = 8.8 Hz, 1H), 7.47 (dd, J = 9.6 Hz, J = 19.6 Hz, 1H), 7.65-7.71 (m, 1H), 7.88 (dd, J = 2.4 Hz, J = 8.8 Hz, 1H), 8.45 (d, J = 2.8 Hz, 1H), 10.97 (s, 1H), 11.25 (s, 1H) | 19-V |

| Example No | Structure and IUPAC Name | Characterization Data | Intermediate from which prepared |
|---|---|---|---|
| D8 | 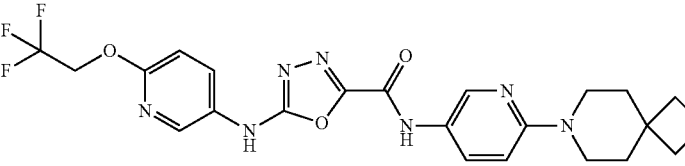<br>N-[6-(2-fluoro-7-azaspiro[3.5]nonan-7-yl)-3-pyridyl]-5-[[6-(2,2,2-trifluoroethoxy)-3-pyridyl]amino]-1,3,4-oxadiazole-2-carboxamide | LCMS: m/z 522.3 (M$^+$ + 1)<br>$^1$HNMR (400 MHz, DMSO-d6): δ 1.56-1 66 (m, 1H), 1.68-1.80 (m, 3H), 2.37 (d, J = 7.2 Hz, 1H), 2.43 (d, J = 7.2 Hz, 1H), 3.12 (t, J = 11.2 Hz, 2H), 4.04 (d, J = 13.2 Hz, 2H), 4.96 (q, J = 9.2 Hz, 2H), 5.11 (d, J = 2.0 Hz, 1H), 5.15 (s, 1H), 5.77-5.87 (m, 1H), 6.91 (d, J = 8.8 Hz, 1H), 7.04 (d, J = 8.8 Hz, 1H), 7.91 (dd, J = 2.4 Hz, J = 9.2 Hz, 1H), 8.01 (dd, J = 2.8 Hz, J = 8.8 Hz, 1H), 8.39 (d, J = 2.8 Hz, 1H), 8.48 (d, J = 2.4 Hz, 1H), 10.88 (s, 1H), 11.16 (bs, 1H) | 19-V |
| D9 | 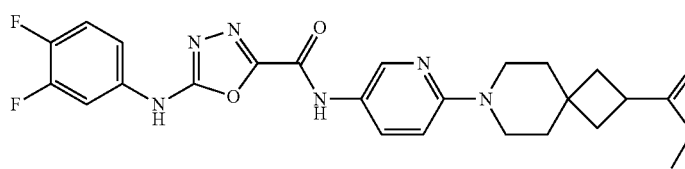<br>5-(3,4-difluoroanilino)-N-[6-[2-(1-methyltetrazol-5-yl)-7-azaspiro[3.5]nonan-7-yl]-3-pyridyl]-1,3,4-oxadiazole-2-carboxamide | LCMS: m/z 523.3 (M$^+$ + 1)<br>$^1$HNMR (400 MHz, DMSO-d6): δ 1.55 (t, J = 5.2 Hz, 2H), 1.73 (t, J = 52 Hz, 2H), 2.13 (t, J = 8.8 Hz, 2H), 2.34 (d, J = 11.2 Hz, 2H), 3.39 (t, J = 5.2 Hz, 2H), 3.51 (t, J = 4.8 Hz, 2H), 3.80-3.84 (m, 1H), 3.90 (s, 3H), 6.86 (d, J = 9.2 Hz, 1H), 7.32 (d, J = 8.8 Hz, 1H), 7.47(dd, J = 9.2 Hz, J = 19.2 Hz, 1H), 7.65-7.70 (m, 1H), 7.86 (dd, J = 2.4 Hz, J = 8.8 Hz, 1H), 8.45 (d, J = 2.4 Hz, 1H), 10.94 (s, 1H), 11.23 (bs, 1H) | 21-IX |

Example E1

5-(3,4-difluoroanilino)-N-[6-[2-(hydroxymethyl)-7-azaspiro[3.5]nonan-7-yl]-3-pyridyl]-1,3,4-oxadiazole-2-carboxamide

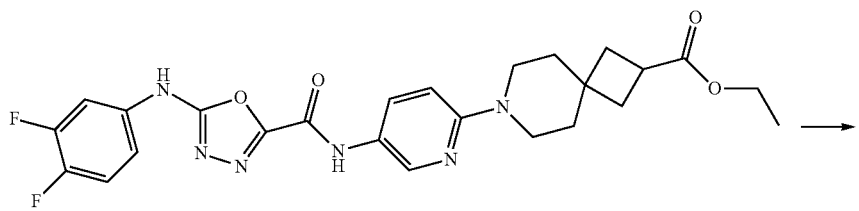
Example A12

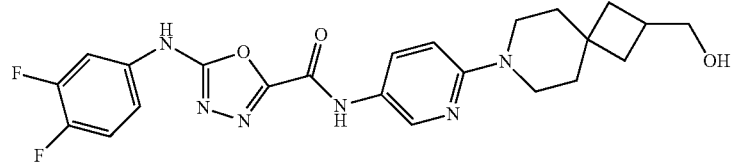
Example E1

To a solution of ethyl 7-[5-[[5-(3,4-difluoroanilino)-1,3,4-oxadiazole-2-carbonyl]amino]-2-pyridyl]-7-azaspiro[3.5]nonane-2-carboxylate Example A12 (0.15 g, 0.29 mmol, 1.0 equiv.) in a mixture of methanol (10 mL) and THF (2 mL) was added sodium borohydride (0.165 g, 4.35 mmol, 15.0 equiv.) in portions. After complete addition, 2 drops of water were added. The reaction mixture was stirred at room temperature for 72 h. Reaction was monitored by TLC. On completion of reaction, volatiles were removed under reduced pressure. Reaction mixture was diluted with water (50 ml) and extracted with ethyl acetate (3×50 mL). Organic layer was washed with brine (50 mL), dried over anhydrous sodium sulfate and solvent was removed under reduced pressure to afford crude product which was purified by preparative HPLC to give pure product Example E1 (0.03 g, 23%)

$^1$H NMR (400 MHz, DMSO-d6): δ 1.46-1.53 (m, 4H), 1.59 (t, J=5.1 Hz, 2H), 1.81 (t, J=9.3 Hz, 2H), 2.30-2.41 (m, 1H), 3.32-3.38 (m, 4H), 3.45 (t, J=5.1 Hz, 2H), 4.46 (t, J=5.3

Hz, 1H), 6.85 (d, J=9.2 Hz, 1H), 7.33-7.35 (m, 1H), 7.49 (q, J=9.3 Hz, 1H), 7.67-7.72 (m, 1H), 7.88 (dd, J=9.3 & 2.7 Hz, 1H), 8.45 (d, J=2.7 Hz, 1H), 10.95 (bs, 2H)

LCMS: MS (EI): m/z 471.3 (M⁺+1)

Example F1

N-[6-(2-carbamoyl-7-azaspiro[3.5]nonan-7-yl)-3-pyridyl]-5-(3,4-difluoroanilino)-1,3,4-oxadiazole-2-carboxamide filtered out and triturated with diethyl ether (10 mL) followed by ethyl acetate (5 mL) to provide pure product Example F1 (42 mg, 71%)

$^1$H NMR (400 MHz, DMSO-d6): δ 1.48 (t, J=5.2 Hz, 2H), 1.58 (t, J=4.9 Hz, 2H), 1.84-1.93 (m, 4H), 2.87-2.98 (m, 1H), 3.20-3.38 (m, 2H), 3.44 (t, J=4.9 Hz, 2H), 6.70 (s, 1H), 6.84 (d, J=9.1 Hz, 1H), 7.14 (s, 1H), 7.30-7.35 (m, 1H), 7.47 (q, J=9.3 Hz, 1H), 7.65-7.71 (m, 1H), 7.86 (dd, J=9.0 & 2.4 Hz, 1H), 8.43 (d, J=2.5 Hz, 1H), 10.95 (s, 1H), 11.24 (bs, 1H).

MS (EI): m/z 484.3 (M⁺+1)

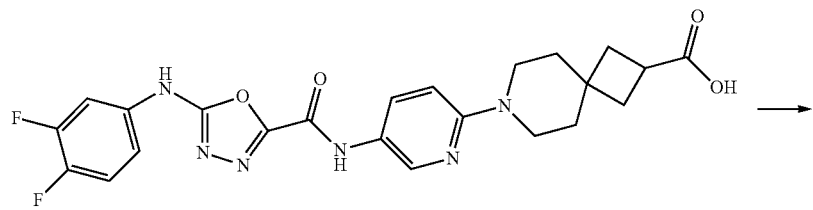
Example B12

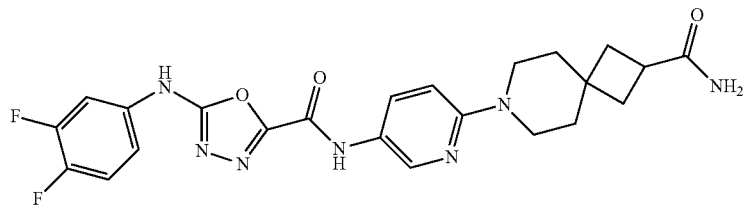
Example F1

To a stirred solution of 7-[5-[[5-(3,4-difluoroanilino)-1,3,4-oxadiazole-2-carbonyl]amino]-2-pyridyl]-7-azaspiro[3.5]nonane-2-carboxylic acid Example B12 (0.06 g, 0.12 mmol, 1.0 equiv.) in N,N dimethyl formamide (5 mL) was added 2M ammonia solution in ethanol (4.0 mL) followed by HATU (0.07 g, 0.18 mmol, 1.5 equiv.) and stirred at room temperature for 15 h. The reaction was monitored by TLC. After completion of the reaction, reaction mixture was poured into ice-water (10 mL). Solid separated out was

Example F2

N-[6-[3-(2-amino-2-oxo-ethyl)-9-azaspiro[5.5]undecan-9-yl]-3-pyridyl]-5-(3,4-difluoroanilino)-1,3,4-oxadiazole-2-carboxamide

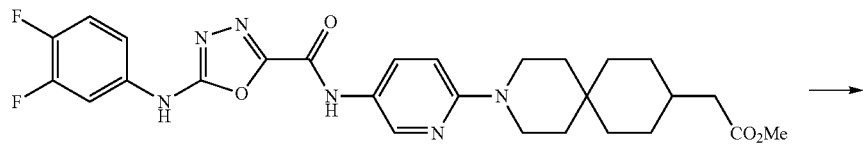
Example B7

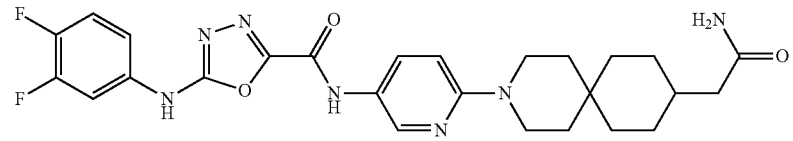
Example F2

Example F2 was prepared from Example B7 using similar procedure as used for the preparation of Example F1 from Example B12.

¹HNMR (400 MHz, DMSO-D6): δ 1.06-1.14 (m, 4H), 1.31-1.36 (m, 2H), 1.46-1.50 (m, 4H), 1.63-1.68 (m, 3H), 1.95 (d, J=7.2 Hz, 2H), 3.43-3.47 (m, 4H), 6.71 (br. s, 1H), 6.82 (d, J=9.2 Hz, 1H), 7.23 (br. s, 1H), 7.27-7.30 (m, 1H), 7.41-7.46 (m, 1H), 7.68 (ddd, J=12.4, 6.8, 4.8 Hz, 1H), 7.88 (dd, J=9.2, 2.4 Hz, 1H), 8.45 (d, J=2.8 Hz, 1H), 10.88 (br. s, 1H), 11.31 (br. s, 1H)

LCMS: m/z 526.2 [M⁺+1]

Example G1
N-[6-(2-benzyloxyspiro[3.5]nonan-7-yl)oxy-3-pyridyl]-5-(3,4-difluoroanilino)-1,3,4-oxadiazole-2-carboxamide Scheme 28

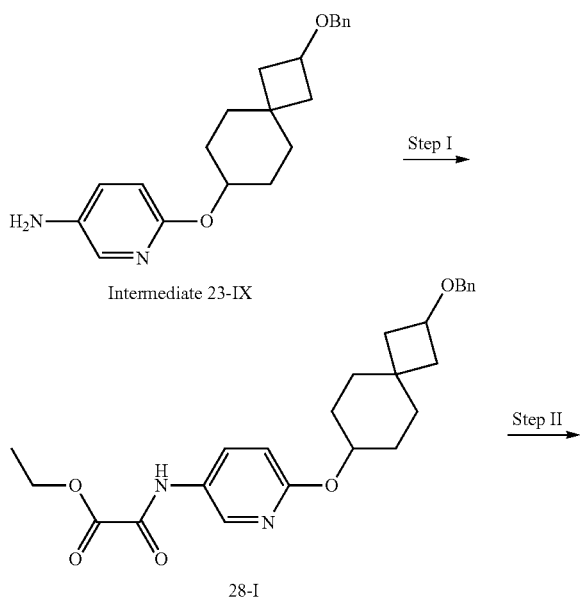

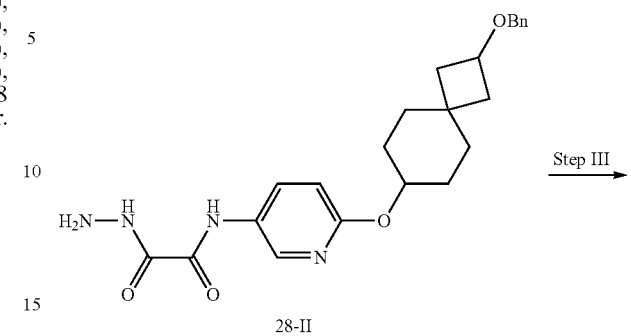

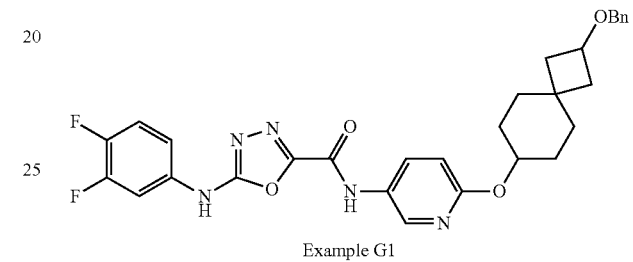

Example G1 was prepared from Intermediate 23-IX following similar procedure as used for the synthesis of Example A1 from Intermediate 1-IX; LCMS: m/z 562.0 (M⁺+1)

Following examples were prepared from Intermediate 23-IX following similar procedure as described for Example G1

| Example No | Structure and IUPAC Name | Characterization Data |
|---|---|---|
| G2 | 5-anilino-N-[6-(2-benzyloxyspiro[3.5]nonan-7-yl)oxy-3-pyridyl]-1,3,4-oxadiazole-2-carboxamide | LCMS: m/z 525 (M⁺ + 1) |

| Example No | Structure and IUPAC Name | Characterization Data |
|---|---|---|
| G3 | 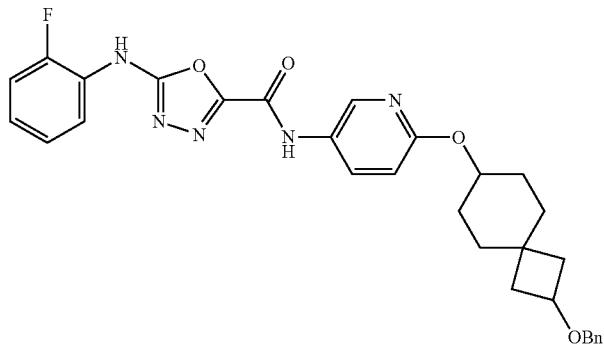<br>N-[6-(2-benzyloxyspiro[3.5]nonan-7-yl)oxy-3-pyridyl]-5-(2-fluoroanilino)-1,3,4-oxadiazole-2-carboxamide | LCMS: m/z 543 (M$^+$ + 1) |

Example G4

5-(3,4-difluoroanilino)-N-[6-(2-hydroxyspiro[3.5]nonan-7-yl)oxy-3-pyridyl]-1,3,4-oxadiazole-2-carboxamide

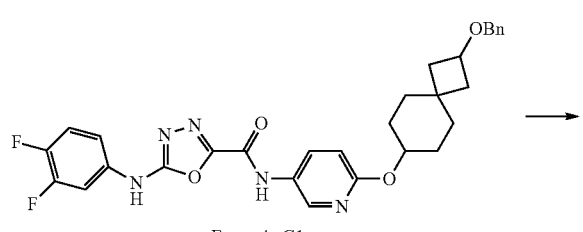
Example G1

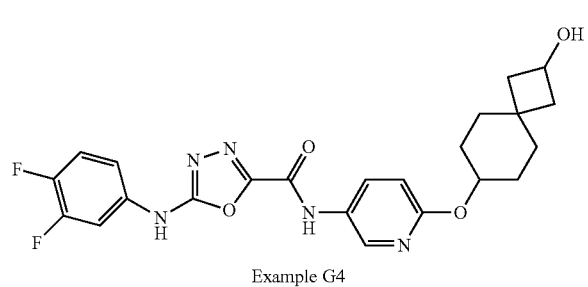
Example G4

To solution of Example G1 (0.12 g, 0.21 mmol) in ethyl acetate (10 mL) was added water (3 mL) followed by Pd/C (10%, 0.025 g). The resulting reaction mixture was degassed using $N_2$ gas for 15 minutes and stirred under hydrogen atmosphere (balloon pressure) for 16 hours. After completion of reaction (monitored by TLC), reaction mixture was filtered through celite pad and washed with excess ethyl acetate. Solvent was concentrated under reduced pressure to yield target compound Example G4 (0.04 g, 82%) as a white solid.

LCMS: m/z 472.1 (M$^+$+1)

$^1$HNMR (400 MHz, DMSO-D6): δ 1.35-1.61 (m, 8H), 1.79-1.82 (m, 2H), 2.06 (m, 1H), 2.16 (m, 1H), 4.04-4.10 (m, 1H), 4.87 (d, J=4 Hz, 2H), 6.77 (d, J=12 Hz, 1H), 7.33-7.35 (br, s, 1H), 7.45-7.52 (dd, J=8 Hz, 20 Hz, 1H), 7.67-7.71 (m, 1H), 8.03 (d, J=8.8 Hz, 1H) 8.49 (s, 1H), 11.13 (s, 1H), 11.28 (s, 1H)

Following examples were prepared from their corresponding starting materials following similar procedures as used for the preparation of Example G4 from Example G1

| Example No | Structure and IUPAC Name | Characterization Data |
|---|---|---|
| G5 | 5-anilino-N-[6-(2-hydroxyspiro[3.5]nonan-7-yl)oxy-3-pyridyl]-1,3,4-oxadiazole-2-carboxamide | LCMS: m/z 436.3 (M$^+$ + 1) $^1$HNMR (400 MHz, DMSO-D6): δ 1.35-1.61 (m, 8H), 1.79-1.82 (m, 2H), 2.06 (m, 1H), 2.16 (m, 1H), 4.04-4.09 (m, 1H), 4.87-4.88 (d, J = 4 Hz, 2H), 6.77-6.79 (d, J = 8.8 Hz, 1H), 7.04-7.08 (t, 1H), 7.42-7.74 (t, 2H), 7.60-7.62 (d, J = 8 Hz, 2H), 8.03-8.06 (dd, J = 2 Hz, J = 2 Hz, 1H), 8.49-8.50 (d, J = 2.4 Hz, 1H) 11.02-11.10 (bs, 2H) |
| G6 | 5-(2-fluoroanilino)-N-[6-(2-hydroxyspiro[3.5]nonan-7-yl)oxy-3-pyridyl]-1,3,4-oxadiazole-2-carboxamide | LCMS: m/z 454.1 (M$^+$ + 1) $^1$HNMR (400 MHz, DMSO-D6): δ 1.35-1.61 (m, 8H), 1.82-1.79 (m, 2H), 2.06 (m, 1H), 2.16 (m, 1H), 4.04-4.10 (m, 1H), 4.87-4.88 (d, J = 4 Hz, 2H), 6.76-6.79 (d, J = 7.6 Hz, 1H), 7.15-7.18 (m, 1H), 7.24-7.33 (m, 2H), 8.02-8.06 (t, 2H), 8.48-8.49 (d, J = 2.4 Hz, 1H) 10.80 (bs, 1H), 11.13 (bs, 1H) |

Example H1

Methyl 2-[9-[4-(4-chloro-5-oxo-7,8-dihydropyrimido[5,4-f][1,4]oxazepin-6-yl)phenyl]spiro[5.5]undecan-3-yl]acetate Example H1 was prepared from 2-VIII (Scheme 2) following similar sequence of procedures as mentioned in WO2009016462; LCMS: 498.20 (M$^+$+1), 500.30 (M$^+$+2)

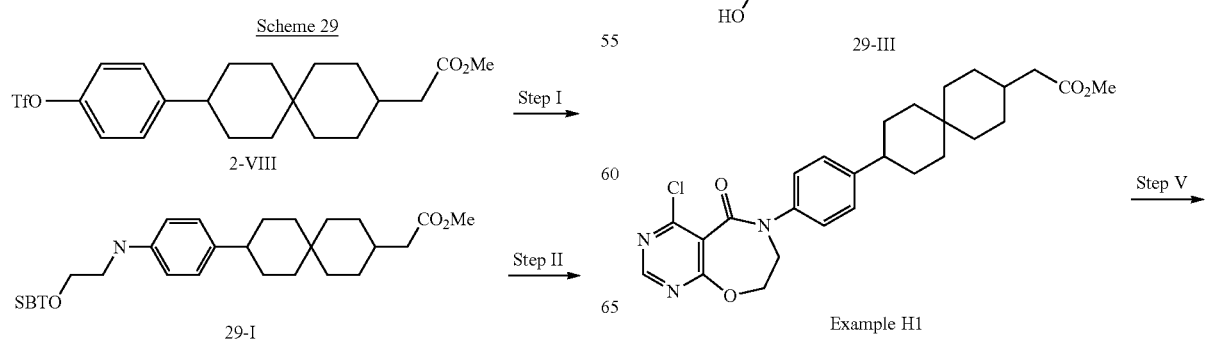

Scheme 29

131

-continued

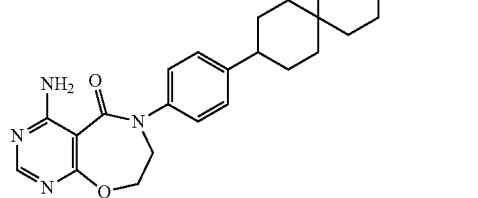

Example H2

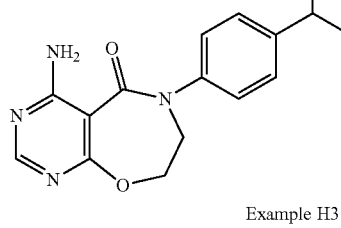

Example H3

Example H2

Methyl 2-[9-[4-(4-amino-5-oxo-7,8-dihydropyrimido[5,4-f][1,4]oxazepin-6-yl)phenyl]spiro[5.5]undecan-3-yl]acetate Example H2 was prepared from Example H1 following similar procedure as mentioned in WO2009016462; LCMS: m/z 479.30 (M$^+$+1)

Example H3

2-[9-[4-(4-amino-5-oxo-7,8-dihydropyrimido[5,4-f][1,4]oxazepin-6-yl)phenyl]spiro[5.5]undecan-3-yl]acetic acid Example H3 was prepared from Example H2 following similar procedure as mentioned in WO2009016462

$^1$HNMR (400 MHz, DMSO-d6): δ 0.92-1.05 (m, 2H), 1.08-1.41 (m, 7H), 1.47-1.65 (m, 7H), 2.02-2.50 (m, 4H), 3.96 (t, J=4.7 Hz, 2H), 4.58 (t, J=4.9 Hz, 2H), 7.26 (d, J=8.6 Hz, 2H), 7.30 (d, J=8.5 Hz, 2H), 7.61 (bs, 1H), 8.17 (s, 1H)

LCMS: m/z 465.20 (M$^+$+1)

Example I1

[4-(4-amino-5-oxo-7,8-dihydropyrimido[5,4-f][1,4]oxazepin-6-yl)phenyl]spiro[2.5]octane-2-carboxylic acid 30-VI was prepared from commercially available 30-I following similar sequence of procedures as mentioned in WO2009016462.

132

Step VI: Methyl 6-[4-(4-amino-5-oxo-7,8-dihydropyrimido[5,4-f][1,4]oxazepin-6-yl)phenyl]spiro[2.5]oct-6-ene-2-carboxylate (Example I1)

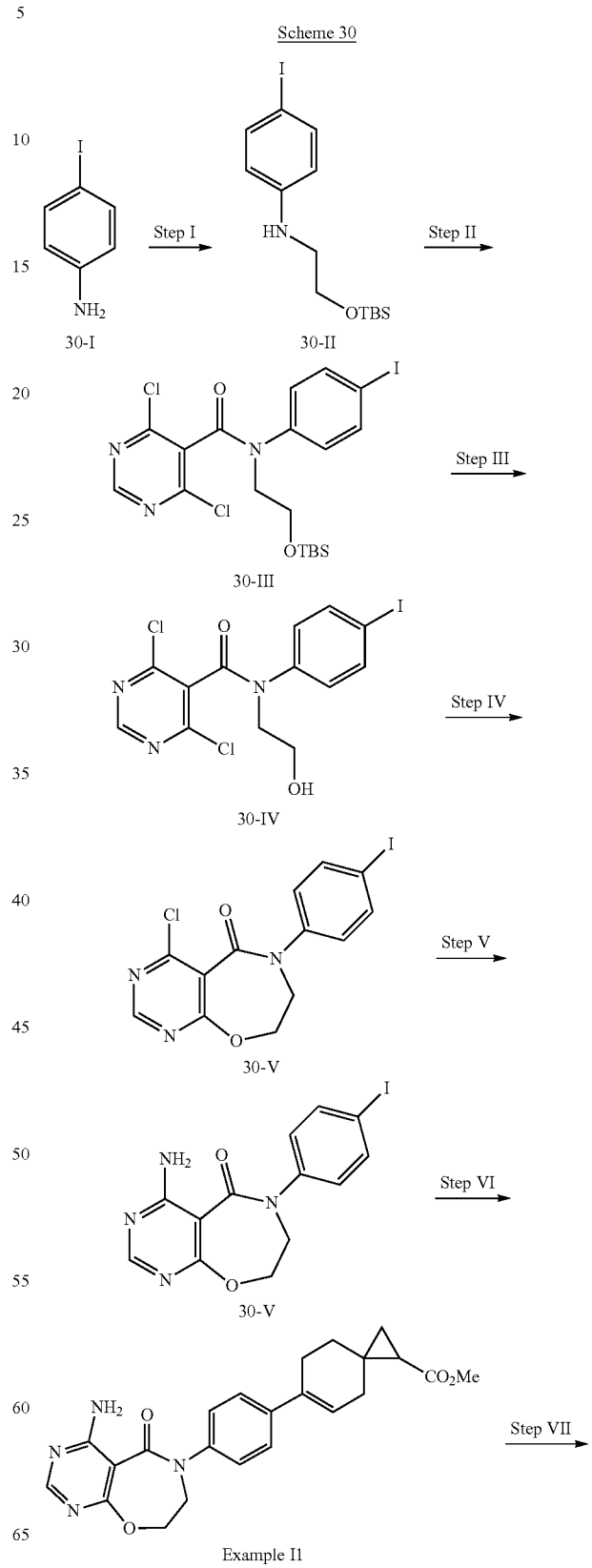

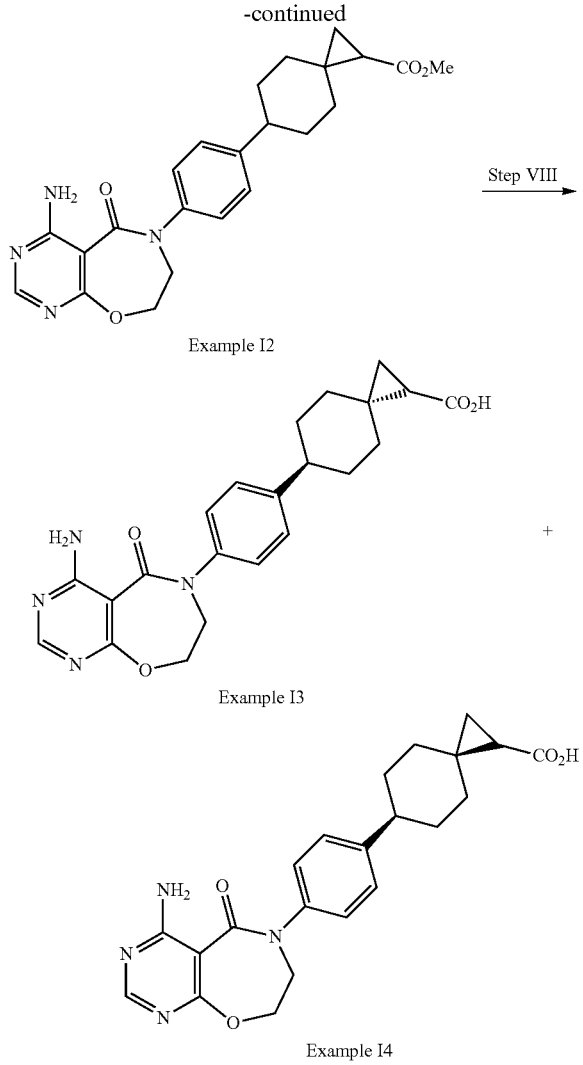

Example I2

Example I3

Example I4

To a solution of 30-VI (0.20 g, 0.52 mmol) in 1,4-dioxane (5.2 mL) was added Intermediate 12-VI (0.23 g, 0.79 mmol) and cesium carbonate (0.51 g, 1.57 mmol). The reaction mixture was degassed with argon for 30 min. Tetrakistriphenylphosphine palladium(0) (0.060 g, 0.052 mmol) was added to degassed reaction mixture then stirred at 80° C. for 15 h. Reaction was monitored by TLC. On completion of reaction, reaction mixture was poured on ice-water (10 mL) extracted with ethyl acetate (3×20 mL). Organic layer was washed with water (20 mL), with brine (20 mL) and dried over anhydrous sodium sulfate. Solvent was removed under reduced pressure to afford crude product which was purified by column chromatography (Silica gel 100-200 mesh, 10% EtOAc:hexane as eluent) to provide pure product Example I1 (0.22 g, 100%); LCMS: m/z 421.20 (M$^+$+1)

Example I2

Methyl 6-[4-(4-amino-5-oxo-7,8-dihydropyrimido[5,4-f][1,4]oxazepin-6-yl)phenyl]spiro[2.5]octane-2-carboxylate Example I2 was prepared from Example I1 following similar procedure as used for the preparation of Intermediate 7-VIII from 7-VII (Scheme 7); LCMS: m/z 423.3 (M$^+$+1)

Examples I3 and I4

Trans and cis-6-[4-(4-amino-5-oxo-7,8-dihydropyrimido[5,4-f][1,4]oxazepin-6-yl)phenyl]spiro[2.5]octane-2-carboxylic acid To a stirred solution of Example I2 (0.22 g, 0.52 mmol) in 1,4-dioxane (5.2 mL) was added LiOH. H$_2$O (0.183 g, 4.36 mmol) in 1.6 mL water. The reaction was stirred at room temperature for 4 h. The reaction mixture was concentrated, diluted with water and acidified with 1N HCl followed by extraction with ethyl acetate (3×20 mL). Organic layer was washed with water (20 mL) and brine (20 mL) and dried over anhydrous sodium sulfate. Solvent was removed under reduced pressure to afford crude product which was purified by preparative HPLC to provide title compounds Example I3 (0.025 g, 13%) and Example I4 (0.015 g, 8%).

$^1$HNMR (Example I3) (400 MHz, DMSO-d6): δ 0.85 (dd, J=7.5 & 3.5 Hz, 1H), 0.90 (t, J=3.9 Hz, 1H), 1.02 (d, J=12.5 Hz, 1H), 1.47-1.61 (m, 4H), 1.70-1.85 (m, 1H), 1.94 (t, J=12.8 Hz, 1H), 2.55-2.66 (m, 1H), 3.95 (t, J=4.4 Hz, 2H), 4.57 (t, J=4.4 Hz, 2H), 7.26 (d, 0.1=8.9 Hz, 2H), 7.30 (d, 0.1=8.8 Hz, 2H), 7.60 (bs, 2H), 8.15 (s, 1H), 11.97 (bs, 1H)
LCMS: m/z: 409.2 (M+1)

$^1$HNMR (Example I4) (400 MHz, DMSO-d6): δ 0.89 (dd, J=7.4 & 3.9 Hz, 1H), 0.96 (t, J=4.6 Hz, 1H), 1.05 (d, J=13.0 Hz, 1H), 1.20-1.32 (m, 1H), 1.49 (dd, J=7.5 & 5.5 Hz, 1H), 1.50-1.65 (m, 1H), 1.69-1.84 (m, 4H), 1.95 (dt, J=16.1, 13.0 & 3.0 Hz, 1H), 2.60-2.65 (m, 1H), 3.97 (t, J=4.6 Hz, 2H), 4.59 (t, J=4.2 Hz, 2H), 7.26 (d, J=8.6 Hz, 2H), 7.30 (d, J=8.4 Hz, 2H), 7.62 (bs, 2H), 8.17 (s, 1H), 12.08 (bs, 1H)
LCMS: m/z 409.2 (M+1)

Example J1

2-[9-(4-amino-5-oxo-7,8-dihydropyrimido[5,4-f][1,4]oxazepin-6-yl)spiro[5.5]undecan-3-yl]acetic acid Scheme 31

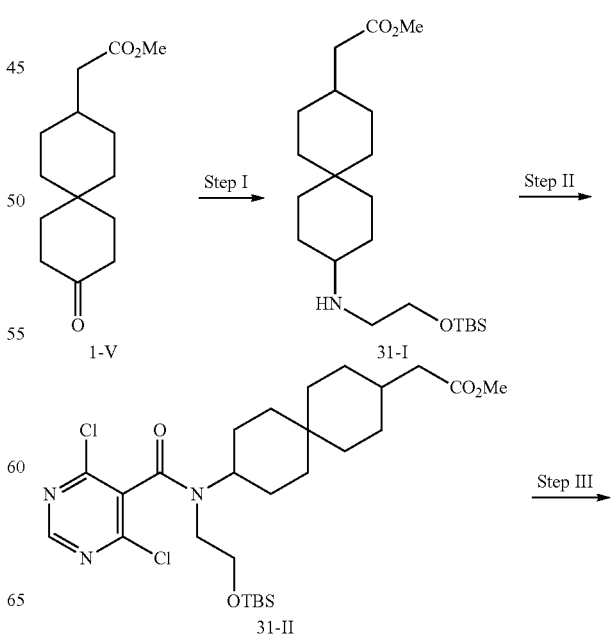

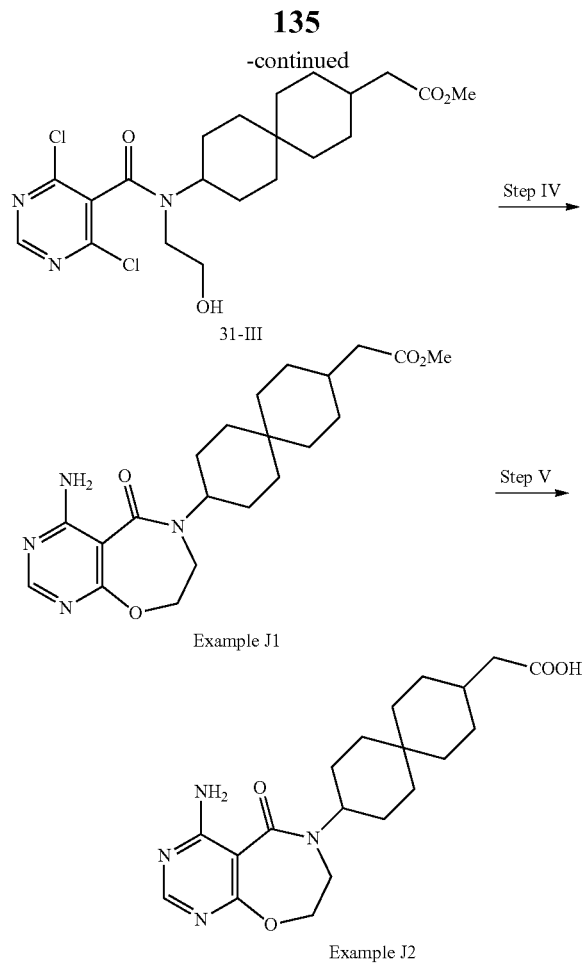

Step I: Methyl 2-[9-[2-[t-butyl(dimethyl)silyl]oxyethylamino]spiro[5.5]undecan-3-yl]acetate (31-I)

To a solution of methyl 2-(9-oxospiro[5.5]undecan-3-yl)acetate (1-V) (Scheme 1) (50 mg, 0.2 mmol) in 1,2-dichloroethane (2 ml) were added 4 Å molecular sieves (200 mg) and 2-[t-butyl (dimethyl)silyl]oxyethanamine (73 mg, 0.42 mmol) and resulting reaction mixture was stirred at room temperature for 2 hrs. Sodium cyanoborohydride (66 mg, 0.31 mmol) was added and stirring was continued for another 18 hrs. Reaction mixture was filtered through celite pad, washed with EtOAc and filtrate was evaporated to yield crude title product 31-I (0.08 g) which was used for next step without further purification.

Example J1

2-[9-(4-amino-5-oxo-7,8-dihydropyrimido[5,4-f][1,4]oxazepin-6-yl)spiro[5.5]undecan-3-yl]acetic acid Example J1 was prepared from 31-I (Step II-Step IV) following similar sequence of procedures as mentioned in WO2009016462; LCMS: m/z 403.3 [M$^+$+1]

Example J2

2-[9-(4-amino-5-oxo-7,8-dihydropyrimido[5,4-f][1,4]oxazepin-6-yl)spiro[5.5]undecan-3-yl]acetic acid Example J2 was prepared from Example J1 following similar procedure as mentioned in WO2009016462.

$^1$HNMR (400 MHz, DMSO-d6): δ 0.83-1.01 (m, 2H), 1.02-1.32 (m, 5H), 1.32-1.55 (m, 6H), 1.56-1.72 (m, 2H), 2.03 (q, J=15.6 Hz, 2H), 2.11 (d, J=8.8 Hz, 2H), 3.57 (t, J=4.4 Hz, 2H), 4.29-4.41 (m, 3H), 7.52 (s, 2H), 8.12 (s, 1H), 11.97 (s, 1H)

LCMS: m/z 389.2 (M$^+$+1)

Example K1

5-chloro-3-[6-(2-methyl-7-azaspiro[3.5]nonan-7-yl)-3-pyridyl]pyrimido[4,5-d]pyrimidin-4-one Scheme 32

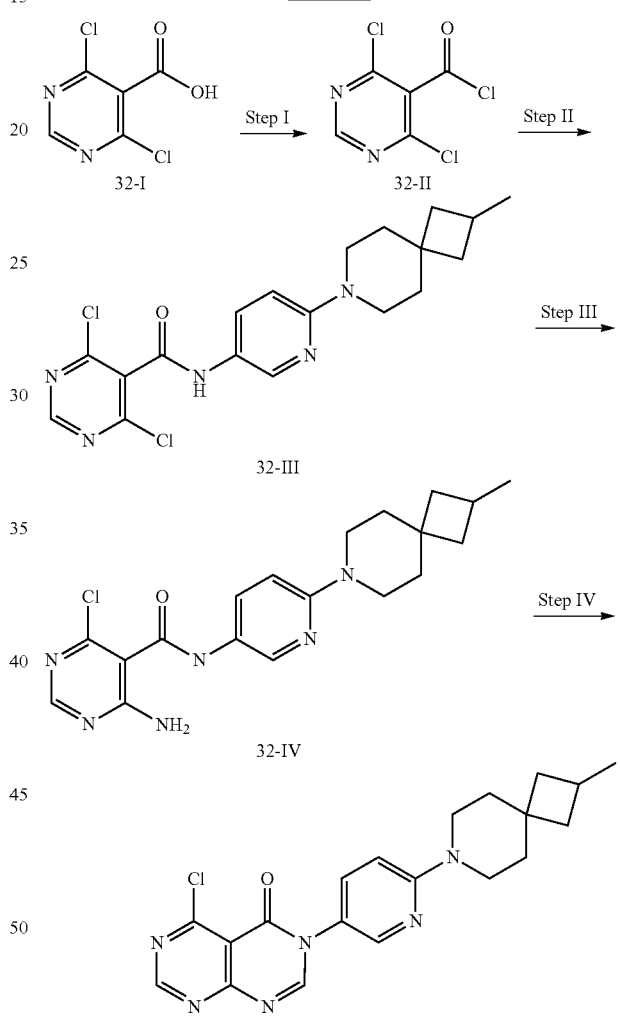

Step I: 4,6-dichloropyrimidine-5-carbonyl chloride (32-II)

To a solution of 4,6-dichloropyrimidine-5-carboxylic acid (32-I) (0.4 g, 2.08 mmol) in DCM (5 mL) at room temperature was added 1 drop of DMF and oxalyl chloride (0.27 ml, 3.12 mmol) and reaction mixture was stirred for 2 hours. After completion of reaction (monitored by TLC), solvents were evaporated under reduced pressure and dried under high vacuum. The crude product 32-II was used as such without purification for next step.

Step II: 4,6-dichloro-N-[6-(2-methyl-7-azaspiro[3.5]nonan-7-yl)-3-pyridyl]pyrimidine-5-carboxamide (32-III)

To a mixture of Intermediate 20-IV (0.29, 1.26 mmol) and triethylamine (0.53 ml, 3.78 mmol) in THF (5 mL) at 0° C. was added 32-II (0.26 g, 1.26 mmol) in THF (1 mL) and reaction mixture was stirred for 4 hours at room temperature. After completion of reaction (monitored by TLC), solvents were evaporated under reduced pressure. Crude product was taken in water and ethyl acetate was added. Layers were separated, aqueous layer was extracted with ethyl acetate and combined organic layers were washed with water and brine, dried over anhydrous sodium sulphate and concentrated under reduced pressure. The crude product so obtained was purified by silica gel column chromatography using 25% ethyl acetate in hexane as eluent to provide target product 32-III (0.2 g, 40%); LCMS: m/z 406.20 (M⁺+1)

Step III: 4-amino-6-chloro-N-[6-(2-methyl-7-azaspiro[3.5]nonan-7-yl)-3-pyridyl]pyrimidine-5-carboxamide (32-IV)

A solution of 32-III (0.2 g, 0.5 mmol) in 0.5 M ammonia in dioxane (5 mL) was stirred for 16 hours at 50° C. After completion of reaction (monitored by TLC), solvents were evaporated under reduced pressure. The residue was taken in water and ethyl acetate was added. The layers were separated and aqueous layer was extracted with ethyl acetate. The combined organic layers were washed with water and brine, dried over anhydrous sodium sulphate and concentrated under reduced pressure to afford target product 32-IV (0.11 g, 56%); LCMS: m/z 387.30 (M⁺+1)

Step IV: 5-chloro-3-[6-(2-methyl-7-azaspiro[3.5]nonan-7-yl)-3-pyridyl]pyrimido[4,5-d]pyrimidin-4-one (Example K1)

A mixture of 32-IV (0.11 g, 0.28 mmol) and triethylorthoformate (4 mL) was heated at 140° C. for 16 hours. After completion of reaction (monitored by TLC), solvent was evaporated under reduced pressure. The residue was taken in water and ethyl acetate was added. Layers were separated and aqueous layer was extracted with ethyl acetate. Combined organic layers were washed with water and brine, dried over anhydrous sodium sulphate and concentrated under reduced pressure. The crude product so obtained was purified by preparative TLC to provide target product Example K1 (0.058 g, 51%); LCMS: m/z 397.3 (M⁺+1), 398.3 (M⁺+2)

Following example was prepared following similar sequence of procedures as used for the preparation of Example K1

| Example No | Structure and IUPAC Name | Characterization Data |
|---|---|---|
| K2 | 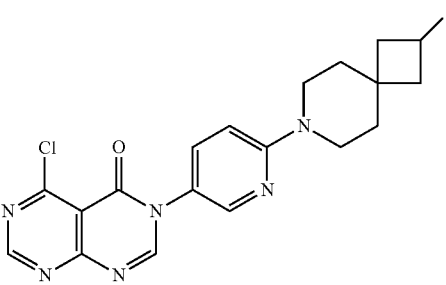<br>5-chloro-3-[6-(2-fluoro-7-azaspiro[3.5]nonan-7-yl)-3-pyridyl]pyrimido[4,5-d]pyrimidin-4-one | LCMS: m/z 401.3 (M⁺ + 1), 402.3 (M⁺ + 2) |

Example K3

5-amino-3-[6-(2-methyl-7-azaspiro[3.5]nonan-7-yl)-3-pyridyl]pyrimido[4,5-d]pyrimidin-4-one

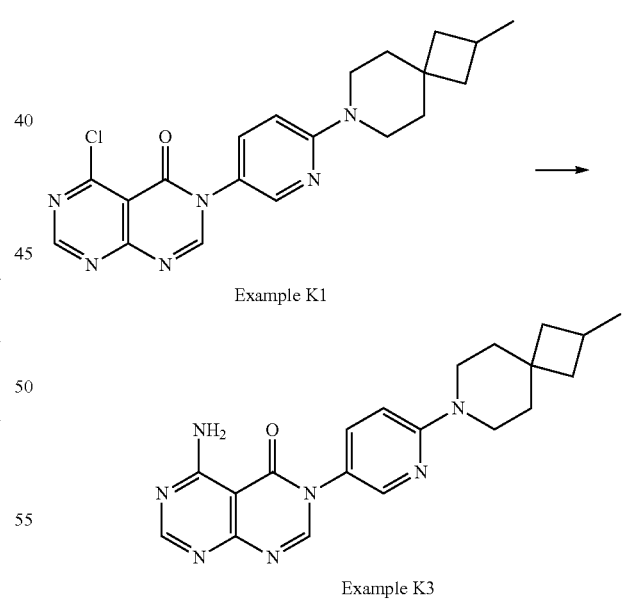

A solution of Example K1 (0.058 g, 0.14 mmol) in 0.5 M ammonia in dioxane (5 mL) was stirred for 16 hours at 50° C. After completion of reaction (monitored by TLC), solvents were evaporated under reduced pressure. The residue was taken in water and ethyl acetate was added. The layers were separated and aqueous layer was extracted with ethyl acetate. Combined organic layers were washed with water and brine, dried over anhydrous sodium sulphate and concentrated under reduced pressure. The crude product so obtained was purified by preparative TLC to afford target product Example K3 (0.015 g, 27%) as an off-white solid; LCMS: m/z 378.4 (M$^+$+1)

$^1$H NMR (400 MHz, CD$_3$OD): δ 1.10 (d, J=6.8 Hz, 3H), 1.38-1.46 (m, 2H), 1.58 (t, J=5.6 Hz, 2H), 1.69 (t, J=5.2 Hz, 2H), 20.4-2.09 (m, 2H), 2.36-2.44 (m, 1H), 3.53 (t, J=5.6 Hz, 2H), 3.61 (t, J=5.2 Hz, 2H), 6.91 (d, J=9.6 Hz, 1H), 7.59 (dd, J=2.4 Hz, J=8.8 Hz, 1H), 8.13 (d, J=2.8 Hz, 1H), 8.48 (d, J=11.2 Hz, 2H)

Following example was prepared following similar procedure as used for the preparation of Example K3 from Example K1

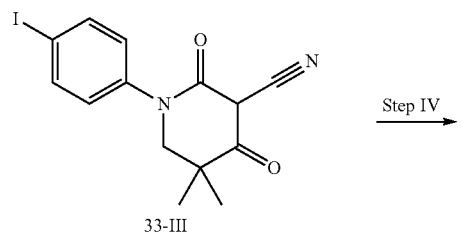

33-III

| Example No | Structure and IUPAC Name | Characterization Data |
|---|---|---|
| K4 | 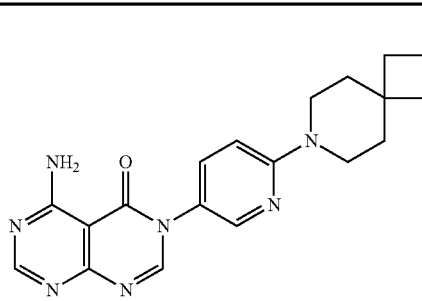<br>5-chloro-3-[6-(2-fluoro-7-azaspiro[3.5]nonan-7-yl)-3-pyridyl]pyrimido[4,5-d]pyrimidin-4-one | LCMS: m/z 382.30 (M + 1)<br>$^1$H NMR (400 MHz, CD$_3$OD): δ 1.66-1.73 (m, 2H), 1.94-1.98 (s, 2H), 2.36-2.44 (m, 2H), 3.25-3.34 (m, 2H), 4.20-4.25 (m, 2H), 5.09-5.13 (m, 2H), 5.81-5.90 (m, 1H), 6.97 (d, J = 8.8 Hz, 1H), 7.63 (dd, J = 2.8 Hz, J = 8.8 Hz, 1H), 8.16 (d, J = 2.8 Hz, 1H), 8.48 (d, J = 9.6 Hz, 2H) |

Example L1 methyl 6-[4-(4-amino-8,8-dimethyl-5-oxo-7H-pyrido[4,3-d]pyrimidin-6-yl)phenyl]spiro[2.5]oct-6-ene-2-carboxylate

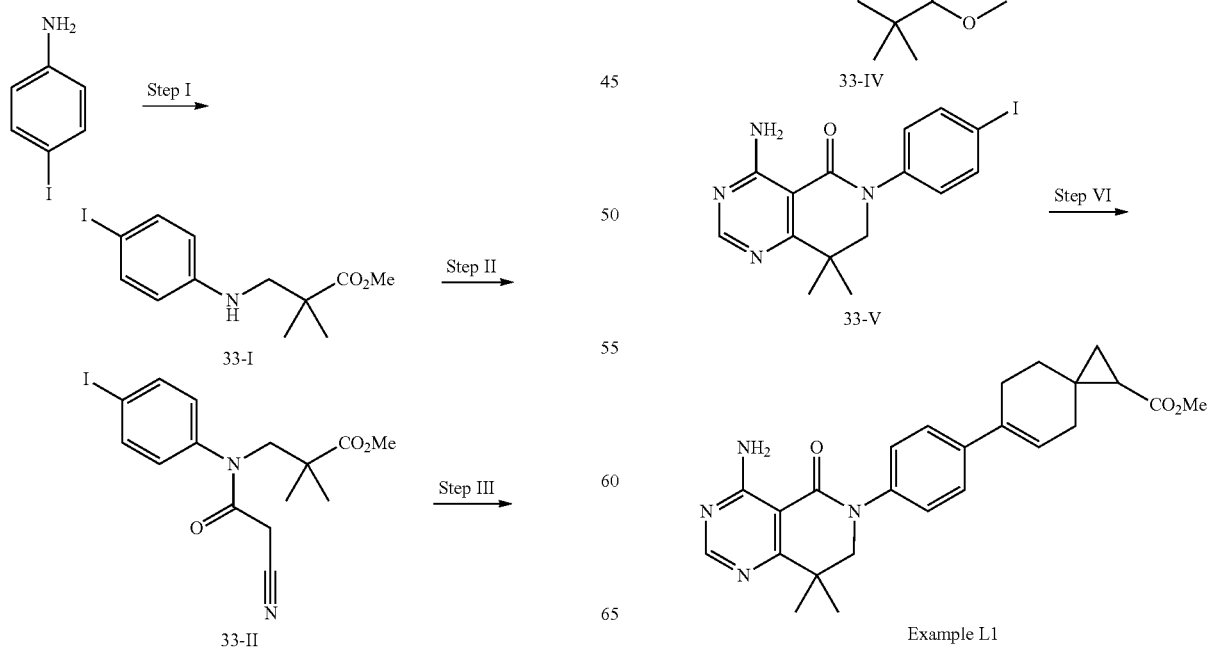

Example L1

Step I: Methyl 3-(4-iodoanilino)-2,2-dimethyl-propanoate (33-I)

To a stirred mixture of Indium chloride (3.7 g, 16.6 mmol) and formaldehyde (2.5 g, 83.2 mmol) in water (250 mL) was added 4-Iodoaniline (21.8 g, 99.9 mmol). After 30 minutes (1-methoxy-2-methyl-prop-1-enoxy)-trimethyl-silane (29 g, 166.5 mmol) was added and reaction mixture was stirred for 24 hours. After completion of reaction (monitored by TLC), reaction mixture was taken into water and ethyl acetate and layers were separated. Aqueous layer was extracted with ethyl acetate, combined organic layer was washed with water and brine, dried over anhydrous sodium sulphate and concentrated under reduced pressure. The crude product thus obtained was purified by column chromatography using 5% ethyl acetate in hexanes as eluent to afford title compound 33-I (8.8 g, 33%); LCMS: m/z 334.0 (M$^+$+1)

Step-II: Methyl 3-(N-(2-cyanoacetyl)-4-iodo-anilino)-2,2-dimethyl-propanoate (33-II)

To a solution of 2-cyanoacetic acid (8.67 g, 102 mmol) in $CH_2Cl_2$ (80 mL) was added oxalyl chloride (7.0 mL, 81.68 mmol) and one drop of DMF and the resulting reaction mixture was stirred for 3 hours at room temperature. After completion of reaction (monitored by TLC), solvent was removed under reduced pressure. Residue was taken in THF (20 mL) and was added to mixture of 33-I (6.8 g, 20.4 mmol) and diisopropyl ethyl amine (18.1 mL, 102 mmol) at 0° C. The reaction mixture was heated at 60° C. for 3 hours, cooled to room temperature and taken into water and ethyl acetate. Layers were separated and aqueous layer was extracted with ethyl acetate. Combined organic layer was washed with water and brine, dried over anhydrous sodium sulphate and concentrated under reduced pressure. The crude product so obtained was purified by column chromatography using 20% ethyl acetate in hexanes as eluent to afford title compound 33-II (3.8 g, 47%); LCMS: 401.0 (M$^+$+1)

Step-III: 1-(4-iodophenyl)-5,5-dimethyl-2,4-dioxo-piperidine-3-carbonitrile (33-III)

To a solution of 33-II (3.4 g, 8.5 mmol) in methanol (35 mL) was added DBU (1.53 mL, 10.2 mmol) and the resulting reaction mixture was heated at 80° C. for 2 hours. After completion of reaction (monitored by TLC), reaction mixture was taken into water and ethyl acetate. Layers were separated and aqueous layer was extracted with ethyl acetate. Combined organic layer was washed with water and brine, dried over anhydrous sodium sulphate and concentrated under reduced pressure. The crude product so obtained was purified by column chromatography using 5% methanol in dichloromethane as eluent to afford title compound 33-III (1.0 g, 32%); LCMS: 369.0 (M+1)

Step-IV: 1-(4-iodophenyl)-4-methoxy-3,3-dimethyl-6-oxo-2H-pyridine-5-carbonitrile (33-IV)

To a solution of 33-III (0.9 g, 2.44 mmol) in $CH_2Cl_2$ (8 mL) was added oxalyl chloride (0.65 mL, 7.58 mmol) and one drop of DMF. The resulting reaction mixture was stirred for 1 hour at room temperature. After completion of reaction (monitored by TLC), solvent was removed under reduced pressure and anhydrous methanol (10 mL) was added. The reaction mixture was heated at 80° C. for 4 hours. Solvent was removed under reduced pressure to afford title compound 33-IV (0.9 g) which was used as such for next step without any further purification; LCMS: m/z 383.1 (M++1)

Step-V: 4-amino-6-(4-iodophenyl)-8,8-dimethyl-7H-pyrido[4,3-d]pyrimidin-5-one (33-V)

To a solution of 33-IV (0.9 g, 2.35 mmol) in methanol (10 mL) was added formamidine.HCl (1.5 g, 18.8 mmol) and diisopropylethyl amine (2.43 g, 18.8 mmol). The resulting reaction mixture was heated at reflux for 1 hour. After completion of reaction (monitored by TLC), solvent was removed under reduced pressure. The crude product so obtained was purified by column chromatography using 30% ethyl acetate in hexanes as eluent to afford title compound 33-V (0.14 g, 14%); LCMS: 395.0 (M$^+$+1)

Step VI: Methyl 6-[4-(4-amino-8,8-dimethyl-5-oxo-7H-pyrido[4,3-d]pyrimidin-6-yl)phenyl]spiro[2.5]oct-6-ene-2-carboxylate (Example L1)

A mixture of 33-V (0.14 g, 0.35 mmol), Intermediate 12-VI (0.15 g, 0.53 mmol) and $K_3PO_4$ (0.22 g, 1.06 mmol) in dioxane:water (4:1, 5 mL) was degassed with argon for 30 minutes. Pd(PPh$_3$)$_4$ (0.04 g, 0.035 mmol) was added and reaction mixture was heated at 100° C. for 16 hours. After completion of reaction (monitored by TLC), the reaction mixture was taken into water and ethyl acetate. Layers were separated and aqueous layer was extracted with ethyl acetate. Combined organic layer was washed with water and brine, dried over anhydrous sodium sulphate and concentrated under reduced pressure. The crude product so obtained was purified by preparative TLC using 50% ethyl acetate in hexane as solvent system to afford title compound Example L1 (0.1 g, 65%); LCMS: 433.3 (M$^+$+1)

Example L2 was prepared from 33-V and 1-VII following similar procedure as used for the preparation of Example L1 from 33-V and Intermediate 12-VI

| Example No | Structure and IUPAC Name | Characterization Data |
|---|---|---|
| L2 | 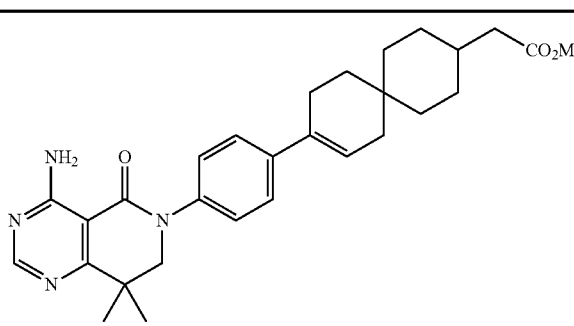<br>Methyl 2-[9-[4-(4-amino-8,8-dimethyl-5-oxo-7H-pyrido[4,3-d]pyrimidin-6-yl)phenyl]spiro[5.5]undec-9-en-3-yl]acetate | LCMS: m/z 489.4 (M$^+$ + 1) |

Example L3

Methyl 6-[4-(4-amino-8,8-dimethyl-5-oxo-7H-pyrido[4,3-d]pyrimidin-6-yl)phenyl]spiro[2.5]octane-2-carboxylate

Example L5

6-[4-(4-amino-8,8-dimethyl-5-oxo-7H-pyrido[4,3-d]pyrimidin-6-yl)phenyl]spiro[2.5]octane-2-carboxylic acid

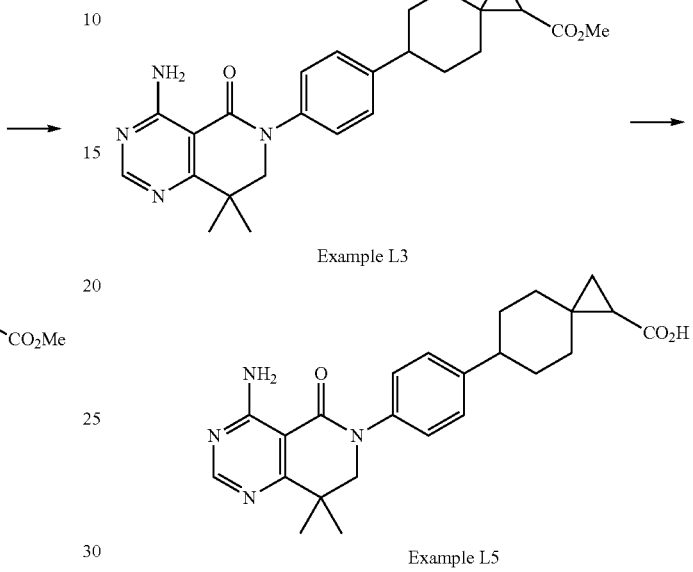

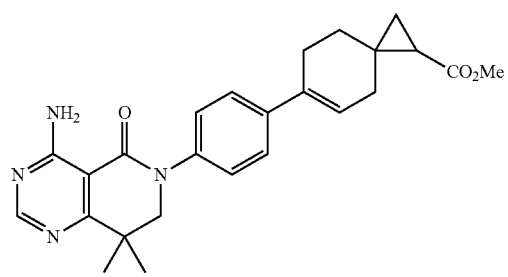

To a solution of Example L1 (0.1 g, 0.23 mmol) in ethyl acetate (3 mL) was added. Palladium hydroxide (0.01 g 10% w/w) and the reaction mixture was stirred under hydrogen atmosphere for 16 hours. After completion of reaction (monitored by TLC), the reaction mixture was filtered through a pad of celite and filtrate was concentrated under reduced pressure. The crude product so obtained was purified by preparative TLC using 50% ethyl acetate in hexanes as solvent system to afford title compound Example L3 (0.07 g, 70%); LCMS: m/z 435.3 (M$^+$+1)

Example L4 was prepared from Example L2 following similar procedure as used for the preparation of Example L3 from Example L1

To a solution of Example L3 (0.07 g, 0.23 mmol) in a mixture of THF/MeOH/H$_2$O (3:1:1, 5 mL) was added lithium hydroxide monohydrate (0.038 g, 0.92 mmol) and reaction mixture was stirred at 40° C. for 16 hours. After completion of reaction (monitored by TLC), solvent was removed under reduced pressure. The residue was taken into water and extracted with diethyl ether. The aqueous layer was acidified with 1 N HCl and extracted with ethyl acetate. Combined organic layer was washed with water and brine, dried over anhydrous sodium sulphate and concentrated under reduced pressure. The crude product so obtained was purified by preparative TLC using 80% ethyl acetate in hexanes as solvent system to afford title compound Example L5 (0.025 g, 37%); LCMS: m/z 421.3 (M$^+$+1)

| Example No | Structure and IUPAC Name | Characterization Data |
|---|---|---|
| L4 | Methyl 2-[9-[4-(4-amino-8,8-dimethyl-5-oxo-7H-pyrido[4,3-d]pyrimidin-6-yl)phenyl]spiro[5.5]undecan-3-yl]acetate | LCMS: m/z 491.4 (M$^+$ + 1) |

¹H NMR (400 MHz, DMSO-d6): δ 0.80-0.91 (m, 6H), 0.95-0.97 (m, 1H), 0.98-1.03 (m, 1H), 1.06-1.13 (m, 1H), 1.47-1.62 (m, 4H), 1.72-1.86 (m, 4H), 2.59-2.64 (m, 1H), 3.73 (s, 2H), 7.24-7.33 (m, 4H), 7.82 (d, J=4.4 Hz, 1H), 8.37 (s, 1H), 8.45 (s, 1H). 12.05 (bs, 1H)

Example L6 was prepared from Example L4 following similar procedure as used for the preparation of Example L5 from Example L3

| Example No | Structure and IUPAC Name | Characterization Data |
|---|---|---|
| L6 | 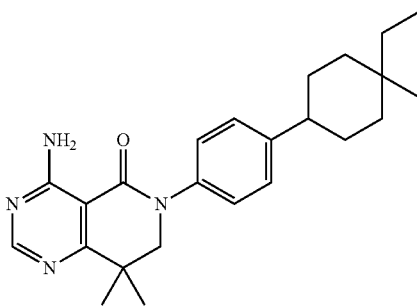<br>2-[9-[4-(4-amino-8,8-dimethyl-5-oxo-7H-pyrido[4,3-d]pyrimidin-6-yl)phenyl]spiro[5.5]undecan-3-yl]acetic acid | LCMS: m/z 477.4 (M⁺ + 1)<br>¹H NMR (400 MHz, DMS0-d6): δ 0.95-0.98 (m, 2H), 1.15-1.20 (m, 2H), 1.21-1.25 (m, 3H), 1.27 (s, 6H), 1.32-1.38 (m, 2H), 1.47-1.65 (m, 7H), 2.05-2.13 (m, 3H), 2.47-2.49 (m, 1H), 3.72 (s, 2H), 7.24-7.30 (m, 4H), 7.80 (d, J = 4.0 Hz, 1H), 8.36 (d, J = 3.2 Hz, 1H), 8.45 (s, 1H), 11.29 (s, 1H) |

The list of examples below, but not limited to these, can also be synthesized following general synthesis described above:

2-[9-[4-[(5-anilino-1,3,4-thiadiazole-2-carbonyl)amino]phenyl]spiro[5.5]undecan-3-yl]acetic acid;
6-[4-[(5-anilino-1,3,4-thiadiazole-2-carbonyl)amino]phenyl]spiro[2.5]octane-2-carboxylic acid;
6-[4-[(5-anilino-1,3,4-thiadiazole-2-carbonyl)amino]phenyl]spiro[2.5]octane-2-carboxylic acid;
2-[7-[4-[(5-phenyl-1,3,4-oxadiazole-2-carbonyl)amino]phenyl]spiro[3.5]nonan-2-yl]acetic acid;
2-[9-[4-[(5-phenyl-1,3,4-oxadiazole-2-carbonyl)amino]phenyl]spiro[5.5]undecan-3-yl]acetic acid;
2-[9-[4-[(5-anilino-4H-1,2,4-triazole-3-carbonyl)amino]phenyl]spiro[5.5]undecan-3-yl]acetic acid;
2-[9-[5-[(5-anilino-4H-1,2,4-triazole-3-carbonyl)amino]-2-pyridyl]spiro[5.5]undecan-3-yl]acetic acid;
2-[9-[5-[(5-phenoxy-4H-1,2,4-triazole-3-carbonyl)amino]-2-pyridyl]spiro[5.5]undecan-3-yl]acetic acid;
2-[9-[5-[(5-benzyl-4H-1,2,4-triazole-3-carbonyl)amino]-2-pyridyl]spiro[5.5]undecan-3-yl]acetic acid;
2-[9-[5-[(5-phenylsulfanyl-4H-1,2,4-triazole-3-carbonyl)amino]-2-pyridyl]spiro[5.5]undecan-3-yl]acetic acid;
2-[9-[5-[(5-phenylsulfanyl-1,3,4-oxadiazole-2-carbonyl)amino]-2-pyridyl]spiro[5.5]undecan-3-yl]acetic acid;
2-[9-[5-[[5-(benzenesulfonamido)-1,3,4-oxadiazole-2-carbonyl]amino]-2-pyridyl]spiro[5.5]undecan-3-yl]acetic acid;
2-[9-[5-[(5-benzyloxy-1,3,4-oxadiazole-2-carbonyl)amino]-2-pyridyl]spiro[5.5]undecan-3-yl]acetic acid;
2-[9-[5-[[5-(benzylamino)-1,3,4-oxadiazole-2-carbonyl]amino]-2-pyridyl]spiro[5.5]undecan-3-yl]acetic acid;
2-[9-[5-[[5-(benzylamino)-1,3,4-thiadiazole-2-carbonyl]amino]-2-pyridyl]spiro[5.5]undecan-3-yl]acetic acid;
2-[9-[5-[[3-(benzylamino)-1,2,4-oxadiazole-5-carbonyl]amino]-2-pyridyl]spiro[5.5]undecan-3-yl]acetic acid;
2-[9-[5-[(3-benzyloxy-1,2,4-oxadiazole-5-carbonyl)amino]-2-pyridyl]spiro[5.5]undecan-3-yl]acetic acid;
2-[9-[5-[[[5-[(3,4-difluorobenzoyl)amino]-1,3,4-oxadiazole-2-carbonyl]amino]methoxy]-2-pyridyl]spiro[5.5]undecan-3-yl]acetic acid;
2-[9-[5-[[[5-[(3,4-difluorophenyl)carbamoyl]-1,3,4-oxadiazole-2-carbonyl]amino]methoxy]-2-pyridyl]spiro[5.5]undecan-3-yl]acetic acid;
2-[9-[5-[[(5-anilino-1,3,4-oxadiazole-2-carbonyl)amino]methyl]-2-pyridyl]spiro[5.5]undecan-3-yl]acetic acid;
2-[9-[5-[[(5-anilino-1,3,4-oxadiazole-2-carbonyl)amino]methoxy]-2-pyridyl]spiro[5.5]undecan-3-yl]acetic acid;
2-[9-[[5-[(5-anilino-1,3,4-oxadiazole-2-carbonyl)amino]-2-pyridyl]oxy]spiro[5.5]undecan-3-yl]acetic acid;
2-[9-[[5-[(5-anilino-1,3,4-thiadiazole-2-carbonyl)amino]-2-pyridyl]oxy]spiro[5.5]undecan-3-yl]acetic acid;
2-[9-[[5-[(5-benzyl-1,3,4-thiadiazole-2-carbonyl)amino]-2-pyridyl]oxy]spiro[5.5]undecan-3-yl]acetic acid;
7-[[5-[(5-benzyl-1,3,4-thiadiazole-2-carbonyl)amino]-2-pyridyl]oxy]spiro[3.5]nonane-2-carboxylic acid;
7-[4-[(5-phenoxy-1,3,4-thiadiazole-2-carbonyl)amino]phenoxy]spiro[3.5]nonane-2-carboxylic acid;
7-[4-[[5-[(6-methyl-3-pyridyl)oxy]-1,3,4-thiadiazole-2 carbonyl]amino]phenyl]sulfonylspiro[3.5]nonane-2-carboxylic acid;
N-[4-(2-carbamoylspiro[3.5]nonan-7-yl)sulfonylphenyl]-5-[[6-(2,2,2-trifluoroethoxy)-3-pyridyl]amino]-1,3,4-thiadiazole-2-carboxamide;
5-(3,4-difluoroanilino)-N-[4-[[2-(pyrrolidine-1-carbonyl)-7-azaspiro[3.5]nonan-7-yl]methyl]phenyl]-1,3,4-thiadiazole-2-carboxamide;
5-(3,4-difluoroanilino)-N-[4-[(2-fluoro-7-azaspiro[3.5]nonan-7-yl)methyl]phenyl]-1,3,4-thiadiazole-2-carboxamide;
5-(3,4-difluorophenoxy)-N-[4-[(2-fluoro-7-azaspiro[3.5]nonan-7-yl)methyl]phenyl]-4H-1,2,4-triazole-3-carboxamide;
5-(3-fluorophenoxy)-N-[4-[(3-hydroxy-8-azaspiro[4.5]decan-8-yl)methyl]phenyl]-4H-1,2,4-triazole-3-carboxamide;
5-(3-fluorophenoxy)-N-[6-(3-hydroxy-8-azaspiro[4.5]decan-8-yl)-3-pyridyl]-4H-1,2,4-triazole-3-carboxamide;
N-[6-(3,3-difluoro-8-azaspiro[4.5]decan-8-yl)-3-pyridyl]-5-(3-fluorophenoxy)-4H-1,2,4-triazole-3-carboxamide;

5-[(6-chloro-3-pyridyl)oxy]-N-[6-(3,3-dimethyl-10-oxo-8-azaspiro[4.5]decan-8-yl)-3-pyridyl]-4H-1,2,4-triazole-3-carboxamide;

5-[(6-chloro-3-pyridyl)oxy]-N-[6-[2-(2,2,2-trifluoroethoxy)-7-azaspiro[3.5]nonan-7-yl]-3-pyridyl]-4H-1,2,4-triazole-3-carboxamide;

5-anilino-N-[6-[[2-(2,2,2-trifluoroethoxy)spiro[3.5]nonan-7-yl]methyl]-3-pyridyl]-4H-1,2,4-triazole-3-carboxamide;

8-[[5-[(3-fluorophenoxy)-4H-1,2,4-triazole-3-carbonyl]amino]-2-pyridyl]-9-oxaspiro[4.5]decane-3-carboxylic acid;

5-(3-fluorophenoxy)-N-[6-(3-methyl-10-oxaspiro[5.5]undecan-9-yl)-3-pyridyl]-1,3,4-oxadiazole-2-carboxamide;

9-[5-[[5-[(3-fluorophenyl)methyl]-1,3,4-oxadiazole-2-carbonyl]amino]-2-pyridyl]-10-oxaspiro[5.5]undecane-3-carboxylic acid;

9-[5-[[[5-[(3-fluorophenyl)methyl]-1,3,4-oxadiazole-2-carbonyl]amino]methyl]-2-pyridyl]-10-oxaspiro [5.5]undecane-3-carboxylic acid;

9-[5-[[5-(3-fluoroanilino)-1,3,4-oxadiazole-2-carbothioyl]amino]-2-pyridyl]-9-azaspiro[5.5]undecane-3-carboxylic acid;

3-[9-[5-[[5-(3-fluoroanilino)-1,3,4-oxadiazole-2-carbothioyl]amino]-2-pyridyl]-9-azaspiro[5.5]undecan-3-yl]propanoic acid;

3-[9-[5-[[5-(1H-indol-6-ylamino)-1,3,4-oxadiazole-2-carbothioyl]amino]-2-pyridyl]-9-azaspiro[5.5]undecan-3-yl]propanoic acid;

2-[7-[5-[[5-(3H-benzimidazol-5-ylamino)-1,3,4-oxadiazole-2-carbothioyl]amino]-2-pyridyl]-7-azaspiro[3.5]nonan-2-yl]acetic acid;

2-[7-[5-[[5-[(3-phenylbenzimidazol-5-yl)amino]-1,3,4-oxadiazole-2-carbothioyl]amino]-2-pyridyl]-7-azaspiro[3.5]nonan-2-yl]acetic acid;

2-[7-[5-[[5-(3H-benzotriazol-5-ylamino)-1,3,4-oxadiazole-2-carbothioyl]amino]-2-pyridyl]-7-azaspiro[3.5]nonan-2-yl]acetic acid;

2-[7-[5-[[5-[(2-phenylbenzotriazol-5-yl)amino]-1,3,4-oxadiazole-2-carbothioyl]amino]-2-pyridyl]-7-azaspiro[3.5]nonan-2-yl]acetic acid;

6-[5-[[5-(1H-indol-2-ylamino)-1,3,4-oxadiazole-2-carbothioyl]amino]-2-pyridyl]-6-azaspiro[2.5]octane-2-carboxylic acid;

N-[6-(2-methyl-8-azaspiro[3.5]nonan-8-yl)-3-pyridyl]-5-[(2-phenylbenzotriazol-5-yl)amino]-1,3,4-oxadiazole-2-carbothioamide;

4-[5-[[5-(cyclohexa-1,5-dien-1-ylamino)-1,3,4-oxadiazole-2-carbonyl]amino]-2-pyridyl]-4-azaspiro[5.5]undecane-9-carboxylic acid;

5-(cyclohexa-1,5-dien-1-ylamino)-N-(4-spiro[5.5]undecan-10-ylphenyl)-1,3,4-thiadiazole-2-carboxamide;

4-[4-[[5-(propylamino)-1,3,4-thiadiazole-2-carbonyl]amino]phenyl]spiro[5.5]undecane-9-carboxylic acid;

5-(cyclopentylamino)-N-[4-(2-hydroxyspiro[3.5]nonan-7-yl)phenyl]-1,3,4-oxadiazole-2-carboxamide;

7-[4-(4-amino-5-oxo-7,8-dihydropyrimido[5,4-f][1,4]oxazepin-6-yl)phenyl]spiro[3.5]nonane-2-carboxylic acid;

7-[5-(4-amino-5-oxo-7,8-dihydropyrimido[5,4-f][1,4]oxazepin-6-yl)-2-pyridyl]spiro[3.5]nonane-2-carboxylic acid;

7-[5-(4-amino-5-oxo-7,8-dihydropyrimido[5,4-f][1,4]oxazepin-6-yl)-2-pyridyl]-7-azaspiro[3.5]nonane-2-carboxylic acid;

2-[7-[4-(4-amino-5-oxo-7,8-dihydropyrimido[5,4-f][1,4]oxazepin-6-yl)phenyl]spiro[3.5]nonan-2-yl]acetic acid;

2-[7-[5-(4-amino-5-oxo-7,8-dihydropyrimido[5,4-f][1,4]oxazepin-6-yl)-2-pyridyl]spiro[3.5]nonan-2-yl]acetic acid;

7-[4-(4-amino-5-oxo-7,8-dihydropyrimido[5,4-f][1,4]oxazepin-6-yl)phenyl]spiro[3.5]nonane-2-carboxylic acid;

7-[5-(4-amino-5-oxo-7,8-dihydropyrimido[5,4-f][1,4]oxazepin-6-yl)-2-pyridyl]spiro[3.5]nonane-2-carboxylic acid;

7-[5-(4-amino-5-oxo-7,8-dihydropyrimido[5,4-f][1,4]oxazepin-6-yl)-2-pyridyl]-7-azaspiro[3.5]nonane-2-carboxylic acid;

2-[7-[4-(4-amino-5-oxo-7,8-dihydropyrimido[5,4-f][1,4]oxazepin-6-yl)phenyl]spiro[3.5]nonan-2-yl]acetic acid;

2-[7-[5-(4-amino-5-oxo-7,8-dihydropyrimido[5,4-f][1,4]oxazepin-6-yl)-2-pyridyl]spiro[3.5]nonan-2-yl]acetic acid;

2-[7-[5-(4-amino-5-oxo-7,8-dihydropyrimido[5,4-f][1,4]oxazepin-6-yl)-2-pyridyl]-7-azaspiro[3.5]nonan-2-yl]acetic acid;

2-[9-[5-[(8R)-4-amino-8-methyl-5-oxo-7,8-dihydropyrimido[5,4-f][1,4]oxazepin-6-yl]-2-pyridyl]-9-azaspiro[5.5]undecan-3-yl]acetic acid;

2-[9-[5-[(8R)-4-amino-8-methyl-5-oxo-7,8-dihydropyrimido[5,4-f][1,4]oxazepin-6-yl]-2-pyridyl]-9-azaspiro[5.5]undecan-3-yl]acetic acid;

2-[9-[4-[(7S)-4-amino-7-methyl-5-oxo-7,8-dihydropyrimido[5,4-f][1,4]oxazepin-6-yl]phenyl]spiro[5.5]undecan-3-yl]acetic acid;

2-[9-[4-(4-amino-8,8-dimethyl-5-oxo-7H-pyrimido[5,4-f][1,4]oxazepin-6-yl)phenyl]spiro[5.5]undecan-3-yl]acetic acid;

2-[9-[5-(4-amino-5-oxo-7,8-dihydropyrimido[5,4-f][1,4]oxazepin-6-yl)-2-pyridyl]-9-azaspiro[5.5]undecan-3-yl]acetic acid;

7-[5-(4-amino-2-methoxy-5-oxo-7,8-dihydropyrimido[5,4-f][1,4]oxazepin-6-yl)-2-pyridyl]-7-azaspiro[3.5]nonane-2-carboxylic acid;

8-[5-(4-amino-5-oxo-7,8-dihydropyrimido[5,4-f][1,4]oxazepin-6-yl)-2-pyridyl]spiro[8-azabicyclo[3.2.1]octane-3,2'-cyclopropane]-1'-carboxylic acid;

7-[5-(4-amino-5-oxo-2-phenoxy-7,8-dihydropyrimido[5,4-f][1,4]oxazepin-6-yl)-2-pyridyl]-7-azaspiro[3.5]nonane-2-carboxylic acid;

8-[5-(4-amino-5-oxo-7,8-dihydropyrimido[5,4-f][1,4]oxazepin-6-yl)-2-pyridyl]spiro[8-azabicyclo[3.2.1]octane-3,3'-cyclobutane]-1'-carboxylic acid;

8-[5-(4-amino-2-methyl-5-oxo-7,8-di hydropyrimido[5,4-f][1,4]oxazepin-6-yl)-2-pyridyl]spiro[8-azabicyclo[3.2.1]octane-3,3'-cyclobutane]-1'-carboxylic acid;

8-[5-(4-amino-8,8-dimethyl-5-oxo-7H-pyrido[4,3-d]pyrimidin-6-yl)-2-pyridyl]spiro[8-azabicyclo[3.2.1]octane-3,3'-cyclobutane]-1'-carboxylic acid;

8-[5-(4-amino-8,8-dimethyl-5-oxo-7H-pyrido[4,3-d]pyrimidin-6-yl)-2-pyridyl]spiro[8-azabicyclo[3.2.1]octane-3,2'-cyclopropane]-1'-carboxylic acid;

7-[5-(4-amino-8,8-dimethyl-5-oxo-7H-pyrido[4,3-d]pyrimidin-6-yl)-2-pyridyl]spiro[3.5]nonane-2-carboxylic acid;

2-[9-[5-(4-amino-8,8-dimethyl-5-oxo-7H-pyrido[4,3-d]pyrimidin-6-yl)-2-pyridyl]spiro[5.5]undecan-3-yl]acetic acid;

2-[7-[5-(4-amino-8,8-dimethyl-5-oxo-7H-pyrido[4,3-d]pyrimidin-6-yl)-2-pyridyl]spiro[3.5]nonan-2-yl]acetic acid;

2-[7-[5-(4-amino-2,8,8-trimethyl-5-oxo-7H-pyrido[4,3-d]pyrimidin-6-yl)-2-pyridyl]spiro[3.5]nonan-2-yl]acetic acid;

2-[7-[5-(4-amino-8-methyl-5-oxo-pyrimido[4,5-d] pyridazin-6-yl)-2-pyridyl]spiro[3.5]nonan-2-yl]acetic acid;

7-[5-(4-amino-8-methyl-5-oxo-pyrimido[4,5-d]pyridazin-6-yl)-2-pyridyl]-7-azaspiro[3.5]nonane-2-carboxylic acid;

7-[4-(4-amino-8-methyl-5-oxo-pyrimido[4,5-d]pyridazin-6-yl)phenyl]spiro[3.5]nonane-2-carboxylic acid;

6-[5-(4-amino-8-methyl-5-oxo-pyrimido[4,5-d]pyridazin-6-yl)-2-pyridyl]spiro[2.5]octane-2-carboxylic acid;

2-[9-[5-(4-amino-8-methyl-5-oxo-pyrimido[4,5-d] pyridazin-6-yl)-2-pyridyl]spiro[5.5]undecan-3-yl]acetic acid;

8-[5-(4-amino-8-methyl-5-oxo-pyrimido[4,5-d]pyridazin-6-yl)-2-pyridyl]spiro[8-azabicyclo[3.2.1]octane-3,2'-cyclopropane]-1'-carboxylic acid;

8-[5-(4-amino-8-methyl-5-oxo-pyrimido[4,5-d]pyridazin-6-yl)-2-pyridyl]spiro[8-azabicyclo[3.2.1]octane-3,3'-cyclobutane]-1'-carboxylic acid;

7-[5-[4-amino-8-methyl-5-oxo-2-(trifluoromethyl)pyrimido [4,5-d]pyridazin-6-yl]-2-pyridyl]-7-azaspiro[3.5]nonane-2-carboxylic acid;

2-[7-[5-(5-amino-4-oxo-pyrimido[4,5-d]pyrimidin-3-yl)-2-pyridyl]-7-azaspiro[3.5]nonan-2-yl]acetic acid;

2-[7-[4-(5-amino-4-oxo-pyrimido[4,5-d]pyrimidin-3-yl) phenyl]spiro[3.5]nonan-2-yl]acetic acid;

2-[9-[4-(5-amino-4-oxo-pyrimido[4,5-d]pyrimidin-3-yl) phenyl]spiro[5.5]undecan-3-yl]acetic acid;

2-[9-[5-(5-amino-4-oxo-pyrimido[4,5-d]pyrimidin-3-yl)-2-pyridyl]-9-azaspiro[5.5]undecan-3-yl]acetic acid;

8-[5-(5-amino-4-oxo-pyrimido[4,5-d]pyrimidin-3-yl)-2-pyridyl]spiro[8-azabicyclo[3.2.1]octane-3,3'-cyclobutane]-1'-carboxylic acid;

8-[5-(5-amino-2-methyl-4-oxo-pyrimido[4,5-d]pyrimidin-3-yl)-2-pyridyl]spiro[8-azabicyclo[3.2.1]octane-3,3'-cyclobutane]-1'-carboxylic acid;

8-[5-(4-amino-2-methoxy-7-methyl-5-oxo-pyrimido[4,5-d] pyrimidin-6-yl)-2-pyridyl]spiro[8-azabicyclo[3.2.1]octane-3,3'-cyclobutane]-1'-carboxylic acid;

8-[5-(4-amino-7-methyl-5-oxo-2-phenoxy-pyrimido[4,5-d] pyrimidin-6-yl)-2-pyridyl]spiro[8-azabicyclo[3.2.1]octane-3,3'-cyclobutane]-1'-carboxylic acid;

2-[9-[4-(4-amino-5-oxo-8,9-dihydro-7H-pyrimido[4,5-b][1,5]oxazocin-6-yl)phenyl]spiro[5.5]undecan-3-yl]acetic acid;

7-[4-(4-amino-5-oxo-8,9-dihydro-7H-pyrimido[4,5-b][1,5] oxazocin-6-yl)phenyl]spiro[3.5]nonane-2-carboxylic acid;

2-[7-[4-(4-amino-5-oxo-8,9-dihydro-7H-pyrimido[4,5-b][1,5]oxazocin-6-yl)phenyl]spiro[3.5]nonan-2-yl]acetic acid;

7-[4-(4-amino-5-oxo-8,9-dihydro-7H-pyrimido[4,5-b][1,5] oxazocin-6-yl)phenyl]-7-azaspiro[3.5]nonane-2-carboxylic acid;

2-[7-[4-(4-amino-5-oxo-8,9-dihydro-7H-pyrimido[4,5-b][1,5]oxazocin-6-yl)phenyl]-7-azaspiro[3.5]nonan-2-yl]acetic acid;

7-[4-(4-amino-9-methyl-5-oxo-8,9-dihydro-7H-pyrimido[4,5-b][1,5]oxazocin-6-yl)phenyl]spiro[3.5]nonane-2-carboxylic acid;

7-[4-(4-amino-8-methyl-5-oxo-8,9-dihydro-7H-pyrimido[4,5-b][1,5]oxazocin-6-yl)phenyl]spiro[3.5]nonane-2-carboxylic acid;

4-amino-6-[4-(2,2-difluorospiro[3.5]nonan-7-yl)phenyl]-8,9-dihydro-7H-pyrimido[4,5-b][1,5]oxazocin-5-one;

4-amino-6-[4-(2-methylspiro[3.5]nonan-7-yl)phenyl]-8,9-dihydro-7H-pyrimido[4,5-b][1,5]oxazocin-5-one;

2-[9-[4-(9-amino-1,1-dioxo-3,4-dihydropyrimido[4,5-b][1,4,5]oxathiazepin-2-yl)phenyl]spiro[5.5]undecan-3-yl] acetic acid;

2-[9-[4-(9-amino-1,1-dioxo-3,4-dihydropyrimido[4,5-b][1,4,5]oxathiazepin-2-yl)phenyl]spiro[5.5]undecan-3-yl] acetic acid;

2-[9-[4-(9-amino-1,1-dioxo-3,4-dihydropyrimido[4,5-b][1,4,5]oxathiazepin-2-yl)phenyl]-9-azaspiro[5.5]undecan-3-yl]acetic acid;

7-[4-(9-amino-1,1-dioxo-3,4-dihydropyrimido[4,5-b][1,4,5] oxathiazepin-2-yl)phenyl]-7-azaspiro[3.5]nonane-2-carboxylic acid;

2-[7-[4-(9-amino-1,1-dioxo-3,4-dihydropyrimido[4,5-b][1,4,5]oxathiazepin-2-yl)phenyl]spiro[3.5]nonan-2-yl]acetic acid;

2-[4-(2,2-difluorospiro[3.5]nonan-7-yl)phenyl]-1,1-dioxo-3,4-dihydropyrimido[4,5-b][1,4,5]oxathiazepin-9-amine;

2-[9-[4-(4-amino-7,7-dimethyl-5-oxo-pyrrolo[3,4-d]pyrimidin-6-yl)phenyl]spiro[5.5]undecan-3-yl]acetic acid;

6-[4-(4-amino-7,7-dimethyl-5-oxo-pyrrolo[3,4-d]pyrimidin-6-yl)phenyl]spiro[2.5]octane-2-carboxylic acid;

6-[4-(4'-amino-5'-oxo-spiro[cyclopropane-1,7'-pyrrolo[3,4-d]pyrimidine]-6'-yl)phenyl]spiro[2.5]octane-2-carboxylic acid; and 7-[4-(4'-amino-5'-oxo-spiro[cyclopropane-1,7'-pyrrolo[3,4-d]pyrimidine]-6'-yl)phenyl]spiro[3.5]nonane-2-carboxylic acid In Vitro hDGAT1 Assays:

Measurement of Membrane-Based Recombinant hDGAT1 Inhibitory Activity Using LCMS Method (Method A)

The determination of recombinant human DGAT1 (hDGAT1) activity was carried, out using a LC-MS-based assay system based on literature report [*Journal of Lipid Research* (2010), 51(12), 3559-3567]. In brief, baculovirus expression system (Sf9) membranes expressing hDGAT1 were employed for the membrane based assay. DGAT1 activity in membrane preparations was assayed in buffer (0.1 M Tris (pH 7.5), 250 mM sucrose, 0.1% BSA, 1 mM EDTA, 10 mM $MgCl_2$) containing 40 µM oleoyl-CoA, 40 µM DCG, and 100 nM of [1,3-di-heptadecanoyl-2-(10Z-heptadecanoyl)-sn-glycerol-d5) serving as an internal standard in a 96-well plate in the presence of different concentrations of compounds. The final DMSO concentration in the reaction was 0.1%. The plates were incubated for 1 hour at room temperature. The formed TG product was separated from the sample solution by butanol extraction followed by evaporation of organic phase and reconstituting the samples in Isopropanol:THF (90:10). An Applied Biosystems API3200 LC/MS system interfaced with a triplequadrupole mass spectrophotometer through a turbo ion spray source was employed for separation of the analytes using a Hi-Purity ADVANCE column eluted with 10 mM ammonium formate: isopropanol (80:20) at a flow rate of 0.4 mL/min. The potencies of DGAT-1 inhibition for the compounds were determined by calculating the $IC_{50}$ values, based on percent inhibition calculated on the basis of area ratio of product (TG) and internal standard (IS).

Measurement of Membrane-Based Recombinant hDGAT1 Inhibitory Activity Using Radiometry Method (Method B):

The determination of recombinant human DGAT1 (hDGAT1) activity was carried out using a Radiometry based assay system based on literature report [*European Journal of Medicinal Chemistry* (2012), August; 54:324-42]. In brief, baculovirus expression system (Sf9) membranes expressing hDGAT1 were employed for the membrane based assay.

Radiometry hDGAT1 assays were performed using 1 µg of the hDGAT1, pre-incubated with 100 µl of the assay buffer [100 mM Tris-HCl (pH 7.5), 250 mM sucrose, and 1.25 mg/ml fatty acid free BSA] containing a known concentration of the inhibitor and supplemented with 300 µM of 1,2-dioleoylglycerol. The hDGAT1 reaction was initiated following an addition of 16.8 nCi of [14C]-oleoyl CoA. The reaction was terminated after 30 minutes of incubation at 37° C. using 300 µl alkaline ethanol stop solution mix (AESSM) [12.5% of 100% non-denatured ethanol, 10% deionized water, 2.5% NaOH, and 75% stop solution (78.4% isopropanol, 19.6% n-heptane, 2% deionized water)]. The $^{14}C$ triglyceride formed in this reaction was extracted using 600 µl of heptane. 250 µl of this extracted heptane was added to scintillation fluid and subjected to radioactivity measurement.

Measurement of Cell Based hDGAT1 Inhibitory Activity:

HEK293H cells were seeded in a 96-well poly-D-lysine plate at a density of 80000 cells per well. Following day, cells were washed with assay buffer-DMEM high glucose supplemented with 25 mM Hepes (pH7.5) carrying 0.25% fatty acid-free bovine serum. The cells were starved in assay buffer at 37° C./5% CO2 followed by removal of media and treatment with appropriate concentrations of the test compound at a final concentration of 0.2% DMSO for 20 min. 13C-Oleic acid pre-complexed with BSA (300 uM) was added and cells were incubated further at 370 C/5% CO2 for 120 min. The supernatant was removed and the cells were allowed to air dry briefly. The extraction solvent (90% isopropyl alcohol and 10% tetrahydrofuran with 20 nM of the internal standard [1,3-di-heptadecanoyl-2-(10Z-heptadecanoyl)-sn-glycerol-d5] was added to the cells, and allowed to shake at room temperature for 15 min. The extract was then transferred to glass vials for LC-MS analysis. An Applied Biosystems API3200 LC/MS system interfaced with a triplequadrupole mass spectrophotometer through a Turbo ion spray source was employed for the LC separation of the analytes using a Hi-Purity ADVANCE column eluted with 10 mM ammonium formate in IPA-H2O (80:20) at a flow rate of 0.4 mL/min. A characteristic in-source fragment ion m/z 639.7 formed from the precursor ion $^{13}C$-54-triolein (m/z 956.8, ammonium adduct) at a collision energy of 30 and declustering potential 70 was monitored. $IC_{50}$ values of the compounds were determined based on percent inhibition calculated on the basis of area ratio of product (TG) and internal standard (IS).

Compounds of present disclosure are considered to be active if $IC_{50}$ of hDGAT1 enzyme inhibition is between 0.01 nM to 100 µM, more specifically below 10 µM. Data for representative compounds of the present disclosure are given below in Table 2:

TABLE 2 hDGAT1 membrane based and HEK293H cell based $IC_{50}$ values:

| Example No | hDGAT1 membrane $IC_{50}$ (nM) | HEK293H cell $IC_{50}$ (nM) |
|---|---|---|
| A9 | — | 31 |
| A12 | — | 22 |
| B1 | 22 | 17.6 |
| B2 | 30 | 15 |
| B3 | 48 | 15 |
| B4 | 117 | 16 |
| B5 | 1300 | — |
| B6 | 28 | 12 |
| B7 | 23 | 10 |
| B8 | 79 | 21 |
| B9 | 11 | 7.8 |
| B10 | 13 | 8.6 |

TABLE 2-continued hDGAT1 membrane based and HEK293H cell based $IC_{50}$ values:

| Example No | hDGAT1 membrane $IC_{50}$ (nM) | HEK293H cell $IC_{50}$ (nM) |
|---|---|---|
| B11 | 26 | 6 |
| B12 | 20 | 20 |
| B13 | — | 47 |
| B14 | — | 21 |
| B15 | — | 10 |
| B16 | — | 16 |
| B17 | 92 | 54 |
| B18 | 59 | 54 |
| B19 | 59 | 68 |
| B20 | 87 | 62 |
| B21 | — | 64 |
| B22 | 53 | 465 |
| B23 | 7.6 | 8.8 |
| B24 | — | 49% Inhibition at 1 uM |
| B25 | 4.5 | 20 |
| B26 | — | 37% Inhibition at 1 uM |
| B27 | 167 | 47 |
| B28 | 92 | 48 |
| B29 | 175 | 35 |
| B30 | 130 | 450 |
| B31 | — | 37 |
| [(−) - isomer of B3] | 64 | 24 |
| [(+) - isomer of B3] | 75 | 23 |
| B32 | 6.9* | — |
| B33 | 26* | — |
| B34 | 24* | — |
| B35 | 19* | — |
| B36 | 25* | — |
| B37 | 22* | — |
| B38 | 50* | — |
| B39 | 47* | — |
| B40 | 20* | — |
| C1 | — | 86% Inhibition at 1 uM |
| C2 | — | 88% Inhibition at 1 uM |
| C3 | — | 84% Inhibition at 1 uM |
| C4 | — | 84% Inhibition at 1 uM |
| C5 | — | 90% Inhibition at 1 uM |
| C6 | — | 33 |
| C7 | — | — |
| C8 | — | 11 |
| C9 | — | 92% Inhibition at 1 µM |
| D1 | — | 85 |
| D2 | — | 64 |
| D3 | — | 32 |
| D4 | — | 26 |
| D5 | — | 4 |
| D6 | — | 4.2 |
| D7 | — | 87% Inhibition at 1 uM |
| D8 | — | 77% Inhibition at 1 uM |
| D9 | — | 91% Inhibition at 1 uM |
| E1 | — | 10 |
| F1 | — | 44 |
| F2 | — | 19 |
| H3 | 42 | 15 |
| I3 | 54 | 26 |
| I4 | 94 | 35 |
| J2 | 2500 | — |
| K4 | — | 19% inhibition at 1 µM |
| L5 | — | No inhibition at 1 µM |
| L6 | — | 3% inhibition at 1 µM |

*hDGAT1 membrane $IC_{50}$ was determined using Method B

Although the subject matter has been described in considerable detail with reference to certain preferred embodiments thereof, other embodiments are possible. As such, the spirit and scope of the appended claims should not be limited to the description of the preferred embodiment contained therein.

We claim:

1. A compound of Formula (Ia)

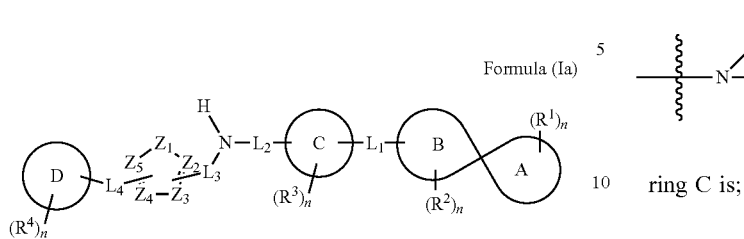

Formula (Ia)

or its tautomers, polymorphs, stereoisomers, solvates, hydrates, N-Oxides, co-crystals or a pharmaceutically acceptable salts thereof, wherein, rings A and B together form a spiro ring system which is selected from the group consisting of

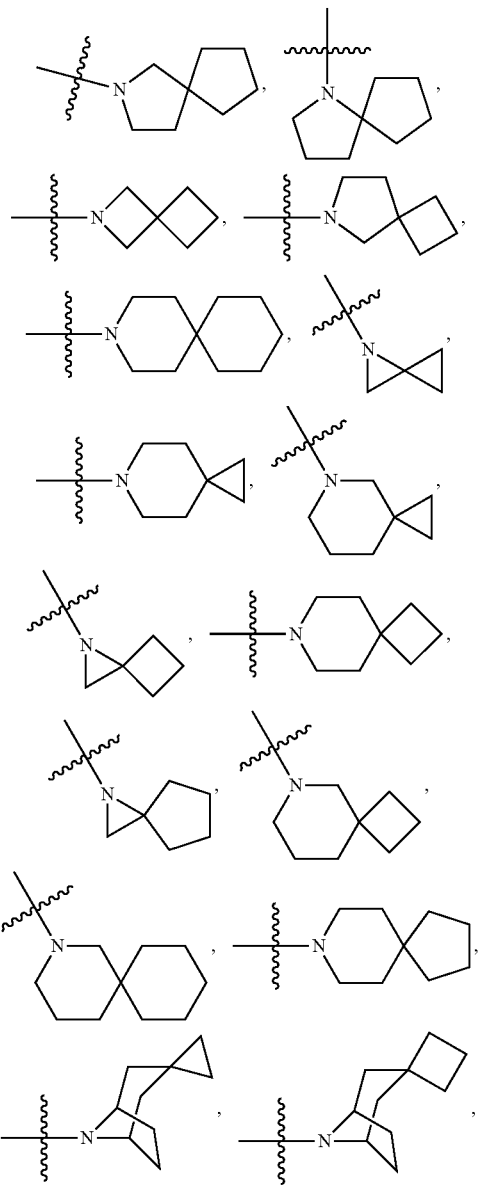

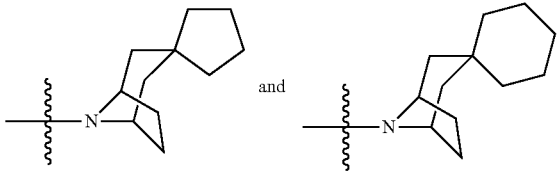

ring C is;

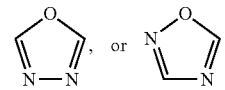 [SMILES: c1nnco1 ; c1ncon1]

ring D is;

$L_1$ and $L_2$ are absent;

$L_3$ and $L_4$ are independently selected from the group consisting of —O—, —S(O)$_p$—, —N(R$^6$)—, —C(O)—, —C(S)— and —(CR$^a$R$^b$)—;

$Z_1$, $Z_2$, $Z_3$, $Z_4$ and $Z_5$ together form a ring which is $R^1$ and $R^4$ are independently selected from the group consisting of hydrogen, halo, cyano, nitro, —(CR$^a$R$^b$)$_n$OR$^7$, —(CR$^a$R$^b$)$_n$C(O)R$^7$, —(CR$^a$R$^b$)$_n$SR$^7$, —(CR$^a$R$^b$)$_n$COOR$^7$, —(CR$^a$R$^b$)$_n$NR$^8$R$^9$, —(CR$^a$R$^b$)$_n$C(O)NR$^8$R$^9$, —(CR$^a$R$^b$)$_n$NR$^8$C(O)OR$^7$, —(CR$^a$R$^b$)$_n$NR$^8$C(O)NR$^8$R$^9$, —NR$^8$S(O)$_2$R$^7$, —S(O)$_p$R$^7$, —SO$_3$H, —S(O)$_2$NR$^8$R$^9$, azido, oxo, thiocarbonyl, C$_{1-6}$alkyl, C$_{2-6}$alkenyl, C$_{2-6}$alkynyl, cyanoalkyl, cyanoalkylcarbonyl, haloalkyl, perhaloalkyl, haloalkoxy, perhaloalkoxy, alkoxyalkoxy, and alkoxyalkoxyalkyl, wherein each substituent is unsubstituted or substituted with 1, 2, or 3 substituents independently selected from alkyl, halogen, haloalkyl, perhaloalkyl, haloalkoxy, perhaloalkoxy, cyano —(CR$^a$R$^b$)$_n$OR$^7$, —(CR$^a$R$^b$)$_n$COOR$^7$, —(CR$^a$R$^b$)—NR$^8$R$^9$, —(CR$^a$R$^b$)$_n$C(O)NR$^8$R$^9$, —S(O)$_p$R$^7$ or —SO$_3$H;

$R^2$ and $R^3$ are hydrogen;

$R^6$ is hydrogen, cyano, alkyl or haloalkyl;

$R^7$ is hydrogen, alkyl, haloalkyl, aminocarbonyl, cycloalkyl, cycloalkylalkyl, aryl, arylalkyl, heteroaryl, heteroarylalkyl, heterocyclyl or heterocyclylalkyl;

$R^8$ and $R^9$ are independently selected from the group consisting of hydrogen, alkyl, haloalkyl, —(CR$^a$R$^b$)$_n$OR$^7$, —(CR$^a$R$^b$)$_n$C(O)R$^7$, aryl, arylalkyl, heteroaryl, heteroarylalkyl, cycloalkyl, cycloalkylalkyl, heterocyclyl and heterocyclylalkyl, $R^a$ and $R^b$ are independently selected from the group consisting of hydrogen, —OR$^7$, halogen, haloalkyl, perhaloalkyl and alkyl;

p=0-2; and n=0-4.

2. A compound according to claim 1, or its tautomers, polymorphs, stereoisomers, solvates, hydrates, N-Oxides, co-crystals or a pharmaceutically acceptable salts thereof, wherein the compound is selected from a group consisting of:

methyl 2-[9-[5-[(5-anilino-1,3,4-oxadiazole-2-carbonyl)amino]-2-pyridyl]-9-azaspiro [5.5]undecan-3-yl]acetate;
methyl 2-[9-[5-[[5-(3,4-difluoroanilino)-1,3,4-oxadiazole-2-carbonyl]amino]-2-pyridyl]-9-azaspiro[5.5]undecan-3-yl]acetate;
ethyl 2-[7-[5-[(5-anilino-1,3,4-oxadiazole-2-carbonyl)amino]-2-pyridyl]-7-azaspiro [3.5]nonan-2-yl]acetate;
ethyl 7-[5-[[5-(3,4-difluoroanilino)-1,3,4-oxadiazole-2-carbonyl]amino]-2-pyridyl]-7-azaspiro[3.5]nonane-2-carboxylate;
ethyl 7-[5-[[5-[[6-(2,2,2-trifluoroethoxy)-3-pyridyl]amino]-1,3,4-oxadiazole-2-carbonyl]amino]-2-pyridyl]-7-azaspiro[3.5]nonane-2-carboxylate;
ethyl 6-[5-[(5-anilino-1,3,4-oxadiazole-2-carbonyl)amino]-2-pyridyl]-6-azaspiro [2.5]octane-2-carboxylate;
ethyl 6-[5-[[5-(4-fluoroanilino)-1,3,4-oxadiazole-2-carbonyl]amino]-2-pyridyl]-6-azaspiro [2.5]octane-2-carboxylate;
ethyl 6-[5-[[5-(3,4-difluoroanilino)-1,3,4-oxadiazole-2-carbonyl]amino]-2-pyridyl]-6-azaspiro [2.5]octane-2-carboxylate;
ethyl 6-[5-[[5-(4-methylanilino)-1,3,4-oxadiazole-2-carbonyl]amino]-2-pyridyl]-6-azaspiro [2.5]octane-2-carboxylate;
ethyl 6-[5-[[5-[[6-(2,2,2-trifluoroethoxy)-3-pyridyl]amino]-1,3,4-oxadiazole-2-carbonyl]amino]-2-pyridyl]-6-azaspiro[2.5]octane-2-carboxylate;
ethyl 7-[5-[[5-(3,4-difluoroanilino)-1,3,4-oxadiazole-2-carbonyl]amino]-2-pyridyl]-7-azaspiro[2.5]octane-2-carboxylate;
ethyl 6-[4-[(5-anilino-1,3,4-oxadiazole-2-carbonyl)amino]phenyl]-6-azaspiro [2.5]octane-2-carboxylate;
ethyl 6-[4-[[5-(3,4-difluoroanilino)-1,3,4-oxadiazole-2-carbonyl]amino]phenyl]-6-azaspiro[2.5]octane-2-carboxylate;
ethyl 6-[4-[[5-(4-fluoroanilino)-1,3,4-oxadiazole-2-carbonyl]amino]phenyl]-6-azaspiro [2.5]octane-2-carboxylate;
ethyl 8-[5-[[5-(3,4-difluoroanilino)-1,3,4-oxadiazole-2-carbonyl]amino]-2-pyridyl]spiro[8-azabicyclo [3.2.1]octane-3,2'-cyclopropane]-1'-carboxylate;
ethyl 8-[5-[[5-(3,4-difluoroanilino)-1,3,4-oxadiazole-2-carbonyl]amino]-2-pyridyl]spiro[8-azabicyclo [3.2.1]octane-3,3'-cyclobutane]-1'-carboxylate;
ethyl 2-[7-[5-[[5-(3,4-difluoroanilino)-1,3,4-oxadiazole-2-carbonyl]amino]-2-pyridyl]-7-azaspiro[3.5]nonan-2-yl]acetate;
ethyl 2-[7-[5-[[5-(2-fluoroanilino)-1,3,4-oxadiazole-2-carbonyl]amino]-2-pyridyl]-7-azaspiro[3.5]nonan-2-yl]acetate;
ethyl 7-[5-[(5-anilino-1,3,4-oxadiazole-2-carbonyl)amino]-2-pyridyl]-7-azaspiro [3.5]nonane-2-carboxylate;
ethyl 7-[5-[[5-(3-fluoroanilino)-1,3,4-oxadiazole-2-carbonyl]amino]-2-pyridyl]-7-azaspiro [3.5]nonane-2-carboxylate;
ethyl 7-[5-[[5-(4-chloroanilino)-1,3,4-oxadiazole-2-carbonyl]amino]-2-pyridyl]-7-azaspiro [3.5]nonane-2-carboxylate;
ethyl 7-[5-[[5-[3-(trifluoromethyl)anilino]-1,3,4-oxadiazole-2-carbonyl]amino]-2-pyridyl]-7-azaspiro[3.5]nonane-2-carboxylate;
ethyl 2-[7-[4-[[5-(2-fluoroanilino)-1,3,4-oxadiazole-2-carbonyl]amino]phenyl]-7-azaspiro [3.5]nonan-2-yl]acetate;
ethyl 2-[7-[4-[(5-anilino-1,3,4-oxadiazole-2-carbonyl)amino]phenyl]-7-azaspiro [3.5]nonan-2-yl]acetate;
ethyl 2-[7-[4-[[5-(3,4-difluoroanilino)-1,3,4-oxadiazole-2-carbonyl]amino]phenyl]-7-azaspiro [3.5]nonan-2-yl]acetate;
ethyl 7-[4-[(5-anilino-1,3,4-oxadiazole-2-carbonyl)amino]phenyl]-7-azaspiro [3.5]nonane-2-carboxylate;
ethyl 7-[4-[[5-(3,4-difluoroanilino)-1,3,4-oxadiazole-2-carbonyl]amino]phenyl]-7-azaspiro [3.5]nonane-2-carboxylate;
ethyl 2-[6-[5-[[5-(2-fluoroanilino)-1,3,4-oxadiazole-2-carbonyl]amino]-2-pyridyl]-6-azaspiro[3.3]heptan-2-yl]acetate;
ethyl 2-[6-[5-[(5-anilino-1,3,4-oxadiazole-2-carbonyl)amino]-2-pyridyl]-6-azaspiro [3.3]heptan-2-yl]acetate;
ethyl 2-[6-[5-[[5-(3,4-difluoroanilino)-1,3,4-oxadiazole-2-carbonyl]amino]-2-pyridyl]-6-azaspiro[3.3]heptan-2-yl]acetate;
2-[9-[5-[(5-anilino-1,3,4-oxadiazole-2-carbonyl)amino]-2-pyridyl]-9-azaspiro[5.5]undecan-3-yl]acetate;
2-[9-[5-[[5-(3,4-difluoroanilino)-1,3,4-oxadiazole-2-carbonyl]amino]-2-pyridyl]-9-azaspiro[5.5]undecan-3-yl]acetate;
2-[7-[5-[(5-anilino-1,3,4-oxadiazole-2-carbonyl)amino]-2-pyridyl]-7-azaspiro[3.5]nonan-2-yl]acetate;
7-[5-[[5-(3,4-difluoroanilino)-1,3,4-oxadiazole-2-carbonyl]amino]-2-pyridyl]-7-azaspiro[3.5]nonane-2-carboxylate;
7-[5-[[5-[[6-(2,2,2-trifluoroethoxy)-3-pyridyl]amino]-1,3,4-oxadiazole-2-carbonyl]amino]-2-pyridyl]-7-azaspiro[3.5]nonane-2-carboxylate;
6-[5-[(5-anilino-1,3,4-oxadiazole-2-carbonyl)amino]-2-pyridyl]-6-azaspiro[2.5]octane-2-carboxylate;
6-[5-[[5-(4-fluoroanilino)-1,3,4-oxadiazole-2-carbonyl]amino]-2-pyridyl]-6-azaspiro [2.5]octane-2-carboxylate;
6-[5-[[5-(3,4-difluoroanilino)-1,3,4-oxadiazole-2-carbonyl]amino]-2-pyridyl]-6-azaspiro [2.5]octane-2-carboxylate;
6-[5-[[5-(4-methylanilino)-1,3,4-oxadiazole-2-carbonyl]amino]-2-pyridyl]-6-azaspiro [2.5]octane-2-carboxylate;
6-[5-[[5-[[6-(2,2,2-trifluoroethoxy)-3-pyridyl]amino]-1,3,4-oxadiazole-2-carbonyl]amino]-2-pyridyl]-6-azaspiro[2.5]octane-2-carboxylate;
7-[5-[[5-(3,4-difluoroanilino)-1,3,4-oxadiazole-2-carbonyl]amino]-2-pyridyl]-7-azaspiro[2.5]octane-2-carboxylate;
6-[4-[(5-anilino-1,3,4-oxadiazole-2-carbonyl)amino]phenyl]-6-azaspiro[2.5]octane-2-carboxylate;
6-[4-[[5-(3,4-difluoroanilino)-1,3,4-oxadiazole-2-carbonyl]amino]phenyl]-6-azaspiro[2.5]octane-2-carboxylate;
6-[4-[[5-(4-fluoroanilino)-1,3,4-oxadiazole-2-carbonyl]amino]phenyl]-6-azaspiro [2.5]octane-2-carboxylate;
8-[5-[[5-(3,4-difluoroanilino)-1,3,4-oxadiazole-2-carbonyl]amino]-2-pyridyl]spiro[8-azabicyclo[3.2.1]octane-3,2'-cyclopropane]-1'-carboxylate;
8-[5-[[5-(3,4-difluoroanilino)-1,3,4-oxadiazole-2-carbonyl]amino]-2-pyridyl]spiro[8-azabicyclo[3.2.1]octane-3,3'-cyclobutane]-1'-carboxylate;
2-[7-[5-[[5-(3,4-difluoroanilino)-1,3,4-oxadiazole-2-carbonyl]amino]-2-pyridyl]-7-azaspiro[3.5]nonan-2-yl]acetate;
2-[7-[5-[[5-(2-fluoroanilino)-1,3,4-oxadiazole-2-carbonyl]amino]-2-pyridyl]-7-azaspiro[3.5]nonan-2-yl]acetate;

7-[5-[(5-anilino-1,3,4-oxadiazole-2-carbonyl)amino]-2-pyridyl]-7-azaspiro[3.5]nonane-2-carboxylate;

7-[5-[[5-(3-fluoroanilino)-1,3,4-oxadiazole-2-carbonyl]amino]-2-pyridyl]-7-azaspiro [3.5]nonane-2-carboxylate;

7-[5-[[5-(4-chloroanilino)-1,3,4-oxadiazole-2-carbonyl]amino]-2-pyridyl]-7-azaspiro [3.5]nonane-2-carboxylate;

7-[5-[[5-[3-(trifluoromethyl)anilino]-1,3,4-oxadiazole-2-carbonyl]amino]-2-pyridyl]-7-azaspiro[3.5]nonane-2-carboxylate;

2-[7-[4-[[5-(2-fluoroanilino)-1,3,4-oxadiazole-2-carbonyl]amino]phenyl]-7-azaspiro [3.5]nonan-2-yl]acetate;

2-[7-[4-[(5-anilino-1,3,4-oxadiazole-2-carbonyl)amino]phenyl]-7-azaspiro[3.5]nonan-2-yl]acetate;

2-[7-[4-[[5-(3,4-difluoroanilino)-1,3,4-oxadiazole-2-carbonyl]amino]phenyl]-7-azaspiro[3.5]nonan-2-yl]acetate;

7-[4-[(5-anilino-1,3,4-oxadiazole-2-carbonyl)amino]phenyl]-7-azaspiro[3.5]nonane-2-carboxylate;

7-[4-[[5-(3,4-difluoroanilino)-1,3,4-oxadiazole-2-carbonyl]amino]phenyl]-7-azaspiro [3.5]nonane-2-carboxylate;

2-[6-[5-[[5-(2-fluoroanilino)-1,3,4-oxadiazole-2-carbonyl]amino]-2-pyridyl]-6-azaspiro[3.3]heptan-2-yl]acetate;

2-[6-[5-[(5-anilino-1,3,4-oxadiazole-2-carbonyl)amino]-2-pyridyl]-6-azaspiro [3.3]heptan-2-yl]acetate;

2-[6-[5-[[5-(3,4-difluoroanilino)-1,3,4-oxadiazole-2-carbonyl]amino]-2-pyridyl]-6-azaspiro[3.3]heptan-2-yl]acetate;

5-(3,4-difluoroanilino)-N-[6-[2-(pyrrolidine-1-carbonyl)-7-azaspiro [3.5]nonan-7-yl]-3-pyridyl]-1,3,4-oxadiazole-2-carboxamide;

5-(3,4-difluoroanilino)-N-[6-[2-(2-methylpiperidine-1-carbonyl)-7-azaspiro[3.5]nonan-7-yl]-3-pyridyl]-1,3,4-oxadiazole-2-carboxamide;

5-(3,4-difluoroanilino)-N-[6-[2-(morpholine-4-carbonyl)-7-azaspiro[3.5]nonan-7-yl]-3-pyridyl]-1,3,4-oxadiazole-2-carboxamide;

5-(3,4-difluoroanilino)-N-[6-[2-(2,2,2-trifluoroethylcarbamoyl)-7-azaspiro[3.5]nonan-7-yl]-3-pyridyl]-1,3,4-oxadiazole-2-carboxamide;

5-(3,4-difluoroanilino)-N-[6-[2-(4-methoxypiperidine-1-carbonyl)-7-azaspiro[3.5]nonan-7-yl]-3-pyridyl]-1,3,4-oxadiazole-2-carboxamide;

5-(3,4-difluoroanilino)-N-6-[2-(4-hydroxypiperidine-1-carbonyl)-7-azaspiro[3.5]nonan-7-yl]-3-pyridyl]-1,3,4-oxadiazole-2-carboxamide;

5-(3,4-difluoroanilino)-N-[6-[2-[3-(trifluoromethyl)-6,8-dihydro-5H-[1,2,4]triazolo[4,3-a]pyrazine-7-carbonyl]-7-azaspiro[3.5]nonan-7-yl]-3-pyridyl]-1,3,4-oxadiazole-2-carboxamide;

5-(3,4-difluoroanilino)-N-[6-[2-(3-hydroxyazetidine-1-carbonyl)-7-azaspiro[3.5]nonan-7-yl]-3-pyridyl]-1,3,4-oxadiazole-2-carboxamide;

5-(3,4-difluoroanilino)-N-[6-[2-(4-oxopiperidine-1-carbonyl)-7-azaspiro[3.5]nonan-7-yl]-3-pyridyl]-1,3,4-oxadiazole-2-carboxamide;

5-(3,4-difluoroanilino)-N-[6-(2,2-difluoro-7-azaspiro[3.5]nonan-7-yl)-3-pyridyl]-1,3,4-oxadiazole-2-carboxamide;

N-[6-(2,2-difluoro-7-azaspiro[3.5]nonan-7-yl)-3-pyridyl]-5-[[6-(2,2,2-trifluoroethoxy)-3-pyridyl]amino]-1,3,4-oxadiazole-2-carboxamide;

5-(3,4-difluoroanilino)-N-[6-(2-methyl-7-azaspiro[3.5]nonan-7-yl)-3-pyridyl]-1,3,4-oxadiazole-2-carboxamide;

N-[6-(2-methyl-7-azaspiro[3.5]nonan-7-yl)-3-pyridyl]-5-[[6-(2,2,2-trifluoroethoxy)-3-pyridyl]amino]-1,3,4-oxadiazole-2-carboxamide;

5-(3,4-difluoroanilino)-N-[6-(2-hydroxy-7-azaspiro[3.5]nonan-7-yl)-3-pyridyl]-1,3,4-oxadiazole-2-carboxamide;

N-[6-(2-hydroxy-7-azaspiro[3.5]nonan-7-yl)-3-pyridyl]-5-[[6-(2,2,2-trifluoroethoxy)-3-pyridyl]amino]-1,3,4-oxadiazole-2-carboxamide;

5-(3,4-difluoroanilino)-N-[6-(2-fluoro-7-azaspiro[3.5]nonan-7-yl)-3-pyridyl]-1,3,4-oxadiazole-2-carboxamide;

N-[6-(2-fluoro-7-azaspiro[3.5]nonan-7-yl)-3-pyridyl]-5-[[6-(2,2,2-trifluoroethoxy)-3-pyridyl]amino]-1,3,4-oxadiazole-2-carboxamide;

5-(3,4-difluoroanilino)-N-[6-[2-(1-methyltetrazol-5-yl)-7-azaspiro[3.5]nonan-7-yl]-3-pyridyl]-1,3,4-oxadiazole-2-carboxamide;

5-(3,4-difluoroanilino)-N-[6-[2-(hydroxymethyl)-7-azaspiro[3.5]nonan-7-yl]-3-pyridyl]-1,3,4-oxadiazole-2-carboxamide;

N-[6-(2-carbamoyl-7-azaspiro [3.5]nonan-7-yl)-3-pyridyl]-5-(3,4-difluoroanilino)-1, 3,4-oxadiazole-2-carboxamide;

N-[6-[3-(2-amino-2-oxo-ethyl)-9-azaspiro [5.5]undecan-9-yl]-3-pyridyl]-5-(3,4-difluoroanilino)-1,3,4-oxadiazole-2-carboxamide;

5-(3,4-difluoroanilino)-N-[4-[(2-fluoro-7-azaspiro [3.5]nonan-7-yl)methyl]phenyl]-1,3,4-thiadiazole-2-carboxamide;

5-(3,4-difluorophenoxy)-N-[4-[(2-fluoro-7-azaspiro [3.5]nonan-7-yl)methyl]phenyl]-4H-1,2,4-triazole-3-carboxamide;

5-(3-fluorophenoxy)-N-[4-[(3-hydroxy-8-azaspiro [4.5]decan-8-yl)methyl]phenyl]-4H-1,2,4-triazole-3-carboxamide;

5-(3-fluorophenoxy)-N-[6-(3-hydroxy-8-azaspiro[4.5]decan-8-yl)-3-pyridyl]-4H-1,2,4-triazole-3-carboxamide;

N-[6-(3,3-difluoro-8-azaspiro [4.5]decan-8-yl)-3-pyridyl]-5-(3-fluorophenoxy)-4H-1,2,4-triazole-3-carboxamide;

5-[(6-chloro-3-pyridyl)oxy]-N-[6-(3,3-dimethyl-10-oxo-8-azaspiro [4.5]decan-8-yl)-3-pyridyl]-4H-1,2,4-triazole-3-carboxamide;

5-[(6-chloro-3-pyridyl)oxy]-N-[6-[2-(2,2,2-trifluoroethoxy)-7-azaspiro [3.5]nonan-7-yl]-3-pyridyl]-4H-1,2,4-triazole-3-carboxamide;

9-[5-[[5-(3-fluoroanilino)-1,3,4-oxadiazole-2-carbothioyl]amino]-2-pyridyl]-9-azaspiro [5.5]undecane-3-carboxylic acid;

3-[9-[5-[[5-(3-fluoroanilino)-1,3,4-oxadiazole-2-carbothioyl]amino]-2-pyridyl]-9-azaspiro [5.5]undecan-3-yl]propanoic acid;

3-[9-[5-[[5-(1H-indol-6-ylamino)-1,3,4-oxadiazole-2-carbothioyl]amino]-2-pyridyl]-9-azaspiro [5.5]undecan-3-yl]propanoic acid;

2-[7-[5-[[5-(3H-benzimidazol-5-ylamino)-1,3,4-oxadiazole-2-carbothioyl]amino]-2-pyridyl]-7-azaspiro [3.5]nonan-2-yl]acetic acid;

2-[7-[5-[[5-(3-phenylbenzimidazol-5-yl)amino]-1,3,4-oxadiazole-2-carbothioyl]amino]-2-pyridyl]-7-azaspiro [3.5]nonan-2-yl]acetic acid;

2-[7-[5-[[5-(3H-benzotriazol-5-ylamino)-1,3,4-oxadiazole-2-carbothioyl]amino]-2-pyridyl]-7-azaspiro [3.5]nonan-2-yl]acetic acid;

2-[7-[5-[[5-[(2-phenylbenzotriazol-5-yl)amino]-1,3,4-oxadiazole-2-carbothioyl]amino]-2-pyridyl]-7-azaspiro [3.5]nonan-2-yl]acetic acid;

6-[5-[[5-(1H-indol-2-ylamino)-1,3,4-oxadiazole-2-carbothioyl]amino]-2-pyridyl]-6-azaspiro [2.5]octane-2-carboxylic acid;

N-[6-(2-methyl-8-azaspiro [3.5]nonan-8-yl)-3-pyridyl]-5-[(2-phenylbenzotriazol-5-yl)amino]-1,3,4-oxadiazole-2-carbothioamide;

4-[5-[[5-(cyclohexa-1, 5-dien-1-ylamino)-1,3,4-oxadiazole-2-carbonyl]amino]-2-pyridyl]-4-azaspiro [5.5]undecane-9-carboxylic acid.

3. A pharmaceutical composition comprising a compound of formula (Ia) or a pharmaceutically acceptable salt thereof according to claim 1, together with a pharmaceutically acceptable carrier, optionally in combination with one or more other pharmaceutical compositions.

4. The compound of claim 1, having the formula:

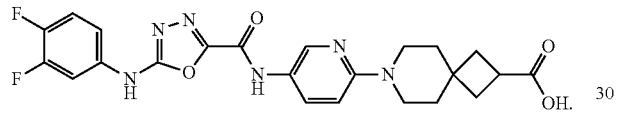

5. The composition of claim 3, wherein the compound has the formula:

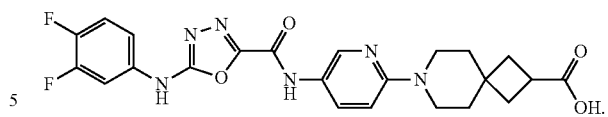

6. The composition of claim 3, wherein rings A and B together form a spiro ring system which is selected from the group consisting of:

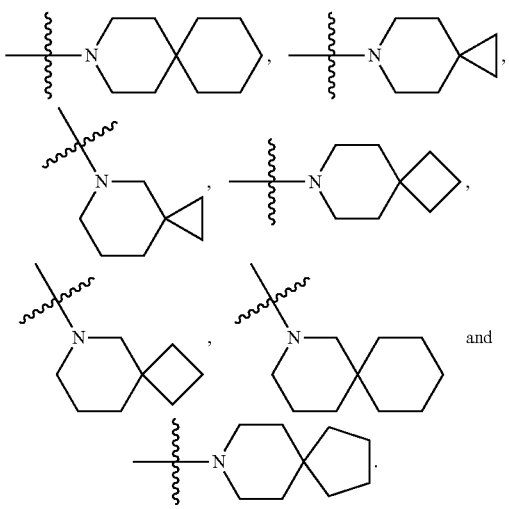

7. The compound of claim 1, wherein Ring C is pyridyl.

* * * * *